US008849581B2

(12) United States Patent
Hellerstein

(10) Patent No.: US 8,849,581 B2
(45) Date of Patent: *Sep. 30, 2014

(54) MOLECULAR FLUX RATES THROUGH CRITICAL PATHWAYS MEASURED BY STABLE ISOTOPE LABELING IN VIVO, AS BIOMARKERS OF DRUG ACTION AND DISEASE ACTIVITY

(71) Applicant: The Regents of the University of California, Oakland, CA (US)

(72) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/781,505

(22) Filed: Feb. 28, 2013

(65) Prior Publication Data
US 2013/0273533 A1 Oct. 17, 2013

Related U.S. Application Data

(60) Continuation of application No. 13/215,110, filed on Aug. 22, 2011, now Pat. No. 8,401,800, which is a division of application No. 11/064,197, filed on Feb. 22, 2005, now Pat. No. 8,005,623.

(60) Provisional application No. 60/581,028, filed on Jun. 17, 2004, provisional application No. 60/546,580, filed on Feb. 20, 2004.

(51) Int. Cl.
G06F 19/00 (2011.01)
G01N 33/50 (2006.01)
G01N 33/68 (2006.01)
G01N 33/92 (2006.01)
G01N 33/60 (2006.01)

(52) U.S. Cl.
CPC ........ G01N 33/5011 (2013.01); G01N 33/5014 (2013.01); G01N 33/6893 (2013.01); G01N 33/5088 (2013.01); G01N 2800/044 (2013.01); G01N 33/92 (2013.01); G01N 33/5008 (2013.01); G01N 2500/00 (2013.01); G01N 33/60 (2013.01); G01N 2800/323 (2013.01); G01N 2800/042 (2013.01); G01N 33/5038 (2013.01)
USPC .......................................................... 702/19

(58) Field of Classification Search
CPC ..... G06F 19/10; G06F 19/20; G01N 33/5088; G01N 33/60; G01N 33/6893; G01N 33/5014; G01N 33/5008; G01N 2500/00
See application file for complete search history.

(56) References Cited

U.S. PATENT DOCUMENTS

| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zoltarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |

(Continued)

FOREIGN PATENT DOCUMENTS

| CA | 2494715 A1 | 2/2004 |
| EP | 0826377 B1 | 11/2002 |

(Continued)

OTHER PUBLICATIONS

Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.
Price et al., "Measurement of Human Plasma Proteome Dynamics with 2H2O and Liquid Chromatography Tandem Mass Spectrometry", Analytical Biochemistry, vol. 420, 2012, pp. 73-83.

(Continued)

Primary Examiner — Lori A Clow
(74) Attorney, Agent, or Firm — Morrison & Foerster LLP

(57) ABSTRACT

The methods described herein enable the evaluation of compounds on subjects to assess their therapeutic efficacy or toxic effects. The target of analysis is the underlying biochemical process or processes (i.e., metabolic process) thought to be involved in disease pathogenesis. Molecular flux rates within the one or more biochemical processes serve as biomarkers and are quantitated and compared with the molecular flux rates (i.e., biomarker)from control subjects (i.e., subjects not exposed to the compounds). Any change in the biomarker in the subject relative to the biomarker in the control subject provides information to evaluate therapeutic efficacy of an administered drug or a toxic effect and to develop the compound further if desired. In one aspect of the invention, stable isotope-labeled substrate molecules are administered to a subject and the label is incorporated into targeted molecules in a manner that reveals molecular flux rates through metabolic pathways of interest.

19 Claims, 30 Drawing Sheets

(56) References Cited

U.S. PATENT DOCUMENTS

| | | | |
|---|---|---|---|
| 5,961,470 | A | 10/1999 | Wagner et al. |
| 6,010,846 | A | 1/2000 | Hellerstein |
| 6,031,228 | A | 2/2000 | Abramson |
| 6,071,245 | A | 6/2000 | Kohno et al. |
| 6,117,656 | A | 9/2000 | Seed |
| 6,284,219 | B1 | 9/2001 | Ajami |
| 6,329,208 | B1 | 12/2001 | Jones et al. |
| 6,355,416 | B1 | 3/2002 | Abramson |
| 6,461,806 | B1 | 10/2002 | Hellerstein |
| 6,461,870 | B2 | 10/2002 | Yatscoff et al. |
| 6,468,802 | B1 | 10/2002 | Yatscoff et al. |
| 6,599,750 | B2 | 7/2003 | Yatscoff et al. |
| 6,602,715 | B2 | 8/2003 | Yatscoff et al. |
| 6,610,270 | B1 | 8/2003 | Ajami |
| 6,625,547 | B1 | 9/2003 | Korzekwa et al. |
| 6,642,059 | B2 | 11/2003 | Chait et al. |
| 6,653,076 | B1 | 11/2003 | Franza, Jr. et al. |
| 6,653,090 | B1 | 11/2003 | Lopaschuk |
| 6,670,194 | B1 | 12/2003 | Aebersold et al. |
| 6,680,203 | B2 | 1/2004 | Dasseux et al. |
| 6,764,817 | B1 | 7/2004 | Schneider |
| 6,783,751 | B2 | 8/2004 | Heumann |
| 6,808,875 | B2 | 10/2004 | Hellerstein |
| 6,835,927 | B2 | 12/2004 | Becker et al. |
| 6,849,396 | B2 | 2/2005 | Schneider |
| 6,872,575 | B2 | 3/2005 | Regnier |
| 6,887,712 | B1 | 5/2005 | Medford et al. |
| 6,902,719 | B2 | 6/2005 | Wagner |
| 6,906,320 | B2 | 6/2005 | Sachs et al. |
| 7,001,587 | B2 | 2/2006 | Hellerstein |
| 7,022,834 | B2 | 4/2006 | Hellerstein |
| 7,048,907 | B2 | 5/2006 | Groman et al. |
| 7,057,168 | B2 | 6/2006 | Miller et al. |
| 7,084,396 | B2 | 8/2006 | Schneider |
| 7,255,850 | B2 | 8/2007 | Hellerstein |
| 7,256,047 | B2 | 8/2007 | Malloy et al. |
| 7,262,020 | B2 | 8/2007 | Hellerstein |
| 7,307,059 | B2 | 12/2007 | Hellerstein |
| 7,357,913 | B2 | 4/2008 | Hellerstein |
| 7,410,633 | B2 | 8/2008 | Hellerstein |
| 7,449,171 | B2 | 11/2008 | Hellerstein |
| 7,504,233 | B2 | 3/2009 | Hellerstein |
| 7,910,323 | B2 | 3/2011 | Hellerstein |
| 8,005,623 | B2 | 8/2011 | Hellerstein |
| 8,021,644 | B2 | 9/2011 | Hellerstein |
| 8,129,335 | B2 | 3/2012 | Hellerstein |
| 2003/0068634 | A1 | 4/2003 | Hellerstein |
| 2003/0119069 | A1 | 6/2003 | Schneider et al. |
| 2003/0133871 | A1 | 7/2003 | Hellerstein |
| 2003/0148533 | A1 | 8/2003 | Malloy et al. |
| 2003/0180710 | A1 | 9/2003 | Lee et al. |
| 2003/0180800 | A1 | 9/2003 | Lee et al. |
| 2003/0211036 | A1 | 11/2003 | Degani et al. |
| 2003/0224420 | A1 | 12/2003 | Hellerstein et al. |
| 2003/0228259 | A1 | 12/2003 | Hellerstein |
| 2004/0081994 | A1 | 4/2004 | Hellerstein |
| 2004/0091943 | A1 | 5/2004 | Schneider |
| 2004/0115131 | A1 | 6/2004 | Hellerstein |
| 2004/0121305 | A1 | 6/2004 | Wiegand et al. |
| 2004/0152994 | A1 | 8/2004 | Meier-Augenstein |
| 2004/0191916 | A1 | 9/2004 | Gross et al. |
| 2004/0253647 | A1 | 12/2004 | Mathews et al. |
| 2005/0003375 | A1 | 1/2005 | Franza, Jr. et al. |
| 2005/0014181 | A1 | 1/2005 | Galis et al. |
| 2005/0092910 | A1 | 5/2005 | Geromanos et al. |
| 2005/0118724 | A1 | 6/2005 | Bateman et al. |
| 2005/0147558 | A1 | 7/2005 | Hellerstein |
| 2005/0153346 | A1 | 7/2005 | Schneider |
| 2005/0175982 | A1 | 8/2005 | Iwatani et al. |
| 2005/0180949 | A1 | 8/2005 | Emtage et al. |
| 2005/0201937 | A1 | 9/2005 | Hellerstein |
| 2005/0202406 | A1 | 9/2005 | Hellerstein |
| 2005/0221278 | A1 | 10/2005 | Iwatani et al. |
| 2005/0238577 | A1 | 10/2005 | Hellerstein |
| 2005/0238581 | A1 | 10/2005 | Kurland et al. |
| 2005/0255509 | A1 | 11/2005 | Hellerstein et al. |
| 2005/0281745 | A1 | 12/2005 | Lee et al. |
| 2006/0008796 | A1 | 1/2006 | Hellerstein |
| 2006/0029549 | A1 | 2/2006 | Hellerstein |
| 2006/0094057 | A1 | 5/2006 | Hellerstein |
| 2006/0100903 | A1 | 5/2006 | Lee et al. |
| 2006/0105322 | A1 | 5/2006 | Iwatani et al. |
| 2006/0105339 | A1 | 5/2006 | Hellerstein |
| 2006/0120961 | A1 | 6/2006 | Schneider et al. |
| 2006/0204439 | A1 | 9/2006 | Hellerstein |
| 2006/0251576 | A1 | 11/2006 | Hellerstein |
| 2006/0280682 | A1 | 12/2006 | Hellerstein |
| 2007/0248540 | A1 | 10/2007 | Hellerstein |
| 2008/0003179 | A1 | 1/2008 | Hellerstein |
| 2009/0041661 | A1 | 2/2009 | Hellerstein |

FOREIGN PATENT DOCUMENTS

| | | |
|---|---|---|
| JP | 2001-211782 A | 8/2001 |
| JP | 2003-502016 A | 1/2003 |
| JP | 2003-79270 A | 3/2003 |
| SU | 968036 A1 | 10/1982 |
| WO | 90/11371 A1 | 10/1990 |
| WO | 93/20800 A1 | 10/1993 |
| WO | 93/25705 A1 | 12/1993 |
| WO | 95/13096 A1 | 5/1995 |
| WO | 98/51820 A1 | 11/1998 |
| WO | 00/12535 A2 | 3/2000 |
| WO | 00/13025 A1 | 3/2000 |
| WO | 00/55355 A2 | 9/2000 |
| WO | 00/63683 A1 | 10/2000 |
| WO | 01/80715 A2 | 11/2001 |
| WO | 01/84143 A1 | 11/2001 |
| WO | 03/061479 A1 | 7/2003 |
| WO | 03/068919 A2 | 8/2003 |
| WO | 03/087314 A2 | 10/2003 |
| WO | 2004/003493 A2 | 1/2004 |
| WO | 2004/011426 A2 | 2/2004 |
| WO | 2004/016156 A2 | 2/2004 |
| WO | 2004/021863 A2 | 3/2004 |
| WO | 2004/024941 A2 | 3/2004 |
| WO | 2004/025270 A2 | 3/2004 |
| WO | 2004/042360 A2 | 5/2004 |
| WO | 2004/016156 A3 | 6/2004 |
| WO | 2005/009597 A2 | 2/2005 |
| WO | 2005/015155 A2 | 2/2005 |
| WO | 2005/033652 A2 | 4/2005 |
| WO | 2006/050130 A2 | 5/2006 |
| WO | 2006/081521 A2 | 8/2006 |
| WO | 2006/107814 A2 | 10/2006 |

OTHER PUBLICATIONS

Hinkson et al., "The Dynamic State of Protein Turnover: It's About Time", Trends in Cell Biology, vol. 21, No. 5, May 2011, pp. 293-303.

Linn et al., "Effect of Long-Term Dietary Protein Intake on Glucose Metabolism in Humans", Diabetologia, vol. 43, 2000, pp. 1257-1265.

Nordhoff et al., "Mass Spectrometry of Nucleic Acids", Mass Spectrometry Reviews, vol. 15, 1996, pp. 67-138.

Previs et al., "A Critical Evaluation of Mass Isotopomer Distribution Analysis of Gluconeogenesis in Vivo", American Journal of Physiology-Endocrinology and Metabolism, vol. 277, 1999, E154-E160.

Szymanski et al., "Beyond the Proteome: Non-Coding Regulatory RNAs", Genome Biology, vol. 3, No. 5, Apr. 15, 2002, pp. 1-8.

Boros et al., "Metabolic Profiling of Cell Growth and Death in Cancer: Applications in Drug Discovery", Drug Discovery Today, vol. 7, No. 6, Mar. 2002, pp. 364-372.

Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1088-1095.

Brown et al., "Treating Patients with Documented Atherosclerosis to National Cholesterol Education Program—Recommended Low-Density-Lipoprotein Cholesterol Goals with Atorvastatin, Fluvastatin, Lovastatin and Simvastatin", Journal of the American College of Cardiology, vol. 32, 1998, pp. 665-672.

(56) References Cited

OTHER PUBLICATIONS

Bucy et al., "Analysis of Lymph Node Biopsies in HIV Infected Patients Before and After HAART", 5th Conference on Retroviruses and Opportunistic Infections, Session 66, vol. 519, 1998, 177 Pages (Abstract only).
Caldwell et al., "Quantification of Peptide Isotopomer Abundances and Determination of Protein (sic) Turnover Rates by Using Mass Isotopomer Distribution Analysis", 41st Annual Amer. Society Mass Spectrometry on Mass Spectrometry, 1993, p. 331a (Abstract only).
Cassella et al., "Mechanisms of Lymphocyte Killing by HIV", Current Opinion in Hematology, vol. 4, 1997, pp. 24-31.
Cesar et al., "Direct Measurement of CD4+ and CD8+ T Cell Proliferation Rates in Vivo in AIDS Patients Using a Stable Isotope-Mass Spectrometric Technique", 5th Conference on Retroviruses and Opportunistic Infections, Chicago Illinois, 1998, Abstract only.
Chinkes et al., "Comparison of Mass Isotopomer Dilution Methods Used to Compute VLDL Production In Vivo", The American Journal of Physiology, vol. 271, 1996, pp. E373-E383.
Christiansen et al., "Effect of Dietary Energy Restriction on Glucose Production and Substrate Utilization in Type 2 Diabetes", Diabetes, vol. 49, Oct. 2000, pp. 1691-1699.
Clarke, R. B., "Isolation and Characterization of Human Mammary Stem Cells", Cell Proliferation, vol. 38, 2005, pp. 375-386.
Clayton, "Replication and Transcription of Vertebrate Mitochondrial DNA", Annual Review of Cell Biology, vol. 7, 1991, pp. 453-478.
Cohen et al., "Purine and Pyrimidine Metabolism in Human T Lymphocytes. Regulation of Deoxyribonucleotide Metabolism", The Journal of Biological Chemistry, vol. 258, No. 20, 1983, pp. 12334-12340.
Cohen, J. "Failure Isn't What It Used to Be . . . But Neither is Success", Science, vol. 279, 1998, pp. 1133-1134.
Collins et al., "A Method for Measuring Mitochondrial Proliferation In Vivo Using 2H2O Incorporation Into Mitochondria DNA", FASEB Journal, vol. 14, No. 4, Mar. 15, 2000, p. A620.
Collins et al., "Measurement of Mitochondrial DNA Synthesis In Vivo Using a Stable Isotope-Mass Spectrometric Technique", Journal of Applied Physiology, vol. 94, 2003, pp. 2203-2211.
Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, 1997, pp. 533-540.
Conrads et al., "Stable Isotope Labeling in Proteomics", The Synthesis Cambridge Isotope Laboratories, vol. 3, No. 2, Jan. 2002, pp. 1-3.
Craig et al., "The Impact of Physical Activity on Lipids, Lipoproteins, and Blood Pressure in Preadolescent Girls", Pediatrics, vol. 98, 1996, pp. 389-395.
Crain, "Preparation and Enzymatic Hydrolysis of DNA and RNA for Mass Spectrometry", Methods in Enzymology, vol. 193, 1990, pp. 782-790.
Dalvie, D. "Recent Advances in the Applications of Radioisotopes in Drug Metabolism, Toxicology and Pharmacokinetics", Current Pharmaceutical Design, vol. 6, 2000, pp. 1009-1028.
Davis et al., "Effect of Pinitol Treatment on Insulin Action in Subjects with Insulin Resistance", Diabetes Care, vol. 23, No. 7, Jul. 2000, pp. 1000-1005.
Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.
Deeks et al., "Viral Load and CD4+ T Cell Changes in Patients Failing Potent Protease Inhibitor Therapy", 5th Conference on Retroviruses and Opportunistic Infections, Session 53, vol. 419, 1998, p. 158 (Abstract only).
Dekker et al., "Glucose Homeostasis in Children with Falciparum Malaria: Precursor Supply Limits Gluconeogenesis and Glucose Production", J. Clin. Endocrinol. Metabol., vol. 82, 1997, pp. 2514-2521.

Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.
Dimitrov et al., "Scientific Correspondence", Nature, vol. 375, 1995, pp. 194-195.
Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.
Emken et al., "Incorporation of Deuterium-Labeled Trans- and CIS-13-Octadeconoic Acids in Human Plasma Lipids", Journal of Lipid Research, vol. 24, 1983, pp. 34-41.
Etnier et al., "Metabolism of Organically Bound Tritium in Man", Radiation Research, vol. 100, 1984, pp. 487-502.
Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.
Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.
Gasparini et al., "Amplification of DNA from Epithelial Cells in Urine", The New England Journal of Medicine, vol. 320, No. 12, 1989, p. 809.
Gerling et al., "Prediction of Liver Fibrosis According to Serum Collagen VI Level in Children with Cystic Fibrosis", The New England Journal of Medicine, vol. 336, No. 22, 1997, pp. 1611-1612.
Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.
Goz, "The Effects of Incorporation of 5-Halogenated Deoxyuridines into the DNA of Eukaryotic Cells", Pharmacological Reviews, vol. 29, 1977, pp. 249-272.
Gratzner, "Monoclonal Antibody to 5-Bromo- and 5-Iododeoxyuridine: A New Reagent for Detection of DNA Replication", Science, vol. 218, 1982, pp. 474-475.
Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.
Gygi et al., "Using Mass Spectrometry for Quantitative Proteomics", Proteomics: A Trends Guide, 2000, pp. 31-36.
Hansen et al., "A Practical Method for Uniform Isotopic Labeling of Recombinant Proteins in Mammalian Cells", Biochemistry, vol. 31, 1992, pp. 12713-12718.
Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.
Hellerstein, "Mass Isotopomer Distribution Analysis: A Technique for Measuring Biosynthesis and Turnover of Polymers", The American Journal of Physiology, vol. 263, 1992, pp. E988-E1001.
Hellerstein et al., "Altered Fluxes Responsible for Reduced Hepatic Glucose Production and Gluconeogenesis by Exogenous Glucose in Rats", The American Journal of Physiology, vol. 272, 1997, pp. E163-E172.
Hellerstein et al., "Directly Measured Kinetics of Circulating T Lymphocytes in Normal and HIV-1-Infected Humans", Nature Medicine, vol. 5, 1999, pp. 83-89.
Hellerstein et al., "Effects of Cigarette Smoking and its Cessation on Lipid Metabolism and Energy Expenditure in Heavy Smokers", J. Clin. Invest., vol. 93, 1994, pp. 265-272.
Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.
Hellerstein et al., "Hepatic Gluconeogenic Fluxes and Glycogen Turnover During Fasting in Humans. A Stable Isotope Study", The Journal of Clinical Investigation, vol. 100, No. 5, Sep. 1997, pp. 1305-1319.

(56) References Cited

OTHER PUBLICATIONS

Hellerstein et al., "Mass Isotopomer Distribution Analysis at Eight Years: Theoretical, Analytic, and Experimental Considerations", The American Journal of Physiology, vol. 276, 1999, pp. E1146-E1170.

Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.

Hellerstein et al., "Measurement of Hepatic Ra UDP-Glucose in Vivo in Rats: Relation to Glycogen Deposition and Labeling Patterns", The American Journal of Physiology, vol. 272, 1997, pp. E155-E162.

Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology, Meeting, vol. 16, 2002, p. A256 (Abstract only).

McLean et al., "In Vivo Estimates of Division and Death Rates of Human T Lymphocytes", Proc. Natl. Acad. Sci USA, vol. 92, 1995, pp. 3707-3711.

Meier et al., "Rates of Protein Synthesis and Turnover in Fetal Life", Am J Physiol., vol. 240, No. 3, 1981, pp. E320-E324.

Mellors et al., "Prognosis in HIV-1 Infection Predicted by the Quantity of Virus in Plasma", Science, vol. 272, 1996, pp. 1167-1170.

Mellors et al., "Quantitation of HIV-1 RNA in Plasma Predicts Outcome after Seroconversion", Ann. Intern. Med., vol. 122, 1995, pp. 573-579.

Messmer et al., "In Vivo Measurements Document the Dynamic Cellular Kinetics of Chronic Lymphocytic Leukemia B Cells", J. Clin. Invest., vol. 115, Feb. 10, 2005, pp. 755-764.

Mewissen et al., "Comparative Incorporation of Tritium from Tritiated Water Versus Tritiated Thymidine, Uridine or Leucine", Curr. Top Rad. Res. Quart., vol. 12, 1977, pp. 225-254.

Michie et al., "Lifespan of Human Lymphocyte Subsets Defined by CD45 Isoforms,", Nature, vol. 360, 1992, pp. 264-265.

Mikkola et al., "Serum Cholesterol Efflux Potential is an Independent Predictor of Coronary Artery Atherosclerosis", Atherosclerosis, vol. 170, 2003, pp. 31-38.

Mindham et al., "Application of Simultaneous Spleen and Liver Perfusion to the Study of Reverse Cholesterol Transport", Biochemical Journal, vol. 302, 1994, pp. 207-213.

Misell et al., "A new in Vivo Stable Isotope Method for Measuring Mammary Epithelial Cell Proliferation", Faseb Journal Experimental Biology, vol. 14, No. 4, 2000, p. 550.

Mohri et al., "Increased Turnover of T Lymphocytes in HIV-1 Infection and its Reduction by Antiretroviral Therapy", J. Exp. Med., vol. 194, No. 9, 2001, pp. 1277-1287.

Morris et al., "Evidence that a Slowly Cycling Subpopulation of Adult Murine Epidermal Cells Retains Carcinogen", Cancer Research, vol. 46, 1997, pp. 3061-3066.

Morris et al., "Evidence that Cutaneous Carcinogen-Initiated Epithelial Cells from Mice are Quiescent Rather than Actively Cycling", Cancer Research, vol. 57, 1997, pp. 3436-3443.

Morsches, "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.

Mosier, D. E., "CD4.sup.+ Cell Turnover", Nature, vol. 375, 1995, pp. 193-194.

Murali-Krishna et al., "Counting Antigen-Specific CD8 T Cells: A Reevaluation of Bystander Activation during Viral Infection", Immunity, vol. 8, 1998, pp. 177-187.

Nagasaka et al., "Endogenous Glucose Production and Glucose Effectiveness in Type 2 Diabetic Subjects Derived From Stable-Labeled Minimal Modal Approach", Diabetes, vol. 48, May 1999, pp. 1054-1056.

Naik et al., "Pharmacological Activation of Liver X Receptors Promotes Reverse Cholesterol Transport In Vivo", Circulation, vol. 113, 2006, pp. 90-97.

Nanjee et al., "Intravenous apoA-I/lecithin Discs Increase Pre-Beta-HDL Concentration in Tissue Fluid and Stimulate Reverse Cholesterol Transport in Humans", Journal of Lipid Research, vol. 42, 2001, pp. 1586-1593.

Neese et al., "Advances in the Stable Isotope-Mass Spectrometric Measurement of DNA Synthesis and Cell Proliferation", Analytical Biochemistry, vol. 298, No. 2, 2001, pp. 189-195.

Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.

Neese et al., "Measurement of Endogenous Synthesis of Plasma Cholesterol in Rats and Humans Using MIDA", Am. J. Physiol., vol. 264, 1993, pp. E139-E147.

Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350.

Ong et al., "Stable Isotope Labeling by Amino Acids in Cell Culture, SILAC, as a Simple and Accurate Approach to Expression Proteomics", Molecular and Cellular Proteomics, vol. 1, 2002, pp. 376-386.

Oshima et al., "COX Selectivity and Animal Models for Colon Cancer", Current Pharmaceutical Design, vol. 8, 2002, pp. 1021-1034.

Ouguerram et al., "A New Labeling Approach Using Stable Isotopes to Study In Vivo Plasma Cholesterol Metabolism in Humans", Metabolism, vol. 51, No. 1, Jan. 2002, pp. 5-11.

Oyaizu et al., "Role of Apoptosis in HIV Disease Pathogenesis", J. of Clinical Immunology, vol. 15, No. 5, 1995, pp. 217-231.

Paku, S. "Origin and Structural Evolution of the Early Proliferating Oval Cells in Rat Liver", American Journal of Pathology, vol. 158, No. 4, Apr. 2001, pp. 1313-1323.

Palmer et al., "Telomere Length, Telomerase Activity, and Replicative Potential in HIV Infection: Analysis of CD4+ and CD8+ T Cells from HIV-discordant Monozygotic Twins", J. Experimental Medicine, vol. 185, No. 7, 1997, pp. 1381-1386.

Panteleo, Giuseppe, "Unraveling the Strands of HIV's Web", Nature Medicine, vol. 5, No. 1, 1999, pp. 27-28.

Papageorgopoulos et al., "Measuring Protein Synthesis by Mass Isotopomer Distribution Analysis (MIDA)", Analytical Biochemistry, vol. 267, 1999, pp. 1-16.

Papageorgopoulos et al., "Toward the Measurement of Protein Synthesis by Mass Isotopomer Distribution Analysis (MIDA):Resolution of Isotopomers in a [d.sub.3]-Leucine Enriched Synthetic Oligopeptide Using Electrospray/Quadrupole Mass Spectrometry (ESI/MS)", Federation of American Societies for Experimental Biology, vol. 1022, 1993, p. A177.

Park et al., "Measurement of Small Intestinal Cell Turnover with [6,6, 2H2] Glucose", Berkeley Scientific, Abstract, vol. 1, No. 2, 1997, pp. 41-43.

Parks et al., "Carbohydrate-induced Hypertriacylglycerolemia: Historical Perspective and Review of Biological Mechanisms", Am. J. Nutr., vol. 71, 2000, pp. 412-433.

Parks et al., "Dependence of Plasma a-Tocopherol Flux on Very Low-Density Triglyceride Clearance in Humans", Free Radical Biology & Medicine, vol. 29, No. 11, 2000, pp. 1151-1159.

Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.

Paša-Tolic et al., "High Throughput Proteome-Wide Precision Measurements of Protein expression Using Mass Spectrometry", J. Am. Chem. Soc., vol. 121, 1999, pp. 7949-7950.

Patsalos et al., "Pattern of Myelin Breakdown During Sciatic Nerve Wallerian Degeneration: Reversal of the Order of Assembly", The Journal of Cell Biology, vol. 87, 1980, pp. 1-5.

Patterson et al., "Concentration Dependence of Methyl-Palmitate Isotope Ratios by Electron Impact Ionization Gas Chromatography/Mass Spectrometry", Biol. Mass Spectrom., vol. 22, 1993, pp. 481-486.

Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.

(56) References Cited

OTHER PUBLICATIONS

Patton et al., "Measurements of Fatty Acid Synthesis by Incorporation of Deuterium from Deuterated Water", Biochemistry, vol. 18, No. 14, 1979, pp. 3186-3188.

Perelson et al., "Decay Characteristics of HIV-1-Infected Compartments During Combination Therapy", Nature 387, 1997, pp. 188-191.

Perelson et al., "HIV-1 Dynamics in Vivo: Virion Clearance Rate, Infected Cell Life-Span, and Viral Generation Time", Science, vol. 271, 1996, pp. 1582-1586.

Perochon et al., "Radiolabeling of the Lipids of Chinese Hamster Ovary Cells with the Probe [3-(Trifluoromethyl)-3-(m-[4125]iodophenyl)diazirine", Analytical Biochemistry, vol. 254, 1997, pp. 109-118.

Previs et al., "Estimation of Protein Turnover In Vivo Using D2O", Diabetes Abstract Book, 61st Scientific Sessions, vol. 50, Supplement 2, A301, 2001, 1248-p.

Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.

Ramakers et al., "Chronic Suppression of Bioelectric Activity and Cell Survival in Primary Cultures of Rat Cerebral Cortex Biochemical Observations", European Journal of Neuroscience, vol. 3, No. 2, 1991, pp. 154-161.

Ravichandran et al., "In Vivo Labeling Studies on the Biosynthesis and Degradation of Collagen in Experimental Myocardial Infarction", Biochemistry Journal, vol. 24, No. 3, 1991, pp. 405-414.

Reichard, P., "From Deoxynucleotides to DNA Synthesis", Federation Proceedings, vol. 37, No. 1, 1978, pp. 9-14.

Reichard, P., "Interactions Between Deoxyribonucleotide and DNA Synthesis", Ann. Rev. Biochem. vol. 57, 1988, pp. 349-374.

Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.

Rittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.

Rittler et al., "Effect of Tumor Removal on Mucosal Protein Synthesis in Patients with Colorectal Cancer", American Journal of Physiology-Endocrinology and Metabolism, vol. 284, 2003, pp. E1018-E1021.

Roberts, "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.

Robin et al., "Mitochondria DNA Molecules and Virtual Number of Mitochondria per Cell in Mammalian Cells", Journal of Cellular Physiology, vol. 136, 1988, pp. 507-513.

Robosky, L. C., "In Vivo Toxicity Screening Programs Using Metabonomics", Combinatorial Chemistry & High Throughput Screening., vol. 5, 2002, pp. 651-662.

Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.

Roda et al., "Results with Six 'Kit' Radioimmunoassays for Primary Bile Acids in Human Serum Intercompared", Clin. Chem., vol. 26, No. 12, 1980, pp. 1677-1682.

Roederer, M. "T-Cell Dynamics of Immunodeficiency", Nature Medicine, vol. 1, No. 7, Jul. 1995, pp. 621-622.

Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.

Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.

Royale et al., "Techniques for Investigating Substrate Metabolism in Patients", Annals of the Royal College of Surgeons of England, vol. 63, 1981, pp. 415-419.

Santarelli et al., "Requirement of Hippocampal Neurogenesis for the Behavioral Effects of Antidepressants", Science, vol. 301, No. 5634, Aug. 8, 2003, pp. 805-809.

Sawada et al., "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver", Mutation Research, vol. 344, 1995, pp. 109-116.

Scalise, K., "Tracking T-Cells in AIDS Patients: A Safe Reliable Method of Measuring Human Cell Generation Rates", Berkeleyan, Feb. 11-17, 1998, 3 pages.

Scheibner et al., "Bile Acid Synthesis from Newly Synthesized Vs. Preformed Cholesterol Precursor Pools in the Rat", Hepatology, vol. 17, 1993, pp. 1095-1102.

Scheibner et al., "Complex Feedback Regulation of Bile Acid Synthesis in the Hamster: The Role of Newly Synthsized Cholesterol", Hepatology, vol. 30, 1999, pp. 230-237.

Schneiter et al., "Kinetics of Dexamethasone Induced Alterations of Glucose Metabolism in Healthy Humans", American Journal of Physiology, 1998, pp. E806-E813.

Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.

Schwarz et al., "Short-Term Alterations in Carbohydrate Energy Intake in Humans", J. Clin. Invest., vol. 96, 1995, pp. 2735-2743.

Australian Patent Office Search Report mailed Aug. 26, 2005, for Singapore patent application No. SG 200500571-5, filed Jul. 25, 2003, 5 pages.

Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.

Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.

Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.

Siler et al., "The Inhibition of Gluconeogenesis Following Alcohol in Humans", Am. J. Physiol., vol. 275, 1998, pp. E897-E907.

Siler et al., "VLDL-Triglyceride Production After Alcohol Ingestion, Studied Using [2-13C1] Glycerol", J. Lipid Res., vol. 39, 1998, pp. 2319-2328.

Smith et al., "The Phosphogluconate Odixative Pathway", in Principles of Biochemistry, 7th edition, McGraw-Hill Book Company, 1983, pp. 417-423.

Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.

Sprent et al., "CD4+ Cell Turnover", Nature, vol. 375, 1995, 194 pages.

Stingl, et al., "Purification and Unique Properties of Mammary Epithelial Stem Cells", Nature, vol. 439, Feb. 2006, pp. 993-997.

Stingl et al., "Characterization of Bipotent Mammary Epithelial Progenitor Cells in Normal Adult Human Breast Tissue", Breast Can Res and Treatment, vol. 67, 2001, pp. 93-109.

Sunter et al., "Cell Population Kinetics in the Epithelium of the Colon of the Male Rat", Virchows Archiv. B Cell Path., vol. 26, 1978, pp. 275-287.

Teixeira et al., "Poor CD4 T Cell Restoration After Supression of HIV-1 Replication May Reflect Lower Thymic Function", AIDS, vol. 15, No. 14, 2001, pp. 1749-1756.

Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.

(56) References Cited

OTHER PUBLICATIONS

Traber et al., "Isolation of Intestinal Epithelial Cells for the Study of Differential Gene Expression Along the Crypt-Villus Axis", Am. J. Physiol., vol. 260, 1991, pp. G895-G903.
Trappe et al., "Effect of Ibuprofen and Acetaminophen on Postexercise Muscle Protein Synthesis", Am J Physiology Endocronol Metab, vol. 282, 2002, pp. E551-E556.
Turner, S. M., "Stable Isotopes, Mass Spectrometry, and Molecular Fluxes: Applications to Toxicology", Journal of Pharmacological and Toxicological Methods, vol. 53, 2006, pp. 75-85.
Turner et al., "Emerging Applications of Kinetic Biomarkers in Preclinical and Clinical Drug Development", Current Opinion in Drug Discovery & Development, vol. 8, No. 1, 2005, pp. 115-126.
Turner et al., "Measurement of Triglyceride (TG) Synthesis in Vivo 2H2O Incorporation into TG-Glycerol and Application of Mass Isotopomer Distribution Analysis (MIDA)", Experimental Biology, 2002 16 [Meeting Abstract 361.9], A400.
Van Hinsbergh et al., "Palmitate Oxidation by Rat Skeletal Muscle Mitochondria", Archives of Biochemistry and Biophysics, vol. 190, No. 2, 1978, pp. 762-771.
Van Loan et al., "Monitoring Changes in Fat-Free Mass in HIV-Positive Men with Hypotestosteronemia and AIDS Wasting Syndrome Treated with Gonadal Hormone Replacement Therapy", AIDS, vol. 13, 1999, pp. 241-248.
Veenstra et al., "Proteome Analysis Using Selective Incorporation of Isotopically Labeled Amino Acids", J. Am. Soc. Mass. Spectrom., vol. 11, 2000, pp. 78-82.
Veerkamp et al., "14CO2 Production is no Adequate Measure of [14C]Fatty Acid Oxidation", Biochemical Medicine and Metabolic Biology, vol. 35, 1986, pp. 248-259.
Véniant et al., "Defining the Atherogenicity of Large and Small Lipoproteins Containing Apolipoproteins B100", J. Clin. Invest., vol. 106, No. 12, 2000, pp. 1501-1510.
Wadke, "Fatty Acid Synthesis by Liver Perfused with Deuterated and Tritiated Water", Biochemistry, vol. 12, No. 14, 1973, pp. 2619-2624.
Wain-Hobson, S., "Virological Mayhem", Nature, vol. 373, 1995, 102 pages.
Waldeman et al., "A Comparison Between Bromodeoxyuridine and 3 H Thymidine Labeling in Human Breast Tumors", Modern Path., vol. 4, No. 6, 1991, pp. 718-722.
Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.
Waterlow, "Protein Turnover in the Whole Animal", Invest. Cell Pathol. vol. 3, 1980, pp. 107-119.
Wei et al., "Viral Dynamics in Human Immunodeficiency Virus Type 1 Infection", Nature, vol. 373, 1995, pp. 117-122.
Whittmann et al., "Application of MALDI-TOF MS to lysine-Producing *Corynebacterium glutamicum*: A Novel Approach for Metabolic Flux Analysis", Eur. J. Biochem., vol. 268, 2001, pp. 2441-2455.
Winett et al., "Exercise Regimens for Men With HIV", JAMA, vol. 284, No. 2, 2000, pp. 175-176.
Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.
Wolfe, "Isotopic Measurement of Glucose and Lactate Kinetics", Ann. Med., vol. 22, 1990, pp. 163-170.
Wolfe et al., "Glucose Metabolism in Humans", ACS Symposium Series 258, Chapter 12, Turnund et al. ed., 1984, pp. 175-189.
Wolthers et al., "Rapid CD4+ T-Cell Turnover in HIV-1 Infection: A Paradigm Revisited", Immunology Today, vol. 19, No. 1, 1998, pp. 44-48.
Wolthers et al., "T Cell Telomere Length in HIV-1 Infection: No Evidence for Increased CD4+ T Cell Turnover", Science, vol. 274, 1996, pp. 1543-1547.
Wong et al., "From monoamines to genomic targets: a paradigm shift for drug discovery in depression", Nature Reviews Drug Discovery, vol. 3, Feb. 2004, pp. 136-151.

Wood et al., "Estimation of Pathways of Carbohydrate Metabolism", Biochemische Zeitschrift, vol. 338, 1963, pp. 809-847.
Zhang et al., "Deuterium NMR Study of the Origin of Hydrogen in Fatty Acids Produced In Vivo in Chicken.", European Journal of Lipid Science and Technology, vol. 108, 2006, pp. 125-133.
Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.
Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.
Pozharisski et al., "Study of Kinetics of Epithelial Cell Populations in Normal Tissues of the Rat's Intestines and in Carcinogenesis", Exp. Path., Bd., vol. 18, 1980, pp. 387-406.
Landau et al., "Use of 2H2O for Estimating Rates of Gluconeogenesis", Journal of Clinical Investigation, vol. 95, Jan. 1995, pp. 172-178.
Office Action received for Canadian Patent Application No. 2,555,702, mailed on Jan. 27, 2012, 5 pages.
Extended European Search Report received for European Patent Application No. 06784805.1, mailed on Mar. 21, 2011, 7 pages.
Extended European Search Report received for European Patent Application No. 06759050.5, mailed on Mar. 31, 2011, 7 pages.
Notice of Allowance received for U.S. Appl. No. 13/215,110, mailed on Nov. 16, 2012, 7 pages.
Abou-Donia et al., "Mechanisms of Joint Neurotoxicity of n-Hexane, Methyl Isobutyl Ketone and O-Ethyl 0-4-Nitrophenyl Phenylphosphonothioate in Hens", The Journal of Pharmacology and Experimental Therapeutics, vol. 257, No. 1, 1991, pp. 282-289.
Abu-Qare et al., "Quantification of Nicotine, Chlorpyrifos and Their Metabolites in Rat Plasma and Urine Using High-Performance Liquid Chromatography", Journal of Chromatography B., vol. 757, 2001, pp. 295-300.
Aydemir et al., "Effects of Defibrotide on Aorta and Brain Malondialdehyde and Antioxidants in Cholesterol-Induced Atherosclerotic Rabbits", International Journal of Clinical & Laboratory Research, vol. 30, 2000, pp. 101-107.
Bantscheff et al., "Quantitative Mass Spectrometry in Proteomics: A Critical Review", Anal. Bioanal. Chem., vol. 389, 2007, pp. 1017-1031.
Buchanan, T. A., "Pancreatic Beta-Cell Loss and Preservation in Type 2 Diabetes", Clinical Therapeutics, vol. 25, 2003, pp. B32-B46.
Chobanian et al., "Body cholesterol Metabolism in Man. II. Measurement of the Body Cholesterol Miscible Pool and Turnover Rate", Journal of Clinical Investigation, vol. 41, No. 9, 1962, pp. 1738-1744.
Duane, William C., "Measurement of Bile Acid Synthesis by Three Different Methods in Hypertriglyceridemic and Control Subjects", Journal of Lipid Research, vol. 38, 1997, pp. 183-188.
Edes et al., "Glycemic Index and Insulin Response to a Liquid Nutritional Formula Compared with a Standard Meal", Journal of the American College of Nutrition, vol. 17, No. 1, 1998, pp. 30-35.
Feldman et al., "Chlordiazepoxide-Fluoxetine Interactions on Food Intake in Free-Feeding Rats", Pharmacology Biochemistry & Behavior, vol. 8, No. 6, 1978, pp. 749-752.
Ferezou et al., "Origins of Neutral Sterols in Human Feces Studied by Stable Isotope Labeling (Deuterium and Carbon-13) Existence of an External Secretion of Cholesterol", Digestion, vol. 21, No. 5, 1981, pp. 232-243.
Futami et al., "An Application of the On-Line Respiratory Mass Spectrometer to the Detection of *Helicobacter pylori* Infection Using 13C-Labeled Urea", Journal of the Mass Spectrometry Society of Japan, vol. 47, No. 6, 1999, pp. 386-388.
Jones et al., "Modulation of Plasma Lipid Levels and Cholesterol Kinetics by Phytosterol Versus Phytostanol Esters", Journal of Lipid Research, vol. 41, 2000, pp. 697-705.
Murphy et al., "A New, Sensitive in Vivo Diagnostic Test of Insulin Resistance: The Deuterated Oral Glucose Tolerance Test (2H-OGTT)", Diabetes, American Diabetes Association, US, vol. 53, No. Suppl. 02, Jan. 1, 2004, 2 pages.
Neher et al., "Pyruvate and Thiamine Pyrophosphate Potentiate Cyclic Nucleotide-Induced Steroidogenesis in Isolated Rat Adrenocortical Cells", J.Steroid Biochem., vol. 18, 1983, pp. 1-6.

(56) References Cited

OTHER PUBLICATIONS

Radziuk, J. "Insulin Sensitivity and its Measurement: Structural Commonalities among the Methods", The Journal of Endocrinology & Metabolism, vol. 85, No. 12, 2000, pp. 4426-4433.
Sakurai, Y. "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.
Schoenheimer et al., "Deuterium as an Indicator in the Study of Intermediary Metabolism—III. The Role of the Fat Tissues", The Journal of Biological Chemistry, vol. 111, 1935, pp. 175-181.
Schoenheimer et al., "Deuterium as an Indicator in the Study of Intermediary Metabolism—IX. The Conversion of Stearic Acid into Palmitic Acid in the Organism", The Journal of Biological Chemistry, vol. 120, 1937, pp. 155-165.
Seiler et al., "The Influence of Catabolic Reactions on Polyamine Excretion", Biochem. J., vol. 225, 1985, pp. 219-226.
Shen et al., "Purification of Oligodendrocyte and Its Myelination to the Demyelinated Culture Model in Vitro", Acta Histochem. Cytochem, vol. 35, No. 2, 2002, p. 123.
Tayek et al., "Glucose Production, Recycling, and Gluconeogenesis in Normals and Diabetics: A Mass Isotopomer [U_13C] Glucose Study", Am. J. Physiol. Endocrino.l Metab., vol. 270, No. 4, Apr. 1, 1996, pp. E709-E717.
Wang et al., "Validation of a Single-Isotope-Labeled Cholesterol Tracer Approach for Measuring Human Cholesterol Absorption", Lipids, vol. 39, No. 1, 2004, pp. 87-91.
Non Final Office Action received for U.S. Appl. No. 13/215,110, mailed on Jul. 20, 2012, 8 pages.
Non Final Office Action received for U.S. Appl. No. 11/064,197, mailed on Oct. 29, 2010, 8 pages.
Notice of Allowance received for U.S. Appl. No. 11/064,197, mailed on Apr. 11, 2011, 10 pages.
Hellerstein et al., "Model for Measuring Absolute Rates of Hepatic de Novo Lipogenesis and Reesterification of Free Fatty Acids", The American Journal of Physiology, vol. 265, 1993, pp. E814-E820.
Hellerstein et al., "Subpopulations of Long-Lived and Short-Lived T Cells in Advanced HIV-1 Infection", The Journal of Clinical Investigation, vol. 112, No. 6, 2003, pp. 956-966.
Hellerstein et al., "T Cell Turnover in HIV-1 Disease", Immunity, vol. 7, 1997, pp. 583-589.
Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.
Hellerstein, M. K., "Measurement of T-Cell Kinetics: Recent Methodologic Advances", Trends Immunology Today, vol. 20, No. 10, 1999, pp. 438-441.
Hellerstein, M. K., "Methods for Measurement of Fatty Acid and Cholesterol Metabolism", Current Opinion in Lipidology,vol. 6, 1995, pp. 172-181.
Hellerstein, M. K., "New Stable Isotope-Mass Spectrometric Techniques for Measuring Fluxes through Intact Metabolic Pathways in Mammalian Systems: Introduction of Moving Pictures into Functional Genomics and Biochemical Phenotyping", Metabolic Engineering, vol. 6, 2004, pp. 85-100.
Hellerstein, M. K., "No Common Energy: de Novo Lipogenesis as the Road Less Traveled", The American Journal of Clinical Nutrition, vol. 74, 2001, pp. 707-708.
Hellerstein, M. K., "Synthesis of Fat in Response to Alterations in Diet: Insights from New Stable Isotope Methodologies", Lipids, vol. 31 (Supp) 1996, pp. S117-S125.
Hellerstein, M. K., "The Changing Face of AIDS: Translators Needed", The American Journal of Clinical Nutrition, vol. 70, 1999, pp. 787-788.
Hellerstein, Marc K., "In Vivo Measurement of Fluxes Through Metabolic Pathways: The Missing Link in Functional Genomics and Pharaceutical Research", Annu. Rev. Nutr., vol. 3, 2003, pp. 379-402.
Ho et al., "Rapid Turnover of Plasma Virions and CD4 Lymphocytes in HIV-1 Infection", Nature, vol. 373, 1995, pp. 123-126.
Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.
Hsieh et al., "Dynamics of Keratinocytes in Vivo Using 2H2O Labeling: A Sensitive Marker of Epidermal Proliferation State", J Invest Dermatol, vol. 123, 2004, pp. 530-536.
Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.
Hudgins et al., "Relationship Between Carbohydrate-Induced Hypertriglyceridemia and Fatty Synthesis in Lean and Obese Subjects", J. Lipid Res., vol. 41, 2000, pp. 595-604.
Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.
Humphrey et al., "A New Method for the Measurement of Protein Turnover", Biochem. J., vol. 148, 1975, pp. 119-127.
Humphrey et al., "A Sensitive Method for Measuring Protein Turnover Based on the Measurement of 2-3H-labeled Amino Acids in Proteins", Biochem. J., vol. 156, 1976, pp. 561-568.
Iyengar et al., "Human Stools as a Source of Viable Colonic Epithelial Cells", The FASEB Journal, vol. 5, 1991, pp. 2856-2859.
James, J. S., "Clinical Implications of Virological Failure: Interview with Steven Deeks, M.D., San Francisco General Hospital", AIDS Treatment News, vol. 289, 1998, pp. 6-7.
Jennings et al., "The Use of Infrared Spectrophotometry for Measuring Body Water Spaces", Clinical Chemistry, vol. 45, No. 7, Jul. 1999, pp. 1077-1081.
Jones et al., "An Integrated 2H and 13C NMR Study of Gluconeogenesis and TCA Cycle Flux in Humans", American Journal of Physiology—Endocrinology and Metabolism, vol. 281, 2001, pp. E848-856.
Jones et al., "Evidence for Diurnal Periodicity in Human Cholesterol Synthesis", Journal of Lipid Research, vol. 31, 1990, pp. 667-673.
Jung et al., "Metabolic Adaptations to Dietary Fat Malabsorption in Chylomicron-Deficient Mice", Biochem. J., vol. 343, 1999, pp. 473-478.
Jungas, "Fatty Acid Synthesis in Adipose Tissue Incubated in Tritiated Water", Biochemistry, vol. 7, No. 10, 1968, pp. 3708-3717.
Katz, "Futile Cycles in the Metabolism of Glucose", Curr. Top Cell Regul., vol. 10, 1976, pp. 237-289.
Kelleher et al., "Model Equations for Condensation Biosynthesis Using Stable Isotopes and Radioisotopes", Am. J. Physiol., vol. 262, 1992, pp. E118-E125.
Khairallah et al., "Assessment of Protein Turnover in Perfused Rat Liver: Evidence for Amino Acid Compartmentation from Differential Labeling of Free and tRNA-bound Valine", J Biol Chem, vol. 251, No. 5, 1976, pp. 1375-1384.
Kim et al., "A New Stable Isotope-Mass Spectrometric (MS) Method to Measure Proliferation Rates of Colon Epithelial Cells", Faseb Journal, vol. 14, No. 4, 2000, p. A718.
Lammert et al., "Effects of Isoenergetic Overfeeding of Either Carbohydrate or Fat in Young Men", British Journal of Nutrition, vol. 84, 2000, pp. 233-245.
Lee, "Cardiorespiratory Fitness, Body Composition, and All-Cause and Cardiovascular Disease Mortality in Men 1-3", Am. J. Clin. Nutr., vol. 69, 1999, pp. 373-380.
Lefebvre, "Naturally Labeled 13C-Glucose: A New Tool to Measure Oxidation Rates of Exogenous Glucose", Diabetes, vol. 28 (Suppl. 1), Jan. 1979, pp. 63-65.
Leung et al., "A Deficiency of Microsomal Triglyceride Transfer Protein Reduces Apolipoprotein B Secretion", The Journal of Biological Chemistry, vol. 275, No. 11, 2000, pp. 7515-7520.
Lewanczuk et al., "Comparison of the [13 C] Glucose Breath Test to the Hyperinsulinemic-Euglycemic Clamp When Determining Insulin Resistance", Diabetes Care, vol. 27, No. 2, 2004, pp. 441-447.
Lipkin, "Cell Proliferation Kinetics in the Gastrointestinal Tract of Man. I. Cell Renewal in Colon and Rectum", Journal of Clinical Investigations, vol. 42, No. 6, 1963, pp. 767-776.

(56) References Cited

OTHER PUBLICATIONS

Lipkin, "Proliferation and Differentiation of Normal and Diseased Gastrointestinal Cells", In Physiology of the Gastrointestinal Tract, L.R. Johnson ed., Raven Press, New York, 1987, pp. 255-284.
Lutton et al., "Critical analysis of the Use of 14C-acetate for Measuring In Vivo Rat Cholesterol Synthesis", Reprod. Nutr. Dev., vol. 30, 1990, pp. 71-84.
MacAllan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.
Maentausta et al., "Radioimmunoassay of Conjugated Cholic Acid, Chenodeoxycholic Acid, and Deoxycholic Acid from Human Serum, with Use of 125I-Labeled Ligands", Clin. Chem., vol. 25, No. 2, 1979, pp. 264-268.
Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.
Margolick et al., "Failure of T-cell Homeostasis Preceding AIDS in HIV-1 Infection", Nature Medicine, vol. 1, No. 7, 1995, pp. 674-680.
Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.
Marin et al., "Dynamic Profiling of the Glucose Metabolic Network in Fasted Rat Hepatocytes using [1,2-13C2] Glucose", Biochemical Journal, vol. 381, 2004, pp. 287-294.
Martin et al., "Discovery of a Human Liver Glycogen Phosphorylase Inhibitor That Lowers Blood Glucose in Vivo", Proc. Natl. Acad. Sci. USA, vol. 95, No. 4, 1998, pp. 1776-1781.
Mathur-De Vre et al., "Molecular Aspects of Tritiated Water and Natural Water in Radiation Biology", Prog. Biophys. Molec. Biol., vol. 43, 1984, pp. 161-193.
McCloskey, "ElectronIonization Mass Spectra of Trimethylsilyl Derivatives of Nucleosides", Meth. Enz., vol. 193, 1990, pp. 825-841.
McCune et al., "Factors Influencing T-Cell Turnover in HIV-1-Seropositive Patients", J. Clin. Invest., vol. 105, 2000, pp. R1-R8.
McCune, J. M., "Thymic Function in HIV-1 Disease", Seminars in Immunology, vol. 9, 1997, pp. 397-404.
McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.
Written Opinion mailed Jul. 14, 2006, by the Australian Patent Office for Singapore patent application No. 200502593-7, filed on Nov. 4, 2003, 5 pages.
Australian Search Report and Written Opinion mailed Aug. 5, 2009, for SG Application No. 200717391-7, filed on May 3, 2006, 7 pages.
Supplementary Partial Search Report Received for European Patent Application No. 02806603.3, mailed on Jul. 25, 2006, 5 pages.
Supplementary Partial Search Report received for European Patent Application No. 03713429.3, mailed on Mar. 9, 2006, 6 pages.
Supplementary Partial Search Report received for European Patent Application No. 03749756.7, mailed on Aug. 17, 2005, 6 pages.
Supplementary Partial Search Report received for European Patent Application No. 03768624.3, mailed on Sep. 22, 2006, 4 pages.
Supplementary Search Report received for European Patent Application No. 04809469.2, mailed on Jul. 28, 2009, 4 pages.
Search Report received for European Patent Application No. 04812281.6, mailed on Oct. 6, 2010, 4 pages.
Supplementary Search Report received for European Patent Application No. 05725448.4, mailed on Jun. 30, 2009, 7 pages.
Office Action received for European Patent Application No. 05733311, mailed on Aug. 4, 2010, 13 pages.
Supplementary Search Report received for European Patent Application No. 05733311.4, mailed on Sep. 19, 2008, 9 pages.
International Search Report received for for PCT Patent Application No. PCT/US2003/004183, mailed on Jun. 29, 2004, 4 pages.
International Search Report received for for PCT Patent Application No. PCT/US2003/010554, mailed on Aug. 20, 2004, 4 pages.
International Search Report received for PCT Patent Application No. PCT/US2003/020052, mailed on Apr. 13, 2004, 3 pages.
International Search Report received for PCT Patent Application No. PCT/US2003/023340, mailed on Aug. 18, 2004, 4 pages.
International Search Report received for PCT Patent Application No. PCT/US2003/027623, mailed on Jul. 8, 2004, 4 pages.
International Search Report received for PCT Patent Application No. PCT/US2003/029361, mailed on Jan. 19, 2005, 4 pages.
International Search Report received for PCT Patent Application No. PCT/US2003/29526, mailed on Aug. 18, 2004, 3 pages.
International Search Report received for PCT Patent Application No. PCT/US2003/035107, mailed on Jul. 9, 2004, 2 pages.
International Search Report received for PCT Patent Application No. PCT/US2004/21063, mailed on Apr. 4, 2005, 2 pages.
International Search Report received for PCT Patent Application No. PCT/US2004/039722, mailed on Mar. 25, 2005, 3 pages.
International Search Report and Written Opinion received for PCT Patent Application No. PCT/US2005/005660, mailed on Oct. 11, 2007, 11 pages.
International Search Report and Written Opinion received for PCT Patent Application No. PCT/US2005/010429, mailed on Aug. 8, 2006, 15 pages.
International Search Report received for PCT Patent Application No. PCT/US2005/08265, mailed on Aug. 1, 2005, 4 pages.
International Search Report and Written Opinion received for PCT Patent Application No. PCT/US2006/017167, mailed on Feb. 5, 2008, 11 pages.
"NCBI Blast: Protein Sequence (17 letters)", Available at: <http://blast.ncbi.nlm.nih.gov/Blast.cgi>, Visited on May 29, 2008, 5 pages.
"New Diagnostic Technique Could Help Treat AIDS", Agence France-Presse, Dow Jones News, Feb. 17, 1998, pp. 1-2.
Zilversmit et al., "On the Calculation of 'Turnover Time' and 'Turnover Rate' from Experiments Involving the Use of Labeling Agents", J. of General Physiology, vol. 26, No. 3, 1943, pp. 325-331.
Ackermans et al., "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol", The Journal of Clinical Endocrinology & Metabolism, vol. 86, No. 5, 2001, pp. 2220-2226.
Adami et al., "The Aetiology and Pathogenesis of Human Breast Cancer", Mutation Research, vol. 333, 1995, pp. 29-35.
Airhart et al., "Compartmentation of Free Amino Acids for Protein Synthesis in Rat Liver", The Biochemical Journal, vol. 140, 1974, pp. 539-545.
Ajie et al., "In Vivo Study of the Biosynthesis of Long-Chain Fatty Acids Using Deuterated Water", The American Journal of Physiology, vol. 269, 1995, pp. E247-E252.
Anderson et al., "Direct HIV Cytopathicity Cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.
Antelo et al., "Adipose Triglyceride (TG) Turnover and De Novo Lipogenesis (DNL) in Humans: Measurement by Long-Term 2H2O Labeling and Mass Isotopomer Distribution Analysis (MIDA)", Experimental Biology, FASEB#361.10, 2002, p. A400 (Abstract only).
Asher et al., "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine", Leukemia & Lymphoma, vol. 19, 1995, pp. 107-119.
Attardi et al., "Biogenesis of Mitochondria", Annual Review of Cell Biology, vol. 4, 1988, pp. 289-333.
Bach et al., "Stem Cells: The Intestinal Stem Cell as a Paradigm", Carcinogenesis, vol. 21, No. 3, 2000, pp. 469-476.
Backhouse et al., "Effects of Haloperidol on Cell Proliferation in the Early Postnatal Rat Brain", Neuropathology and Applied Neurobiology, vol. 8, No. 2, 1982, pp. 109-116.
Bandsma et al., "Contribution of Newly Synthesized Cholesterol to Rat Plasma and Bile Determined by Mass Isotopomer Distribution

(56) References Cited

OTHER PUBLICATIONS

Analysis: Bile-Salt Flux Promotes Secretion of Newly Synthesized Cholesterol into Bile", The Biochemical Journal, vol. 329, 1998, pp. 699-703.

Bandsma et al., "The Contribution of Newly Synthesized Cholesterol to Bile Salt Synthesis in Rats Quantified by Mass Isotopomer Distribution Analysis", Biochemica et Biophysica Acta, vol. 1483, 2000, pp. 343-351.

Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.

Bickenbach, "Identification and Behavior of Label-Retaining Cells in Oral Mucosa and Skin", Journal of Dental Research, vol. 60, 1981, pp. 1611-1620.

Bier, D. M., "The Use of Stable Isotopes in Metabolic Investigation", Balliere's Clinical Endocrinology and Metabolism, vol. 1, No. 4, Nov. 1987, pp. 817-836.

Bier, D. M., "Stable Isotopes in Biosciences, their Measurement and Models for Amino Acid Metabolism", European Journal of Pediatrics, vol. 156, 1997, pp. S2-S8.

Bingham, Sheila A., "The Use of 24-h Urine Samples and Energy Expenditure to Validate Dietary Assessments", The American Journal of Clinical Nutrition, vol. 59(suppl), 1994, pp. 227S-231S.

Black et al., "Labeling DNA with Stable Isotopes: Economical and Practical Considerations", BioTechniques, vol. 30, 2001, pp. 134-138, 140.

Blair et al., "Changes in Physical Fitness and All-Cause Mortality. A Prospective Study of Healthy and Unhealthy Men", JAMA, vol. 273, 1995, pp. 1093-1098.

Blau et al., "Handbook of Derivatives for Chromatography", 2nd Edition, John Wiley & Sons Ltd., England, 1993.

Bonotto et al., "Study of the Distribution and Biological Effects of 3H in the Algae *Acetabularia, Chlamydomonas* and *Porphyra*", Current Topics in Radiation Research Quarterly, vol. 12, 1978, pp. 115-132.

Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.

MOLECULAR FLUX RATES THROUGH CRITICAL PATHWAYS MEASURED BY STABLE ISOTOPE LABELING IN VIVO, AS BIOMARKERS OF DRUG ACTION AND DISEASE ACTIVITY

CROSS-REFERENCE TO RELATED APPLICATIONS

This application is a Continuation application of U.S. application Ser. No. 13/215,110, filed Aug. 22, 2011, which was a Divisional application of U.S. application Ser. No. 11/064,197 (now Letters U.S. Pat. No. 8,005,623), which claims priority to U.S. Provisional Application Ser. No. 60/546,580 filed on Feb. 20, 2004, and U.S. Provisional Application No. 60/581,028 filed on Jun. 17, 2004, all of which are hereby incorporated by reference in their entirety.

FIELD OF THE INVENTION

The invention relates to methods for measuring changes in biochemical processes that underlie various diseases and disorders. More specifically, the invention relates to measuring the molecular flux rates of these biochemical processes for diagnostic, prognostic, and therapeutic purposes.

BACKGROUND OF THE INVENTION

It is generally accepted in the fields of biology and medicine that the signs and symptoms of most diseases (the clinical phenotype) are secondary consequences of underlying biochemical and molecular processes which, in turn, are the fundamental driving forces and etiologic factors responsible for the disease. In biochemical terms, the processes that underlie most diseases can best be described as molecular fluxes through complex biochemical pathways. These underlying biochemical processes (i.e., the flow of molecules through highly complex, adaptive metabolic pathways or networks) are responsible for the initiation and/or progression of a disease or disorder from pre-clinical to frank clinical or morbid stages and are therefore the true targets of contemporary medical therapeutics (e.g., drug, dietary, behavioral or genetic therapies).

Current drug research and medical diagnostics lack validated, reproducible high-throughput measurement tools for measuring changes in key biochemical processes in vivo, despite the central importance of these processes in driving disease progression. The main explanation for this gap in the contemporary biochemical repertoire is methodologic: molecular fluxes through complex pathways and networks underlie most diseases but effective tools for measuring molecular flux rates are lacking. This state of affairs reflects the fact that measurement of dynamic processes (flux rates, kinetics) in living organisms requires different tools and models than measurement of static molecular parameters (e.g., concentration, structure, or composition of molecules). Accordingly, the notion of targeting rates of biochemical processes, rather than the physical entities or components that comprise the biological system of interest (e.g., genes, proteins) per se as targets or biomarkers of drug action or of disease activity, is not only new but had previously lacked the technical tools for implementation.

Disclosed herein are methods for testing the effects of compounds, combinations of compounds, or mixtures of compounds (i.e., chemical entities (whether new or old) drugs (e.g., already-approved drugs or known drugs), drug leads, or drug candidates, toxic agents, biological factors) on molecular flux rates through metabolic pathways and networks in living systems as biomarkers for drug discovery, development and approval (DDA), medical diagnosis and prognosis, and toxicology.

SUMMARY OF THE INVENTION

The invention is directed toward analyzing biochemical processes that are involved in, or are believed to be involved in, the etiology or progression of a disease or disorder. The biochemical process (i.e., the flow of molecules through a targeted metabolic pathway or network) is the focus of analysis (as disclosed herein) since it is the underlying changes of the biochemical process (i.e., molecular flux rates) that may be the significant or authentic target for treatment or diagnostic monitoring of the disease or disorder.

The invention allows for the comparison between the molecular flux rates within one or more metabolic pathways of interest measured from cells, tissues, or organisms that have been exposed to one or more compounds including agents (e.g., drugs, drug candidates, or drug leads) to the molecular flux rates from the one or more metabolic pathways of interest measured from non-exposed cells, tissues, or organisms. Non-exposed cells, tissues, or organisms may be cells, tissues, or organisms having a disease or condition of interest but not yet having been exposed to one or more agents (i.e., compounds) or non-exposed cells, tissues, or organisms may be cells, tissues, or organisms not having the disease or condition of interest. Differences between the exposed and non-exposed molecular flux rates are identified and this information is then used to determine whether the one or more compounds including agents (or combinations or mixtures thereof) elicit a change in the one or more metabolic pathways of interest in the exposed cell, tissue, or organism. The one or more compounds including agents may be administered to a mammal and the molecular flux rates calculated and evaluated against the molecular flux rates calculated from an unexposed mammal of the same species. Alternatively, the molecular flux rates from the same mammal may be calculated prior to exposure of the one or more compounds including agents and then the molecular flux rates may be calculated in the same mammal after exposure to the one or more compounds and then compared. The mammal may be a human.

In another embodiment, the molecular flux rates are measured in one or more metabolic pathways involved in the molecular pathogenesis of a disease. In a further embodiment, the one or more metabolic pathways are the cause of the disease or contribute to the initiation, progression, activity, pathologic consequences, symptoms, or severity of the disease.

In another embodiment, the molecular flux rates are measured in one or more metabolic pathways of interest from a living organism prior to and after exposure to one or more compounds to evaluate toxicity. Such compounds may be chemical entities or agents. In one variation, the one or more compounds may be industrial or occupational chemicals. In another variation, the one or more compounds may be cosmetics. In yet another variation, the one or more compounds may be food additives. And in yet another variation, the one or more compounds may be environmental pollutants. The toxicity of interest may be end-organ toxicity or any other toxic endpoint.

Alternatively, exposure of one or more compounds or chemical entities may be to one living organism and the molecular flux rates from the one or more metabolic pathways may be compared to another unexposed living organism of the same species to evaluate toxicity. The toxicity of interest may be end-organ toxicity or any other toxic endpoint.

In another embodiment, the molecular flux rates two or more metabolic pathways are measured concurrently. In a further embodiment, the molecular flux rates are measured using stable isotope labeling techniques. The isotope label may include specific heavy isotopes of elements present in biomolecules, such as $^2$H, $^{13}$C, $^{15}$N, $^{18}$O, $^{33}$S, $^{34}$S, or may contain other isotopes of elements present in biomolecules such as $^3$H, $^{14}$C, $^{32}$P, $^{33}$P, $^{35}$S, $^{125}$I, $^{131}$I. Isotope labeled precursors include, but are not limited to $^2$H$_2$O, $^{15}$NH$_3$, $^{13}$CO$_2$, H$^{13}$CO$_3$, $^2$H-labeled amino acids, $^{13}$C-labeled amino acids, $^{15}$N-labeled amino acids, $^{18}$O-labeled amino acids, $^{34}$S or $^{33}$S-labeled amino acids, $^3$H$_2$O, $^3$H-labeled amino acids, and $^{14}$C-labeled amino acids. The stable isotope substrate may be chosen from $^2$H$_2$O, $^2$H-glucose, $^2$H-labeled amino acids, $^{13}$C-labeled amino acids, $^2$H-labeled organic molecules, $^{13}$C-labeled organic molecules, and $^{15}$N-labeled organic molecules labeled water. The stable isotope substrate may be labeled water. The labeled water may be $^2$H$_2$O.

Stable isotope-labeled substrates are incorporated into one or more molecules comprising one or more metabolic pathways of interest. In this manner, the molecular flux rates can be determined by measuring, over specific time intervals, isotopic content and/or pattern or rate of change of isotopic content and/or pattern in the targeted molecules, for example by using mass spectrometry, allowing for the determination of the molecular flux rates within the one or more metabolic pathways of interest, by use of analytic and calculation methods known in the art.

Alternatively, radiolabeled substrates are contemplated for use in the present application wherein the radiolabeled substrates are incorporated into one or more molecules comprising one or more metabolic pathways of interest. In this manner, the molecular flux rates can be determined by measuring radiation and/or radioactivity of the targeted molecules of interest within the one or more metabolic pathways of interest by using techniques known in the art such as scintillation counting. The molecular flux rates within the one or more metabolic pathways of interest are then calculated, using methods known in the art.

The invention is further directed to one or more isotopically perturbed molecules. The isotopically perturbed molecules may include one or more stable isotopes. The isotopically perturbed molecules are products of the labeling methods described herein. The isotopically perturbed molecules are collected by sampling techniques known in the art and are analyzed using appropriate analytical tools such as those described herein.

In yet another embodiment, the isotopically perturbed molecules are labeled with one or more radioactive isotopes.

In yet another embodiment, one or more kits are provided that include isotope-labeled precursors and instructions for using them. The kits may contain stable-isotope labeled precursors or radioactive-labeled isotope precursors or both. Stable-isotope labeled precursors and radioactive-labeled isotope precursors may be provided in one kit or they may be separated and provided in two or more kits. The kits may further include one or more tools for administering the isotope-labeled precursors. The kits may also include one or more tools for collecting samples from a subject.

In yet another embodiment, one or more information storage devices are provided that include data generated from the methods of the present invention. The data may be analyzed, partially analyzed, or unanalyzed. The data may be imprinted onto paper, plastic, magnetic, optical, or other medium for storage and display.

The application is further directed to one or more compounds identified and at least partially characterized by the methods of the present invention.

The present application is further directed to a method for evaluating the action of one or more compounds on a molecular flux rate through a critical pathway as an authentic biomarker of disease, wherein the method includes: a) exposing a living system to one or more compounds; b) administering an isotope-labeled substrate to the living system for a period of time sufficient for the isotope-labeled substrate to enter into one or more metabolic pathways of interest and thereby enter into and label at least one targeted molecule of interest within the one or more metabolic pathways of interest in the living system; c) obtaining one or more samples from the living system, wherein the one or more samples include at least one isotope-labeled targeted molecule of interest; d) measuring the content, rate of incorporation and/or pattern or rate of change in content and/or pattern of isotope labeling of the at least one targeted molecule of interest; e) calculating molecular flux rates in the one or more metabolic pathways of interest based on the content and/or pattern or rate of change of content and/or pattern of isotopic labeling in the at least one targeted molecule of interest; f) measuring the molecular flux rates in the one or more metabolic pathways of interest according to steps b) through e) in at least one living system not exposed to the one or more compounds as provided by step a); and g) comparing the molecular flux rates in the one or more metabolic pathways of interest in the living system administered the one or more compounds to the molecular flux rates in the one or more metabolic pathways of interest in the living system not administered the one or more compounds to evaluate the action of the one or more compounds on the molecular flux rates. An authentic biomarker is the flow of molecules through a targeted metabolic pathway that is involved in the progression of a disease or disorder.

The molecular flux rates in the one or more metabolic pathways of interest may be relevant to an underlying molecular pathogenesis, or causation of, one or more diseases. Further, the molecular flux rates in the one or more metabolic pathways of interest may contribute to the initiation, progression, severity, pathology, aggressiveness, grade, activity, disability, mortality, morbidity, disease sub-classification or other underlying pathogenic or pathologic feature of the one or more diseases. Further, the molecular flux rates in the metabolic pathways of interest may contribute to the prognosis, survival, morbidity, mortality, stage, therapeutic response, symptomology, disability or other clinical factor of the one or more diseases.

In one format of the method, the molecular flux rates of two or more metabolic pathways of interest are measured concurrently. In another format of the invention, the one or more samples may be collected at known times or intervals after administration or contacting the living system to the isotope-labeled substrate and after exposing the living system to the one or more compounds.

The concurrent measurement of the molecular flux rates from the metabolic pathways of interest may be achieved by use of stable isotopic labeling techniques. The isotope label used may be stable (i.e., non-radioactive) isotope. The stable isotope may be isotope-labeled water, e.g. $^2$H$_2$O.

In one format, the concurrent measurement of the molecular flux rates from the metabolic pathways of interest may be achieved by use of radioisotope labeling techniques.

In another format, the one or more compounds may be an already-approved drug, e.g., a Federal Food and Drug Administration-approved drug or a drug approved by a similar agency outside the United States. In one format, the already-approved drug is selected randomly. In another format, the already-approved drug may be selected on the basis of a specific biochemical rationale or hypothesis concerning a hypothesized role in the molecular pathogenesis of one or more diseases. In another format, the one or more compounds is a chemical entity (whether new or old) or a biological factor. The already-approved drug may be chosen from statins, glitazones, COX-2 inhibitors, NSAIDS, β-blockers, calcium channel blockers, ACE inhibitors, antibiotics, anti-viral agents, hypolipidemic agents, antihypertensives, anti-inflammatory agents, antidepressants, anxiolytics, anti-psychotics, sedatives, analgesics, antihistamines, oral hypoglycemic agents, antispasmodics, antineoplastics, cancer chemotherapeutic agents, sex steroids, pituitary hormones, cytokines, chemokines, appetite suppressant agents, thyromimetics, anti-seizure agents, sympathomimetics, sulfa drugs, biguanides, and other classes of agents.

In one format of the invention, one or more animal models of disease are used for evaluating the actions on molecular flux rates in one or more metabolic pathways potentially related to disease in living systems. The one or more animal models of disease may be chosen from Alzheimer's disease, heart failure, renal disease, diabetic nephropathy, osteoporosis, hepatic fibrosis, cirrhosis, hepatocellular necrosis, pulmonary fibrosis, scleroderma, renal fibrosis, multiple sclerosis, arteriosclerosis, osteoarthritis, rheumatoid arthritis, psoriasis, skin photoaging, skin rashes, breast cancer, prostate cancer, colon cancer, pancreatic cancer, lung cancer, acquired immunodeficiency syndrome, immune defects, multiple myeloma, chronic lymphocytic leukemia, chronic myelocytic leukemia, diabetes, diabetic complications, insulin resistance, obesity, lipodystrophy, muscle wasting, frailty, deconditioning, angiogenesis, hyperlipidemia, infertility, viral or bacterial infections, auto-immune disorders, and immune flares.

In one format of the invention, the one or more metabolic pathways of interest are measured in response to a specific dose or a range of doses of the one or more compounds.

The one or more metabolic pathways of interest may be chosen from hepatocyte proliferation and destruction, total liver cell proliferation and destruction, renal tubular cell turnover, lymphocyte turnover, spermatocyte turnover, protein synthesis and breakdown in muscle and heart, liver collagen synthesis and breakdown, myelin synthesis and breakdown in brain or peripheral nerves, breast epithelial cell proliferation, colon epithelial cell proliferation, prostate epithelial cell proliferation, ovarian epithelial cell proliferation, endometrial cell proliferation, bronchial epithelial cell proliferation, pancreatic epithelial cell proliferation, keratin synthesis in skin, keratinocyte proliferation, immunoglobulin synthesis, synthesis and breakdown of mitochondrial DNA, synthesis and breakdown of mitochondrial phospholipids, synthesis and breakdown of mitochondrial proteins, synthesis and breakdown of adipose lipids, and synthesis and breakdown of adipose cells.

In yet another format of the invention, the already-approved drug is screened for actions on multiple biochemical processes concurrently.

In one format, the living system is chosen from prokaryotic cells, eukaryotic cells, cell lines, cell cultures, isolated tissue preparations, rabbits, dogs, mice, rats, guinea pigs, pigs non-human primates, and humans.

In another format, the isotope labeled substrate is chosen from $^2H_2O$, $^2H$-glucose, $^2H$-labeled amino acids, $^2H$-labeled organic molecules, $^{13}C$-labeled organic molecules, $^{13}CO_2$, $^{15}N$-labeled organic molecules, $^3H_2O$, $^3H$-labeled glucose, $^3H$-labeled amino acids, $^3H$-labeled organic molecules, $^{14}C$-labeled organic molecules and $^{14}CO_2$.

The one or more compounds may be administered according to established or hypothesized dose ranges that have the potential for biological activity in the living system.

In another format of the invention, combinations of two or more compounds are exposed to the living system. In this format, synergistic, complementary, or antagonistic actions of combinations of compounds on molecular flux rates through the one or more metabolic pathways are determined by comparing the molecular flux rates in the living systems exposed to the combination of compounds to the molecular flux rates in the living systems exposed to a single compound alone or not exposed to any of the compounds being tested. In one format, the combinations of compounds are selected randomly. The combinations of compounds may be selected on the basis of a specific biochemical rationale or hypothesis concerning a hypothesized role of one or more of the compounds in the molecular pathogenesis of the one or more diseases.

The present invention is further directed to a method for evaluating an action on a molecular flux rate through a critical pathway as an authentic biomarker of toxicity, the method including: a) exposing a living system to one or more compounds; b) administering an isotope-labeled substrate to a living system for a period of time sufficient for the isotope-labeled substrate to enter into one or more metabolic pathways of interest and thereby enter into and label one or more targeted molecules of interest within the one or more metabolic pathways of interest in the living system wherein the one or more metabolic pathways of interest are related to one or more toxic effects; c) obtaining one or more samples from the living system, wherein the one or more samples include one or more isotope-labeled targeted molecules of interest; d) measuring the content, rate of incorporation and/or pattern or rate of change in content and/or pattern of isotope labeling of the targeted molecule or molecules of interest; e) calculating molecular flux rates in the one or more metabolic pathways of interest based on the content and/or pattern or rate of change of content and/or pattern of isotopic labeling in the molecule or molecules of interest; f) measuring the molecular flux rates in the one or more metabolic pathways of interest according to steps b) through e) in a living system or systems not administered the one or more compounds; and g) comparing the molecular flux rates in the one or more metabolic pathways of interest in the living system administered the one or more compounds to the molecular flux rates in the one or more metabolic pathways in the living system or systems not administered the one or more compounds.

The one or more toxic actions may include at least one end-organ toxicity. The end-organ toxicity may be chosen from hepatocyte proliferation and destruction, total liver cell proliferation and destruction, renal tubular cell turnover, lymphocyte turnover, spermatocyte turnover, protein synthesis and breakdown in muscle and heart, liver collagen synthesis and breakdown, myelin synthesis and breakdown in brain or peripheral nerves, breast epithelial cell proliferation, colon epithelial cell proliferation, prostate epithelial cell proliferation, ovarian epithelial cell proliferation, endometrial cell proliferation, bronchial epithelial cell proliferation, pancreatic epithelial cell proliferation, keratin synthesis in skin, keratinocyte proliferation, immunoglobulin synthesis, synthesis and breakdown of mitochondrial DNA, synthesis and breakdown of mitochondrial phospholipids, synthesis and breakdown of mitochondrial proteins, synthesis and breakdown of adipose lipids, and synthesis and breakdown of adipose cells.

The one or more metabolic pathways of interest related to end-organ toxicity may be measured in response to a specific dose or a range of doses of the one or more compounds of interest.

The living system may be chosen from prokaryotic cells, eukaryotic cells, cell lines, cell cultures, isolated tissue preparations, rabbits, dogs, mice, rats, guinea pigs, pigs, and non-human primates. Such toxic effects can be analyzed on isolated human cells or tissue preparations but are not performed on humans in vivo. The living system may be exposed to combinations of two or more compounds. Synergistic, complementary, or antagonistic actions of combinations of compounds on molecular flux rates through the one or more metabolic pathways of interest may be determined by comparing the molecular flux rates in the living systems exposed to the combination of compounds to the molecular flux rates in the living systems exposed to a single compound alone or not exposed to any of said one or more compounds being tested.

The information generated using the methods of the invention may be stored in an information storage device. The device may be a printed report. The medium in which the report is printed on may be chosen from paper, plastic, and microfiche. The device may be a computer disc. The disc may be chosen from a compact disc, a digital video disc, an optical disc, and a magnetic disc. The device may also be a computer.

The present application is further directed to an isotopically-perturbed molecule generated by the methods of the invention. The molecule may be chosen from protein, lipid, nucleic acid, glycosaminoglycan, proteoglycan, porphyrin, and carbohydrate molecules. In one format the isotopically perturbed molecule is myelin, amyloid-β, deoxyribonucleic acid, ribonucleic acid, collagen or a triglyceride.

The present application is further directed to a kit for determining screening of one or more compounds for actions on molecular flux rates in one or more metabolic pathways potentially related to disease in a subject, including: a) one or more isotope-labeled precursors and b) instructions for use of the kit. The kit may further include a tool for administration of precursor molecules or an instrument for collecting a sample from the subject.

The present application is further directed to a kit for screening of one or more compounds for actions on molecular flux rates in one or more metabolic pathways potentially related to one or more toxic effects in a subject, including: a) one or more isotope-labeled precursors, and b) instructions for use of the kit. The kit may further include a tool for administration of precursor molecules or an instrument for collecting a sample from the subject.

The methods of the application may further include the step of manufacturing one or more compounds at least partially identified by the methods of the invention. The methods of the invention may further include the step of developing one or more compounds at least partially identified by the methods of the invention.

The present application is further directed to a method including: measuring a molecular flux rate of an authentic biomarker of interest using an isotope; comparing the results of step a) with the molecular flux rate of the authentic biomarker of interest in the presence of a compound of interest; if the compound of interest changes a molecular flux rate of interest, the compound is then further developed.

The present application is further directed to a method for monitoring or diagnosing a clinical or medical disease or condition, the method including: a) administering an isotope-labeled substrate to a living system for a period of time sufficient for the isotope-labeled substrate to enter into one or more metabolic pathways of interest and thereby enter into and label at least one targeted molecule of interest within the one or more metabolic pathways of interest in the living system; b) obtaining one or more samples from the living system, wherein the one or more samples include at least one isotope-labeled targeted molecule of interest; c) measuring the content, rate of incorporation and/or pattern or rate of change in content and/or pattern of isotope labeling of the at least one targeted molecule of interest; d) calculating molecular flux rates in the one or more metabolic pathways/biomarker of interest based on the content and/or pattern or rate of change of content and/or pattern of isotopic labeling in the at least one targeted molecule of interest to monitor or diagnose the clinical or medical disease or condition.

Table 1 depicts examples of authentic biomarkers, the related clinical or medical diseases or conditions and the molecule of interest to be detected using the methods of the application. Taking into account Table 1, the present application is further directed to a method for monitoring or diagnosing a clinical or medical disease or condition, the method including: a) administering an isotope-labeled substrate to the living system for a period of time sufficient for the isotope-labeled substrate to enter into one or more metabolic pathways of interest and thereby enter into and label at least one targeted molecule of interest within the one or more metabolic pathways of interest in the living system; b) obtaining one or more samples from the living system, wherein the one or more samples include at least one isotope-labeled targeted molecule of interest; c) measuring the content, rate of incorporation and/or pattern or rate of change in content and/or pattern of isotope labeling of the at least one targeted molecule of interest; d) calculating molecular flux rates in the one or more metabolic pathways/biomarker of interest based on the content and/or pattern or rate of change of content and/or pattern of isotopic labeling in the at least one targeted molecule of interest to monitor or diagnose the clinical or medical disease or condition. In another format, one or more compounds are administered to the living system before or after the determination of the molecular flux rates of the one or more metabolic pathways of interest in the living system in order to evaluate the action of the one or more compounds on the biomarker as a predictor of an effect of the compound on the clinical or medical disease or condition.

Various clinical or medical diseases or conditions can be diagnosed or monitored using the methods of the invention as depicted in Table 1. Each of the clinical or medical diseases or conditions explained in more detail below can be monitored using the methods of the invention before and after the administration of one or more compounds to evaluate the action of the one or more compounds as a potential treatment, diagnostic or causative agent.

For example, obesity, lipoatrophy, fat distribution, or hyperplasia-hypertrophy can be monitored or diagnosed by measuring or detecting adipose triglyceride dynamics. In this method, the targeted molecule of interest is triglyceride glycerol or one or more fatty acids. As such, the present application is further directed to a method for monitoring or diagnosing obesity; lipoatrophy; fat distribution or hyperplasia-hypertrophy in a living system, the method including: a) administering an isotope-labeled substrate to a living system for a period of time sufficient for the isotope-labeled substrate to enter into the adipose triglyceride metabolic pathway and thereby enter into and label at least one triglyceride glycerol or fatty acid within the adipose triglyceride metabolic pathway in the living system; b) obtaining one or more samples from the living system, wherein the one or more samples include at least one isotope-labeled triglyceride glycerol or fatty acid; c) measuring the content, rate of incorporation and/or pattern or rate of change in content and/or pattern of isotope labeling of the triglyceride glycerol or fatty acid; d) calculating molecular flux rates in the adipose triglyceride metabolic pathway based on the content and/or pattern or rate of change of content and/or pattern of isotopic labeling in the triglyceride glycerol or fatty acid to monitor or diagnose obesity; lipoatrophy; fat distribution and/or hyperplasia-hypertrophy.

Hyperplasia-hypertrophy can be monitored or diagnosed by measuring or detecting adipocyte dynamics. In this method, the targeted molecule of interest is DNA isolated from adipocytes. In this format, the present application is further directed to a method for monitoring or diagnosing hyperplasia-hypertrophy in a living system, the method including: a) administering an isotope-labeled substrate to the living system for a period of time sufficient for the isotope-labeled substrate to enter into the adipose metabolic pathway and thereby enter into and label at least one DNA molecule isolated from adipocytes within the adipose metabolic pathway in the living system; b) obtaining one or more samples from the living system, wherein the one or more samples include at least one isotope-labeled DNA molecule isolated from adipocytes; c) measuring the content, rate of incorporation and/or pattern or rate of change in content and/or pattern of isotope labeling of the DNA isolated from adipocytes; d) calculating molecular flux rates in the adipose metabolic pathway based on the content and/or pattern or rate of change of content and/or pattern of isotopic labeling in the DNA isolated from adipocytes to monitor or diagnose hyperplasia-hypertrophy.

Unfitness, cardiovascular disease risk, autotoxicity drugs, deconditioning or frailty can be monitored or diagnosed by measuring or detecting muscle mitochondrial DNA or phospholipid dynamics. In this method, the targeted molecules of interest are DNA from muscle mitochondria or phospholipids from muscle mitochondria. In this format, the present application is further directed to a method for monitoring or diagnosing unfitness, cardiovascular disease risk, autotoxicity drugs, deconditioning or frailty in a living system, the method including: a) administering an isotope-labeled substrate to the living system for a period of time sufficient for the isotope-labeled substrate to enter into the muscle mitochondrial DNA or phospholipid metabolic pathway and thereby enter into and label at least one DNA molecule from muscle mitochondria or one phospholipid from muscle mitochondria within the muscle mitochondrial DNA or phospholipid metabolic pathway in the living system; b) obtaining one or more samples from the living system, wherein the one or more samples include at least one isotope-labeled DNA molecule from muscle mitochondria or one phospholipid from muscle mitochondria; c) measuring the content, rate of incorporation and/or pattern or rate of change in content and/or pattern of isotope labeling of the DNA from muscle mitochondria or phospholipids from muscle mitochondria; d) calculating molecular flux rates in the muscle mitochondrial DNA or phospholipid metabolic pathway based on the content and/or pattern or rate of change of content and/or pattern of isotopic labeling in the DNA from muscle mitochondria or phospholipids from muscle mitochondria to monitor or diagnose unfitness, cardiovascular disease risk, autotoxicity drugs, deconditioning or frailty.

Frailty, wasting or dystrophies can be monitored or diagnosed by measuring or detecting muscle protein dynamics. In this method, the targeted molecule of interest is protein derived from muscle. In this format, the present application is further directed to a method for monitoring or diagnosing frailty, wasting or dystrophies in a living system, the method including: a) administering an isotope-labeled substrate to the living system for a period of time sufficient for the isotope-labeled substrate to enter into the muscle protein metabolic pathway and thereby enter into and label at least one protein derived from muscle within the muscle protein metabolic pathway in the living system; b) obtaining one or more samples from the living system, wherein the one or more samples include at least one isotope-labeled protein derived from muscle; c) measuring the content, rate of incorporation and/or pattern or rate of change in content and/or pattern of isotope labeling of the protein derived from muscle; d) calculating molecular flux rates in the muscle protein metabolic pathway based on the content and/or pattern or rate of change of content and/or pattern of isotopic labeling in the protein derived from muscle to monitor or diagnose frailty, wasting or dystrophies.

Atherosclerosis or risk of diabetes mellitus can be monitored or diagnosed by measuring or detecting dynamics of adipose lipolysis. In this method, the targeted molecule of interest is triglyceride glycerol or one or more fatty acids. In this format, the present application is further directed to a method for monitoring or diagnosing atherosclerosis or assessing the risk of diabetes mellitus in a living system, the method including: a) administering an isotope-labeled substrate to the living system for a period of time sufficient for the isotope-labeled substrate to enter into the adipose lipolysis pathway and thereby enter into and label at least one triglyceride glycerol or fatty acid within the adipose lipolysis pathway in the living system; b) obtaining one or more samples from the living system, wherein the one or more samples include at least one isotope-labeled triglyceride glycerol or fatty acid; c) measuring the content, rate of incorporation and/or pattern or rate of change in content and/or pattern of isotope labeling of the triglyceride glycerol or fatty acid; d) calculating molecular flux rates in the adipose lipolysis pathway based on the content and/or pattern or rate of change of content and/or pattern of isotopic labeling in the triglyceride glycerol or fatty acid to monitor or diagnose atherosclerosis or assess the risk of diabetes mellitus.

Carbohydrate overfeeding, anabolic block, impaired fat oxidation or energy balance can be monitored or diagnosed by measuring or detecting the dynamics of adipose or hepatic de novo lipogenesis. In this method, the targeted molecule of interest is one or more fatty acids. In this format, the present application is further directed to a method for monitoring or diagnosing carbohydrate overfeeding, anabolic block, impaired fat oxidation or energy balance in a living system, the method including: a) administering an isotope-labeled substrate to the living system for a period of time sufficient for the isotope-labeled substrate to enter into the adipose metabolic pathway or hepatic de novo lipogenesis pathway and thereby enter into and label at least one or more fatty acids within the adipose metabolic pathway or hepatic de novo lipogenesis pathway in the living system; b) obtaining one or more samples from the living system, wherein the one or more samples include at least one isotope-labeled fatty acid; c) measuring the content, rate of incorporation and/or pattern or rate of change in content and/or pattern of isotope labeling of the fatty acid; d) calculating molecular flux rates in the adipose metabolic pathway or hepatic de novo lipogenesis pathway based on the content and/or pattern or rate of change of content and/or pattern of isotopic labeling in the fatty acid to monitor or diagnose carbohydrate overfeeding, anabolic block, impaired fat oxidation or energy balance.

Insulin resistance, impaired glucose tolerance or diabetes mellitus risk can be monitored or diagnosed by measuring or detecting the dynamics of glycolysis. In this method, the targeted molecule of interest is water. In this format, the present application is further directed to a method for monitoring or diagnosing insulin resistance, impaired glucose tolerance or diabetes mellitus risk in a living system, the method including: a) administering an isotope-labeled substrate to the living system for a period of time sufficient for the isotope-labeled substrate to enter into glycolysis and thereby enter into and label at least one water molecule within the glycolysis pathway in the living system; b) obtaining one or more samples from the living system, wherein the one or more samples include at least one isotope-labeled water molecule; c) measuring the content, rate of incorporation and/or pattern or rate of change in content and/or pattern of isotope labeling of the water; d) calculating molecular flux rates in the glycolysis pathway based on the content and/or pattern or rate of change of content and/or pattern of isotopic labeling in the water to monitor or diagnose insulin resistance, impaired glucose tolerance or diabetes mellitus risk.

Obesity risk, hypometabolism or hypermetabolism, or response to compounds or therapeutics can be monitored or diagnosed by measuring or detecting the dynamics of metabolic $H_2O$ or $CO_2$ production. In this method, the targeted molecule of interest is water or $CO_2$. In this format, the present application is further directed to a method for monitoring or diagnosing obesity risk, hypo or hypermetabolism, or response to compounds or therapeutics in a living system, the method including: a) administering an isotope-labeled substrate to the living system for a period of time sufficient for the isotope-labeled substrate to enter into the metabolic $H_2O$ or $CO_2$ production pathway and thereby enter into and label at least one water molecule or one $CO_2$ molecule within the metabolic $H_2O$ or $CO_2$ production pathway in the living system; b) obtaining one or more samples from the living system, wherein the one or more samples include at least one isotope-labeled water molecule; c) measuring the content, rate of incorporation and/or pattern or rate of change in content and/or pattern of isotope labeling of the water; d) calculating molecular flux rates in the metabolic $H_2O$ or $CO_2$ production pathway based on the content and/or pattern or rate of change of content and/or pattern of isotopic labeling in the water to monitor or diagnose obesity risk, hypometabolism or hypermetabolism, or response to compounds or therapeutics.

Obesity risk or insulin resistance can be monitored or diagnosed by measuring or detecting the dynamics of fatty acid oxidation. In this method, the targeted molecule of interest is water. In this format, the present application is further directed to a method for monitoring or diagnosing obesity risk or insulin resistance in a living system, the method including: a) administering an isotope-labeled substrate to the living system for a period of time sufficient for the isotope-labeled substrate to enter into the fatty acid oxidation pathway and thereby enter into and label at least one water molecule within the fatty acid oxidation pathway in the living system; b) obtaining one or more samples from the living system, wherein the one or more samples include at least one isotope-labeled water molecule; c) measuring the content, rate of incorporation and/or pattern or rate of change in content and/or pattern of isotope labeling of the water; d) calculating molecular flux rates in the fatty acid oxidation pathway based on the content and/or pattern or rate of change of content and/or pattern of isotopic labeling in the water to monitor or diagnose obesity risk or insulin resistance.

Hepatic insulin resistance, hypometabolism or hypermetabolism or treatment thereof can be monitored or diagnosed by measuring or detecting the dynamics of hepatic glucose production. In this method, the targeted molecule of interest is glucose. In this format, the present application is further directed to a method for monitoring or diagnosing hepatic insulin resistance or hypo or hypermetabolism in a living system, the method including: a) administering an isotope-labeled substrate to the living system for a period of time sufficient for the isotope-labeled substrate to enter into the hepatic glucose production pathway and thereby enter into and label at least one glucose molecule within the hepatic glucose production pathway in the living system; b) obtaining one or more samples from the living system, wherein the one or more samples include at least one isotope-labeled glucose molecule; c) measuring the content, rate of incorporation and/or pattern or rate of change in content and/or pattern of isotope labeling of the glucose; d) calculating molecular flux rates in the hepatic glucose production pathway based on the content and/or pattern or rate of change of content and/or pattern of isotopic labeling in the glucose to monitor or diagnose hepatic insulin resistance, hypometabolism or hypermetabolism or treatment thereof.

Hepatic steatosis (including tumors and cirrhosis) or treatment thereof can be monitored or diagnosed by measuring or detecting the dynamics of hepatic triglyceride synthesis. In this method, the targeted molecule of interest is triglyceride glycerol or one or more fatty acids. In this format, the present application is further directed to a method for monitoring or diagnosing hepatic steatosis in a living system, the method including: a) administering an isotope-labeled substrate to the living system for a period of time sufficient for the isotope-labeled substrate to enter into the hepatic triglyceride synthesis pathway and thereby enter into and label at least one triglyceride glycerol or fatty acid within the hepatic triglyceride synthesis pathway in the living system; b) obtaining one or more samples from the living system, wherein the one or more samples include at least one isotope-labeled triglyceride glycerol or fatty acid; c) measuring the content, rate of incorporation and/or pattern or rate of change in content and/or pattern of isotope labeling of the triglyceride glycerol or fatty acid; d) calculating molecular flux rates in the hepatic triglyceride synthesis pathway based on the content and/or pattern or rate of change of content and/or pattern of isotopic labeling in the triglyceride glycerol or fatty acid to monitor or diagnose hepatic steatosis.

Pancreatic burden, pancreatic reserve or diabetes mellitus risk or treatment thereof can be monitored or diagnosed by measuring or detecting (β-Cell DNA dynamics. In this method, the targeted molecule of interest is DNA derived from pancreatic beta cells. In this format, the present application is further directed to a method for monitoring or diagnosing pancreatic burden, pancreatic reserve or diabetes mellitus risk in a living system, the method including: a) administering an isotope-labeled substrate to the living system for a period of time sufficient for the isotope-labeled substrate to enter into the β-Cell DNA and thereby enter into and label at least one DNA molecule derived from pancreatic beta cells within the β-Cell DNA in the living system; b) obtaining one or more samples from the living system, wherein the one or more samples include at least one isotope-labeled DNA molecule derived from pancreatic beta cells; c) measuring the content, rate of incorporation and/or pattern or rate of change in content and/or pattern of isotope labeling of the DNA derived from pancreatic beta cells; d) calculating molecular flux rates in the β-Cell DNA based on the content and/or pattern or rate of change of content and/or pattern of isotopic labeling in the DNA derived from pancreatic beta cells to monitor or diagnose pancreatic burden, pancreatic reserve or diabetes mellitus risk or treatment thereof.

Pancreatic burden or pancreatic reserve or treatment thereof can be monitored or diagnosed by measuring or detecting insulin dynamics. In this method, the targeted molecule of interest is insulin. In this format, the present application is further directed to a method for monitoring or diagnosing pancreatic burden/pancreatic reserve in a living system, the method including: a) administering an isotope-labeled substrate to the living system for a period of time sufficient for the isotope-labeled substrate to enter into the insulin metabolic pathway and thereby enter into and label at least one insulin molecule within the insulin metabolic pathway in the living system; b) obtaining one or more samples from the living system, wherein the one or more samples include at least one isotope-labeled insulin molecule; c) measuring the content, rate of incorporation and/or pattern or rate of change in content and/or pattern of isotope labeling of the insulin; d) calculating molecular flux rates in the insulin metabolic pathway based on the content and/or pattern or rate of change of content and/or pattern of isotopic labeling in the insulin to monitor or diagnose pancreatic burden and/or pancreatic reserve.

Diabetes mellitus complications or treatment thereof can be monitored or diagnosed by measuring or detecting advanced glycation end product dynamics or advanced glycation end product glycosylation dynamics. In this method, the targeted molecules of interest are advanced glycation end products. In this format, the present application is further directed to a method for monitoring or diagnosing Diabetes mellitus complications in a living system, the method including: a) administering an isotope-labeled substrate to the living system for a period of time sufficient for the isotope-labeled substrate to enter into the advanced glycation end product pathway; advanced glycation end product glycosylation pathway and thereby enter into and label at least one advanced glycation end product within the advanced glycation end product pathway or advanced glycation end product glycosylation pathway in the living system; b) obtaining one or more samples from the living system, wherein the one or more samples include at least one isotope-labeled advanced glycation end product; c) measuring the content, rate of incorporation and/or pattern or rate of change in content and/or pattern of isotope labeling of the advanced glycation end products; d) calculating molecular flux rates in the glycation end product pathway or advanced glycation end product glycosylation pathway based on the content and/or pattern or rate of change of content and/or pattern of isotopic labeling in the advanced glycation end products to monitor or diagnose Diabetes mellitus complications or treatment thereof.

Caloric restriction/longevity regimens can be monitored or diagnosed by measuring or detecting keratinocyte or mammary epithelial cell dynamics. In this method, the targeted molecule of interest is DNA derived from keratinocytes or mammary epithelial cells. In this format, the present application is further directed to a method for monitoring or diagnosing caloric restriction/longevity regimens in a living system, the method including: a) administering an isotope-labeled substrate to the living system for a period of time sufficient for the isotope-labeled substrate to enter into the keratinocyte or mammary epithelial cell production pathway and thereby enter into and label at least one DNA molecule derived from keratinocytes or mammary epithelial cells within the keratinocyte or mammary epithelial cell production pathway in the living system; b) obtaining one or more samples from the living system, wherein the one or more samples include at least one isotope-labeled DNA molecule derived from keratinocytes or mammary epithelial cells; c) measuring the content, rate of incorporation and/or pattern or rate of change in content and/or pattern of isotope labeling of the DNA derived from keratinocytes or mammary epithelial cells; d) calculating molecular flux rates in the keratinocyte or mammary epithelial cell production pathway based on the content and/or pattern or rate of change of content and/or pattern of isotopic labeling in the DNA derived from keratinocytes or mammary epithelial cells to monitor or diagnose caloric restriction/longevity regimens.

Hyperlipoproteinemia or treatment thereof can be monitored or diagnosed by measuring or detecting hepatic bile acid dynamics. In this method, the targeted molecule of interest is one or more hepatic bile acids. In this format, the present application is further directed to a method for monitoring or diagnosing hyperlipoproteinemia in a living system, the method including: a) administering an isotope-labeled substrate to the living system for a period of time sufficient for the isotope-labeled substrate to enter into the hepatic bile acid synthesis pathway and thereby enter into and label at least one hepatic bile acid within the hepatic bile acid synthesis pathway in the living system; b) obtaining one or more samples from the living system, wherein the one or more samples include at least one isotope-labeled hepatic bile acid; c) measuring the content, rate of incorporation and/or pattern or rate of change in content and/or pattern of isotope labeling of the hepatic bile acid; d) calculating molecular flux rates in the hepatic bile acid synthesis pathway based on the content and/or pattern or rate of change of content and/or pattern of isotopic labeling in the hepatic bile acid to monitor or diagnose hyperlipoproteinemia or treatment thereof.

Hyperlipoproteinemia or cirrhosis/steatosis risk or treatment thereof can be monitored or diagnosed by measuring or detecting the dynamics of conversion of ethanol to acetate and triglyceride. In this method, the targeted molecule of interest is one or more fatty acids or acetate. In this format, the present application is further directed to a method for monitoring or diagnosing hyperlipoproteinemia or cirrhosis/steatosis risk in a living system, the method including: a) administering an isotope-labeled substrate to the living system for a period of time sufficient for the isotope-labeled substrate to enter into the pathway of conversion of ethanol to acetate and triglyceride and thereby enter into and label at least one fatty acid or acetate within the pathway of conversion of ethanol to acetate and triglyceride in the living system; b) obtaining one or more samples from the living system, wherein the one or more samples include at least one isotope-labeled fatty acid or acetate; c) measuring the content, rate of incorporation and/or pattern or rate of change in content and/or pattern of isotope labeling of the fatty acid or acetate; d) calculating molecular flux rates in the pathway of conversion of ethanol to acetate and triglyceride based on the content and/or pattern or rate of change of content and/or pattern of isotopic labeling in the fatty acid or acetate to monitor or diagnose hyperlipoproteinemia or cirrhosis/steatosis risk or treatment thereof.

Coronary artery disease risk or treatment of coronary artery disease can be monitored or diagnosed by measuring or detecting apolipoprotein B dynamics. In this method, the targeted molecule of interest is apolipoprotein B. In this format, the present application is further directed to a method for monitoring or diagnosing coronary artery disease risk in a living system, the method including: a) administering an isotope-labeled substrate to the living system for a period of time sufficient for the isotope-labeled substrate to enter into the apolipoprotein B metabolic pathway and thereby enter into and label at least one apolipoprotein B molecule within the apolipoprotein B metabolic pathway in the living system; b) obtaining one or more samples from the living system, wherein the one or more samples include at least one isotope-labeled apolipoprotein B molecule; c) measuring the content, rate of incorporation and/or pattern or rate of change in content and/or pattern of isotope labeling of the apolipoprotein B; d) calculating molecular flux rates in the apolipoprotein B metabolic pathway based on the content and/or pattern or rate of change of content and/or pattern of isotopic labeling in the apolipoprotein B to monitor or diagnose coronary artery disease risk or treatment of coronary artery disease.

Coronary artery disease risk, pancreatitis or hyperlipoproteinemia or treatment thereof can be monitored or diagnosed by measuring or detecting very low density lipoprotein (VLDL)—triglyceride dynamics. In this method, the targeted molecules of interest are Apolipoprotein B and triglyceride glycerol. In this format, the present application is further directed to a method for monitoring or diagnosing coronary artery disease risk, pancreatitis or hyperlipoproteinemia in a living system, the method including: a) administering an isotope-labeled substrate to the living system for a period of time sufficient for the isotope-labeled substrate to enter into the VLDL/triglyceride metabolic pathway and thereby enter into and label at least one Apolipoprotein B or triglyceride glycerol molecule within the VLDL/triglyceride metabolic pathway in the living system; b) obtaining one or more samples from the living system, wherein the one or more samples include at least one isotope-labeled Apolipoprotein B or triglyceride glycerol molecule; c) measuring the content, rate of incorporation and/or pattern or rate of change in content and/or pattern of isotope labeling of the Apolipoprotein B and triglyceride glycerol; d) calculating molecular flux rates in the VLDL/triglyceride metabolic pathway based on the content and/or pattern or rate of change of content and/or pattern of isotopic labeling in the Apolipoprotein B and triglyceride glycerol to monitor or diagnose coronary artery disease risk, pancreatitis or hyperlipoproteinemia or treatment thereof.

Statin response or coronary artery disease risk can be monitored or diagnosed by measuring or detecting cholesterol dynamics. In this method, the targeted molecule of interest is cholesterol from serum or blood. In this format, the present application is further directed to a method for monitoring or diagnosing statin response or coronary artery disease risk in a living system, the method including: a) administering an isotope-labeled substrate to the living system in the presence or absence of a statin for a period of time sufficient for the isotope-labeled substrate to enter into the cholesterol synthesis pathway and thereby enter into and label at least one cholesterol molecule from serum or blood within the cholesterol synthesis pathway in the living system; b) obtaining one or more samples from the living system, wherein the one or more samples include at least one isotope-labeled cholesterol molecule from serum or blood; c) measuring the content, rate of incorporation and/or pattern or rate of change in content and/or pattern of isotope labeling of the cholesterol from serum or blood; d) calculating molecular flux rates in the cholesterol synthesis pathway based on the content and/or pattern or rate of change of content and/or pattern of isotopic labeling in the cholesterol from serum or blood to monitor or diagnose statin response or coronary artery disease risk.

Atherosclerosis risk or treatment of atherosclerosis can be monitored or diagnosed by measuring or detecting vascular smooth muscle cell dynamics. In this method, the targeted molecule of interest is DNA derived from vascular smooth muscle cells. In this format, the present application is further directed to a method for monitoring or diagnosing atherosclerosis risk in a living system, the method including: a) administering an isotope-labeled substrate to the living system for a period of time sufficient for the isotope-labeled substrate to enter into the vascular smooth muscle cell production pathway and thereby enter into and label at least one DNA molecule derived from vascular smooth muscle cells within the vascular smooth muscle cell production pathway in the living system; b) obtaining one or more samples from the living system, wherein the one or more samples include at least one isotope-labeled DNA molecule derived from vascular smooth muscle cells; c) measuring the content, rate of incorporation and/or pattern or rate of change in content and/or pattern of isotope labeling of the DNA derived from vascular smooth muscle cells; d) calculating molecular flux rates in the vascular smooth muscle cell production pathway based on the content and/or pattern or rate of change of content and/or pattern of isotopic labeling in the DNA derived from vascular smooth muscle cells to monitor or diagnose atherosclerosis risk or treatment of atherosclerosis.

Coronary artery disease risk or treatment thereof can be monitored or diagnosed by measuring or detecting cholesterol transport dynamics (reverse cholesterol transport). In this method, the targeted molecules of interest are bile acids and cholesterol. In this format, the present application is further directed to a method for monitoring or diagnosing coronary artery disease risk in a living system, the method including: a) administering an isotope-labeled substrate to the living system for a period of time sufficient for the isotope-labeled substrate to enter into the reverse cholesterol transport pathway and thereby enter into and label at least one bile acid and cholesterol molecule within the reverse cholesterol transport pathway in the living system; b) obtaining one or more samples from the living system, wherein the one or more samples include at least one isotope-labeled bile acid and cholesterol molecule; c) measuring the content, rate of incorporation and/or pattern or rate of change in content and/or pattern of isotope labeling of the bile acids and cholesterol; d) calculating molecular flux rates in the reverse cholesterol transport pathway based on the content and/or pattern or rate of change of content and/or pattern of isotopic labeling in the bile acids and cholesterol to monitor or diagnose coronary artery disease risk.

Cardiomyopathy or treatment thereof can be monitored or diagnosed by measuring or detecting cardiac muscle protein dynamics. In this method, the targeted molecule of interest is protein derived from cardiac muscle. In this format, the present application is further directed to a method for monitoring or diagnosing cardiomyopathy in a living system, the method including: a) administering an isotope-labeled substrate to the living system for a period of time sufficient for the isotope-labeled substrate to enter into the cardiac muscle protein synthesis pathway and thereby enter into and label at least one protein derived from cardiac muscle within the cardiac muscle protein synthesis pathway in the living system; b) obtaining one or more samples from the living system, wherein the one or more samples include at least one isotope-labeled protein derived from cardiac muscle; c) measuring the content, rate of incorporation and/or pattern or rate of change in content and/or pattern of isotope labeling of the protein derived from cardiac muscle; d) calculating molecular flux rates in the cardiac muscle protein synthesis pathway based on the content and/or pattern or rate of change of content and/or pattern of isotopic labeling in the protein derived from cardiac muscle to monitor or diagnose cardiomyopathy or treatment thereof.

Cardiac fitness or congestive heart failure or treatment thereof can be monitored or diagnosed by measuring or detecting cardiac collagen dynamics. In this method, the targeted molecule of interest is collagen derived from cardiac tissue. In this format, the present application is further directed to a method for monitoring or diagnosing cardiac fitness or congestive heart failure in a living system, the method including: a) administering an isotope-labeled substrate to the living system for a period of time sufficient for the isotope-labeled substrate to enter into the cardiac collagen synthesis pathway and thereby enter into and label at least one collagen molecule derived from cardiac tissue within the cardiac collagen synthesis pathway in the living system; b) obtaining one or more samples from the living system, wherein the one or more samples include at least one isotope-labeled collagen molecule derived from cardiac tissue; c) measuring the content, rate of incorporation and/or pattern or rate of change in content and/or pattern of isotope labeling of the collagen derived from cardiac tissue; d) calculating molecular flux rates in the cardiac collagen synthesis pathway based on the content and/or pattern or rate of change of content and/or pattern of isotopic labeling in the collagen derived from cardiac tissue to monitor or diagnose cardiac fitness or congestive heart failure or treatment thereof.

Vasculitis or treatment thereof can be monitored or diagnosed by measuring or detecting vascular smooth muscle cell or endothelial cell dynamics. In this method, the targeted molecule of interest is DNA derived from vascular smooth muscle cells or endothelial cells. In this format, the present application is further directed to a method for monitoring or diagnosing vasculitis in a living system, the method including: a) administering an isotope-labeled substrate to the living system for a period of time sufficient for the isotope-labeled substrate to enter into the vascular smooth muscle cell or endothelial cell production pathway and thereby enter into and label at least one DNA molecule derived from vascular smooth muscle cells or endothelial cells within the vascular smooth muscle cell or endothelial cell production pathway in the living system; b) obtaining one or more samples from the living system, wherein the one or more samples include at least one isotope-labeled DNA molecule derived from vascular smooth muscle cells or endothelial cells; c) measuring the content, rate of incorporation and/or pattern or rate of change in content and/or pattern of isotope labeling of the DNA derived from vascular smooth muscle cells or endothelial cells; d) calculating molecular flux rates in the vascular smooth muscle cell or endothelial cell production pathway based on the content and/or pattern or rate of change of content and/or pattern of isotopic labeling in the DNA derived from vascular smooth muscle cells or endothelial cells to monitor or diagnose vasculitis or treatment thereto.

Psoriasis, skin hyperproliferation or ectopy or response of treatment thereto with one or more compounds can be monitored or diagnosed by measuring or detecting keratinocyte dynamics. In this method, the targeted molecule of interest is DNA derived from keratinocytes. In this format, the present application is further directed to a method for monitoring or diagnosing psoriasis, skin hyperproliferation or ectopy in a living system, the method including: a) administering an isotope-labeled substrate to the living system for a period of time sufficient for the isotope-labeled substrate to enter into the keratinocyte production pathway and thereby enter into and label at least one DNA molecule derived from keratinocytes within the keratinocyte production pathway in the living system; b) obtaining one or more samples from the living system, wherein the one or more samples include at least one isotope-labeled DNA molecule derived from keratinocytes; c) measuring the content, rate of incorporation and/or pattern or rate of change in content and/or pattern of isotope labeling of the DNA derived from keratinocytes; d) calculating molecular flux rates in the keratinocyte production pathway based on the content and/or pattern or rate of change of content and/or pattern of isotopic labeling in the DNA derived from keratinocytes to monitor or diagnose psoriasis, skin hyperproliferation or ectopy or response of treatment thereto with one or more compounds.

Psoriasis or skin barrier can be monitored or diagnosed by measuring or detecting skin keratin dynamics. In this method, the targeted molecule of interest is skin keratin. In this format, the present application is further directed to a method for monitoring or diagnosing psoriasis or skin barrier in a living system, the method including: a) administering an isotope-labeled substrate to the living system for a period of time sufficient for the isotope-labeled substrate to enter into the skin keratin synthesis pathway and thereby enter into and label at least one skin keratin molecule within the skin keratin synthesis pathway in the living system; b) obtaining one or more samples from the living system, wherein the one or more samples include at least one isotope-labeled skin keratin molecule; c) measuring the content, rate of incorporation and/or pattern or rate of change in content and/or pattern of isotope labeling of the skin keratin; d) calculating molecular flux rates in the skin keratin synthesis pathway based on the content and/or pattern or rate of change of content and/or pattern of isotopic labeling in the skin keratin to monitor or diagnose psoriasis or skin barrier.

Skin wrinkles, dermatomyolitis or scleroderma or response to treatment of same with one or more compounds can be monitored or diagnosed by measuring or detecting skin collagen dynamics and elastin dynamics. In this method, the targeted molecule of interest is collagen from skin (epidermis or dermis). In this format, the present application is further directed to a method for monitoring or diagnosing skin wrinkles, dermatomyolitis or scleroderma in a living system, the method including: a) administering an isotope-labeled substrate to the living system for a period of time sufficient for the isotope-labeled substrate to enter into the skin collagen and elastin synthesis pathways and thereby enter into and label at least one collagen molecule from skin within the skin collagen and elastin synthesis pathways in the living system; b) obtaining one or more samples from the living system, wherein the one or more samples include at least one isotope-labeled collagen molecule from skin; c) measuring the content, rate of incorporation and/or pattern or rate of change in content and/or pattern of isotope labeling of the collagen from skin; d) calculating molecular flux rates in the skin collagen and elastin synthesis pathways based on the content and/or pattern or rate of change of content and/or pattern of isotopic labeling in the collagen from skin to monitor or diagnose skin wrinkles, dermatomyolitis or scleroderma or response to treatment of same with one or more compounds.

Wound healing, adjunctive compound or therapeutic response to treatment thereto within one or more compounds can be monitored or diagnosed by measuring or detecting wound collagen dynamics. In this method, the targeted molecule of interest is collagen from skin and other wounded tissues. In this format, the present application is further directed to a method for monitoring or diagnosing wound healing, adjunctive compound or therapeutic response in a living system, the method including: a) administering an isotope-labeled substrate to the living system for a period of time sufficient for the isotope-labeled substrate to enter into the wound collagen production pathway and thereby enter into and label at least one collagen molecule from skin and other wounded tissues within the wound collagen production pathway in the living system; b) obtaining one or more samples from the living system, wherein the one or more samples include at least one isotope-labeled collagen molecule from skin and other wounded tissues; c) measuring the content, rate of incorporation and/or pattern or rate of change in content and/or pattern of isotope labeling of the collagen from skin and other wounded tissues; d) calculating molecular flux rates in the wound collagen production pathway based on the content and/or pattern or rate of change of content and/or pattern of isotopic labeling in the collagen from skin and other wounded tissues to monitor or diagnose wound healing, adjunctive compound or therapeutic response to treatment thereto.

Osteoarthritis, rheumatoid arthritis, joint protection/destruction or diet or response to treatment of same with one or more compounds can be monitored or diagnosed by measuring or detecting synovial space hyaluronic acid or chondroitin sulfate dynamics. In this method, the targeted molecules of interest are hyaluronic acid from synovial fluid or cartilage and chondroitin sulfate from synovial fluid or cartilage. In this format, the present application is further directed to a method for monitoring or diagnosing osteoarthritis, rheumatoid arthritis, joint protection/destruction or diet in a living system, the method including: a) administering an isotope-labeled substrate to the living system for a period of time sufficient for the isotope-labeled substrate to enter into the synovial space hyaluronic acid or chondroitin sulfate pathways and thereby enter into and label at least one hyaluronic acid from synovial fluid or cartilage and one chondroitin sulfate molecule from synovial fluid or cartilage within the synovial space hyaluronic acid or chondroitin sulfate pathways in the living system; b) obtaining one or more samples from the living system, wherein the one or more samples include at least one isotope-labeled hyaluronic acid from synovial fluid or cartilage and one chondroitin sulfate molecule from synovial fluid or cartilage; c) measuring the content, rate of incorporation and/or pattern or rate of change in content and/or pattern of isotope labeling of the hyaluronic acid from synovial fluid or cartilage and chondroitin sulfate from synovial fluid or cartilage; d) calculating molecular flux rates in the synovial space hyaluronic acid or chondroitin sulfate pathways based on the content and/or pattern or rate of change of content and/or pattern of isotopic labeling in the hyaluronic acid from synovial fluid or cartilage and chondroitin sulfate from synovial fluid or cartilage to monitor or diagnose osteoarthritis, rheumatoid arthritis, joint protection/destruction or diet.

Osteoporosis, pagets or healing of bone fractures or response to treatment of same with one or more compounds can be monitored or diagnosed by measuring or detecting bone collagen dynamics. In this method, the targeted molecule of interest is collagen from bone. In this format, the present application is further directed to a method for monitoring or diagnosing osteoporosis, pagets or healing of bone fractures in a living system, the method including: a) administering an isotope-labeled substrate to the living system for a period of time sufficient for the isotope-labeled substrate to enter into the bone collagen synthesis pathway and thereby enter into and label at least one collagen molecule from bone within the bone collagen synthesis pathway in the living system; b) obtaining one or more samples from the living system, wherein the one or more samples include at least one isotope-labeled collagen molecule from bone; c) measuring the content, rate of incorporation and/or pattern or rate of change in content and/or pattern of isotope labeling of the collagen from bone; d) calculating molecular flux rates in the bone collagen synthesis pathway based on the content and/or pattern or rate of change of content and/or pattern of isotopic labeling in the collagen from bone to monitor or diagnose osteoporosis, pagets or healing of bone fractures or response to treatment of same with one or more compounds.

Osteoarthritis, rheumatoid arthritis, joint protection or response to treatment of same with one or more compounds can be monitored or diagnosed by measuring or detecting joint collagen dynamics. In this method, the targeted molecule of interest is collagen from synovial fluid or cartilage. In this format, the present application is further directed to a method for monitoring or diagnosing osteoarthritis, rheumatoid arthritis, joint protection or response to treatment in a living system, the method including: a) administering an isotope-labeled substrate to the living system for a period of time sufficient for the isotope-labeled substrate to enter into the joint collagen synthesis pathway and thereby enter into and label at least one collagen molecule from synovial fluid or cartilage within the joint collagen synthesis pathway in the living system; b) obtaining one or more samples from the living system, wherein the one or more samples include at least one isotope-labeled collagen molecule from synovial fluid or cartilage; c) measuring the content, rate of incorporation and/or pattern or rate of change in content and/or pattern of isotope labeling of the collagen from synovial fluid or cartilage; d) calculating molecular flux rates in the joint collagen synthesis pathway based on the content and/or pattern or rate of change of content and/or pattern of isotopic labeling in the collagen from synovial fluid or cartilage to monitor or diagnose osteoarthritis, rheumatoid arthritis, joint protection or response to treatment of same with one or more compounds.

Rheumatoid arthritis or joint destruction or response to treatment of same with one or more compounds can be monitored or diagnosed by measuring or detecting synovial leukocyte/T-cell dynamics. In this method, the targeted molecule of interest is DNA from leukocytes or T-cells in synovial fluid or associated with joints. In this format, the present application is further directed to a method for monitoring or diagnosing rheumatoid arthritis or joint destruction in a living system, the method including: a) administering an isotope-labeled substrate to the living system for a period of time sufficient for the isotope-labeled substrate to enter into the synovial leukocyte/T-cell production pathways and thereby enter into and label at least one DNA molecule from leukocytes or T-cells in synovial fluid or associated with joints within the synovial leukocyte/T-cell production pathways in the living system; b) obtaining one or more samples from the living system, wherein the one or more samples include at least one isotope-labeled DNA molecule from leukocytes or T-cells in synovial fluid or associated with joints; c) measuring the content, rate of incorporation and/or pattern or rate of change in content and/or pattern of isotope labeling of the DNA from leukocytes or T-cells in synovial fluid or associated with joints; d) calculating molecular flux rates in the synovial leukocyte/T-cell production pathways based on the content and/or pattern or rate of change of content and/or pattern of isotopic labeling in the DNA from leukocytes or T-cells in synovial fluid or associated with joints to monitor or diagnose rheumatoid arthritis or joint destruction or response to treatment thereof.

Risk for cancer or therapeutic response to a treatment thereof can be monitored or diagnosed by measuring or detecting mammary epithelial cell dynamics. In this method, the targeted molecule of interest is DNA from mammary epithelial cells. In this format, the present application is further directed to a method for monitoring or diagnosing risk for cancer or compound or therapeutic response in a living system, the method including: a) administering an isotope-labeled substrate to the living system for a period of time sufficient for the isotope-labeled substrate to enter into the mammary epithelial cell production pathway and thereby enter into and label at least one DNA molecule from mammary epithelial cells within the mammary epithelial cell production pathway in the living system; b) obtaining one or more samples from the living system, wherein the one or more samples include at least one isotope-labeled DNA molecule from mammary epithelial cells; c) measuring the content, rate of incorporation and/or pattern or rate of change in content and/or pattern of isotope labeling of the DNA from mammary epithelial cells; d) calculating molecular flux rates in the mammary epithelial cell production pathway based on the content and/or pattern or rate of change of content and/or pattern of isotopic labeling in the DNA from mammary epithelial cells to monitor or diagnose risk for cancer or therapeutic treatment thereof.

Risk for cancer or therapeutic treatment thereof can be monitored or diagnosed by measuring or detecting colon epithelial cell dynamics. In this method, the targeted molecule of interest is DNA from colon epithelial cells. In this format, the present application is further directed to a method for monitoring or diagnosing risk for cancer or compound or therapeutic response in a living system, the method including: a) administering an isotope-labeled substrate to the living system for a period of time sufficient for the isotope-labeled substrate to enter into the colon epithelial cell production pathway and thereby enter into and label at least one DNA molecule from colon epithelial cells within the colon epithelial cell production pathway in the living system; b) obtaining one or more samples from the living system, wherein the one or more samples include at least one isotope-labeled DNA molecule from colon epithelial cells; c) measuring the content, rate of incorporation and/or pattern or rate of change in content and/or pattern of isotope labeling of the DNA from colon epithelial cells; d) calculating molecular flux rates in the colon epithelial cell production pathway based on the content and/or pattern or rate of change of content and/or pattern of isotopic labeling in the DNA from colon epithelial cells to monitor or diagnose risk for cancer or compound or therapeutic response.

Risk for cancer or therapeutic treatment thereof can be monitored or diagnosed by measuring or detecting bronchial cell or tissue dynamics. In this method, the targeted molecule of interest is DNA from bronchial tissue. In this format, the present application is further directed to a method for monitoring or diagnosing risk for cancer or compound or therapeutic response in a living system, the method including: a) administering an isotope-labeled substrate to the living system for a period of time sufficient for the isotope-labeled substrate to enter into the bronchial cell or tissue production pathway and thereby enter into and label at least one DNA molecule from bronchial tissue within the bronchial cell or tissue production pathway in the living system; b) obtaining one or more samples from the living system, wherein the one or more samples include at least one isotope-labeled DNA molecule from bronchial tissue; c) measuring the content, rate of incorporation and/or pattern or rate of change in content and/or pattern of isotope labeling of the DNA from bronchial tissue; d) calculating molecular flux rates in the bronchial cell or tissue production pathway based on the content and/or pattern or rate of change of content and/or pattern of isotopic labeling in the DNA from bronchial tissue to monitor or diagnose risk for cancer or therapeutic treatment thereof.

Risk for cancer, benign prostatic hyperplasia or therapeutic thereof can be monitored or diagnosed by measuring or detecting prostate epithelial cell dynamics. In this method, the targeted molecule of interest is DNA from prostate epithelial cells. In this format, the present application is further directed to a method for monitoring or diagnosing risk for cancer, benign prostatic hyperplasia or compound or therapeutic response in a living system, the method including: a) administering an isotope-labeled substrate to the living system for a period of time sufficient for the isotope-labeled substrate to enter into the prostate epithelial cell production pathway and thereby enter into and label at least one DNA molecule from prostate epithelial cells within the prostate epithelial cell production pathway in the living system; b) obtaining one or more samples from the living system, wherein the one or more samples include at least one isotope-labeled DNA molecule from prostate epithelial cells; c) measuring the content, rate of incorporation and/or pattern or rate of change in content and/or pattern of isotope labeling of the DNA from prostate epithelial cells; d) calculating molecular flux rates in the prostate epithelial cell production pathway based on the content and/or pattern or rate of change of content and/or pattern of isotopic labeling in the DNA from prostate epithelial cells to monitor or diagnose risk for cancer, benign prostatic hyperplasia or therapeutic treatment thereof.

Risk for cancer or therapeutic treatment thereof can be monitored or diagnosed by measuring or detecting the dynamics of tumors of pancreas, bladder, gastric, brain, ovary, or cervix. In this method, the targeted molecule of interest is DNA from cells from which tumors may derive (e.g., epithelial cells) or pre-cancerous cells, or cells whose proliferative behavior is associated with increased risk of cancer. In this format, the present application is further directed to a method for monitoring or diagnosing risk for cancer or compound or therapeutic response in a living system, the method including: a) administering an isotope-labeled substrate to the living system for a period of time sufficient for the isotope-labeled substrate to enter into the tumorigenesis pathway of pancreas, bladder, gastric, brain, ovary, or cervix cancer and thereby enter into and label at least one DNA molecule from cells from which tumors may derive from the tumorigenesis of pancreas, bladder, gastric, brain, ovary, or cervix in the living system; b) obtaining one or more samples from the living system, wherein the one or more samples include at least one isotope-labeled DNA molecule from cells from which tumors may derive; c) measuring the content, rate of incorporation and/or pattern or rate of change in content and/or pattern of isotope labeling of the DNA from cells from which tumors may derive; d) calculating molecular flux rates in the tumorigenesis of pancreas, bladder, gastric, brain, ovary, or cervix cancer based on the content and/or pattern or rate of change of content and/or pattern of isotopic labeling in the DNA from cells from which tumors may derive to monitor or diagnose risk for cancer or therapeutic treatment thereof.

Tumor growth, grade, prognosis, aggressiveness, or therapeutic treatment thereof can be monitored or diagnosed by measuring or detecting the dynamics of solid tumors (including breast, colon, lung, and lymphoma). In this method, the targeted molecule of interest is DNA derived from solid tumor cells. In this format, the present application is further directed to a method for monitoring or diagnosing tumor growth, grade, prognosis, aggressiveness, or therapeutic response in a living system, the method including: a) administering an isotope-labeled substrate to the living system for a period of time sufficient for the isotope-labeled substrate to enter into the solid tumor formation pathway and thereby enter into and label at least one DNA molecule derived from solid tumor cells within the solid tumor formation pathway in the living system; b) obtaining one or more samples from the living system, wherein the one or more samples include at least one isotope-labeled DNA molecule derived from solid tumor cells; c) measuring the content, rate of incorporation and/or pattern or rate of change in content and/or pattern of isotope labeling of the DNA derived from solid tumor cells; d) calculating molecular flux rates in the solid tumor formation pathway based on the content and/or pattern or rate of change of content and/or pattern of isotopic labeling in the DNA derived from solid tumor cells to monitor or diagnose tumor growth, grade, prognosis, aggressiveness, or therapeutic treatment thereof.

Cancer growth, prognosis, or therapeutic treatment thereof can be monitored or diagnosed by measuring or detecting the dynamics of liquid tumors. In this method, the targeted molecule of interest is DNA derived from liquid tumor cells. In this format, the present application is further directed to a method for monitoring or diagnosing cancer growth, prognosis, or compound or therapeutic response in a living system, the method including: a) administering an isotope-labeled substrate to the living system for a period of time sufficient for the isotope-labeled substrate to enter into the liquid tumor formation pathway and thereby enter into and label at least one DNA molecule derived from liquid tumor cells within the liquid tumor formation pathway in the living system; b) obtaining one or more samples from the living system, wherein the one or more samples include at least one isotope-labeled DNA molecule derived from liquid tumor cells; c) measuring the content, rate of incorporation and/or pattern or rate of change in content and/or pattern of isotope labeling of the DNA derived from liquid tumor cells; d) calculating molecular flux rates in the liquid tumor formation pathway based on the content and/or pattern or rate of change of content and/or pattern of isotopic labeling in the DNA derived from liquid tumor cells to monitor or diagnose cancer growth, prognosis, or therapeutic treatment thereof.

Multiple myeloma activity, prognosis, growth, mass or therapeutic treatment thereof can be monitored or diagnosed by measuring or detecting immunoglobulin, albumin, myeloma-protein dynamics or myeloma cell dynamics. In this method, the targeted molecule of interest is myeloma protein, immunoglobulin or albumin derived from serum or bone marrow, or DNA from myeloma cells. In this format, the present application is further directed to a method for monitoring or diagnosing multiple myeloma activity, prognosis, growth, mass or therapeutic response to treatment thereof in a living system, the method including: a) administering an isotope-labeled substrate to the living system for a period of time sufficient for the isotope-labeled substrate to enter into the immunoglobulin, albumin, myeloma-protein or myeloma cell production pathways and thereby enter into and label at least one myeloma protein, immunoglobulin, or albumin derived from serum or bone marrow, or one DNA molecule from myeloma cells within the immunoglobulin, albumin, myeloma-protein or myeloma cell production pathways in the living system; b) obtaining one or more samples from the living system, wherein the one or more samples include at least one isotope-labeled myeloma protein, immunoglobulin, or albumin derived from serum or bone marrow, or one DNA molecule from myeloma cells; c) measuring the content, rate of incorporation and/or pattern or rate of change in content and/or pattern of isotope labeling of the myeloma protein, immunoglobulin, or albumin derived from serum or bone marrow, or DNA from myeloma cells; d) calculating molecular flux rates in the immunoglobulin, albumin, myeloma-protein or myeloma cell production pathways based on the content and/or pattern or rate of change of content and/or pattern of isotopic labeling in the myeloma protein, immunoglobulin, or albumin derived from serum or bone marrow, or DNA from myeloma cells to monitor or diagnose multiple myeloma activity, prognosis, growth, mass or therapeutic treatment thereof.

Angiogenesis or therapeutic treatment thereof can be monitored or diagnosed by measuring or detecting tumor endothelial cell dynamics. In this method, the targeted molecule of interest is DNA from tumor endothelial cells. In this format, the present application is further directed to a method for monitoring or diagnosing angiogenesis or compound or therapeutic response in a living system, the method including: a) administering an isotope-labeled substrate to the living system for a period of time sufficient for the isotope-labeled substrate to enter into the tumor endothelial cell production pathway and thereby enter into and label at least one DNA molecule from tumor endothelial cells within the tumor endothelial cell production pathway in the living system; b) obtaining one or more samples from the living system, wherein the one or more samples include at least one isotope-labeled DNA molecule from tumor endothelial cells; c) measuring the content, rate of incorporation and/or pattern or rate of change in content and/or pattern of isotope labeling of the DNA from tumor endothelial cells; d) calculating molecular flux rates in the tumor endothelial cell production pathway based on the content and/or pattern or rate of change of content and/or pattern of isotopic labeling in the DNA from tumor endothelial cells to monitor or diagnose angiogenesis or therapeutic treatment thereof.

Angiogenesis or therapeutic treatment thereof can be monitored or diagnosed by measuring or detecting the dynamics of ribonucleotide reductase substrates and metabolites (flux vs. salvage). In this method, the targeted molecule of interest is deoxyadenosine and deoxythymidine. In this format, the present application is further directed to a method for monitoring or diagnosing compound or therapeutic response in a living system, the method including: a) administering an isotope-labeled substrate to the living system for a period of time sufficient for the isotope-labeled substrate to enter into the metabolism of ribonucleotide reductase substrates and thereby enter into and label at least one molecule of deoxyadenosine and deoxythymidine within the metabolism of ribonucleotide reductase substrates in the living system; b) obtaining one or more samples from the living system, wherein the one or more samples include at least one isotope-labeled molecule of deoxyadenosine and deoxythymidine; c) measuring the content, rate of incorporation and/or pattern or rate of change in content and/or pattern of isotope labeling of the deoxyadenosine and deoxythymidine; d) calculating molecular flux rates in the metabolism of ribonucleotide reductase substrates based on the content and/or pattern or rate of change of content and/or pattern of isotopic labeling in the deoxyadenosine and deoxythymidine to monitor or diagnose angiogenesis or therapeutic response to treatment thereof.

Cancer risk or therapeutic response to treatment thereto can be monitored or diagnosed by measuring or detecting epithelial stem cell dynamics. In this method, the targeted molecule of interest is DNA from epithelial stem cells. In this format, the present application is further directed to a method for monitoring or diagnosing cancer risk or compound or therapeutic response in a living system, the method including: a) administering an isotope-labeled substrate to the living system for a period of time sufficient for the isotope-labeled substrate to enter into the epithelial stem cell production pathway and thereby enter into and label at least one DNA molecule from epithelial stem cells within the epithelial stem cell production pathway in the living system; b) obtaining one or more samples from the living system, wherein the one or more samples include at least one isotope-labeled DNA molecule from epithelial stem cells; c) measuring the content, rate of incorporation and/or pattern or rate of change in content and/or pattern of isotope labeling of the DNA from epithelial stem cells; d) calculating molecular flux rates in the epithelial stem cell production pathway based on the content and/or pattern or rate of change of content and/or pattern of isotopic labeling in the DNA from epithelial stem cells to monitor or diagnose cancer risk or therapeutic response to treatment thereto.

Tumor grade, prognosis, treatment target, or therapeutic response to treatment thereto can be monitored or diagnosed by measuring or detecting tumor cell RNA dynamics. In this method, the targeted molecule of interest is RNA from tumor cells, either total or transcript-specific. In this format, the present application is further directed to a method for monitoring or diagnosing tumor grade, prognosis, treatment target, or compound or therapeutic response in a living system, the method including: a) administering an isotope-labeled substrate to the living system for a period of time sufficient for the isotope-labeled substrate to enter into tumor cell transcription and thereby enter into and label at least one RNA molecule from tumor cells within tumor cell transcription in the living system; b) obtaining one or more samples from the living system, wherein the one or more samples include at least one isotope-labeled RNA molecule from tumor cells; c) measuring the content, rate of incorporation and/or pattern or rate of change in content and/or pattern of isotope labeling of the RNA from tumor cells; d) calculating molecular flux rates in tumor cell transcription based on the content and/or pattern or rate of change of content and/or pattern of isotopic labeling in the RNA from tumor cells to monitor or diagnose tumor grade, prognosis, treatment target, or therapeutic response to treatment thereto.

Proliferation and growth of transplant can be monitored or diagnosed by measuring or detecting T-cell or other blood cell dynamics (post bone marrow transplant). In this method, the targeted molecule of interest is DNA from transplanted cells, or from cells maturing from transplanted cells. In this format, the present application is further directed to a method for monitoring or diagnosing proliferation and growth of transplant in a living system, the method including: a) administering an isotope-labeled substrate to the living system for a period of time sufficient for the isotope-labeled substrate to enter into the T-cell or other blood cell production pathway and thereby enter into and label at least one DNA molecule from transplanted cells, or from cells maturing from transplanted cells within the T-cell or other blood cell production pathway in the living system; b) obtaining one or more samples from the living system, wherein the one or more samples include at least one isotope-labeled DNA molecule from transplanted cells, or from cells maturing from transplanted cells; c) measuring the content, rate of incorporation and/or pattern or rate of change in content and/or pattern of isotope labeling of the DNA from transplanted cells, or from cells maturing from transplanted cells; d) calculating molecular flux rates in the T-cell or other blood cell production pathway based on the content and/or pattern or rate of change of content and/or pattern of isotopic labeling in the DNA from transplanted cells, or from cells maturing from transplanted cells to monitor or diagnose proliferation and growth of transplant.

Adequacy of surgery can be monitored or diagnosed by measuring or detecting cell dynamics at the surgical margin of a tumor. In this method, the targeted molecule of interest is DNA from the surgical margin of the tumor. In this format, the present application is further directed to a method for monitoring or diagnosing adequacy of surgery in a living system, the method including: a) administering an isotope-labeled substrate to the living system for a period of time sufficient for the isotope-labeled substrate to enter into the pathway whereby cells are formed at the surgical margin of a tumor and thereby enter into and label at least one DNA molecule from the surgical margin of the tumor within the pathway whereby cells are formed at the surgical margin of a tumor in the living system; b) obtaining one or more samples from the living system, wherein the one or more samples include at least one isotope-labeled DNA molecule from the surgical margin of the tumor; c) measuring the content, rate of incorporation and/or pattern or rate of change in content and/or pattern of isotope labeling of the DNA from the surgical margin of the tumor; d) calculating molecular flux rates in the pathway whereby cells are formed at the surgical margin of a tumor based on the content and/or pattern or rate of change of content and/or pattern of isotopic labeling in the DNA from the surgical margin of the tumor to monitor or diagnose adequacy of surgery.

Grade, aggressiveness, or graft-versus-host-disease treatment response can be monitored or diagnosed by measuring or detecting grafted tissue dynamics. In this method, the targeted molecule of interest is DNA from the grafted tissue. In this format, the present application is further directed to a method for monitoring or diagnosing grade, aggressiveness, or graft-versus-host-disease treatment response in a living system, the method including: a) administering an isotope-labeled substrate to the living system for a period of time sufficient for the isotope-labeled substrate to enter into the pathway of incorporation of grafted tissue and thereby enter into and label at least one DNA molecule from the grafted tissue within the pathway of incorporation of grafted tissue in the living system; b) obtaining one or more samples from the living system, wherein the one or more samples include at least one isotope-labeled DNA molecule from the grafted tissue; c) measuring the content, rate of incorporation and/or pattern or rate of change in content and/or pattern of isotope labeling of the DNA from the grafted tissue; d) calculating molecular flux rates in the pathway of incorporation of grafted tissue based on the content and/or pattern or rate of change of content and/or pattern of isotopic labeling in the DNA from the grafted tissue to monitor or diagnose grade, aggressiveness, or graft-versus-host-disease treatment response.

Diagnosis of cancer, monitoring of cancer progression and treatment of cancer by gene silencing can be monitored or diagnosed by measuring or detecting the dynamics of methylcytosine (methyl deoxycytosine methylation/hypo methylation). In this method, the targeted molecule of interest is methyl deoxycytosine from DNA from cells of interest. In this format, the present application is further directed to a method for monitoring or diagnosing gene silencing, prognosis; or compound or therapeutic response in a living system, the method including: a) administering an isotope-labeled substrate to the living system for a period of time sufficient for the isotope-labeled substrate to enter into the methyl deoxycytosine methylation pathway and thereby enter into and label at least one methyl deoxycytosine molecule from DNA from cells of interest within the methyl deoxycytosine methylation pathway in the living system; b) obtaining one or more samples from the living system, wherein the one or more samples include at least one isotope-labeled methyl deoxycytosine molecule from DNA from cells of interest; c) measuring the content, rate of incorporation and/or pattern or rate of change in content and/or pattern of isotope labeling of the methyl deoxycytosine from DNA from cells of interest; d) calculating molecular flux rates in the methyl deoxycytosine methylation pathway based on the content and/or pattern or rate of change of content and/or pattern of isotopic labeling in the methyl deoxycytosine from DNA from cells of interest to monitor or diagnose cancer, or cancer progression or cancer treatments by gene silencing.

Alzheimer's disease risk or response to treatment thereto can be monitored or diagnosed by measuring or detecting brain amyloid-β or amyloid precursor protein dynamics. In this method, the targeted molecule of interest is amyloid beta peptide or amyloid precursor protein or subfragments of either. In this format, the present application is further directed to a method for monitoring or diagnosing Alzheimer's disease risk or response to treatment in a living system, the method including: a) administering an isotope-labeled substrate to the living system for a period of time sufficient for the isotope-labeled substrate to enter into the brain amyloid-β or amyloid precursor protein synthesis pathway and thereby enter into and label at least one amyloid beta peptide or amyloid precursor protein or subfragments of either within the brain amyloid-β or amyloid precursor protein synthesis pathway in the living system; b) obtaining one or more samples from the living system, wherein the one or more samples include at least one isotope-labeled amyloid beta peptide or amyloid precursor protein or subfragments of either; c) measuring the content, rate of incorporation and/or pattern or rate of change in content and/or pattern of isotope labeling of the amyloid beta peptide or amyloid precursor protein or subfragments of either; d) calculating molecular flux rates in the brain amyloid-β or amyloid precursor protein synthesis pathway based on the content and/or pattern or rate of change of content and/or pattern of isotopic labeling in the amyloid beta peptide or amyloid precursor protein or subfragments of either to monitor or diagnose Alzheimer's disease risk or response to treatment thereto.

Multiple sclerosis (MS) activity, MS response to treatment, spinal cord and brain injury recovery or therapeutic response to treatment thereto can be monitored or diagnosed by measuring or detecting brain or peripheral nervous system myelin dynamics. In this method, the targeted molecule of interest is galactocerebroside from brain, peripheral nervous system, or blood. In this format, the present application is further directed to a method for monitoring or diagnosing multiple sclerosis (MS) activity, MS response to treatment, spinal cord and brain injury recovery and/or compound or therapeutic response in a living system, the method including: a) administering an isotope-labeled substrate to the living system for a period of time sufficient for the isotope-labeled substrate to enter into the brain or peripheral nervous system myelin production pathway and thereby enter into and label at least one galactocerebroside molecule within the brain or peripheral nervous system myelin production pathway in the living system; b) obtaining one or more samples from the living system, wherein the one or more samples include at least one isotope-labeled galactocerebroside molecule; c) measuring the content, rate of incorporation and/or pattern or rate of change in content and/or pattern of isotope labeling of the galactocerebroside; d) calculating molecular flux rates in the brain or peripheral nervous system myelin production pathway based on the content and/or pattern or rate of change of content and/or pattern of isotopic labeling in the galactocerebroside to monitor or diagnose multiple sclerosis (MS) activity, MS response to treatment, spinal cord and brain injury recovery or therapeutic response to treatment thereto or therapeutic response to treatment thereto.

Neurogenesis, x-ray therapy toxicity, development, stress or depression or therapeutic response to treatment thereto can be monitored or diagnosed by measuring or detecting neuron dynamics. In this method, the targeted molecule of interest is DNA from neurons. In this format, the present application is further directed to a method for monitoring or diagnosing neurogenesis, x-ray therapy toxicity, development, stress or depression in a living system, the method including: a) administering an isotope-labeled substrate to the living system for a period of time sufficient for the isotope-labeled substrate to enter into the neurogenesis pathway and thereby enter into and label at least one DNA molecule from neurons within the neurogenesis pathway in the living system; b) obtaining one or more samples from the living system, wherein the one or more samples include at least one isotope-labeled DNA molecule from neurons; c) measuring the content, rate of incorporation and/or pattern or rate of change in content and/or pattern of isotope labeling of the DNA from neurons; d) calculating molecular flux rates in the neurogenesis pathway based on the content and/or pattern or rate of change of content and/or pattern of isotopic labeling in the DNA from neurons to monitor or diagnose neurogenesis, x-ray therapy toxicity, development, stress or depression or therapeutic response to treatment thereto.

Psychiatric disorders or treatment thereof can be monitored or diagnosed by measuring or detecting neurotransmitter dynamics. In this method, the targeted molecules of interest are neurotransmitters from brain, or circulating or degraded neurotransmitters found in other tissues. In this format, the present application is further directed to a method for monitoring or diagnosing psychiatric disorders in a living system, the method including: a) administering an isotope-labeled substrate to the living system for a period of time sufficient for the isotope-labeled substrate to enter into the neurotransmitter synthesis pathway and thereby enter into and label at least one neurotransmitter within the neurotransmitter synthesis pathway in the living system; b) obtaining one or more samples from the living system, wherein the one or more samples include at least one isotope-labeled neurotransmitter; c) measuring the content, rate of incorporation and/or pattern or rate of change in content and/or pattern of isotope labeling of the neurotransmitter; d) calculating molecular flux rates in the neurotransmitter synthesis pathway based on the content and/or pattern or rate of change of content and/or pattern of isotopic labeling in the neurotransmitter to monitor or diagnose psychiatric disorders or treatment thereof.

Neurogenesis, depression or therapeutic response to treatment thereto can be monitored or diagnosed by measuring or detecting neuroprogenitor cell dynamics. In this method, the targeted molecule of interest is DNA from neuroprogenitor cells. In this format, the present application is further directed to a method for monitoring or diagnosing neurogenesis, depression or compound or therapeutic response in a living system, the method including: a) administering an isotope-labeled substrate to the living system for a period of time sufficient for the isotope-labeled substrate to enter into the neuroprogenitor cell production pathway and thereby enter into and label at least one DNA molecule from neuroprogenitor cells within the neuroprogenitor cell production pathway in the living system; b) obtaining one or more samples from the living system, wherein the one or more samples include at least one isotope-labeled DNA molecule from neuroprogenitor cells; c) measuring the content, rate of incorporation and/or pattern or rate of change in content and/or pattern of isotope labeling of the DNA from neuroprogenitor cells; d) calculating molecular flux rates in the neuroprogenitor cell production pathway based on the content and/or pattern or rate of change of content and/or pattern of isotopic labeling in the DNA from neuroprogenitor cells to monitor or diagnose neurogenesis, depression or therapeutic response to treatment thereto.

Neuroinflammation, multiple sclerosis, Alzheimer's disease, stroke, autism, depression, chronic pain, amyotrophic lateral sclerosis, cerebral amyloid angiopathy, excitotoxic injury or therapeutic response to treatment thereto can be monitored or diagnosed by measuring or detecting microglial cell dynamics. In this method, the targeted molecule of interest is DNA from microglia. In this format, the present application is further directed to a method for monitoring or diagnosing neuroinflammation, multiple sclerosis, Alzheimer's disease, stroke, autism, depression, chronic pain, amyotrophic lateral sclerosis, cerebral amyloid angiopathy, excitotoxic injury or therapeutic response in a living system, the method including: a) administering an isotope-labeled substrate to the living system for a period of time sufficient for the isotope-labeled substrate to enter into the microglial cell production pathway and thereby enter into and label at least one DNA molecule from microglia within the microglial cell production pathway in the living system; b) obtaining one or more samples from the living system, wherein the one or more samples include at least one isotope-labeled DNA molecule from microglia; c) measuring the content, rate of incorporation and/or pattern or rate of change in content and/or pattern of isotope labeling of the DNA from microglia; d) calculating molecular flux rates in the microglial cell production pathway based on the content and/or pattern or rate of change of content and/or pattern of isotopic labeling in the DNA from microglia to monitor or diagnose neuroinflammation, multiple sclerosis, Alzheimer's disease, stroke, autism, depression, chronic pain, amyotrophic lateral sclerosis, cerebral amyloid angiopathy, excitotoxic injury or therapeutic response to treatment thereto.

Alzheimer's disease, excitotoxic injury, neurogenesis, neurodegenerative diseases or therapeutic response to treatment thereto can be monitored or diagnosed by measuring or detecting brain microtubule dynamics. In this method, the targeted molecules of interest are microtubules from central or peripheral nervous system or microtubule subfractions (e.g., tau-associated, dimeric, polymeric). In this format, the present application is further directed to a method for monitoring or diagnosing Alzheimer's disease, excitotoxic injury, neurogenesis, neurodegenerative diseases or therapeutic response in a living system, the method including: a) administering an isotope-labeled substrate to the living system for a period of time sufficient for the isotope-labeled substrate to enter into the brain microtubule production pathway and thereby enter into and label at least one microtubule from central or peripheral nervous system or one microtubule subfraction within the brain microtubule production pathway in the living system; b) obtaining one or more samples from the living system, wherein the one or more samples include at least one isotope-labeled microtubule from central or peripheral nervous system or one microtubule subfraction; c) measuring the content, rate of incorporation and/or pattern or rate of change in content and/or pattern of isotope labeling of the microtubules from central or peripheral nervous system or microtubule subfractions; d) calculating molecular flux rates in the brain microtubule production pathway based on the content and/or pattern or rate of change of content and/or pattern of isotopic labeling in the microtubules from central or peripheral nervous system or microtubule subfractions to monitor or diagnose Alzheimer's disease, excitotoxic injury, neurogenesis, neurodegenerative diseases or therapeutic response to treatment thereto.

Hepatic necrosis, toxin exposure, hepatitis or response to treatment thereof can be monitored or diagnosed by measuring or detecting hepatocyte dynamics. In this method, the targeted molecule of interest is DNA from hepatocytes. In this format, the present application is further directed to a method for monitoring or diagnosing hepatic necrosis, toxin exposure, hepatitis or response to treatment in a living system, the method including: a) administering an isotope-labeled substrate to the living system for a period of time sufficient for the isotope-labeled substrate to enter into the hepatocyte production pathway and thereby enter into and label at least one DNA molecule from hepatocytes within the hepatocyte production pathway in the living system; b) obtaining one or more samples from the living system, wherein the one or more samples include at least one isotope-labeled DNA molecule from hepatocytes; c) measuring the content, rate of incorporation and/or pattern or rate of change in content and/or pattern of isotope labeling of the DNA from hepatocytes; d) calculating molecular flux rates in the hepatocyte production pathway based on the content and/or pattern or rate of change of content and/or pattern of isotopic labeling in the DNA from hepatocytes to monitor or diagnose hepatic necrosis, toxin exposure, hepatitis or response to treatment thereof.

Hepatic fibrosis, cirrhosis risk, prognosis, disease activity or response to treatment thereof can be monitored or diagnosed by measuring or detecting hepatic collagen dynamics. In this method, the targeted molecule of interest is collagen from liver. In this format, the present application is further directed to a method for monitoring or diagnosing hepatic fibrosis, cirrhosis risk, prognosis, disease activity or response to treatment in a living system, the method including: a) administering an isotope-labeled substrate to the living system for a period of time sufficient for the isotope-labeled substrate to enter into the hepatic collagen production pathway and thereby enter into and label at least one collagen molecule from liver within the hepatic collagen production pathway in the living system; b) obtaining one or more samples from the living system, wherein the one or more samples include at least one isotope-labeled collagen molecule from liver; c) measuring the content, rate of incorporation and/or pattern or rate of change in content and/or pattern of isotope labeling of the collagen from liver; d) calculating molecular flux rates in the hepatic collagen production pathway based on the content and/or pattern or rate of change of content and/or pattern of isotopic labeling in the collagen from liver to monitor or diagnose hepatic fibrosis, cirrhosis risk, prognosis, disease activity or response to treatment thereof.

Effects from exposure to hepatic toxins, mitochondrial toxins, recovery or response to treatment can be monitored or diagnosed by measuring or detecting hepatic mitochondrial dynamics. In this method, the targeted molecules of interest are DNA or phospholipids from hepatic mitochondria. In this format, the present application is further directed to a method for monitoring or diagnosing effects from exposure to hepatic toxins, mitochondrial toxins, recovery or response to treatment in a living system, the method including: a) administering an isotope-labeled substrate to the living system for a period of time sufficient for the isotope-labeled substrate to enter into the hepatic mitochondrial production pathway and thereby enter into and label at least one DNA molecule or phospholipid from hepatic mitochondria within the hepatic mitochondrial production pathway in the living system; b) obtaining one or more samples from the living system, wherein the one or more samples include at least one isotope-labeled DNA molecule or phospholipid from hepatic mitochondria; c) measuring the content, rate of incorporation and/or pattern or rate of change in content and/or pattern of isotope labeling of the DNA or phospholipids from hepatic mitochondria; d) calculating molecular flux rates in the hepatic mitochondrial production pathway based on the content and/or pattern or rate of change of content and/or pattern of isotopic labeling in the DNA or phospholipids from hepatic mitochondria to monitor or diagnose effects from exposure to hepatic toxins, mitochondrial toxins, recovery or response to treatment.

Effects from exposure to nephrotoxins, recovery or response to treatment can be monitored or diagnosed by measuring or detecting renal epithelial cell dynamics. In this method, the targeted molecule of interest is DNA from renal epithelial cells. In this format, the present application is further directed to a method for monitoring or diagnosing effects from exposure to nephrotoxins, recovery or response to treatment in a living system, the method including: a) administering an isotope-labeled substrate to the living system for a period of time sufficient for the isotope-labeled substrate to enter into the renal epithelial cell production pathway and thereby enter into and label at least one DNA molecule from renal epithelial cells within the renal epithelial cell production pathway in the living system; b) obtaining one or more samples from the living system, wherein the one or more samples include at least one isotope-labeled DNA molecule from renal epithelial cells; c) measuring the content, rate of incorporation and/or pattern or rate of change in content and/or pattern of isotope labeling of the DNA from renal epithelial cells; d) calculating molecular flux rates in the renal epithelial cell production pathway based on the content and/or pattern or rate of change of content and/or pattern of isotopic labeling in the DNA from renal epithelial cells to monitor or diagnose effects from exposure to nephrotoxins, recovery or response to treatment.

Diabetes Mellitus nephropathy risk and activity or response to treatment can be monitored or diagnosed by measuring or detecting renal collagen dynamics. In this method, the targeted molecule of interest is collagen from kidney. In this format, the present application is further directed to a method for monitoring or diagnosing DM nephropathy risk and activity or response to treatment in a living system, the method including: a) administering an isotope-labeled substrate to the living system for a period of time sufficient for the isotope-labeled substrate to enter into the renal collagen production pathway and thereby enter into and label at least one collagen molecule from kidney within the renal collagen production pathway in the living system; b) obtaining one or more samples from the living system, wherein the one or more samples include at least one isotope-labeled collagen molecule from kidney; c) measuring the content, rate of incorporation and/or pattern or rate of change in content and/or pattern of isotope labeling of the collagen from kidney; d) calculating molecular flux rates in the renal collagen production pathway based on the content and/or pattern or rate of change of content and/or pattern of isotopic labeling in the collagen from kidney to monitor or diagnose Diabetes Mellitus nephropathy risk and activity or response to treatment.

Pulmonary fibrosis disease activity, black lung, hypersensitivity pneumonitis, asbestosis, silicosis or chronic obstructive pulmonary disease or response to treatment thereof can be monitored or diagnosed by measuring or detecting pulmonary collagen dynamics. In this method, the targeted molecule of interest is pulmonary collagen. In this format, the present application is further directed to a method for monitoring or diagnosing pulmonary fibrosis disease activity, response to treatment; black lung, hypersensitivity pneumonitis, asbestosis, silicosis or chronic obstructive pulmonary disease in a living system, the method including: a) administering an isotope-labeled substrate to the living system for a period of time sufficient for the isotope-labeled substrate to enter into the pulmonary collagen production pathway and thereby enter into and label at least one pulmonary collagen molecule within the pulmonary collagen production pathway in the living system; b) obtaining one or more samples from the living system, wherein the one or more samples include at least one isotope-labeled pulmonary collagen molecule; c) measuring the content, rate of incorporation and/or pattern or rate of change in content and/or pattern of isotope labeling of the pulmonary collagen; d) calculating molecular flux rates in the pulmonary collagen production pathway based on the content and/or pattern or rate of change of content and/or pattern of isotopic labeling in the pulmonary collagen to monitor or diagnose pulmonary fibrosis disease activity, black lung, hypersensitivity pneumonitis, asbestosis, silicosis or chronic obstructive pulmonary disease or monitor response to treatment thereof.

Emphysema prognosis or therapeutic response to treatment thereto can be monitored or diagnosed by measuring or detecting pulmonary elastin dynamics. In this method, the targeted molecule of interest is pulmonary elastin. In this format, the present application is further directed to a method for monitoring or diagnosing Emphysema prognosis or therapeutic response in a living system, the method including: a) administering an isotope-labeled substrate to the living system for a period of time sufficient for the isotope-labeled substrate to enter into the pulmonary elastin production pathway and thereby enter into and label at least one pulmonary elastin molecule within the pulmonary elastin production pathway in the living system; b) obtaining one or more samples from the living system, wherein the one or more samples include at least one isotope-labeled pulmonary elastin molecule; c) measuring the content, rate of incorporation and/or pattern or rate of change in content and/or pattern of isotope labeling of the pulmonary elastin; d) calculating molecular flux rates in the pulmonary elastin production pathway based on the content and/or pattern or rate of change of content and/or pattern of isotopic labeling in the pulmonary elastin to monitor or diagnose emphysema prognosis or therapeutic response to treatment thereto.

Inflammatory bowel disease activity, prognosis or therapeutic response to treatment thereto can be monitored or diagnosed by measuring or detecting colonocyte DNA dynamics. In this method, the targeted molecule of interest is DNA from colonocytes isolated from stool, colon biopsy, or other colon tissue sample. In this format, the present application is further directed to a method for monitoring or diagnosing inflammatory bowel disease activity, prognosis or therapeutic response in a living system, the method including: a) administering an isotope-labeled substrate to the living system for a period of time sufficient for the isotope-labeled substrate to enter into the colonocyte DNA replication pathway and thereby enter into and label at least one DNA molecule from colonocytes within the colonocyte DNA replication pathway in the living system; b) obtaining one or more samples from the living system, wherein the one or more samples include at least one isotope-labeled DNA molecule from colonocytes; c) measuring the content, rate of incorporation and/or pattern or rate of change in content and/or pattern of isotope labeling of the DNA from colonocytes; d) calculating molecular flux rates in the colonocyte DNA replication pathway based on the content and/or pattern or rate of change of content and/or pattern of isotopic labeling in the DNA from colonocytes to monitor or diagnose inflammatory bowel disease activity, prognosis or therapeutic response to treatment thereto.

*H. pylori* activity or therapeutic response to treatment thereto, cancer risk or gastric cancer can be monitored or diagnosed by measuring or detecting gastric epithelial DNA dynamics. In this method, the targeted molecule of interest is DNA from gastric epithelial cells. In this format, the present application is further directed to a method for monitoring or diagnosing *H. pylori* activity or therapeutic response, cancer risk or gastric cancer in a living system, the method including: a) administering an isotope-labeled substrate to the living system for a period of time sufficient for the isotope-labeled substrate to enter into the gastric epithelial DNA replication pathway and thereby enter into and label at least one DNA molecule from gastric epithelial cells within the gastric epithelial DNA replication pathway in the living system; b) obtaining one or more samples from the living system, wherein the one or more samples include at least one isotope-labeled DNA molecule from gastric epithelial cells; c) measuring the content, rate of incorporation and/or pattern or rate of change in content and/or pattern of isotope labeling of the DNA from gastric epithelial cells; d) calculating molecular flux rates in the gastric epithelial DNA replication pathway based on the content and/or pattern or rate of change of content and/or pattern of isotopic labeling in the DNA from gastric epithelial cells to monitor or diagnose *H. pylori* activity or therapeutic response to treatment thereto, cancer risk or gastric cancer.

Cell mediated immunity, immune activation, AIDS or therapeutic response to treatment thereto can be monitored or diagnosed by measuring or detecting T-cell dynamics. In this method, the targeted molecule of interest is DNA from T-cells. In this format, the present application is further directed to a method for monitoring or diagnosing cell mediated immunity, immune activation, AIDS or therapeutic response in a living system, the method including: a) administering an isotope-labeled substrate to the living system for a period of time sufficient for the isotope-labeled substrate to enter into the T-cell production pathway and thereby enter into and label at least one DNA molecule from T-cells within the T-cell production pathway in the living system; b) obtaining one or more samples from the living system, wherein the one or more samples include at least one isotope-labeled DNA molecule from T-cells; c) measuring the content, rate of incorporation and/or pattern or rate of change in content and/or pattern of isotope labeling of the DNA from T-cells; d) calculating molecular flux rates in the T-cell production pathway based on the content and/or pattern or rate of change of content and/or pattern of isotopic labeling in the DNA from T-cells to monitor or diagnose cell mediated immunity, immune activation, AIDS or therapeutic response to treatment thereto.

Vaccination response can be monitored or diagnosed by measuring or detecting antigen-specific T-cell dynamics. In this method, the targeted molecule of interest is DNA from T-cells isolated based on their antigen specificity. In this format, the present application is further directed to a method for monitoring or diagnosing Y in a living system, the method including: a) administering an isotope-labeled substrate to the living system for a period of time sufficient for the isotope-labeled substrate to enter into the antigen-specific T-cell production pathway and thereby enter into and label at least one DNA molecule from T-cells isolated based on their antigen specificity within the antigen-specific T-cell production pathway in the living system; b) obtaining one or more samples from the living system, wherein the one or more samples include at least one isotope-labeled DNA molecule from T-cells isolated based on their antigen specificity; c) measuring the content, rate of incorporation and/or pattern or rate of change in content and/or pattern of isotope labeling of the DNA from T-cells isolated based on their antigen specificity; d) calculating molecular flux rates in the antigen-specific T-cell production pathway based on the content and/or pattern or rate of change of content and/or pattern of isotopic labeling in the DNA from T-cells isolated based on their antigen specificity to monitor vaccination response.

Thymopoiesis, thymic failure or therapeutic response to treatment thereto can be monitored or diagnosed by measuring or detecting naïve T-cell dynamics. In this method, the targeted molecule of interest is DNA from naïve T-cells. In this format, the present application is further directed to a method for monitoring or diagnosing thymopoiesis, thymic failure or therapeutic response in a living system, the method including: a) administering an isotope-labeled substrate to the living system for a period of time sufficient for the isotope-labeled substrate to enter into the naïve T-cell production pathway and thereby enter into and label at least one DNA molecule from naïve T-cells within the naïve T-cell production pathway in the living system; b) obtaining one or more samples from the living system, wherein the one or more samples include at least one isotope-labeled DNA molecule from naïve T-cells; c) measuring the content, rate of incorporation and/or pattern or rate of change in content and/or pattern of isotope labeling of the DNA from naïve T-cells; d) calculating molecular flux rates in the naïve T-cell production pathway based on the content and/or pattern or rate of change of content and/or pattern of isotopic labeling in the DNA from naïve T-cells to monitor or diagnose thymopoiesis, thymic failure or therapeutic response to treatment thereto.

B-cell/plasma cell activity, or therapeutic response to treatment thereto or vaccine response can be monitored or diagnosed by measuring or detecting specific antibody dynamics. In this method, the targeted molecule of interest is the antibody specific to the antigen of choice. In this format, the present application is further directed to a method for monitoring or diagnosing B-cell/plasma cell activity, compound or therapeutic response or vaccine response in a living system, the method including: a) administering an isotope-labeled substrate to the living system for a period of time sufficient for the isotope-labeled substrate to enter into the specific antibody production pathway and thereby enter into and label at least one antibody specific to the antigen of choice within the specific antibody production pathway in the living system; b) obtaining one or more samples from the living system, wherein the one or more samples include at least one isotope-labeled antibody specific to the antigen of choice; c) measuring the content, rate of incorporation and/or pattern or rate of change in content and/or pattern of isotope labeling of the antibody specific to the antigen of choice; d) calculating molecular flux rates in the specific antibody production pathway based on the content and/or pattern or rate of change of content and/or pattern of isotopic labeling in the antibody specific to the antigen of choice to monitor or diagnose B-cell/plasma cell activity, or therapeutic response or vaccine response.

Immune activation or disease activity can be monitored or diagnosed by measuring or detecting serum acute-phase reactant dynamics. In this method, the targeted molecules of interest are acute phase proteins. In this format, the present application is further directed to a method for monitoring or diagnosing immune activation or disease activity in a living system, the method including: a) administering an isotope-labeled substrate to the living system for a period of time sufficient for the isotope-labeled substrate to enter into the serum acute-phase reactant production pathway and thereby enter into and label at least one acute phase protein within the serum acute-phase reactant production pathway in the living system; b) obtaining one or more samples from the living system, wherein the one or more samples include at least one isotope-labeled acute phase protein; c) measuring the content, rate of incorporation and/or pattern or rate of change in content and/or pattern of isotope labeling of the acute phase proteins; d) calculating molecular flux rates in the serum acute-phase reactant production pathway based on the content and/or pattern or rate of change of content and/or pattern of isotopic labeling in the acute phase proteins to monitor or diagnose immune activation or disease activity.

Humoral immunity can be monitored or diagnosed by measuring or detecting plasma cell dynamics. In this method, the targeted molecule of interest is DNA from plasma cells. In this format, the present application is further directed to a method for monitoring or diagnosing humoral immunity in a living system, the method including: a) administering an isotope-labeled substrate to the living system for a period of time sufficient for the isotope-labeled substrate to enter into the plasma cell production pathway and thereby enter into and label at least one DNA molecule from plasma cells within the plasma cell production pathway in the living system; b) obtaining one or more samples from the living system, wherein the one or more samples include at least one isotope-labeled DNA molecule from plasma cells; c) measuring the content, rate of incorporation and/or pattern or rate of change in content and/or pattern of isotope labeling of the DNA from plasma cells; d) calculating molecular flux rates in the plasma cell production pathway based on the content and/or pattern or rate of change of content and/or pattern of isotopic labeling in the DNA from plasma cells to monitor or diagnose humoral immunity.

Host defense activity or therapeutic response (e.g., IL-2) can be monitored or diagnosed by measuring or detecting natural killer cell dynamics. In this method, the targeted molecule of interest is DNA from natural killer cells. In this format, the present application is further directed to a method for monitoring or diagnosing host defense activity or therapeutic response in a living system, the method including: a) administering an isotope-labeled substrate to the living system for a period of time sufficient for the isotope-labeled substrate to enter into the natural killer cell production pathway and thereby enter into and label at least one DNA molecule from natural killer cells within the natural killer cell production pathway in the living system; b) obtaining one or more samples from the living system, wherein the one or more samples include at least one isotope-labeled DNA molecule from natural killer cells; c) measuring the content, rate of incorporation and/or pattern or rate of change in content and/or pattern of isotope labeling of the DNA from natural killer cells; d) calculating molecular flux rates in the natural killer cell production pathway based on the content and/or pattern or rate of change of content and/or pattern of isotopic labeling in the DNA from natural killer cells to monitor or diagnose host defense activity or therapeutic response.

Endogenous response to exogenous compound or therapeutic or host defense can be monitored or diagnosed by measuring or detecting cytokine dynamics. In this method, the targeted molecules of interest are secreted or tissue associated cytokines. In this format, the present application is further directed to a method for monitoring or diagnosing endogenous response to exogenous compound or therapeutic or host defense in a living system, the method including: a) administering an isotope-labeled substrate to the living system for a period of time sufficient for the isotope-labeled substrate to enter into the cytokine production pathway and thereby enter into and label at least one secreted or tissue associated cytokine within the cytokine production pathway in the living system; b) obtaining one or more samples from the living system, wherein the one or more samples include at least one isotope-labeled secreted or tissue associated cytokine; c) measuring the content, rate of incorporation and/or pattern or rate of change in content and/or pattern of isotope labeling of the secreted or tissue associated cytokines; d) calculating molecular flux rates in the cytokine production pathway based on the content and/or pattern or rate of change of content and/or pattern of isotopic labeling in the secreted or tissue associated cytokines to monitor or diagnose endogenous response to exogenous compound or therapeutic or host defense.

Viral replication, disease activity, or therapeutic response or sensitivity to antiviral agents can be monitored or diagnosed by measuring or detecting viral DNA/RNA dynamics (e.g., HIV, Hepatitis B). In this method, the targeted molecule of interest is DNA or RNA from the virus of interest. In this format, the present application is further directed to a method for monitoring or diagnosing viral replication, disease activity, compound or therapeutic response or sensitivity to antiviral agents in a living system, the method including: a) administering an isotope-labeled substrate to the living system for a period of time sufficient for the isotope-labeled substrate to enter into the viral DNA/RNA synthesis pathways and thereby enter into and label at least one DNA or RNA molecule from the virus of interest within the viral DNA/RNA synthesis pathways in the living system; b) obtaining one or more samples from the living system, wherein the one or more samples include at least one isotope-labeled DNA or RNA molecule from the virus of interest; c) measuring the content, rate of incorporation and/or pattern or rate of change in content and/or pattern of isotope labeling of the DNA or RNA from the virus of interest; d) calculating molecular flux rates in the viral DNA/RNA synthesis pathways based on the content and/or pattern or rate of change of content and/or pattern of isotopic labeling in the DNA or RNA from the virus of interest to monitor or diagnose viral replication, disease activity, or monitor therapeutic response or sensitivity to antiviral agents.

Viral replication, disease activity, or therapeutic response or sensitivity to antiviral agents can be monitored or diagnosed by measuring or detecting viral protein dynamics. In this method, the targeted molecule of interest is protein from the virus of interest. In this format, the present application is further directed to a method for monitoring or diagnosing viral replication, disease activity, compound or therapeutic response or sensitivity to antiviral agents in a living system, the method including: a) administering an isotope-labeled substrate to the living system for a period of time sufficient for the isotope-labeled substrate to enter into the viral protein synthesis pathway and thereby enter into and label at least one protein from the virus of interest within the viral protein synthesis pathway in the living system; b) obtaining one or more samples from the living system, wherein the one or more samples include at least one isotope-labeled protein from the virus of interest; c) measuring the content, rate of incorporation and/or pattern or rate of change in content and/or pattern of isotope labeling of the protein from the virus of interest; d) calculating molecular flux rates in the viral protein synthesis pathway based on the content and/or pattern or rate of change of content and/or pattern of isotopic labeling in the protein from the virus of interest to monitor or diagnose viral replication, disease activity, or monitor therapeutic response or sensitivity to antiviral agents.

Bacterial cell division, disease activity or response to antibiotics can be monitored or diagnosed by measuring or detecting bacterial dynamics. In this method, the targeted molecule of interest is DNA or other molecule (e.g., protein, carbohydrate, lipid) from the bacteria of interest. In this format, the present application is further directed to a method for monitoring or diagnosing bacterial cell division, disease activity or response to antibiotics in a living system, the method including: a) administering an isotope-labeled substrate to the living system for a period of time sufficient for the isotope-labeled substrate to enter into the bacterial replication pathway and thereby enter into and label at least one DNA or other molecule from the bacteria of interest within the bacterial replication pathway in the living system; b) obtaining one or more samples from the living system, wherein the one or more samples include at least one isotope-labeled DNA or other molecule from the bacteria of interest; c) measuring the content, rate of incorporation and/or pattern or rate of change in content and/or pattern of isotope labeling of the DNA or other molecule from the bacteria of interest; d) calculating molecular flux rates in the bacterial replication pathway based on the content and/or pattern or rate of change of content and/or pattern of isotopic labeling in the DNA or other molecule from the bacteria of interest to monitor or diagnose bacterial cell division, disease activity or response to antibiotics.

Parasite division and growth or therapeutic response (e.g., malaria, schistosomiasis) can be monitored or diagnosed by measuring or detecting parasite dynamics. In this method, the targeted molecule of interest is DNA or other molecule (e.g., protein, carbohydrate, lipid) from the parasite of interest. In this format, the present application is further directed to a method for monitoring or diagnosing parasite division and growth or therapeutic response in a living system, the method including: a) administering an isotope-labeled substrate to the living system for a period of time sufficient for the isotope-labeled substrate to enter into the parasite replication pathway and thereby enter into and label at least one DNA or other molecule from the parasite of interest within the parasite replication pathway in the living system; b) obtaining one or more samples from the living system, wherein the one or more samples include at least one isotope-labeled DNA or other molecule from the parasite of interest; c) measuring the content, rate of incorporation and/or pattern or rate of change in content and/or pattern of isotope labeling of the DNA or other molecule from the parasite of interest; d) calculating molecular flux rates in the parasite replication pathway based on the content and/or pattern or rate of change of content and/or pattern of isotopic labeling in the DNA or other molecule from the parasite of interest to monitor or diagnose parasite division and growth or therapeutic response.

Infectious activity or therapeutic response to treatment thereof can be monitored or diagnosed by measuring or detecting intestinal microbial dynamics. In this method, the targeted molecule of interest is DNA or other molecule (e.g., protein, carbohydrate, lipid) from intestinal bacteria. In this format, the present application is further directed to a method for monitoring or diagnosing infectious activity or therapeutic response in a living system, the method including: a) administering an isotope-labeled substrate to the living system for a period of time sufficient for the isotope-labeled substrate to enter into the intestinal microbial replication pathway and thereby enter into and label at least one DNA or other molecule from intestinal bacteria within the intestinal microbial replication pathway in the living system; b) obtaining one or more samples from the living system, wherein the one or more samples include at least one isotope-labeled DNA or other molecule from intestinal bacteria; c) measuring the content, rate of incorporation and/or pattern or rate of change in content and/or pattern of isotope labeling of the DNA or other molecule from intestinal bacteria; d) calculating molecular flux rates in the intestinal microbial replication pathway based on the content and/or pattern or rate of change of content and/or pattern of isotopic labeling in the DNA or other molecule from intestinal bacteria to monitor or diagnose infectious activity or therapeutic response to treatment thereof.

Abscess, empyema or therapeutic response to treatment thereof can be monitored or diagnosed by measuring or detecting bacterial dynamics in a closed space. In this method, the targeted molecule of interest is bacterial DNA or other molecule (e.g., protein, carbohydrate, lipid) from tissue or abscess or fluid sample. In this format, the present application is further directed to a method for monitoring or diagnosing abscess, empyema or therapeutic response in a living system, the method including: a) administering an isotope-labeled substrate to the living system for a period of time sufficient for the isotope-labeled substrate to enter into the bacterial replication pathway and thereby enter into and label at least one bacterial DNA or other molecule from tissue or abscess or fluid sample within the bacterial replication pathway in the living system; b) obtaining one or more samples from the living system, wherein the one or more samples include at least one isotope-labeled bacterial DNA or other molecule from tissue or abscess or fluid sample; c) measuring the content, rate of incorporation and/or pattern or rate of change in content and/or pattern of isotope labeling of the bacterial DNA or other molecule from tissue or abscess or fluid sample; d) calculating molecular flux rates in the bacterial replication pathway based on the content and/or pattern or rate of change of content and/or pattern of isotopic labeling in the bacterial DNA or other molecule from tissue or abscess or fluid sample to monitor or diagnose abscess, empyema or therapeutic response to treatment thereto.

Endocarditis or therapeutic response to treatment thereto can be monitored or diagnosed by measuring or detecting endovascular bacterial dynamics. In this method, the targeted molecule of interest is DNA or other molecule (e.g., protein, carbohydrate, lipid) from endovascular bacteria. In this format, the present application is further directed to a method for monitoring or diagnosing endocarditis or therapeutic response to treatment thereto in a living system, the method including: a) administering an isotope-labeled substrate to the living system for a period of time sufficient for the isotope-labeled substrate to enter into the endovascular bacterial replication pathway and thereby enter into and label at least one DNA or other molecule from endovascular bacteria within the endovascular bacterial replication pathway in the living system; b) obtaining one or more samples from the living system, wherein the one or more samples include at least one isotope-labeled DNA or other molecule from endovascular bacteria; c) measuring the content, rate of incorporation and/or pattern or rate of change in content and/or pattern of isotope labeling of the DNA or other molecule from endovascular bacteria; d) calculating molecular flux rates in the endovascular bacterial replication pathway based on the content and/or pattern or rate of change of content and/or pattern of isotopic labeling in the DNA or other molecule from endovascular bacteria to monitor or diagnose endocarditis or therapeutic response to treatment thereto.

Stem cell response (transplant, compound or therapeutic) or status of cytopenias can be monitored or diagnosed by measuring or detecting bone marrow precursor/marrow cell dynamics. In this method, the targeted molecule of interest is DNA from bone marrow precursor/marrow cells. In this format, the present application is further directed to a method for monitoring or diagnosing stem cell response or status of cytopenias in a living system, the method including: a) administering an isotope-labeled substrate to the living system for a period of time sufficient for the isotope-labeled substrate to enter into the bone marrow precursor/marrow cell production pathway and thereby enter into and label at least one DNA molecule from bone marrow precursor/marrow cells within the bone marrow precursor/marrow cell production pathway in the living system; b) obtaining one or more samples from the living system, wherein the one or more samples include at least one isotope-labeled DNA molecule from bone marrow precursor/marrow cells; c) measuring the content, rate of incorporation and/or pattern or rate of change in content and/or pattern of isotope labeling of the DNA from bone marrow precursor/marrow cells; d) calculating molecular flux rates in the bone marrow precursor/marrow cell production pathway based on the content and/or pattern or rate of change of content and/or pattern of isotopic labeling in the DNA from bone marrow precursor/marrow cells to monitor or diagnose stem cell response or status of cytopenias.

Hemolysis, anemia response (reticulocytosis), hemoglobinopathies or treatment thereof can be monitored or diagnosed by measuring or detecting hemoglobin dynamics in red blood cells. In this method, the targeted molecule of interest is hemoglobin. In this format, the present application is further directed to a method for monitoring or diagnosing hemolysis, anemia response (reticulocytosis) or hemoglobinopathies in a living system, the method including: a) administering an isotope-labeled substrate to the living system for a period of time sufficient for the isotope-labeled substrate to enter into the hemoglobin synthesis pathway and thereby enter into and label at least one hemoglobin molecule within the hemoglobin synthesis pathway in the living system; b) obtaining one or more samples from the living system, wherein the one or more samples include at least one isotope-labeled hemoglobin molecule; c) measuring the content, rate of incorporation and/or pattern or rate of change in content and/or pattern of isotope labeling of the hemoglobin; d) calculating molecular flux rates in the hemoglobin synthesis pathway based on the content and/or pattern or rate of change of content and/or pattern of isotopic labeling in the hemoglobin to monitor or diagnose hemolysis, anemia response (reticulocytosis), hemoglobinopathies or treatment thereof.

Thrombocytopenia, thrombocytosis or treatment thereof can be monitored or diagnosed by measuring or detecting platelet phospholipid dynamics. In this method, the targeted molecule of interest is one or more phospholipids or DNA from platelets or platelet precursors. In this format, the present application is further directed to a method for monitoring or diagnosing thrombocytopenia or thrombocytosis in a living system, the method including: a) administering an isotope-labeled substrate to the living system for a period of time sufficient for the isotope-labeled substrate to enter into the platelet phospholipid synthesis pathway and thereby enter into and label at least one isotope-labeled phospholipid or DNA molecule from platelets or platelet precursors within the platelet phospholipid synthesis pathway in the living system; b) obtaining one or more samples from the living system, wherein the one or more samples include at least one isotope-labeled phospholipid or DNA molecule from platelets or platelet precursors; c) measuring the content, rate of incorporation and/or pattern or rate of change in content and/or pattern of isotope labeling of the phospholipids or DNA from platelets or platelet precursors; d) calculating molecular flux rates in the platelet phospholipid synthesis pathway based on the content and/or pattern or rate of change of content and/or pattern of isotopic labeling in the phospholipids or DNA from platelets or platelet precursors to monitor or diagnose thrombocytopenia, thrombocytosis or treatment thereof.

Anemia, hemolysis or therapeutic response to treatment thereto can be monitored or diagnosed by measuring or detecting erythrocyte membrane dynamics. In this method, the targeted molecule of interest is phospholipid from erythrocytes. In this format, the present application is further directed to a method for monitoring or diagnosing anemia, hemolysis or therapeutic response to treatment thereto in a living system, the method including: a) administering an isotope-labeled substrate to the living system for a period of time sufficient for the isotope-labeled substrate to enter into the erythrocyte membrane production pathway and thereby enter into and label at least one phospholipid from erythrocytes within the erythrocyte membrane production pathway in the living system; b) obtaining one or more samples from the living system, wherein the one or more samples include at least one isotope-labeled phospholipid from erythrocytes; c) measuring the content, rate of incorporation and/or pattern or rate of change in content and/or pattern of isotope labeling of the phospholipid from erythrocytes; d) calculating molecular flux rates in the erythrocyte membrane production pathway based on the content and/or pattern or rate of change of content and/or pattern of isotopic labeling in the phospholipid from erythrocytes to monitor or diagnose anemia, hemolysis or therapeutic response to treatment thereto.

Spermatogenesis, male infertility, or therapeutic response to treatment thereto or endocrine disruptors can be monitored or diagnosed by measuring or detecting spermatocyte dynamics. In this method, the targeted molecule of interest is DNA from spermatocytes. In this format, the present application is further directed to a method for monitoring or diagnosing spermatogenesis, male infertility, compound or therapeutic response to treatment thereto or endocrine disruptors in a living system, the method including: a) administering an isotope-labeled substrate to the living system for a period of time sufficient for the isotope-labeled substrate to enter into the spermatogenesis pathway and thereby enter into and label at least one DNA molecule from spermatocytes within the spermatogenesis pathway in the living system; b) obtaining one or more samples from the living system, wherein the one or more samples include at least one isotope-labeled DNA molecule from spermatocytes; c) measuring the content, rate of incorporation and/or pattern or rate of change in content and/or pattern of isotope labeling of the DNA from spermatocytes; d) calculating molecular flux rates in the spermatogenesis pathway based on the content and/or pattern or rate of change of content and/or pattern of isotopic labeling in the DNA from spermatocytes to monitor or diagnose spermatogenesis, male infertility, or therapeutic response to treatment thereto or endocrine disruptors.

Developmental biology and disorders thereof can be monitored or diagnosed by measuring or detecting the timing of embryonic protein and lipid dynamics. In this method, the targeted molecules of interest are embryonic proteins, lipids, or DNA. In this format, the present application is further directed to a method for monitoring or diagnosing developmental biology and disorders thereof in a living system, the method including: a) administering an isotope-labeled substrate to the living system for a period of time sufficient for the isotope-labeled substrate to enter into the embryonic protein and lipid production pathways and thereby enter into and label at least one embryonic protein, lipid, or DNA molecule within the embryonic protein and lipid production pathways in the living system; b) obtaining one or more samples from the living system, wherein the one or more samples include at least one isotope-labeled embryonic protein, lipid, or DNA molecule; c) measuring the content, rate of incorporation and/or pattern or rate of change in content and/or pattern of isotope labeling of the embryonic proteins, lipids, or DNA; d) calculating molecular flux rates in the embryonic protein and lipid production pathways based on the content and/or pattern or rate of change of content and/or pattern of isotopic labeling in the embryonic proteins, lipids, or DNA to monitor or diagnose developmental biology and disorders thereof.

Genetic instability or cancer risk can be monitored or diagnosed by measuring or detecting genomic DNA dynamics. In this method, the targeted molecule of interest is genomic DNA (from at risk tissue if appropriate). In this format, the present application is further directed to a method for monitoring or diagnosing genetic instability or cancer risk in a living system, the method including: a) administering an isotope-labeled substrate to the living system for a period of time sufficient for the isotope-labeled substrate to enter into the genomic DNA replication pathway and thereby enter into and label at least one genomic DNA molecule within the genomic DNA replication pathway in the living system; b) obtaining one or more samples from the living system, wherein the one or more samples include at least one isotope-labeled genomic DNA molecule; c) measuring the content, rate of incorporation and/or pattern or rate of change in content and/or pattern of isotope labeling of the genomic DNA; d) calculating molecular flux rates in the genomic DNA replication pathway based on the content and/or pattern or rate of change of content and/or pattern of isotopic labeling in the genomic DNA to monitor or diagnose genetic instability or cancer risk.

DETAILED DESCRIPTION OF THE INVENTION

I. Introduction

Figure 1:
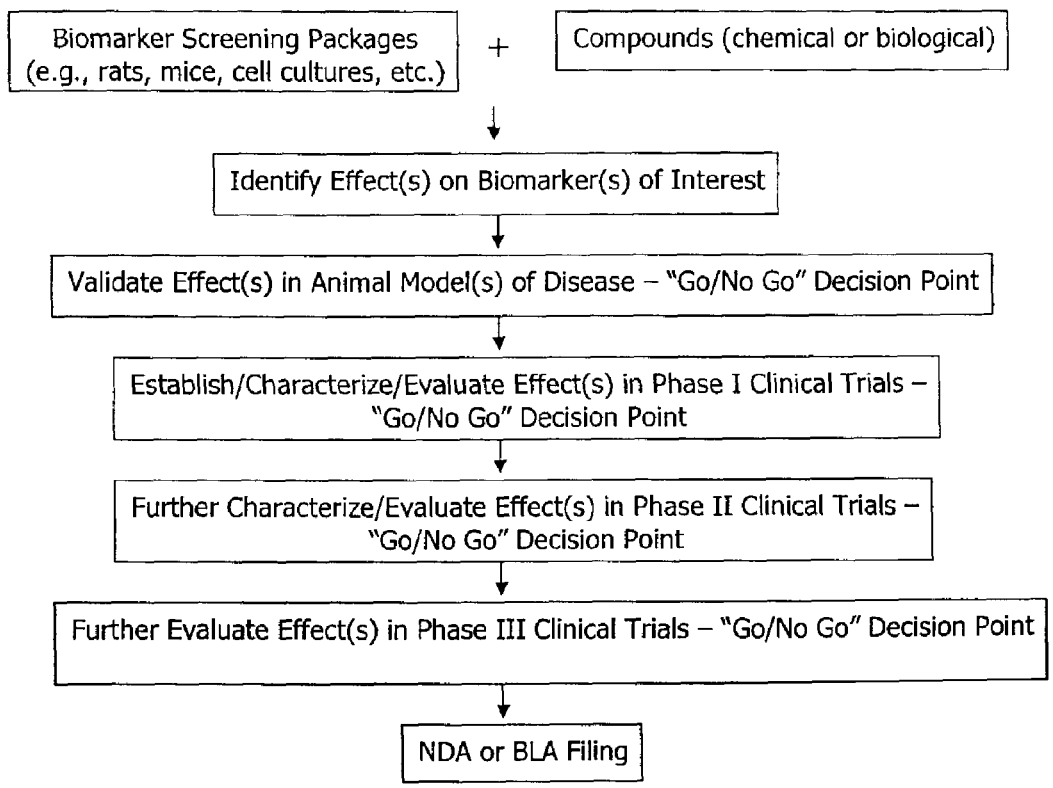
FIG. 1 is a schematic diagram showing the drug discovery, development, and approval (DDA) process using effects on biomarkers (i.e., data collected by the methods of the present invention) as a means for deciding to continue or cease efforts.

In biochemical terms, the processes that underlie most diseases can best be described as molecular fluxes through complex biochemical pathways or networks. Biochemical pathways include linked series of biochemical, physical or spatial transformations typically catalyzed by proteins and occurring in vivo in the context of highly complex networks. The proteins that catalyze the flow of molecules through pathways are coded by genes. Contemporary drug discovery, development and approval (DDA) has therefore largely consisted of strategies for identifying and modulating individual proteins or genes that comprise the elemental components of the pathways that are believed to be critically involved in a disease. Modern drug research tools include gene expression profiling, proteomics, high throughput screening of enzyme activities, and combinatorial chemistry libraries for screening against specific protein targets. Such genes and proteins are termed potential therapeutic targets in contemporary drug research and compounds that may have activity against a target are termed drug leads or candidates.

The true functional targets for therapeutic interventions are not proteins or genes in isolation, however, but are molecular flux rates through fully assembled pathways in the intact biochemical pathway or network. In the final analysis, it is only the flow of molecules through a pathway in the living system, rather than the activity of any catalytic protein or encoding gene in isolation, that has functional consequences for a disease or, indeed, for any organismal phenotype. Moreover, the key regulated parameter in all biochemical systems is flux rates, whether one is discussing enzymatic catalysis or control of complex pathways (see Kacser, H. & Burns, J. A. (1973). The control of flux. In *Rate Control of Biological Processes. Symposium of the Society for Experimental Biology Vol* 27(ed. D. D. Davies), pp. 65-104. Cambridge University Press, Cambridge). The kinetic biomarkers for measuring molecular flux rates through biochemical pathways and networks in vivo in fully assembled living systems thereby differ from currently available non-kinetic, measurement tools used in DDA and in medical diagnosis.

A new measurable target or biomarker of compound action that has broad applications in pharmaceutical research and development, in clinical medicine, and public health is disclosed herein. In the case of DDA, instead of measuring the concentration, structure, state, activity, or composition of proteins, genes, metabolites or other components of biological systems as targets of drug action, as is currently taught for DDA and medical diagnosis, the Applicant has discovered that molecular flux rates through targeted critical metabolic pathways in vivo, measured by introduction of isotope labels, such as stable isotope labels, into a living system, are informative, higher-level targets of drug action and functional measures of disease activity with powerful utility in DDA and clinical medicine.

The methods described herein involve the following steps: identifying a biochemical pathway flux rate that is a potentially critical target for action of a drug in a disease or condition of interest; identifying a target molecule in the metabolic pathway of interest whose kinetics (synthesis, breakdown, input, removal, or turnover) can be used to represent molecular flux rates through the critical metabolic pathway of interest; introducing an isotopic label, such as a non-radioactive (stable) isotope label, into the living system of interest that is designed to result in the formation in vivo of an isotopically perturbed population of the target molecule not otherwise present in nature; isolating the target molecule of interest and measuring its isotopic content and/or pattern, or rate of change of isotopic content and/or pattern, for example by use of mass spectrometry; determining the kinetics of the target molecule of interest, based on its perturbed isotopic content and/or pattern or rate of change of isotopic content and/or pattern and, thereby, calculating molecular flux rates through the targeted metabolic pathway of interest; testing and determining the effect of a compound (e.g., chemical entity (new or old), a drug candidate, a drug lead, an already-approved drug, a biological factor), or combinations or mixtures thereof, on molecular flux rates through the metabolic pathway of interest in model systems or humans with or without the disease of interest. In this manner, the pathway flux rate measurement can be used as a biomarker of compound action in the disease of interest, and the activity of compounds or combinations thereof on molecular flux rates through the targeted metabolic pathway in the living system of interest can be used for identifying potential therapeutic or toxic actions of a compound or combinations thereof.

Procedures for validating the use of molecular flux rates through a pathway (measured by the stable isotope labeling/isotopic measurement method disclosed herein) as a target of compound action for specific diseases of interest, are also disclosed. Also disclosed is the capability of applying the same or closely related stable isotope labeling procedures described herein at all levels of the DDA chain, from cells to human subjects, and from pre-clinical studies to phase IV clinical trials and subsequent routine medical care. The application described herein provides a large number of advantages over currently available non-kinetic biochemical measurement tools for DDA and medical care.

In another embodiment, the application includes the following steps: identifying a biochemical pathway flux rate that is a potentially critical target for action of a compound in a disease or condition of public health interest; identifying a target molecule in the metabolic pathway whose kinetics (synthesis, breakdown, input, removal, or turnover) can be used to represent molecular flux rates through the metabolic pathway; introducing an isotopic label, such as a non-radioactive (stable) isotope label, into the living system of interest that is designed to result in the formation in vivo of an isotopically perturbed population of the target molecule not otherwise present in nature; isolating the target molecule of interest and measuring its isotopic content and/or pattern, or rate of change of isotopic content and/or pattern, for example by use of mass spectrometry; determining the kinetics of the target molecule of interest, based on its perturbed isotopic content and/or pattern or rate of change of isotopic content and/or pattern and, thereby, calculating molecular flux rates through the targeted metabolic pathway; testing and determining the effect of a compound such as a chemical entity (new or old), an industrial chemical, food additive, environmental pollutant, cosmetic, biological factor, or combinations or mixtures thereof, on molecular flux rates through the metabolic pathway in model systems such as cultured cell systems and animals. In this manner, the pathway flux rate measurement can be used as a biomarker of chemical or biological action in the public health disease of interest, and the activity of industrial chemicals, food additives, cosmetics, environmental pollutants, or biological factors, or combinations thereof on molecular flux rates through the targeted metabolic pathway in the living system of interest can be used for identifying potential toxic actions of the industrial chemicals, cosmetics, food additives, environmental pollutants, biological factors, or combinations thereof.

Disclosed herein are methods for testing the effects of compounds such as chemical entities (new or old), drug candidates, drug leads, already-approved drugs, biological factors, or combinations or mixtures thereof on molecular flux rates through metabolic pathways in living systems as biomarkers for DDA and medical diagnosis. Also disclosed are methods for testing the effects of compounds such as chemical entities (new or old), industrial chemicals, food additives, cosmetics, and environmental pollutants on molecular flux rates through metabolic pathways in living systems as biomarkers of chemically-induced or biologically-induced disease or injury (i.e., occupational or industrial toxicological, food toxicological, dermatotoxicological, and environmental toxicological applications).

II. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1146-E1162, 1999). Furthermore, procedures employing commercially available assay kits and reagents will typically be used according to manufacturer-defined protocols unless otherwise noted.

III. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, Mass isotopomer distribution analysis at eight years: theoretical, analytic and experimental considerations by Hellerstein and Neese (Am J Physiol 276 (Endocrinol Metab. 39) E1146-E1162, 1999). As appropriate, procedures involving the use of commercially available kits and reagents are generally carried out in accordance with manufacturer defined protocols and/or parameters unless otherwise noted.

"Molecular flux rates" refers to the dynamic flow or rate of synthesis and/or breakdown of molecules within a cell, tissue, or organism. "Molecular flux rates" also refers to a molecule's input into or removal from a pool of molecules, and is therefore synonymous with the flow into and out of said pool of molecules.

"Metabolic pathway" refers to any linked series of two or more biochemical steps in a living system (i.e., a biochemical process), the net result of which is a chemical, spatial or physical transformation of a molecule or molecules. Metabolic pathways are defined by the direction and flow of molecules through the biochemical steps that comprise the pathway. Molecules within metabolic pathways can be of any biochemical class, e.g., including but not limited to lipids, proteins, amino acids, carbohydrates, nucleic acids, polynucleotides, porphyrins, glycosaminoglycans, glycolipids, intermediary metabolites, inorganic minerals, ions, etc.

"Flux rate through a metabolic pathway" refers to the rate of molecular transformations through a defined metabolic pathway. The unit of flux rates through pathways is chemical mass per time (e.g., moles per minute, grams per hour). Flux rate through a pathway optimally refers to the transformation rate from a clearly defined biochemical starting point to a clearly defined biochemical end-point, including all the stages in between in the defined metabolic pathway of interest.

"Isotopes" refer to atoms with the same number of protons and hence of the same element but with different numbers of neutrons (e.g., $^1H$ vs. $^2H$ or D).

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has an unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Isotope-labeled water" includes water labeled with one or more specific heavy isotopes of either hydrogen or oxygen. Specific examples of isotope-labeled water include $^2H_2O$, $^3H_2O$, and $H_2^{18}O$.

"Chemical entity" includes any chemical, whether new or known, that is administered to a living system for the purpose of screening it for biological or biochemical activity toward the goal of discovering potential therapeutic agents (drugs or drug candidates or drug leads) or uncovering toxic effects (industrial chemicals, pesticides, herbicides, food additives, cosmetics, and the like).

"Drug leads" or "drug candidates" are herein defined as chemical entities or biological molecules that are being evaluated as potential therapeutic agents (drugs). "Drug agents" or "agents" are used interchangeably herein and describe any composition of matter (e.g., chemical entity or biological factor) that is administered, approved or under testing as potential therapeutic agent or is a known therapeutic agent.

"Known drugs" or "known drug agents" or "already-approved drugs" refers to compounds (i.e., chemical entities or biological factors) that have been approved for therapeutic use as drugs in human beings or animals in the United States or other jurisdictions. In the context of the present invention, the term "already-approved drug" means a drug having approval for an indication distinct from an indication being tested for by use of the methods disclosed herein. Using psoriasis and fluoxetine as an example, the methods of the present invention allow one to test fluoxetine, a drug approved by the FDA (and other jurisdictions) for the treatment of depression, for effects on biomarkers of psoriasis (e.g., keratinocyte proliferation or keratin synthesis); treating psoriasis with fluoxetine is an indication not approved by FDA or other jurisdictions. In this manner, one can find new uses (in this example, anti-psoriatic effects) for an already-approved drug (in this example, fluoxetine).

"Biological factor" refers to a compound or compounds made by living organisms having biological or physiological activities (e.g., preventive, therapeutic and/or toxic effects). Examples of biological factors include, but are not limited to, vaccines, polyclonal or monoclonal antibodies, recombinant proteins, isolated proteins, soluble receptors, gene therapy products, environmental toxins, and the like. As used herein, the term "biologics" is synonymous with "biological factor."

"Compound" means, in the context of the present application, any new chemical entity, chemical entity, drug lead, drug candidate, drug, drug agent, agent, known drug, known drug agent, already-approved drug, biologic, or biological factor, food additives, industrial chemicals, environmental pollutants and the like. The term is meant to encompass all chemical and biological molecules.

"Food additive" includes, but is not limited to, organoleptic agents (i.e., those agents conferring flavor, texture, aroma, and color), preservatives such as nitrosamines, nitrosamides, N-nitroso substances and the like, congealants, emulsifiers, dispersants, fumigants, humectants, oxidizing and reducing agents, propellants, sequestrants, solvents, surface-acting agents, surface-finishing agents, synergists, pesticides, chlorinated organic compounds, any chemical ingested by a food animal or taken up by a food plant, and any chemical leaching into (or otherwise finding its way into) food or drink from packaging material. The term is meant to encompass those chemicals which are added into food or drink products at some step in the manufacturing and packaging process, or find their way into food by ingestion by food animals or uptake by food plants, or through microbial byproducts such as endotoxins and exotoxins (pre-formed toxins such as botulinin toxin or aflatoxin), or through the cooking process (such as heterocyclic amines, e.g., 2-amino-3-methyllimidazo[4,5-f]quinolone), or by leaching or some other process from packaging material during manufacturing, packaging, storage, and handling activities.

"Industrial chemical" includes, but is not limited to, volatile organic compounds, semi-volatile organic compounds, cleaners, solvents, thinners, mixers, metallic compounds, metals, organometals, metalloids, substituted and non-substituted aliphatic and acyclic hydrocarbons such as hexane, substituted and non-substituted aromatic hydrocarbons such as benzene and styrene, halogenated hydrocarbons such as vinyl chloride, aminoderivatives and nitroderivatives such as nitrobenzene, glycols and derivatives such as propylene glycol, ketones such as cyclohexanone, aldehydes such as furfural, amides and anhydrides such as acrylamide, phenols, cyanides and nitriles, isocyanates, and pesticides, herbicides, rodenticides, and fungicides.

"Environmental pollutant" includes any chemical not found in nature or chemicals that are found in nature but artificially concentrated to levels exceeding those found in nature (at least found in accessible media in nature). So, for example, environmental pollutants can include any of the non-natural chemicals identified as an occupational or industrial chemical yet found in a non-occupational or industrial setting such as a park, school, or playground. Alternatively, environmental pollutants may comprise naturally occurring chemicals such as lead but at levels exceeding background (for example, lead found in the soil along highways deposited by the exhaust from the burning of leaded gasoline in automobiles). Environmental pollutants may be from a point source such as a factory smokestack or industrial liquid discharge into surface or groundwater, or from a non-point source such as the exhaust from cars traveling along a highway, the diesel exhaust (and all that it contains) from buses traveling along city streets, or pesticides deposited in soil from airborne dust originating in farmlands. As used herein, "environmental contaminant" is synonymous with "environmental pollutant."

"Living system" includes, but is not limited to, cells, cell lines, animal models of disease, guinea pigs, rabbits, dogs, cats, other pet animals, mice, rats, non-human primates, and humans.

A "biological sample" encompasses any sample obtained from a cell, tissue, or organism. The definition encompasses blood and other liquid samples of biological origin, that are accessible from an organism through sampling by invasive means (e.g., surgery, open biopsy, endoscopic biopsy, and other procedures involving non-negligible risk) or by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or organic metabolites. The term "biological sample" also encompasses a clinical sample such as serum, plasma, other biological fluid, or tissue samples, and also includes cells in culture, cell supernatants and cell lysates.

"Biological fluid" refers, but is not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

"Exact mass" refers to mass calculated by summing the exact masses of all the isotopes in the formula of a molecule (e.g., 32.04847 for $CH_3NHD$).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3{}^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3{}^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer envelope" refers to the set of mass isotopomers comprising the family associated with each molecule or ion fragment monitored.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonomously with the term "mass isotopomer pattern."

"Monoisotopic mass" refers to the exact mass of the molecular species that contains all $^1H$, $^{12}C$, $^{14}N$, $^{16}O$, $^{32}S$, etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as $m_0$ and the masses of other mass isotopomers are identified by their mass differences from $m_0$ ($m_1$, $m_2$, etc.).

By "derivatize", "derivatizing", "derivatization", "hydrolysis and derivatization", in the context of the current invention, is meant the process of preparing samples for GC/MS analysis. This preparation can be performed on isolated biomolecules, cells, complex samples, or other samples or molecules and the specific process varies depending on the pathway being analyzed. Such preparation involves multiple procedures, each with many steps, and usually ends with a "derivatization" procedure. As such, the extended process of sample preparation may occasionally be referred to by these terms, as it is the final procedure. In context, the term may also refer only to this final procedure.

"Isotopically perturbed" refers to the state of an element or molecule that results from the explicit incorporation of an element or molecule with a distribution of isotopes that differs from the distribution that is most commonly found in nature, whether a naturally less abundant isotope is present in excess (enriched) or in deficit (depleted).

By "molecule of interest" is meant any molecule (polymer and/or monomer), including but not limited to, amino acids, carbohydrates, fatty acids, peptides, sugars, lipids, nucleic acids, polynucleotides, glycosaminoglycans, polypeptides, or proteins that are present within a metabolic pathway within a living system. In the context of the present invention, a "molecule of interest" may be a "biomarker" of disease and its flux rate, relative to the flux rate of an unexposed or otherwise healthy subject (i.e., control subject), may represent clinically non-observant or subtle pathophysiological occurrences in a subject of interest that may be predictive of future disease or injury in the subject of interest. In this manner, comparing the flux rates of one or more biomarkers of interest in a subject of interest with the flux rates of one or more biomarkers of interest in a control subject, will find use in diagnosing the subject of interest with, or evaluating or quantifying the subject of interest's risk in acquiring, a disease of interest. Moreover, such information will find use in establishing a prognosis for a subject of interest having a disease of interest, monitoring the progression of a disease of interest in a subject of interest, or evaluating the therapeutic efficacy of a treatment regimen in a subject of interest having a disease of interest.

By "subject of interest" is meant a human or animal having a disease of interest or having some level of risk in acquiring a disease of interest.

By "control subject" is meant a human or animal not having the disease of interest or not having some level of risk in acquiring the disease of interest.

"Monomer" refers to a chemical unit that combines during the synthesis of a polymer and which is present two or more times in the polymer.

"Polymer" refers to a molecule synthesized from and containing two or more repeats of a monomer. A "biopolymer" is a polymer synthesized by or in a living system or otherwise associated with a living system.

"Protein" refers to a polymer of amino acids. As used herein, a "protein" may refer to long amino acid polymers as well as short polymers such as peptides.

By "amino acid" is meant any amphoteric organic acid containing the amino group (i.e., $NH_2$). The term encompasses the twenty common (often referred in the art as "standard" or sometimes as "naturally occurring") amino acids as well as the less common (often referred in the art as "nonstandard") amino acids. Examples of the twenty common amino acids include the alpha-amino acids (or α-amino acids), which have the amino group in the alpha position, and generally have the formula RCH—($NH_2$)—COOH. The α-amino acids are the monomeric building blocks of proteins and can be obtained from proteins through hydrolysis. Examples of nonstandard amino acids include, but are not limited to γ-aminobutyric acid, dopamine, histamine, thyroxine, citrulline, ornithine, homocysteine, and S-adenosylmethionine.

"Lipid" refers to any of a heterogeneous group of fats and fatlike substances characterized by being water insoluble and being extractable by nonpolar (or organic) solvents such as alcohol, ether, chloroform, benzene, etc. All contain as a major constituent aliphatic hydrocarbons. The lipids, which are easily stored in the body, serve as a source of fuel, are an important constituent of cell structure, and serve other biological functions. Lipids include, but are not limited to fatty acids, neutral fats (e.g., triacylglycerols), waxes and steroids (e.g., cholesterol). Complex lipids comprise the glycolipids, lipoproteins and phospholipids.

"Fatty acids" are carboxylic acids with long-chain hydrocarbon side groups. They are comprised of organic, monobasic acids, which are derived from hydrocarbons by the equivalent of oxidation of a methyl group to an alcohol, aldehyde, and then acid. Fatty acids can be either saturated or unsaturated.

By "DNA" is meant a polymeric form of deoxyribonucleotides (adenine, guanine, thymine, or cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. The term captures molecules that include the four bases adenine, guanine, thymine, or cytosine, as well as molecules that include base analogs which are known in the art.

A "nucleic acid" sequence refers to a DNA or RNA sequence. The term captures sequences that include any of the known base analogues of DNA and RNA such as, but not limited to 4-acetylcytosine, 8-hydroxy-$N^6$-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethyl-aminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-$N^6$-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

By "carbohydrate" is meant an aldehyde or ketone derivative of a straight-chain polyhydroxyl alcohol containing at least three carbon atoms. The polyhydroxyl alcohol is primarily (but not exclusively) of the pentahydric and hexahydric alcohol varieties. Carbohydrates are so named because the hydrogen and oxygen are usually in the proportion to form water with the general formula $C_n(H_2O)_n$. The most important carbohydrates are the starches, sugars, celluloses and gums. They are classified into mono, di, tri, poly and heterosaccharides. The smallest are monosaccharides like glucose whereas polysaccharides such as starch, cellulose or glycogen can be large and indeterminate in length.

By "sugar" is meant the common name for any sweet, crystalline, simple carbohydrate that is an aldehyde or ketone derivative of a polyhydric alcohol. Sugars are mainly disaccharides like sucrose and monosaccharides like fructose or glucose. The term encompasses monosaccharides, disaccharides, trisaccharides, heterosaccharides, or polysaccharides (which are comprised of monosaccharide residues). Monosaccharides include glucose (both D-glucose and L-glucose), mannose, fructose galactose and sugar derivatives including, but not limited to N-acetylmuramic acid, N-acetylneuraminic acid and other sialic acids, iV-acetylmannosamine, glucuronic acid, glucosamine, etc. Polysaccharides include disaccharides such as sucrose, maltose and lactose and longer chain sugar molecules such as starch, glycogen, cellulose, chitin, etc. By the term "oligosaccharide" is meant a molecule comprised of a few covalently linked monosaccharide monomers.

By "glycosaminoglycan" is meant a polymer comprised of a network of long, unbranched chains made up of repeating units of disaccharides that contain amino group sugars, at least one of which has a negatively charged side group (carboxylate or sulfate). Examples of glycosaminoglycans include, but are not limited to hyaluronate (D-glucuronic acid-N-acetyl-D-glucosamine: MW up to 10 million), chondroitin sulfate (D-glucuronic acid-IV-acetyl-D-galactosamine-4 or 6-sulfate), dermatan sulfate (D-glucuronic acid or L-iduronic acid-IV-acetyl-D-galactosamine), keratan sulfate (D-galactose-N-acetyl-D-glucosamine sulfate), and heparan sulfate (D-glucuronic acid or L-iduronic acid-N-acetyl-D-glucosamine). "Mucopolysaccharide" is a term that is synonymous with glycosaminoglycan.

By "glycoprotein" is meant a protein or polypeptide that is covalently linked to one or more carbohydrate molecules. Glycoproteins include proteoglycans and many, if not most, of the important integral membrane proteins protruding through the exterior leaflet into the extracellular space, as well as many, if not most, of the secreted proteins.

By "proteoglycan" is meant any of a diverse group of macromolecules comprising proteins and glycosaminoglycans. "Mucoprotein" is a term that is synonymous with proteoglycan.

"Isotope labeled substrate" includes any isotope-labeled precursor molecule that is able to be incorporated into a molecule of interest in a living system. Examples of isotope labeled substrates include, but are not limited to, $^2H_2O$, $^3H_2O$, $^2H$-glucose, $^2H$-labeled amino acids, $^2H$-labeled organic molecules, $^{13}C$-labeled organic molecules, $^{14}C$-labeled organic molecules, $^{13}CO_2$, $^{14}CO_2$, $^{15}N$-labeled organic molecules and $^{15}NH_3$.

"Labeled sugar" refers to a sugar incorporating a stable isotope label such as one or more $^2H$ isotopes.

"Labeled fatty acid" refers to a fatty acid incorporating a stable isotope label such as one or more $^2H$ isotopes.

"Deuterated water" refers to water incorporating a stable isotope label such as one or more $^2H$ isotopes.

"Labeled glucose" refers to glucose labeled with one or more $^2H$ isotopes. Specific examples of labeled glucose or $^2H$-labeled glucose include [6,6-$^2H_2$]glucose, [1-$^2H_1$]glucose, and [1,2,3,4,5,6-$^2H_7$]glucose.

"Exposing" a living system to a compound such as a chemical entity or entities can be from, but is not limited to, topical application, oral ingestion, inhalation, subcutaneous injection, intraperitoneal injection, intravenous injection, and intraarterial injection, in animals or other higher organisms.

By "therapeutic action" is meant an effect on a biochemical or molecular process (i.e., the flow of molecules through metabolic pathways or networks) that is believed to be responsible for, or contributing in, a causal manner to the initiation, progression, severity, pathology, aggressiveness, grade, activity, disability, mortality, morbidity, disease sub-classification or other underlying pathogenic or pathologic feature of one or more diseases wherein said effect is beneficial to health or otherwise contributes to a desirable outcome (e.g., a desirable clinical outcome).

By "action" is meant a specific and direct consequence of an intervention such as the administering of a drug.

By "effect" is meant any consequence, including secondary or tangential, not only of an intervention with a compound but a consequence of a natural occurrence such as the effect a gene exerts when naturally expressed or inhibited.

By "toxic effect" is meant an adverse response by a living system exposed to a compound or combinations or mixtures thereof. A toxic effect can include, for example, end-organ toxicity.

An "individual" is a vertebrate, preferably a mammal, more preferably a human.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

"At least partially identified" in the context of drug discovery and development means at least one clinically relevant pharmacological characteristic of a drug agent (i.e., a "compound") has been identified using one or more of the methods of the present invention. This characteristic may be a desirable one, for example, increasing or decreasing molecular flux rates through a metabolic pathway that contributes to a disease process, altering signal transduction pathways or cell surface receptors that alter the activity of metabolic pathways relevant to a disease, inhibiting activation of an enzyme and the like. Alternatively, a pharmacological characteristic of a drug agent may be an undesirable one for example, the production of one or more toxic effects. There are a plethora of desirable and undesirable characteristics of drug agents well known to those skilled in the art and each will be viewed in the context of the particular drug agent being developed and the targeted disease. A drug agent can be more than at least partially identified when, for example, several characteristics have been identified (desirable or undesirable or both) that are sufficient to support a particular milestone decision point along the drug development pathway. Such milestones include, but are not limited to, pre-clinical decisions for in vitro to in vivo transition, pre-IND filing go/no go decision, phase I to phase II transition, phase II to phase III transition, NDA filing, and FDA approval for marketing. Therefore, "at least partially" identified includes the identification of one or more pharmacological characteristics useful in evaluating a drug agent in the drug discovery/drug development process. A pharmacologist or physician or other researcher may evaluate all or a portion of the identified desirable and undesirable characteristics of a drug agent to establish its therapeutic index. This may be accomplished using procedures well known in the art.

"Manufacturing a drug agent" in the context of the present invention includes any means, well known to those skilled in the art, employed for the making of a drug agent product. Manufacturing processes include, but are not limited to, medicinal chemical synthesis (i.e., synthetic organic chemistry), combinatorial chemistry, biotechnology methods such as hybridoma monoclonal antibody production, recombinant DNA technology, and other techniques well known to the skilled artisan. Such a product may be a final drug agent that is marketed for therapeutic use, a component of a combination product that is marketed for therapeutic use, or any intermediate product used in the development of the final drug agent product, whether as part of a combination product or a single product. "Manufacturing drug agent" is synonymous with "manufacturing a compound."

By "authentic biomarker" is meant a physical, biochemical, or physiologic measurement from or on the organism that represents a true or intended mechanistic target of a compound or a mechanistic event believed to be responsible for, or contributing in, a causal manner to the initiation, progression, severity, pathology, aggressiveness, grade, activity, disability, mortality, morbidity, disease sub-classification or other underlying pathogenic or pathologic feature of one or more diseases. A biomarker may be the target for monitoring the outcome of a therapeutic intervention (i.e., the functional or structural target of a drug agent). As defined herein "authentic biomarker" and "biomarkers" are used interchangeably herein and refer to biochemical processes that are involved in, or are believed to be involved in, the etiology or progression of a disease or disorder. The biochemical process (i.e., the flow of molecules through a targeted metabolic pathway or network) is the focus of analysis (as disclosed herein) since it is the underlying changes of the biochemical process (i.e., molecular flux rates) that may be the significant or authentic target for treatment or diagnostic monitoring of the disease or disorder.

By "surrogate biomarker" is meant a physical, biochemical, or physiologic measurement from or on the organism that is often accepted by governmental agencies (e.g., FDA) or medical opinion to be a sufficient therapeutic target in its own right, independent of "hard" clinical outcomes such as mortality, lost work days, morbidity, etc. There are relatively few accepted surrogate biomarkers in the U.S. and these include blood pressure and blood glucose levels. Such surrogate biomarkers are not the subject of this application.

By "evaluate" or "evaluation" or "evaluating," in the context of the present invention, is meant a process whereby the activity, toxicity, relative potency, potential therapeutic value and/or efficacy, significance, or worth of a chemical entity, biological factor, combination of chemical entities, or combination of biological factors is determined through appraisal and study, usually by means of comparing experimental outcomes to established standards and/or conditions. The term embraces the concept of providing sufficient information for a decision-maker to make a "go/no go" decision on a chemical entity or biological factor (or combinations of chemical entities or combinations of biological factors) to proceed further in the drug development process. A "go/no go" decision may be made at any point or milestone in the drug development process including, but not limited to, any stage within pre-clinical development, the pre-clinical to Investigational New Drug (IND) stage, the Phase I to Phase II stage, the Phase II to more advanced phases within Phase II (such as Phase IIb), the Phase II to Phase III stage, the Phase III to the New Drug Application (NDA) or Biologics License Application (BLA) stage, or stages beyond (such as Phase IV or other post-NDA or post-BLA stages). The term also embraces the concept of providing sufficient information to select "best-in-breed" (or "best-of-breed") in a class of compounds (chemical entities, biologics).

By "characterize," "characterizing," or "characterization," in the context of the present invention is meant an effort to describe the character or quality of a chemical entity or combination of chemical entities. As used herein, the term is nearly equivalent to "evaluate," yet lacks the more refined aspects of "evaluate," in which to "evaluate" a drug includes the ability to make a "go/no go" decision (based on an assessment of therapeutic value) on proceeding with that drug or chemical entity through the drug development process.

By "hepatic fibrosis" is meant any fibrotic condition of the liver that impairs hepatocyte or hepatic function and thus total liver function. The fibrosis need not have as its origin the hepatic tissue but may arise, for example, around hepatic venules, which results in a disturbance of blood flow to the hepatocytes. Hepatic fibrosis is commonly termed "fibrosis;" "fibrosis," "liver fibrosis," and "hepatic fibrosis," as used herein, are equivalent terms.

By "condition" or "medical condition" is meant the physical status of the body as a whole or of one of its parts. The term is usually used to indicate a change from a previous physical or mental status, or an abnormality not recognized by medical authorities as a disease or disorder. Examples of "conditions" or "medical conditions" include obesity and pregnancy.

IV. Methods of the Invention

A. Overview of the Methods of the Invention

The present invention is directed to methods of measuring changes in the molecular flux rates of one or more molecules in one or more metabolic pathways of interest within a living system. The metabolic pathways of interest are either known or suspected to be important as driving factors for, or fundamental mechanisms of, diseases or disorders. Changes in metabolic pathways of interest (i.e., molecular flux rates, kinetics) can be elicited by one or more compounds including chemical entities for example, known drugs, drug candidates, drug leads (or combinations thereof), or industrial chemicals such as pesticides, herbicides, plastics, and the like, or cosmetics, or food additives.

At least one isotope-labeled substrate molecule is administered to a cell, tissue or organism for a period of time sufficient to be incorporated in vivo (or intracellularly if the living system is a cultured cell) into one or more molecules of interest within one or more targeted metabolic pathways. In one embodiment, the isotope-labeled substrate molecules are labeled with a stable isotope (i.e., non-radioactive isotope). In another embodiment, the isotope-labeled substrate molecule is labeled with a radioactive isotope. In yet another embodiment, both stable and radioactive isotopes are used to label one or more isotope-labeled substrate molecules.

The targeted molecule of interest is obtained by biochemical isolation procedures from the cell, tissue, or organism, and is identified by mass spectrometry or by other means known in the art. For methods employing stable isotope labels, the relative and absolute abundances of the ions within the mass isotopomeric envelope corresponding to each identified molecule of interest (i.e., the isotopic content and/or pattern of the molecule or the rate of change of the isotopic content and/or pattern of the molecule) are quantified. In one embodiment, the relative and absolute abundances of the ions within the mass isotopomeric envelope corresponding to each identified molecule of interest are quantified by mass spectrometry. Flux rates through the targeted metabolic pathways are then calculated by use of equations known in the art and discussed, infra. Flux rates through the targeted metabolic pathways are compared in the presence or absence of exposure to one or more compounds, one or more chemical entities (i.e., drugs, drug candidates, industrial chemicals, food additives, environmental pollutants, and the like) or combinations of chemical entities (i.e., combinations of drugs, drug candidates, or other chemicals), or in response to different levels of exposure to one or more compounds or one or more chemical entities, or in response to different levels of exposure to combinations of compounds or chemical entities.

In this manner, changes in the targeted underlying biochemical (metabolic) pathways are measured and quantified and related to disease diagnosis; disease prognosis; therapeutic efficacy of administered compounds, drugs, drug candidates, or drug leads; or toxic effects of compounds, chemical entities such as drug candidates, drug leads, known drugs, industrial chemicals, pesticides, herbicides, cosmetics, food additives, and the like.

B. Administering Isotope-Labeled Precursor(s)

As a first step in the methods of the invention, isotope-labeled precursors are administered.

1. Administering an Isotope-Labeled Precursor Molecule

Modes of administering the one or more isotope-labeled substrates may vary, depending upon the absorptive properties of the isotope-labeled substrate and the specific biosynthetic pool into which each compound is targeted. Precursors may be administered to organisms, plants and animals including humans directly for in vivo analysis. In addition, precursors may be administered in vitro to living cells. Specific types of living cells include hepatocytes, adipocytes, myocytes, fibroblasts, microglia, neurons, neuroprogenitor cells, sperm cells, pancreatic β-cells, intestinal epithelial cells, breast epithelial cells, prostate epithelial cells, endothelial cells, leukocytes, lymphocytes, erythrocytes, microbial cells and any other cell-type that can be maintained alive and functional in vitro.

Generally, an appropriate mode of administration is one that produces a steady state level of precursor within the biosynthetic pool and/or in a reservoir supplying such a pool for at least a transient period of time. Intravascular or oral routes of administration are commonly used to administer such precursors to organisms, including humans. Other routes of administration, such as subcutaneous or intra-muscular administration, optionally when used in conjunction with slow release precursor compositions, are also appropriate. Compositions for injection are generally prepared in sterile pharmaceutical excipients.

a. Labeled Precursor Molecules (1) Isotope Labels

The first step in measuring molecular flux rates involves administering an isotope-labeled precursor molecule to a cell, tissue, or organism. The isotope labeled precursor molecule may contain a stable isotope or a radioisotope. Isotope labels that can be used in accordance with the methods of the present invention include, but are not limited to, $^2H$, $^{13}C$, $^{15}N$, $^{18}O$, $^3H$, $^{14}C$, $^{35}S$, $^{32}P$, $^{33}P$, $^{125}I$, $^{131}I$ or other isotopes of elements present in organic systems. These isotopes, and others, are suitable for all classes of chemicals (i.e., precursor molecules) envisioned for use in the present invention. Such precursor molecules include, but are not limited to, protein precursors, lipid precursors, carbohydrate precursors, nucleic acid precursors, porphyrin precursors, glycosaminoglycan precursors, and proteoglycan precursors (see examples of each, infra).

In one embodiment, the isotope label is $^2H$.

(2) Precursor Molecules (Isotope-Labeled Substrates)

The precursor molecule may be any molecule having an isotope label that is incorporated into a molecule of interest by passage through a metabolic pathway in vivo in a living system (or in vitro in a cultured cell). Precursor molecules typically used include, without limitation: $H_2O$; $CO_2$; $NH_3$; acetyl CoA (to form cholesterol, fatty acids); ribonucleic acids (to form RNA); deoxyribonucleic acids (to form DNA); glucose (to form glycogen); amino acids (to form peptides/proteins); phosphoenol-pyruvate (to form glucose/UDP-glucose); and glycine/succinate (to form porphyrin derivatives). Isotope labels may be used to modify all precursor molecules disclosed herein to form isotope-labeled precursor molecules.

The entire precursor molecule may be incorporated into one or more molecules of interest within a metabolic pathway. Alternatively, a portion of the precursor molecule may be incorporated into one or more molecules of interest.

i. Protein Precursors

A protein precursor molecule may be any protein precursor molecule known in the art. These precursor molecules may be amino acids, $CO_2$, $NH_3$, glucose, lactate, $H_2O$, acetate, and fatty acids.

The isotope label may include specific heavy isotopes of elements present in biomolecules, such as $^2H$, $^{13}C$, $^{15}N$, $^{18}O$, $^{33}S$, $^{34}S$, or may contain other isotopes of elements present in biomolecules such as $^3H$, $^{14}C$, $^{35}S$, $^{32}P$ $^{33}P$, $^{125}I$, or $^{131}I$.

Precursor molecules of proteins may also include one or more amino acids. The precursor may be any amino acid. The precursor molecule may be a singly or multiply deuterated amino acid. The precursor molecule may be one or more of $^{13}C$-lysine, $^{15}N$-histidine, $^{13}C$-serine, $^{13}C$-glycine, $^2H$-leucine, $^{15}N$-glycine, $^{13}C$-leucine, $^2H_5$-histidine, and any deuterated amino acid. By way of example, isotope labeled protein precursors include, but are not limited to $^2H_2O$, $^{15}NH_3$, $^{13}CO_2$, $H^{13}CO_3$, $^2H$-labeled amino acids, $^{13}C$ labeled amino acids, $^{15}N$ labeled amino acids, $^{18}O$ labeled amino acids, $^{33}S$ or $^{34}S$ labeled amino acids, $^3H_2O$, $^3H$-labeled amino acids, and $^{14}C$ labeled amino acids. Labeled amino acids may be administered, for example, undiluted or diluted with non-labeled amino acids. All isotope labeled precursors may be purchased commercially, for example, from Cambridge Isotope Labs (Andover, Mass.).

Protein precursor molecules may also include any precursor for post-translational or pre-translationally modified amino acids. These precursors include but are not limited to precursors of methylation such as glycine, serine or $H_2O$; precursors of hydroxylation, such as $H_2O$ or $O_2$; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other pre or post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^2H_2O$ in body water may be identified. The total number of C—H bonds in each non essential amino acid is known—e.g., 4 in alanine, 2 in glycine, etc.

The precursor molecule for proteins may be water. The hydrogen atoms on C—H bonds are the hydrogen atoms on amino acids that are useful for measuring protein synthesis from $^2H_2O$ since the O—H and N—H bonds of proteins are labile in aqueous solution. As such, the exchange of $^2H$-label from $^2H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions. The presence of $^2H$-label in C—H bonds of protein-bound amino acids after $^2H_2O$ administration therefore means that the protein was assembled from amino acids that were in the free form during the period of $^2H_2O$ exposure—i.e., that the protein is newly synthesized.

Analytically, the amino acid derivative used must contain all the C—H bonds but must remove all potentially contaminating N—H and O—H bonds.

Hydrogen atoms from body water may be incorporated into free amino acids. $^2$H or $^3$H from labeled water can enter into free amino acids in the cell through the reactions of intermediary metabolism, but $^2$H or $^3$H cannot enter into amino acids that are present in peptide bonds or that are bound to transfer RNA. Free essential amino acids may incorporate a single hydrogen atom from body water into the α-carbon C—H bond, through rapidly reversible transamination reactions. Free non-essential amino acids contain a larger number of metabolically exchangeable C—H bonds, of course, and are therefore expected to exhibit higher isotopic enrichment values per molecule from $^2$H$_2$O in newly synthesized proteins.

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketogluta rate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histidine, the hydroxyl group in hydroxyproline or hydroxylysine, and others. Other amino acid synthesis pathways are known to those of skill in the art.

Oxygen atoms (H$_2$$^{18}$O) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art. Oxygen atoms may also be incorporated into amino acids from $^{18}$O$_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g., methylation, hydroxylation, phosphorylation, prenylation, sulfation, carboxylation, acetylation or other known post-translational modifications).

Protein precursors that are suitable for administration into a subject include, but are not limited to H$_2$O, CO$_2$, NH$_3$ and HCO$_3$, in addition to the standard amino acids found in proteins.

The individual being administered a labeled protein precursor may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

ii. Precursors of Organic Metabolites

Precursors of organic metabolites may be any precursor molecule capable of entering into the organic metabolite pathway. Organic metabolites and organic metabolite precursors include, but are not limited to, H$_2$O, CO$_2$, NH$_3$, HCO$_3$, amino acids, monosaccharides, carbohydrates, lipids, fatty acids, nucleic acids, glycolytic intermediates, acetic acid, and tricarboxylic acid cycle intermediates.

Isotope labeled organic metabolite precursors include, but are not limited to, $^2$H$_2$O, $^{15}$NH$_3$, $^{13}$CO$_2$, H$^{13}$CO$_3$, $^2$H-labeled amino acids, $^{13}$C-labeled amino acids, $^{15}$N-labeled amino acids, $^{18}$O-labeled amino acids, $^{33}$S or $^{34}$S-labeled amino acids, $^3$H$_2$O, $^3$H-labeled amino acids, $^{14}$C-labeled amino acids, $^{14}$CO$_2$, and H$^{14}$CO$_2$.

Organic metabolite precursors may also be administered directly. Mass isotopes that may be useful in mass isotope labeling of organic metabolite precursors include, but are not limited to, $^2$H, $^3$H, $^{13}$C, $^{14}$C, $^{15}$N, $^{18}$O, $^{33}$S, $^{34}$S, $^{35}$S, $^{32}$P, $^{125}$I, $^{131}$I, or other isotopes of elements present in organic systems. It is often desirable, in order to avoid metabolic loss of isotope labels, that the isotope-labeled atom(s) be relatively non-labile or at least behave in a predictable manner within the subject. By administering the isotope-labeled precursors to the biosynthetic pool, the isotope-labeled precursors can become directly incorporated into organic metabolites formed in the pool.

The individual being administered a labeled organic metabolite precursor may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

iii. Precursors of Nucleic Acids

Precursors of nucleic acids (i.e., RNA, DNA) are any compounds suitable for incorporation into RNA and/or DNA synthetic pathways. Examples of substrates useful in labeling the deoxyribose ring of DNA include, but are not limited to, [6,6-$^2$H$_2$]glucose, [U-$^{13}$C$_6$]glucose and [2-$^{13}$C$_1$]glycerol (see U.S. Pat. No. 6,461,806, herein incorporated by reference). Labeling of the deoxyribose is superior to labeling of the information-carrying nitrogen bases in DNA because it avoids variable dilution sources. The stable isotope labels are readily detectable by mass spectrometric techniques.

In one embodiment, a stable isotope label is used to label the deoxyribose ring of DNA from glucose, precursors of glucose-6-phosphate or precursors of ribose-5-phosphate. In embodiments where glucose is used as the starting material, suitable labels include, but are not limited to, deuterium-labeled glucose such as [6,6-$^2$H$_2$]glucose, [1-$^2$H$_1$]glucose, [3-$^2$H$_1$]glucose, [$^2$H$_7$]glucose, and the like; $^{13}$C-1 labeled glucose such as [1-$^{13}$C$_1$]glucose, [U-$^{13}$C$_6$]glucose and the like; and $^{18}$O-labeled glucose such as [1-$^{18}$O$_2$]glucose and the like.

In embodiments where a glucose-6-phosphate precursor or a ribose-5-phosphate precursor is desired, a gluconeogenic precursor or a metabolite capable of being converted to glucose-6-phosphate or ribose-5-phosphate can be used. Gluconeogenic precursors include, but are not limited to, $^{13}$C-labeled glycerol such as [2-$^{13}$C$_1$]glycerol and the like, a $^{13}$C-labeled amino acid, deuterated water ($^2$H$_2$O) and $^{13}$C-labeled lactate, alanine, pyruvate, propionate or other non-amino acid precursors for gluconeogenesis. Metabolites which are converted to glucose-6-phosphate or ribose-5-phosphate include, but are not limited to, labeled ($^2$H or $^{13}$C) hexoses such as [1-$^2$H$_1$]galactose, [U-$^{13}$C]fructose and the like; labeled ($^2$H or $^{13}$C) pentoses such as [1-$^{13}$C$_1$]ribose, [1-$^2$H$_1$]xylitol and the like, labeled ($^2$H or $^{13}$C) pentose phosphate pathway metabolites such as [1-$^2$H$_1$]seduheptalose and the like, and labeled ($^2$H or $^{13}$C) amino sugars such as [U-$^{13}$C]glucosamine, [1-$^2$H$_1$]N-acetyl-glucosamine and the like.

The present invention also encompasses stable isotope labels which label purine and pyrimidine bases of DNA through the de novo nucleotide synthesis pathway. Various building blocks for endogenous purine synthesis can be used to label purines and they include, but are not limited to, $^{15}$N-labeled amino acids such as [$^{15}$N]glycine, [$^{15}$N]glutamine, [$^{15}$N]aspartate and the like, $^{13}$C-labeled precursors such as [1-$^{13}$C$_1$]glycone, [3-$^{13}$C$_1$]acetate, [$^{13}$C]HCO$_3$, [$^{13}$C]methionine and the like, and H-labeled precursors such as $^2$H$_2$O. Various building blocks for endogenous pyrimidine synthesis can be used to label pyrimidines and they include, but are not limited to, $^{15}$N-labeled amino acids such as [$^{15}$N]glutamine and the like, $^{13}$C-labeled precursors such as [$^{13}$C]HCO$_3$, [U-$^{13}$C$_4$]aspartate and the like, and $^2$H-labeled precursors ($^2$H$_2$O).

It is understood by those skilled in the art that in addition to the list above, other stable isotope labels which are substrates or precursors for any pathways which result in endogenous labeling of DNA are also encompassed within the scope of the invention. The labels suitable for use in the present invention are generally commercially available or can be synthesized by methods well known in the art.

The individual being administered a labeled nucleic acid precursor may be a mammal. In one variation, the individual may be an experimental animal including, without limitation, a rodent, primate, hamster, guinea pig, dog, or pig. In variations involving the administering of drugs, drug candidates, drug leads, biologics, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

iv. Water as a Precursor Molecule

Water is a precursor of proteins and many organic metabolites. As such, labeled water may serve as a precursor in the methods taught herein.

H$_2$O availability is probably never limiting for biosynthetic reactions in a cell (because H$_2$O represents close to 70% of the content of cells, or >35 Molar concentration), but hydrogen and oxygen atoms from H$_2$O contribute stoichiometrically to many reactions involved in biosynthetic pathways: e.g.: R—CO—CH2—COOH+NADPH+H$_2$O→R—CH$_2$CH2COOH (fatty acid synthesis).

As a consequence, isotope labels provided in the form of H- or O-isotope-labeled water is incorporated into biological molecules as part of synthetic pathways. Hydrogen incorporation can occur in two ways: into labile positions in a molecule (i.e., rapidly exchangeable, not requiring enzyme catalyzed reactions) or into stable positions (i.e., not rapidly exchangeable, requiring enzyme catalysis). Oxygen incorporation occurs in stable positions.

Some of the hydrogen-incorporating steps from cellular water into C—H bonds in biological molecules only occur during well-defined enzyme-catalyzed steps in the biosynthetic reaction sequence, and are not labile (exchangeable with solvent water in the tissue) once present in the mature end-product molecules. For example, the C—H bonds on glucose are not exchangeable in solution. In contrast, each of the following C—H positions exchanges with body water during reversal of specific enzymatic reactions: C-1 and C-6, in the oxaloacetate/succinate sequence in the Krebs' cycle and in the lactate/pyruvate reaction; C-2, in the glucose-6-phosphate/fructose-6-phosphate reaction; C-3 and C-4, in the glyceraldehyde-3-phosphate/dihydroxyacetone-phosphate reaction; C-5, in the 3-phosphoglycerate/glyceraldehyde-3-phosphate and glucose-6-phosphate/fructose-6-phosphate reactions.

Labeled hydrogen or oxygen atoms from water that are covalently incorporated into specific non-labile positions of a molecule thereby reveals the molecule's "biosynthetic history"—i.e., label incorporation signifies that the molecule was synthesized during the period that isotope-labeled water was present in cellular water.

The labile hydrogens (non-covalently associated or present in exchangeable covalent bonds) in these biological molecules do not reveal the molecule's biosynthetic history. Labile hydrogen atoms can be easily removed by incubation with unlabelled water (H$_2$O) (i.e., by reversal of the same non-enzymatic exchange reactions through which $^2$H or $^3$H was incorporated in the first place), however:

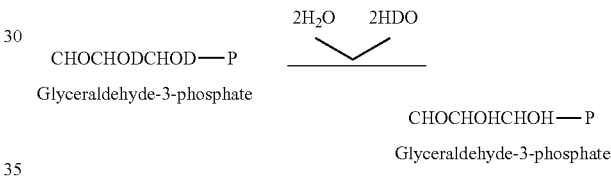

As a consequence, potentially contaminating hydrogen label that does not reflect biosynthetic history, but is incorporated via non-synthetic exchange reactions, can easily be removed in practice by incubation with natural abundance H$_2$O.

Analytic methods are available for measuring quantitatively the incorporation of labeled hydrogen atoms into biological molecules (e.g., liquid scintillation counting for $^3$H; mass spectrometry or NMR spectroscopy for $^2$H and $^{18}$O). For further discussions on the theory of isotope-labeled water incorporation, see, for example, Jungas R L. *Biochemistry.* 1968 7:3708-17, incorporated herein by reference.

Labeled water may be readily obtained commercially. For example, $^2$H$_2$O may be purchased from Cambridge Isotope Labs (Andover, Mass.), and $^3$H$_2$O may be purchased, e.g., from New England Nuclear, Inc. In general, $^2$H$_2$O is non-radioactive and thus, presents fewer toxicity concerns than radioactive $^3$H$_2$O. $^2$H$_2$O may be administered, for example, as a percent of total body water, e.g., 1% of total body water consumed (e.g., for 3 liters water consumed per day, 30 microliters $^2$H$_2$O is consumed). If $^3$H$_2$O is utilized, then a non-toxic amount, which is readily determined by those of skill in the art, is administered.

Relatively high body water enrichments of $^2$H$_2$O (e.g., 1-10% of the total body water is labeled) may be achieved relatively inexpensively using the techniques of the invention. This water enrichment is relatively constant and stable as these levels are maintained for weeks or months in humans and in experimental animals without any evidence of toxicity. This finding in a large number of human subjects (>100 people) is contrary to previous concerns about vestibular toxicities at high doses of $^2H_2O$. The Applicant has discovered that as long as rapid changes in body water enrichment are prevented (e.g., by initial administration in small, divided doses), high body water enrichments of $^2H_2O$ can be maintained with no toxicities. For example, the low expense of commercially available $^2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool, than for 12 hours labeling of $^2H$-leucine at 10% free leucine enrichment, and thus 7-8% enrichment in leucine precursor pool for that period).

Relatively high and relatively constant body water enrichments for administration of $H_2{}^{18}O$ may also be accomplished, since the $^{18}O$ isotope is not toxic, and does not present a significant health risk as a result.

Isotope-labeled water may be administered via continuous isotope-labeled water administration, discontinuous isotope-labeled water administration, or after single or multiple administration of isotope-labeled water administration. In continuous isotope-labeled water administration, isotope-labeled water is administered to an individual for a period of time sufficient to maintain relatively constant water enrichments over time in the individual. For continuous methods, labeled water is optimally administered for a period of sufficient duration to achieve a steady state concentration (e.g., 3-8 weeks in humans, 1-2 weeks in rodents).

In discontinuous isotope-labeled water administration, an amount of isotope-labeled water is measured and then administered, one or more times, and then the exposure to isotope-labeled water is discontinued and wash-out of isotope-labeled water from body water pool is allowed to occur. The time course of delabeling may then be monitored. Water is optimally administered for a period of sufficient duration to achieve detectable levels in biological molecules.

Isotope-labeled water may be administered to an individual or tissue in various ways known in the art. For example, isotope-labeled water may be administered orally, parenterally, subcutaneously, intravascularly (e.g., intravenously, intraarterially), or intraperitoneally. Several commercial sources of $^2H_2O$ and $H_2{}^{18}O$ are available, including Isotec, Inc. (Miamisburg Ohio, and Cambridge Isotopes, Inc. (Andover, Mass.). The isotopic content of isotope labeled water that is administered can range from about 0.001% to about 20% and depends upon the analytic sensitivity of the instrument used to measure the isotopic content of the biological molecules. In one embodiment, 4% $^2H_2O$ in drinking water is orally administered. In another embodiment, a human is administered 50 mL of $^2H_2O$ orally.

The individual being administered labeled water may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

v. Precursors of Carbohydrates

Compositions comprising carbohydrates may include monosaccharides, polysaccharides, or other compounds attached to monosaccharides or polysaccharides.

Isotope labels may be incorporated into carbohydrates or carbohydrate derivatives. These include monosaccharides (including, but not limited to, glucose and galactose), amino sugars (such as N-Acetyl-Galactosamine), polysaccharides (such as glycogen), glycoproteins (such as sialic acid) glycolipids (such as galactocerebrosides), glycosaminoglycans (such as hyaluronic acid, chondroitin-sulfate, and heparan-sulfate) by biochemical pathways known in the art.

$^2H$-labeled sugars may be administered to an individual as monosaccharides or as polymers comprising monosaccharide residues. Labeled monosaccharides may be readily obtained commercially (e.g., Cambridge Isotopes, Massachusetts).

Relatively low quantities of compounds comprising $^2H$-labeled sugars need be administered. Quantities may be on the order of milligrams, $10^1$ mg, $10^2$ mg, $10^3$ mg, $10^4$ mg, $10^5$ mg, or $10^6$ mg. $^2H$-labeled sugar enrichment may be maintained for weeks or months in humans and in animals without any evidence of toxicity. The lower expense of commercially available labeled monosaccharides, and low quantity that need to be administered, allow maintenance of enrichments at low expense.

In one embodiment, the labeled sugar is glucose. Glucose is metabolized by glycolysis and the citric acid cycle. Glycolysis releases most of the H-atoms from C—H bonds of glucose; oxidation via the citric acid cycle ensures that all H-atoms are released to $H_2O$. The loss of $^3H$— or $^2H$-label by glucose has been used to assess glycolysis, an intracellular metabolic pathway for glucose. Some investigators have used release of $^3H$ from intravenously administered $^3H$-glucose into $^3H_2O$ as a measure of glycolysis. Release of $^2H$-glucose into $^2H_2O$ has not been used previously, because of the expectation that the body water pool is too large relative to $^2H$ administration in labeled glucose to achieve measurable 2H2O levels. In a further variation, the labeled glucose may be [6,6-$^2H_2$]glucose, [1-$^2H_1$]glucose, and [1,2,3,4,5,6-$^2H_7$] glucose.

In another embodiment, labeled sugar comprises fructose or galactose. Fructose enters glycolysis via the fructose 1-phosphate pathway, and secondarily through phosphorylation to fructose 6-phosphate by hexokinase. Galactose enters glycolysis via the galactose to glucose interconversion pathway.

Any other sugar is envisioned for use in the present invention. Contemplated monosaccharides include, but are not limited to, trioses, pentoses, hexose, and higher order monosaccharides. Monosaccharides further include, but are not limited to, aldoses and ketoses.

In another embodiment, polymers comprising polysaccharides may be administered. In yet another embodiment, labeled polysaccharides may be administered. In yet another embodiment, labeled sugar monomers may be administered as a component of sucrose (glucose α-(1,2)-fructose), lactose (galactose β-(1,4)-glucose), maltose (glucose α-(1,4)-glucose), starch (glucose polymer), or other polymers.

In one embodiment, the labeled sugar may be administered orally, by gavage, intraperitoneally, intravascularly (e.g., intravenously, intraarterially), subcutaneously, or other bodily routes. In particular, the sugars may be administered to an individual orally, optionally as part of a food or drink.

The individual being administered a labeled carbohydrate precursor may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

vi. Precursors of Lipids and other Fats

Measuring the metabolism of compounds comprising $^2$H-labeled fatty acids are also contemplated by the present invention. Isotope labels from isotope-labeled water may also be incorporated into fatty acids, the glycerol moiety of acylglycerols (including but not limited to, triacylglycerides, phospholipids, and cardiolipin), cholesterol and its derivatives (including but not limited to cholesterol-esters, bile acids, steroid hormones) by biochemical pathways known in the art.

Complex lipids, such as glycolipids and cerebrosides, can also be labeled from isotope-labeled water, which is a precursor for the sugar-moiety of cerebrosides (including, but not limited to, N-acetylgalactosamine, N-acetylglucosamine-sulfate, glucuronic acid, and glucuronic acid-sulfate).

$^2$H-labeled fatty acids may be administered to an individual as fats or other compounds containing the labeled fatty acids. $^2$H-labeled fatty acids may be readily obtained commercially. Relatively low quantities of labeled fatty acids need be administered. Quantities may be on the order of milligrams, $10^1$ mg, $10^2$ mg, $10^3$ mg, $10^4$ mg, $10^5$ mg, or $10^6$ mg. Fatty acid enrichment, particularly with $^2$H, may be maintained for weeks or months in humans and in animals without any evidence of toxicity. The lower expense of commercially available labeled fatty acids, and low quantity that need to be administered, allow maintenance of enrichments at low expense.

The release of labeled fatty acids, particularly $^2$H-fatty acid, to labeled water, particularly $^2$H$_2$O, accurately reflects fat oxidation. Administration of modest amounts of labeled-fatty acid is sufficient to measure release of labeled hydrogen or oxygen to water. In particular, administration of modest amounts of $^2$H-fatty acid is sufficient to measure release of $^2$H to deuterated water.

In another variation, the labeled fatty acids may be administered orally, by gavage, intraperitoneally, intravascularly (e.g., intravenously, intraarterially), subcutaneously, or other bodily routes. In particular, the labeled fatty acids may be administered to an individual orally, optionally as part of a food or drink.

The individual being administered labeled lipid precursors may be a mammal. In one variation, the individual may be an experimental animal including, without limitation, a rodent, primate, hamster, guinea pig, dog, or pig. In variations involving the administering of drugs, drug candidates, drug leads, or combinations thereof, the individual may be a mammal, such as an experimental animal, including an accepted animal model of disease, or a human. In variations involving the administering of food additives, industrial or occupational chemicals, environmental pollutants, or cosmetics, the individual may be any experimental animal such as, without limitation, a rodent, primate, hamster, guinea pig, dog, or pig.

C. Obtaining One or More Targeted Molecules of Interest

In practicing the methods of the invention, in one aspect, targeted molecules of interest are obtained from a cell, tissue, or organism according to methods known in the art. The methods may be specific to the particular molecule of interest. Molecules of interest may be isolated from a biological sample.

A plurality of molecules of interest may be acquired from the cell, tissue, or organism. The one or more biological samples may be obtained, for example, by blood draw, urine collection, biopsy, or other methods known in the art. The one or more biological sample may be one or more biological fluids. The molecule of interest may also be obtained from specific organs or tissues, such as muscle, liver, adrenal tissue, prostate tissue, endometrial tissue, blood, skin, and breast tissue. Molecules of interest may be obtained from a specific group of cells, such as tumor cells or fibroblast cells. Molecules of interest also may be obtained, and optionally partially purified or isolated, from the biological sample using standard biochemical methods known in the art.

The frequency of biological sampling can vary depending on different factors. Such factors include, but are not limited to, the nature of the molecules of interest, ease and safety of sampling, synthesis and breakdown/removal rates of the molecules of interest, and the half-life of a compound (chemical entity, biological factor, already-approved drug, drug candidate, drug lead, etc.).

The molecules of interest may also be purified partially, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the molecules of interest may be hydrolyzed or otherwise degraded to form smaller molecules. Hydrolysis methods include any method known in the art, including, but not limited to, chemical hydrolysis (such as add hydrolysis) and biochemical hydrolysis (such as peptidase degradation). Hydrolysis or degradation may be conducted either before or after purification and/or isolation of the molecules of interest. The molecules of interest also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

D. Analysis

Presently available technologies (static methods) used to identify biological actions of agents measure only composition, structure, or concentrations of molecules in a cell and do so at one point in time. While RNA and protein expression "chips," for example, can be used to detect multiple biological molecules at one time in cells or organisms in a variety of disease states, these techniques fail to determine the molecular flux rates of proteins or transcripts. The methods of the present invention allow determination of the molecular flux rates of a plurality of proteins or transcripts, as well as the molecular flux rates of a plurality of organic metabolites, and their changes over time in a variety of disease states and in response to exposure to one or more drugs, drug candidates, drug leads, or combinations thereof, or in response to exposure to one or more industrial chemicals, food additives, cosmetics, or environmental pollutants.

1. Mass Spectrometry

Isotopic enrichment biomarkers can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrolysis-MS, liquid chromatography-MS, electrospray ionization-MS, matrix assisted laser desorption-time of flight-MS, Fourier-transform-ion-cyclotron-resonance-MS, and cycloidal-MS.

Mass spectrometers convert molecules into rapidly moving gaseous ions and separate them on the basis of their mass-to-charge ratios. The distributions of isotopes or isotopologues of ions, or ion fragments, may thus be used to measure the isotopic enrichment in a plurality of proteins or organic metabolites.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a protein, and then generate secondary fragments of the initial ions. The resulting overlapping sequences allows complete sequencing of the protein, by piecing together overlaying "pieces of the puzzle", based on a single mass spectrometric analysis within a few minutes (plus computer analysis time).

Different ionization methods are also known in the art. One key advance has been the development of techniques for ionization of large, non-volatile macromolecules including proteins and polynucleotides. Techniques of this type have included electrospray ionization (ESI) and matrix assisted laser desorption (MALDI). These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS (or other mass spectrometric modalities that analyze ions of biomolecules, rather than small inorganic gases) is used to measure mass isotopomer abundances of organic molecules, hydrogen-labeled isotope incorporation from isotope-labeled water is amplified 3 to 7-fold, depending on the number of hydrogen atoms incorporated into the organic molecule from isotope-labeled water in vivo.

In general, in order to determine a baseline mass isotopomer frequency distribution for a molecule of interest, such a sample is taken before infusion of an isotopically labeled precursor. Such a measurement is one means of establishing in the cell, tissue or organism, the naturally occurring frequency of mass isotopomers of the molecule of interest. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of $^{13}C$ present in organic carbon in 1.11%. Methods of determining such isotopomer frequency distributions are discussed below. Typically, samples of the molecule of interest are taken prior to and following administration of an isotopically labeled precursor to the subject and analyzed for isotopomer frequency as described below.

a. Measuring Relative and Absolute Mass Isotopomer Abundances

Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the present invention.

2. Calculating Labeled: Unlabeled Proportion of Molecules of Interest

The proportion of labeled and unlabeled molecules of interest is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686, 5,910,403, and 6,010,846, which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety.

In addition to the above-cited references, calculation software implementing the method is publicly available from Professor Marc Hellerstein, University of California, Berkeley.

The comparison of excess molar ratios to the theoretical patterns can be carried out using a table generated for a molecule of interest, or graphically, using determined relationships. From these comparisons, a value, such as the value p, is determined, which describes the probability of mass isotopic enrichment of a subunit in a precursor subunit pool. This enrichment is then used to determine a value, such as the value $A_X^*$, which describes the enrichment of newly synthesized proteins for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M_X$, $$\text{Fractional abundance of } M_X = A_X = \frac{\text{Abundance } M_x}{\sum_{i=0}^{n} \text{Abundance } M_i},$$

where 0 to $n$ is the range of nominal masses relative to the lowest mass ($M_0$) mass isotopomer in which abundances occur.

$$\Delta \text{ Fractional abundance (enrichment or depletion)} =$$

$$(A_x)_e - (A_x)_b = \left( \frac{\text{Abundance } M_x}{\sum_{i=0}^{n} \text{Abundance } M_i} \right)_e - \left( \frac{\text{Abundance } M_x}{\sum_{i=0}^{n} \text{Abundance } M_i} \right)_b,$$

where subscript e refers to enriched and b refers to baseline or natural abundance.

In order to determine the fraction of polymers that were actually newly synthesized during a period of precursor administration, the measured excess molar ratio ($EM_X$) is compared to the calculated enrichment value, $A_X^*$, which describes the enrichment of newly synthesized biopolymers for each mass isotopomer, to reveal the isotopomer excess ratio which would be expected to be present, if all isotopomers were newly synthesized.

3. Calculating Molecular Flux Rates

The method of determining rate of synthesis includes calculating the proportion of mass isotopically labeled subunit present in the molecular precursor pool, and using this proportion to calculate an expected frequency of a molecule of interest containing at least one mass isotopically labeled subunit. This expected frequency is then compared to the actual, experimentally determined isotopomer frequency of the molecule of interest. From these values, the proportion of the molecule of interest which is synthesized from added isotopically labeled precursors during a selected incorporation period can be determined. Thus, the rate of synthesis during such a time period is also determined.

A precursor-product relationship may then be applied. For the continuous labeling method, the isotopic enrichment is compared to asymptotic (i.e., maximal possible) enrichment and kinetic parameters (e.g., synthesis rates) are calculated from precursor-product equations. The fractional synthesis rate ($k_s$) may be determined by applying the continuous labeling, precursor-product formula:

$$k_s = [-\ln(1-f)]/t,$$

where f=fractional synthesis=product enrichment/asymptotic precursor/enrichment and t=time of label administration of contacting in the system studied.

For the discontinuous labeling method, the rate of decline in isotope enrichment is calculated and the kinetic parameters of the molecules of interest are calculated from exponential decay equations. In practicing the method, biopolymers are enriched in mass isotopomers, preferably containing multiple mass isotopically labeled precursors. These higher mass isotopomers of the molecules of interest, e.g., molecules containing 3 or 4 mass isotopically labeled precursors, are formed in negligible amounts in the absence of exogenous precursor, due to the relatively low abundance of natural mass isotopically labeled precursor, but are formed in significant amounts during the period of molecular precursor incorporation. The molecules of interest taken from the cell, tissue, or organism at the sequential time points are analyzed by mass spectrometry, to determine the relative frequencies of a high mass isotopomer. Since the high mass isotopomer is synthesized almost exclusively before the first time point, its decay between the two time points provides a direct measure of the rate of decay of the molecule of interest.

Preferably, the first time point is at least 2-3 hours after administration of precursor has ceased, depending on mode of administration, to ensure that the proportion of mass isotopically labeled subunit has decayed substantially from its highest level following precursor administration. In one embodiment, the following time points are typically 1-4 hours after the first time point, but this timing will depend upon the replacement rate of the biopolymer pool.

The rate of decay of the molecule of interest is determined from the decay curve for the three-isotope molecule of interest. In the present case, where the decay curve is defined by several time points, the decay kinetic can be determined by fitting the curve to an exponential decay curve, and from this, determining a decay constant.

Breakdown rate constants (IQ may be calculated based on an exponential or other kinetic decay curve:

$$k_d = [-\ln f]/t.$$

As described, the method can be used to determine subunit pool composition and rates of synthesis and decay for substantially any biopolymer which is formed from two or more identical subunits which can be mass isotopically labeled. Other well-known calculation techniques and experimental labeling or de-labeling approaches can be used (e.g., see Wolfe, R. R. Radioactive and Stable Isotope Tracers in Biomedicine: Principles and Practice of Kinetic Analysis. John Wiley & Sons; (March 1992)) for calculation flux rates of molecules and flux rates through metabolic pathways of interest.

E. Uses of the Methods of the Present Invention

The disclosed invention allows for the measurement of molecular fluxes within metabolic pathways or networks that are believed to be a driving factor for, or etiologic mechanism of, a disease of interest. Molecular fluxes through the metabolic pathway or network itself is the biomarker for analysis, as it fundamentally represents the physiological and pathophysiological process of the living system. By using the methods of the present invention, one can quantitate the molecular flux rates of one or more molecules of interest within one or more targeted metabolic pathways or networks and use the information as a biomarker of medical diagnosis, prognosis, or therapeutic activity of drug or combination drug treatment. The methods allow for the characterization or evaluation (or both the characterization and evaluation) of compounds and enable one of skill to assess therapeutic efficacy and/or toxic effects.

The methods disclosed herein allow for effects on biomarkers to be observed after a living system is exposed to a compound or combinations of compounds. The data generated and analyzed is therefore useful in the DDA process as it facilitates the DDA decision-making process; i.e., it provides useful information for decision-makers in their decision to continue with further development on a compound or combination of compounds (e.g., if the biomarker data appear promising) or to cease said efforts, for example, if the biomarker data appear unfavorable (see FIG. 1 for a graphical depiction of this process).

Moreover, the methods allow for the skilled artisan to identify, select, and/or characterize "best in breed" in a class of compounds. Once identified, selected, and/or characterized, the skilled artisan, based on the information generated by the methods of the present invention, can decide to evaluate the "best in breed" further or to license the compound to another entity such as a pharmaceutical company or biotechnology company.

In another embodiment, the methods of the present invention allow for the characterization or evaluation (or both the characterization and evaluation) of toxic effects from exposure to industrial chemicals, food additives, cosmetics, and environmental pollutants. The methods of the present invention can be used to establish programs to identify and explore the molecular mechanisms of industrial, food, cosmetic, and environmental toxicants to further public health goals.

In one embodiment, the molecular flux rates in the one or more metabolic pathways being measured may be relevant to an underlying molecular pathogenesis, or causation of, one or more diseases. In another embodiment, the molecular flux rates in one or more metabolic pathways of interest may contribute to the initiation, progression, severity, pathology, aggressiveness, grade, activity, disability, mortality, morbidity, disease sub-classification or other underlying pathogenic or pathologic feature of the disease of interest.

In yet another embodiment, the molecular flux rates in one or more metabolic pathways of interest may contribute to the prognosis, survival, morbidity, mortality, stage, therapeutic response, symptomology, disability or other clinical factor of the disease of interest. Two or more molecular flux rates in metabolic pathways may be measured independently or concurrently.

Such metabolic pathways may include, but are not limited to, hepatocyte proliferation and destruction (or inhibition of proliferation), total liver cell proliferation and destruction (or inhibition of proliferation), renal tubular cell turnover, lymphocyte turnover, spermatocyte turnover, protein synthesis and breakdown in muscle and heart, liver collagen synthesis and breakdown, myelin synthesis and breakdown in brain or peripheral nerves, neuron proliferation and destruction (or inhibition of proliferation), neuroprogenitor cell proliferation and destruction (or inhibition of proliferation), breast epithelial cell proliferation and destruction (or inhibition of proliferation), colon epithelial cell proliferation and destruction (or inhibition of proliferation), prostate epithelial cell proliferation and destruction (or inhibition of proliferation), ovarian epithelial cell proliferation and destruction (or inhibition of proliferation), endometrial cell proliferation and destruction (or inhibition of proliferation), endothelial cell proliferation and destruction (or inhibition of proliferation), bronchial epithelial cell proliferation and destruction (or inhibition of proliferation), pancreatic epithelial cell proliferation and destruction (or inhibition of proliferation), pancreatic β cell proliferation, pancreatic islets of Langerhans proliferation and destruction (or inhibition of proliferation), microglia proliferation and destruction (or inhibition), keratin synthesis in skin, keratinocyte proliferation and destruction (or inhibition of proliferation), immunoglobulin synthesis and breakdown including M protein synthesis and breakdown, synthesis and breakdown of mitochondrial DNA, synthesis and breakdown of mitochondrial phospholipids, DNA methylation and demethylation, synthesis and breakdown of mitochondrial proteins, synthesis and breakdown of adipose lipids, and synthesis and breakdown of adipose cells.

Known animal models of disease may be used as part of the present invention. Such animal models of disease may include, but are not limited to, Alzheimer's disease, heart failure, renal disease, diabetic nephropathy, osteoporosis, hepatic fibrosis, cirrhosis, hepatocellular necrosis, pulmonary fibrosis, scleroderma, renal fibrosis, multiple sclerosis, arteriosclerosis (or atherosclerosis), osteoarthritis, rheumatoid arthritis, psoriasis, skin photoaging, skin rashes, breast cancer, prostate cancer, colon cancer, pancreatic cancer, lung cancer, acquired immunodeficiency syndrome, immune defects, multiple myeloma, chronic lymphocytic leukemia, chronic myelocytic leukemia, diabetes, diabetic complications, insulin resistance, obesity, lipodystrophy, metabolic syndrome (or syndrome X), muscle wasting, frailty, deconditioning, angiogenesis, hyperlipidemia, infertility, viral or bacterial infections, auto-immune disorders, and immune flares.

These interactions between compounds cannot be detected or quantified by use of contemporary or traditional assays that investigate one molecular target and step at a time in a disease-related pathway. A method for systematically evaluating compounds including chemical entities, biologics, combinations of chemical entities, or combinations of biologics for effects on molecular fluxes through pathways had not previously been available. The invention disclosed herein would facilitate the process of identifying, developing and approving effective therapeutic combinations of drug agents.

In another embodiment, the methods of the invention are useful in detecting toxic effects of industrial or occupational chemicals, food additives, cosmetics, or environmental pollutants/contaminants. Such toxic effects may include end-organ toxicity. End-organ toxicity may include, but is not limited to, hepatocyte proliferation and destruction (or inhibition of proliferation), total liver cell proliferation and destruction (or inhibition of proliferation), renal tubular cell turnover, lymphocyte turnover, spermatocyte turnover, protein synthesis and breakdown in muscle and heart, liver collagen synthesis and breakdown, myelin synthesis and breakdown in brain or peripheral nerves, neuron proliferation and destruction (or inhibition of proliferation), neuroprogenitor cell proliferation and destruction (or inhibition of proliferation), breast epithelial cell proliferation and destruction (or inhibition of proliferation), colon epithelial cell proliferation and destruction (or inhibition of proliferation), prostate epithelial cell proliferation and destruction (or inhibition of proliferation), ovarian epithelial cell proliferation and destruction (or inhibition of proliferation), endometrial cell proliferation and destruction (or inhibition of proliferation), endothelial cell proliferation and destruction (or inhibition of proliferation), bronchial epithelial cell proliferation and destruction (or inhibition of proliferation), pancreatic epithelial cell proliferation and destruction (or inhibition of proliferation), pancreatic β cell proliferation, pancreatic islets of Langerhans proliferation and destruction (or inhibition of proliferation), microglia proliferation and destruction (or inhibition), keratin synthesis in skin, keratinocyte proliferation and destruction (or inhibition of proliferation), immunoglobulin synthesis and breakdown including M protein synthesis and breakdown, synthesis and breakdown of mitochondrial DNA, synthesis and breakdown of mitochondrial phospholipids, DNA methylation and demethylation, synthesis and breakdown of mitochondrial proteins, synthesis and breakdown of adipose lipids, and synthesis and breakdown of adipose cells.

Figure 6:
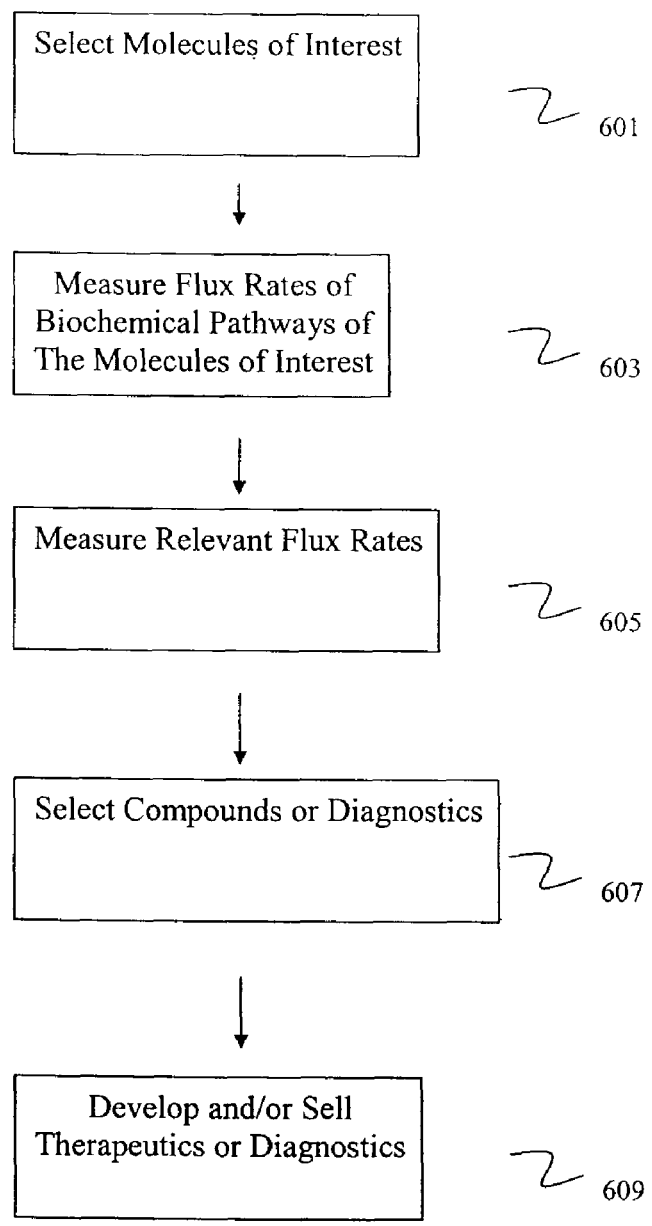
FIG. 6 illustrates use of the inventions herein in a drug discovery process.

FIG. 6 illustrates the use of the inventions herein in a drug discovery process. At step 601 a plurality of drug candidates or other compounds are selected. At step 603 the flux rates of biomarkers are studied within cells, preferably according to the methods discussed herein. In alternative embodiments, step 603 is conducted first when the inventions are used, for example, in a target discovery process. At step 605 relevant flux rates are identified. For example, if it is desirable to reduce the flux rate of a particular biomarker in a particular phenotypic state, a compound that reduces that flux rate will be considered generally more useful, and conversely a compound that increases that flux rate will be considered generally less desirable. In a target discovery process, a particular phenotype that has increased or decreased flux rates with respect to another phenotype (e.g., diseased vs. not diseased) may be considered a good therapeutic or diagnostic target or in the pathway of a good therapeutic or diagnostic target. At step 607 compounds of interest, targets of interest, or diagnostics are selected and further used and further developed. In the case of targets, such targets may be the subject of, for example, well known small molecule screening processes (e.g., high-throughput screening of new chemical entities) and the like. Alternatively, biological factors, or already-approved drugs, or other compounds (or combinations and/or mixtures of compounds) may be used. At step 609 the compounds or diagnostics are sold or distributed. It is recognized of course that one or more of the steps in the process in FIG. 6 will be repeated many times in most cases for optimal results.

Table 1 depicts examples of biomarkers, the related clinical or medical diseases or conditions and the molecule of interest to be detected using the methods of the application. Taking into account Table 1, the present application is further directed to a method for monitoring or diagnosing a clinical or medical disease or condition, the method including: a) administering an isotope-labeled substrate to the living system for a period of time sufficient for the isotope-labeled substrate to enter into one or more metabolic pathways of interest and thereby enter into and label at least one targeted molecule of interest within the one or more metabolic pathways of interest in the living system; b) obtaining one or more samples from the living system, wherein the one or more samples include at least one isotope-labeled targeted molecule of interest; c) measuring the content, rate of incorporation and/or pattern or rate of change in content and/or pattern of isotope labeling of the at least one targeted molecule of interest; d) calculating molecular flux rates in the one or more metabolic pathways/biomarker of interest based on the content and/or pattern or rate of change of content and/or pattern of isotopic labeling in the at least one targeted molecule of interest to monitor or diagnose the clinical or medical disease or condition. In another format, one or more compounds are administered to the living system before or after the determination of the molecular flux rates of the one or more metabolic pathways of interest in the living system in order to evaluate the effect of the one or more compounds on the biomarker as a predictor of an effect of the compound on the clinical or medical disease or condition.

TABLE 1

Dynamic Biomarkers and Applications

| Physiological/Medical Area | Biomarker | Clinical or Medical Disease or Condition | Molecule of interest |
|---|---|---|---|
| Metabolism/Nutrition/Endocrinology | adipose triglyceride dynamics | Obesity; lipoatrophy; fat distribution; hyperplasia-hypertrophy | Glycerol or fatty acids derived from triglyceride. |
| | Adipocyte dynamics | hyperplasia-hypertrophy; response to compounds or therapeutics. | DNA isolated from adipocytes |
| | Muscle mitochondrial DNA or phospholipid dynamics | Unfitness; cardiovascular disease risk; autotoxicity drugs; deconditioning; frailty | DNA from muscle mitochondria or phospholipids (e.g., cardiolipin) from muscle mitochondria. |
| | Muscle protein dynamics | Frailty; wasting; sports; dystrophies | Protein derived from muscle (e.g., total muscle protein or myosin) |
| | Dynamics of adipose lipolysis | Atherosclerosis; diabetes mellitus risk | Glycerol or fatty acids derived from triglyceride. |
| | Dynamics of adipose or hepatic de novo lipogenesis | carbohydrate overfeeding; anabolic block or impaired fat oxidation; energy balance | Fatty acids |
| | Dynamics of glycolysis (whole body, increase or decrease) | Insulin resistance; impaired glucose tolerance; diabetes mellitus risk | Water |
| | Dynamics of metabolic $H_2O$ or $CO_2$ production (whole body) | Obesity risk; hypo or hypermetabolism; thermogenic; response to compounds or therapeutics | Water |
| | Dynamics of fatty acid oxidation | Obesity risk; fuel selector; insulin resistance; | Water |
| | Dynamics of hepatic glucose production (endogenous glucose production) | Hepatic insulin resistance; hypo or hypermetabolism | Glucose |
| | Dynamics of hepatic triglyceride synthesis (de novo lipogeneis + secretion) | Hepatic steatosis (tumors; cirrhosis) | Glycerol or fatty acids derived from triglyceride, fatty acids |
| | β-Cell DNA dynamics | Pancreatic burden/pancreatic reserve; diabetes mellitus risk | DNA derived from pancreatic beta cells. |

TABLE 1-continued

Dynamic Biomarkers and Applications

| Physiological/ Medical Area | Biomarker | Clinical or Medical Disease or Condition | Molecule of interest |
|---|---|---|---|
| | Insulin dynamics | Pancreatic burden/ pancreatic reserve | Insulin |
| | advanced glycation endproduct dynamics; advanced glycation endproduct glycosylation dynamics | Diabetes mellitus complications | Advanced glycation endproducts (glycated proteins). |
| | Keratinocyte or mammary epithelial cell dynamics | Caloric restriction/longevity regiments | DNA derived from keratinocytes or mammary epithelial cells. |
| | Hepatic bile acid dynamics | hyperlipoproteinemia | Hepatic bile acids |
| | Dynamics of conversion of ethanol to acetate and triglyceride | hyperlipoproteinemia; cirrhosis/steatosis risk | Fatty acids and acetate |
| Cardiovascular | Apolipoprotein B dynamics | Coronary artery disease risk | Apolipoprotein B |
| | Very low density lipoprotein (VLDL) - tryglyceride dynamics | Coronary artery disease risk; pancreatitis; hyperlipoproteinemia | Apolipoprotein B, Triglyceride, glycerol |
| | Hepatic + whole body Cholesterol dynamics | Statin response; Coronary artery disease risk; diet treatment | Cholesterol from serum/blood or other biological sample |
| | Vascular smooth muscle cell dynamics | Atherosclerosis risk | DNA derived from vascular smooth muscle cells |
| | Cholesterol transport dynamics (reverse cholesterol transport) | Coronary artery disease risk | Bile acids, Cholesterol |
| | Cardiac muscle protein dynamics | Cardiomyopathy | Protein derived from cardiac muscle (e.g., total protein or myosin) |
| | Cardiac collagen dynamics | Cardiac fitness, congestive heart failure | Collagen (e.g., type III collagen) derived from cardiac tissue |
| | Vascular smooth muscle cell or endothelial cell dynamics | Vasculitis | DNA derived from vascular smooth muscle cells or endothelial cells |
| Skeletal/Rheumatic/ Integument | Keratinocyte dynamics | Psoriasis; skin hyperproliferation; ectopy | DNA derived from keratinocytes |
| | Skin keratin dynamics | Psoriasis, skin barrier | Skin keratin (Type I and/or type II) |
| | Skin collagen dynamics + elastin dynamics | Skin wrinkles; dermatomyolitis; scleroderma | Collagen (e.g., type III collagen) from skin (epidermis or dermis) |
| | Wound collagen dynamics | Wound healing; adjunctive compound or therapeutic response | Collagen (e.g., type III collagen) from skin and other wounded tissues |
| | Synovial space hyaluronic acid or chondroitin sulfate dynamics | osteoarthritis; rheumatoid arthritis; joint protection/destruction; diet or compound or therapeutic response | Hyaluronic acid from synovial fluid or cartilage, chondroitin sulfate from synovial fluid or cartilage |
| | Bone collagen dynamics | Osteoporosis; pagets; healing of bone fractures | Collagen (e.g., type I collagen) from bone |
| | Joint collagen dynamics | osteoarthritis; rheumatoid arthritis; joint protection; response to treatment | Collagen (e.g., type II collagen) from synovial fluid or cartilage |
| | Synovial leukocyte/T-Cell dynamics | rheumatoid arthritis; joint destruction | DNA from leukocytes or T-cells in synovial fluid or associated with joints |

TABLE 1-continued

Dynamic Biomarkers and Applications

| Physiological/ Medical Area | Biomarker | Clinical or Medical Disease or Condition | Molecule of interest |
|---|---|---|---|
| Oncology/Neoplasia | Mammary epithelial cell dynamics | Risk for cancer; compound or therapeutic response | DNA from mammary epithelial cells |
| | Colon epithelial cell dynamics | Risk for cancer; compound or therapeutic response | DNA from colon epithelial cells |
| | Bronchial cell or tissue dynamics | Risk for cancer; compound or therapeutic response | DNA from bronchial tissue |
| | Prostate epithelial cell dynamics | Risk for cancer; benign prostate hyperplasia; compound or therapeutic response | DNA from prostate epithelial cells |
| | Dynamics of tumors of pancreas, bladder, gastric, brain, ovary, cervix | Risk for cancer; compound or therapeutic response | DNA from cells from which tumors may derive (e.g., epithelial cells) or pre-cancerous cells, or cells whose proliferative behavior is associated with increased risk of cancer |
| | Dynamics of solid tumors (including breast, colon, lung, lymphoma) | Tumor growth; grade; prognosis; aggressiveness; Rx response | DNA derived from solid tumor cells |
| | Dynamics of liquid tumors | Cancer growth, prognosis, compound or therapeutic response | DNA derived from liquid tumor cells |
| | Immunoglobulin, albumin, or myeloma-protein dynamics. Myeloma cell dynamics | Multiple myeloma activity, prognosis, growth, mass, compound or therapeutic response | Myeloma protein, immunoglobulins, or albumin derived from serum or bone marrow, DNA from myeloma cells. |
| | Tumor endothelial cell dynamics | Angiogenesis; compound or therapeutic response | DNA from tumor endothelial cells |
| | Dynamics of ribonucleotide reductase substrates and metabolites (flux vs. salvage) | compound or therapeutic response | Deoxyadenosine and deoxythymidine |
| | Epithelial stem cell dynamics | Cancer risk; compound or therapeutic response | DNA from epithelial stem cells |
| | Tumor cell RNA dynamics | Tumor grade; prognosis; treatment target; compound or therapeutic response | RNA from tumor cells, total or transcript specific |
| | T-cell or other blood cell dynamics (post bone marrow transplant) | Proliferation + growth of transplant | DNA from transplanted cells, or from cells maturing from transplanted cells |
| | Cell dynamics at surgical margin of tumor | Adequacy of surgery | DNA from the surgical margin of the tumor |
| | Grafted tissue dynamics | Grade, aggressiveness; graft-versus-host-disease treatment response | DNA from the grafted tissue |
| | Dynamics of methylcytosine, (methyl deoxycytosine methylation/hypo methylation) | Gene silencing; prognosis; compound or therapeutic response | Methyl deoxycytosine from DNA from cells of interest |
| | Dynamics of histone acetylation and deacetylation | Gene expression; prognosis; histone acetylation; compound or therapeutic response | Histones from cells of interest |

TABLE 1-continued

Dynamic Biomarkers and Applications

| Physiological/ Medical Area | Biomarker | Clinical or Medical Disease or Condition | Molecule of interest |
|---|---|---|---|
| Neurology | Brain Amyloid-β or amyloid precursor protein dynamics | Alzheimer's disease risk; response to treatment | Amyloid beta peptide or amyloid precursor protein or subfragments of either |
| | Brain or peripheral nervous system myelin dynamics | Multiple sclerosis (MS) activity; MS response to treatment; spinal cord + brain injury recovery and/or compound or therapeutic response | Galactocerebroside from brain, peripheral nervous system, or blood |
| | Neuron dynamics | Neurogenesis; learning x-ray therapy toxicity; development; stress; depression | DNA from neurons |
| | Neurotransmitter dynamics | Psychiatric disorders | Neurotransmitters from brain or PNS (e.g., serotonin, dopamine, glutamate), or circulating or degraded neurotransmitters found in other tissues |
| | Neuroprogenitor cell dynamics | Neurogenesis, depression, compound or therapeutic response | DNA from neuroprogenitor cells |
| | Microglial cell dynamics | Neuroinflammation, multiple sclerosis, Alzheimer's disease, stroke, autism, depression, chronic pain, amyotrophic lateral sclerosis, cerebral amyloid angiopathy, excitotoxic injury, compound or therapeutic response | DNA from microglia |
| | Brain microtubule dynamics | Memory, learning, alzheimer's disease, excitotoxic injury, neurogenesis, neurodegenerative diseases, compound or therapeutic response | Microtubules (tubulin) from central or peripheral nervous system, microtubule subfractions (e.g., tau-associated, dimeric, polymeric) |
| Gastrointestinal/ Other Internal Organs | Hepatocyte dynamics | Hepatic necrosis; toxin exposure; hepatitis; response to treatment | DNA from hepatocytes |
| | Hepatic collagen dynamics | Hepatic fibrosis, cirrhosis risk, prognosis, disease activity, response to treatment | Collagen (e.g. type I or III collagen) from liver |
| | Hepatic mitochondrial dynamics | Effects from exposure to hepatic toxins, mitochondrial toxins, recovery, response to treatment | DNA or phospholipids (e.g. cardiolipin) from hepatic mitochondria |
| | Renal epithelial cell dynamics | Effects from exposure to nephrotoxins, recovery, response to treatment | DNA from renal epithelial cells. |
| | Renal collagen dynamics | DM nephropathy risk and activity, response to treatment | Collagen (e.g. type III collagen) from kidney |
| | Pulmonary collagen dynamics | Pulmonary fibrosis disease activity, response to treatment; black lung; hypersensitivity | Pulmonary (e.g. type III collagen) collagen |

TABLE 1-continued

Dynamic Biomarkers and Applications

| Physiological/ Medical Area | Biomarker | Clinical or Medical Disease or Condition | Molecule of interest |
|---|---|---|---|
| | | pneumonitis; asbestosis; silicosis; chronic obstructive pulmonary disease | |
| | Pulmonary elastin dynamics | Emphysema: prognosis, compound or therapeutic response | Pulmonary elastin |
| | Colonocyte DNA dynamics | Inflammatory bowel disease: activity, prognosis, compound or therapeutic response | DNA from colonocytes isolated from stool, colon biopsy, or other colon tissue sample |
| | Gastric epithelial DNA dynamics | H. pylori activity, compound or therapeutic response; cancer risk; gastric cancer | DNA from gastric epithelial cells |
| Immunologic/Inflammatory | T-cell dynamics | Cell mediated immunity; immune activation; AIDS, compound or therapeutic response | DNA from T-cells |
| | Antigen-specific T-cell dynamics | Vaccination response; host defense vs. pathogen; adjunctive compound or therapeutic response | DNA from T-cells isolated based on their antigen specificity |
| | Naïve T-Cell dynamics | Thymopoiesis; thymic failure; compound or therapeutic response | DNA from naïve T-cells |
| | Specific antibody dynamics | B-cell/plasma cell: activity, compound or therapeutic response, vaccine response | Immunoglubulin (e.g., IgG) specific to antigen of choice |
| | Serum acute-phase reactant dynamics | Immune activation, disease activity | Acute phase proteins (e.g., c-reactive protein) |
| | Plasma cell dynamics | Humoral immunity | DNA from plasma cells |
| | Natural killer cell dynamics | Host defense activity, compound or therapeutic response (e.g., interleukin-2) | DNA from natural killer cells |
| | Cytokine dynamics | Endogenous response to exogenous compound or therapeutic; host defense | Secreted or tissue associated cytokines (e.g., interleukin-1, interleukin-2, tumor necrosis factor alpha) |
| Infectious | Viral DNA/RNA dynamics (e.g., HIV, Hepatitis B) | Viral replication, disease activity, compound or therapeutic response, sensitivity to antiviral agents | DNA or RNA from virus of interest |
| | Viral protein dynamics | Viral replication, disease activity, compound or therapeutic response, sensitivity to antiviral agents | Protein from virus of interest |
| | Bacterial dynamics | Bacterial cell division; disease activity; response to antibiotics | DNA or other molecule (e.g., protein, carbohydrate, lipid) from bacteria of interest |
| | Parasite dynamics | Parasite division and growth; compound or therapeutic response (e.g., malaria, schistosomiasis) | DNA or other molecule (e.g., protein, carbohydrate, lipid) from parasite of interest |

TABLE 1-continued

Dynamic Biomarkers and Applications

| Physiological/Medical Area | Biomarker | Clinical or Medical Disease or Condition | Molecule of interest |
|---|---|---|---|
| | Intestinal microbial dynamics | Infectious activity; compound or therapeutic response | DNA or other molecule (e.g., protein, carbohydrate, lipid) from intestinal bacteria |
| | Bacterial dynamics (closed space) | Abscess; empyema; compound or therapeutic response | Bacterial DNA or other molecule (e.g., protein, carbohydrate, lipid) from tissue or abscess or fluid sample |
| | Endovascular bacterial dynamics | Endocarditis compound or therapeutic response | DNA or other molecule (e.g., protein, carbohydrate, lipid) from endovascular bacteria |
| Hematologic | Bone marrow precursor cell dynamics. Bone marrow cell dynamics. | Stem cell response (transplant, compound or therapeutic); status of cytopenias | DNA from bone marrow precursor cells. DNA from bone marrow cells. |
| | hemoglobin dynamics (red blood cells) | Hemolysis; anemia response (reticulocytosis); hemoglobinopathies | Hemoglobin |
| | Platelet phospholipid or dynamics | Thrombocytopenia; thrombocytosis | Phospholipids or DNA from platelets or platelet precursors |
| | Erythrocyte membrane dynamics | Anemia; hemolysis; compound or therapeutic response | Phospholipids from erythrocytes |
| Genetic/Developmental/Reproductive | Spermatocyte dynamics | Spermatogenesis; male infertility; compound or therapeutic response; endocrine disruptors | DNA from spermatocytes |
| | Timing of embryonic protein, lipid, and dynamics | Developmental biology and disorders thereof | Embryonic proteins, lipids, or DNA |
| | Genomic DNA dynamics | Genetic instability; cancer risk | Genomic DNA (from at risk tissue if appropriate) |

Table abbreviations:
DNA = deoxyribonucleic acid.

F. Isotopically-Perturbed Molecules

In another variation, the methods provide for the production of isotopically-perturbed molecules (e.g., labeled fatty acids, lipids, carbohydrates, proteins, nucleic acids and the like) or fragments or degradatory products thereof. These isotopically-perturbed molecules or fragments or degradatory products thereof comprise information useful in determining the flux of molecules within the metabolic pathways of interest. Once isolated from a cell and/or a tissue of an organism, one or more isotopically-perturbed molecules or fragments or degradatory products thereof are analyzed to extract information as described, supra.

G. Kits

The invention also provides kits for measuring and comparing molecular flux rates in vivo. The kits may include isotope-labeled precursor molecules, and may additionally include chemical compounds known in the art for separating, purifying, or isolating proteins, and/or chemicals necessary to obtain a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for obtaining samples from the cell, tissue, or organism (e.g., specimen cups, needles, syringes, and tissue sampling devices) may also be optionally provided.

H. Information Storage Devices

The invention also provides for information storage devices such as paper reports or data storage devices comprising data collected from the methods of the present invention. An information storage device includes, but is not limited to, written reports on paper or similar tangible medium, written reports on plastic transparency sheets or microfiche, and data stored on optical or magnetic media (e.g., compact discs, digital video discs, optical discs, magnetic discs, and the like), or computers storing the information whether temporarily or permanently. The data may be at least partially contained within a computer and may be in the form of an electronic mail message or attached to an electronic mail message as a separate electronic file. The data within the information storage devices may be "raw" (i.e., collected but unanalyzed), partially analyzed, or completely analyzed. Data analysis may be by way of computer or some other automated device or may be done manually. The information storage device may be used to download the data onto a separate data storage system (e.g., computer, hand-held computer, and the like) for further analysis or for display or both. Alternatively, the data within the information storage device may be printed onto paper, plastic transparency sheets, or other similar tangible medium for further analysis or for display or both.

I. EXAMPLES

The following non-limiting examples further illustrate the invention disclosed herein:

Example 1

Triglyceride Synthesis (Lipogenesis) and Breakdown (Lipolysis) in Rats as a Biomarker of Obesity-Related Diseases or Conditions Triglyceride synthesis is the fundamental biochemical process (i.e., metabolic pathway) for fat formation (lipogenesis) and therefore is a biomarker for obesity-related diseases or conditions (obesity itself is a condition and is the principal, but not the only, condition of interest herein). Determining whether a compound or a combination of compounds or a mixture of compounds (e.g., a chemical entity such as a new chemical entity (NCE), or combinations of chemical entities such as a combination of NCEs, drug candidate, or a combination of drug candidates, drug lead, or a combination of drug leads, or an already-approved drug such as one listed in the Physician's Desk Reference (PDR) or Merck Index, or a combination of already-approved drugs, or a biological factor, or a combination of biological factors (or any combination of mixtures of NCEs, drug candidates, drug leads, already-approved drugs, and/or biological factors) can inhibit lipogenesis is important in determining whether a compound, or combination of compounds, or mixture of compounds has potential for treating obesity-related diseases or conditions or other metabolic disorders.

To assess whether a compound, or a combination of compounds, or a mixture of compounds inhibits lipogenesis (and therefore, as stated above, a candidate drug specific for treating obesity-related diseases or conditions, or other metabolic disorders) Sprague-Dawley rats (200-300 g Simonsen Labs, Gilroy, Calif.) are either exposed to a compound, or combination of compounds, or mixture of compounds, or left unexposed (i.e., controls). Rats are administered a compound or combination of compounds or a mixture of compounds or vehicle via an appropriate route of administration. One compound, or a combination of compounds, or a mixture of compounds may be administered.

An initial priming dose of 99.8% $^2H_2O$ is given via intraperitoneal injection to achieve ca. 2.5% body water enrichment (assuming 60% body weight as water) followed by administration of 8% $^2H_2O$ in drinking water for up to 12 weeks.

Adipose tissue samples are placed in dual glass tissue grinders (e.g., Kontes tissue grinders, Kimble Kontes, Vineland, N.J.) with 1 ml methanol:chloroform (2:1), ground until homogenous then centrifuged to remove protein. The solution is extracted with 2 ml each chloroform and water. The aqueous phase is discarded and the lipid fraction is transesterified by incubation with 3N methanolic HCL (Sigma-Aldrich) at 55° C. for 60 min. Fatty acid methyl esters are separated from glycerol by the Folch technique, with the modification that pure water rather than 5% NaCl is used for the aqueous phase. The aqueous phase containing glycerol is then lyophilized and glycerol is converted to glycerol triacetate by incubation with acetic anhydride:pyridine, 2:1 as described elsewhere (Hellerstein, M. K., R. A. Neese, and J. M. Schwarz. *Am J Physiol* 265:E814-20, 1993, herein incorporated by reference). Some samples are extracted and then TG separated from other acyfglycerides by thin layer chromatography (TLC) as described elsewhere (Jung, H. R., S. M. Turner, R. A. Neese, S. G. Young, and M. K. Hellerstein. *Biochem J* 343 Pt 2:473-8, 1999, herein incorporated by reference), then analyzed as described, supra.

Glycerol-triacetate is analyzed for isotope enrichment by GC/MS, as described, supra.

The fraction of TG that is newly synthesized, (f) is calculated as described, supra.

The theoretical plateau or asymptotic value ($A_1^\infty$) in TG-glycerol during $^2H_2O$ labeling is determined in two ways: by mass isotopomer distribution analysis (MIDA) of the combinatorial labeling pattern in glycerol ($A_1^\infty{}_{mida}$) and by measurement of plateau enrichments reached in "fully replaced" TG depots ($A_1^\infty$ plateau) (see below). The standard precursor-product equation is then applied:

$$f=1-e-ks*t$$

$$ks=-\ln(1-f)/t$$

Where ks represents the fractional replacement or synthesis rate constant and t is time of labeling.

The absolute synthesis rate of adipose TG is calculated by multiplying the measured fractional synthesis (ks) over the period of labeling times the pool size of TG. For the purpose of this calculation, TG content is assumed to be 10% of body weight in non-obese young rodents. The absolute synthesis rate of adipose tissue TG can be calculated as follows, $$\text{Absolute synthesis (mg/d)}=ks(d-1)\times TG \text{ content (mg)}$$

For statistical analysis, ANOVA is used to compare groups with p<0.05 as the criteria for significance. Curve fitting of label incorporation data is performed using Delta Graph (Delta Point, Inc.).

TG synthesis rates are then compared between exposed animals and unexposed animals to determine whether a compound, or a combination of compounds, or a mixture of compounds inhibits lipogenesis, which provides a basis for selecting compounds, combinations of compounds, or mixtures of compounds for development and evaluation for treating such obesity-related diseases and conditions.

One can also assess whether a compound, or a combination of compounds, or a mixture of compounds stimulates lipolysis using the protocols as described, supra. Stimulating lipolysis is also important in treating obesity-related diseases and conditions or other metabolic disorders; therefore, determining whether a compound, or a combination of compounds, or a mixture of compounds stimulates lipolysis is important in determining whether the compound, or combination of compounds, or mixture of compounds has potential to treat obesity-related diseases or conditions.

The net lipolytic (TG breakdown) rate in individual fat depots is calculated from the difference between the absolute rate of TG synthesis and the net rate of TG accumulation, where the latter is determined from the change in weight over time in a fat pad or in the whole body:

Net lipolysis (mg/d) = Absolute $TG$ synthesis − net $TG$ accumulation =

$([ks(d-1) \times TG \text{ content (mg)}] - [(\text{change in } TG \text{ content})/\text{time (d)}]$ Exposed animals are then compared to unexposed animals to determine if a compound or a combination of compounds or a mixture of compounds has lipolytic activity, which provides a basis for selecting and/or characterizing compounds for development and evaluation in treating indications such as obesity-related diseases and conditions and for evaluating efficacy, dose, etc.

Figure 21:
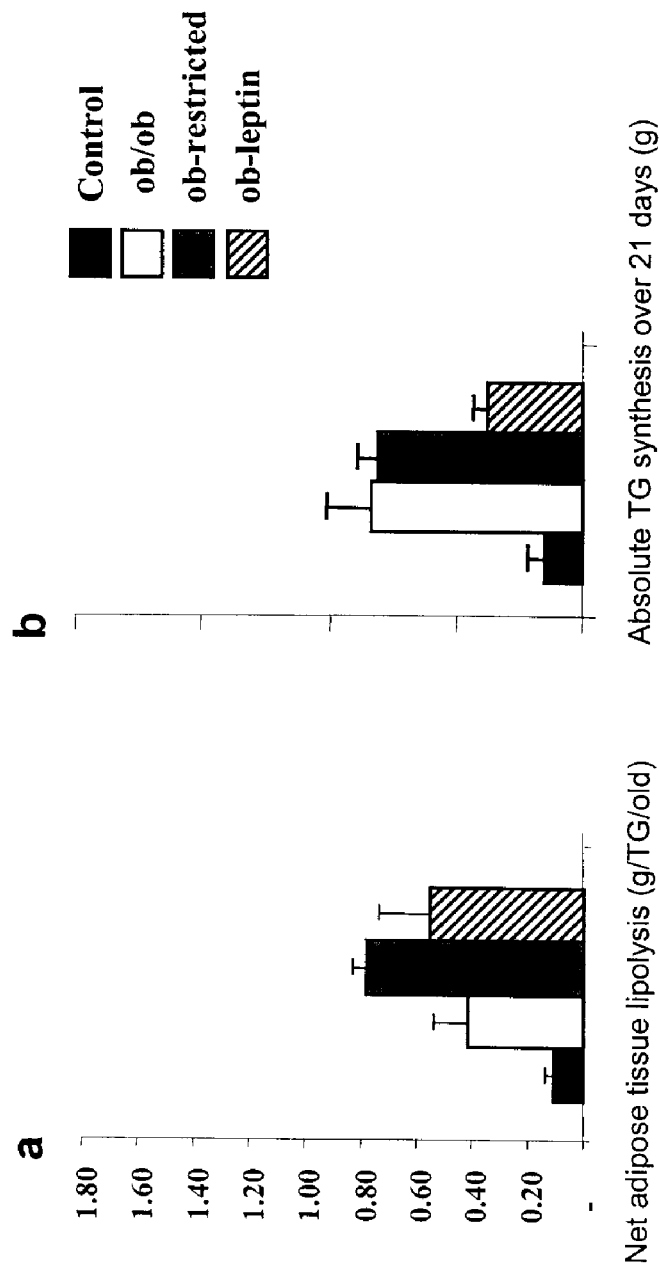
FIG. 21 depicts lipolysis (a) and adipose tissue TG synthesis (b) in mice. Lipolysis and adipose tissue TG synthesis were measured in normal mice, untreated ob/ob mice, ob/ob mice pair fed against control mice, and ob/ob mice treated with leptin. Leptin-treated mice showed a significant decrease in TG synthesis over the course of the study. Abbreviations: TG=triglyceride; g=grams.

As shown in FIG. 21, adipose lipolysis and triglyceride synthesis are increased in obese mice, which can be suppressed by leptin administration.

Example 2

DNA Synthesis in Rats as a Biomarker of Cell Proliferation

DNA synthesis is the fundamental biochemical process (i.e., metabolic pathway) for cell proliferation and is therefore a biomarker for cell proliferation. In some settings it may be desirable to stimulate cell proliferation (e.g., wound healing) while in other settings it may be desirable to inhibit cell proliferation (e.g., cancer).

Figure 2:
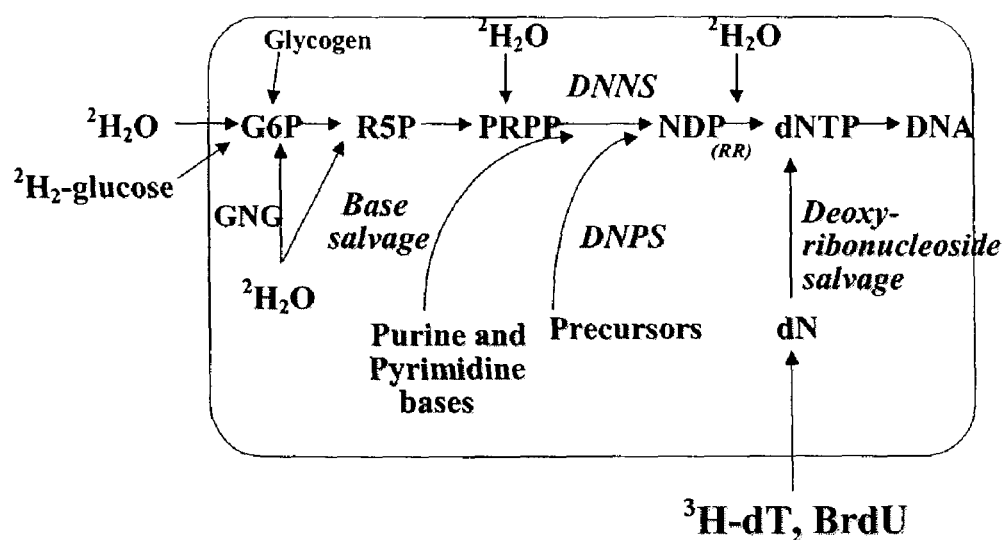
FIG. 2 shows a schematic diagram of an example metabolic pathway (DNA synthesis, both de novo and salvage) and various component elements. Locations of stable or radioactive isotope labeling are shown. G6P=Glucose-6-phosphate. R5P=ribose-5-phosphate. PRPP=5-phosphoribosyl-α-pyrophospate. NDP=nucleotide diphosphate. dNTP=deoxynucleotide triphosphate. RR=ribonucleotide reductase. dN=deoxynucleotide. $^3$H-dT=tritiated deoxythymidine. BrdU=5-bromo-2-deoxyuridine. GNG=gluconeogenesis. DNNS=de novo nucleotide synthesis. DNPS=de novo precursor synthesis.
Figure 3:
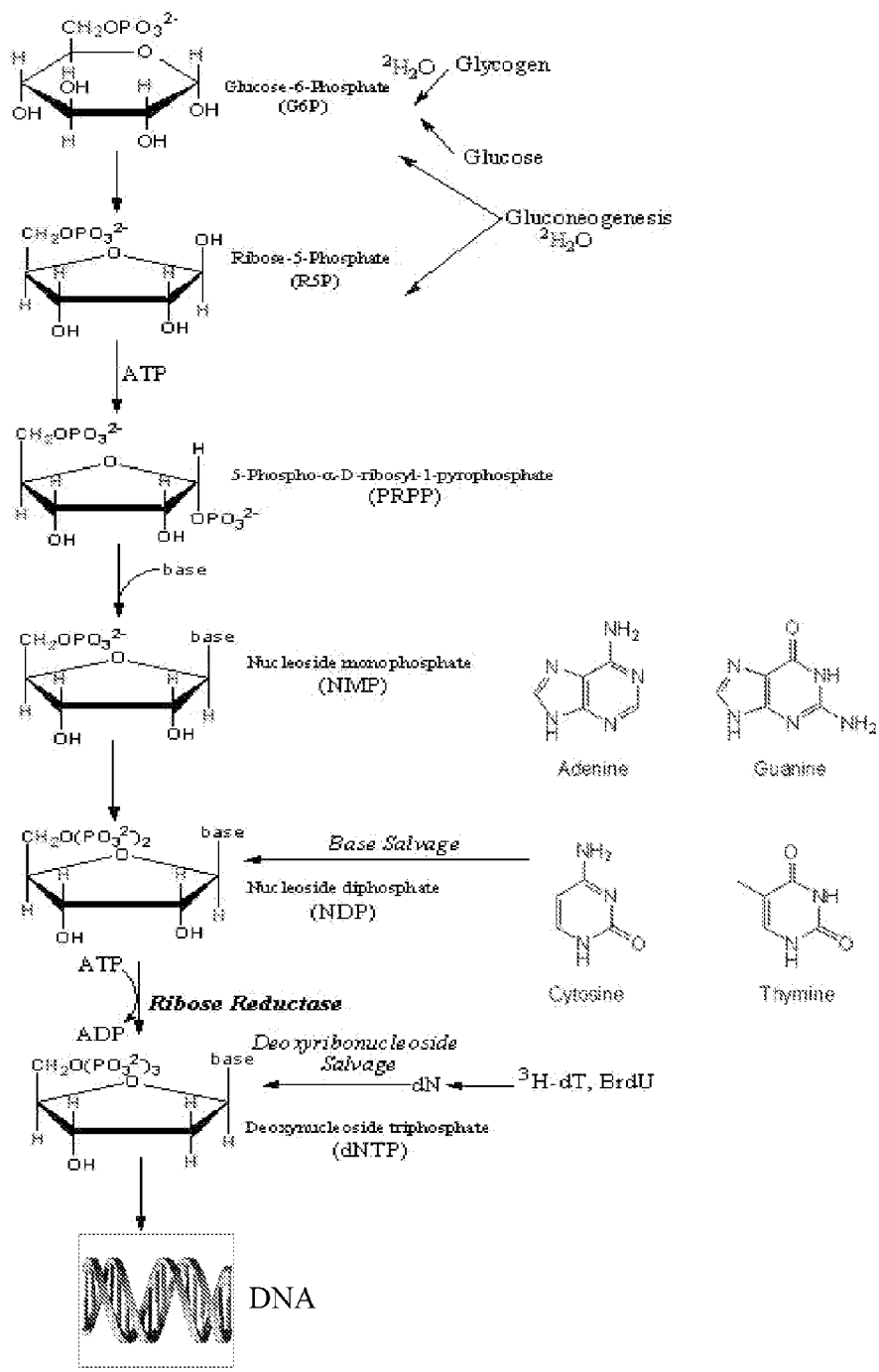
FIG. 3 shows label (i.e., $^2$H from $^2$H$_2$O) being incorporated into DNA.

Rats are administered $^2H_2O$ as discussed in Example 1, supra. DNA is labeled by $^2H$ as shown in FIGS. 2 and 3.

Rats are administered a compound or a combination of compounds or a mixture of compounds or vehicle (controls) as discussed in Example 1, supra.

DNA is then isolated from the tissue or cell of interest using a Qiagen kit (Qiagen, Valencia, Calif.), following the manufacturer's protocol. Isolated DNA, eluted in water, is adjusted to pH 9-10 and hydrolyzed enzymatically; deoxyribose is released selectively from purine (dA/dG) deoxynucleotides and converted to the pentane tetraacetate derivative. Alternatively, a pentafluorobenzyl derivative is prepared by reaction with excess pentafluorobenzyl hydroxylamine under acidic conditions, followed by acetylation with acetic anhydride. Either type of derivative is subsequently extracted with an organic solvent, dried with sodium sulfate, and analyzed by GC/MS as described, supra.

Isotope enrichment is then analyzed and flux rates calculated as described, supra. DNA synthesis is then determined as described, supra, and in U.S. Pat. No. 5,910,403. Exposed animals are then compared to unexposed animals to determine if the compound or combination of compounds or mixture of compounds has an effect on DNA synthesis (i.e., stimulation or inhibition of DNA synthesis). If a compound or combination of compounds or mixture of compounds inhibits DNA synthesis, this provides a basis for selecting and/or characterizing compounds for development and evaluation in indications benefiting from decreased cell proliferation (e.g., cancer including proliferating malignant cells and proliferating endothelial cells) and for evaluating efficacy, dosage, etc. If a compound or combination of compounds or mixture of compounds stimulates DNA synthesis, then this provides a basis for selecting and/or characterizing compounds for development and evaluation in treating indications benefiting from increased cell proliferation (e.g., wound healing) and for evaluating efficacy, dosage, etc.

Figure 20:
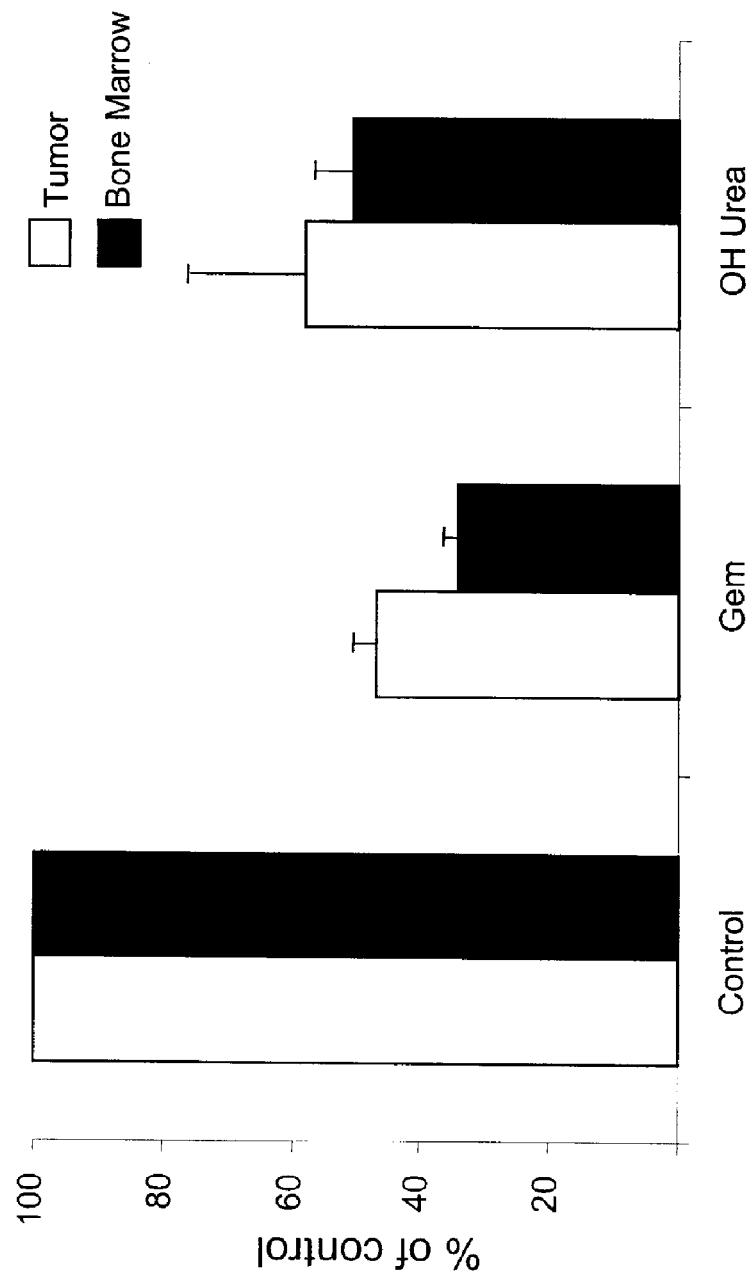
FIG. 20 depicts in vivo tumor cell proliferation over 5 days of chemotherapy treatment. Female balb/C mice were implanted subcutaneously with approximately 106 EMT7 mouse mammary carcinoma cells in matrigel and allowed to reach ca. 1500 $mm^3$. Mice were labeled with $^2H_2O$ with an i.p. bolus followed by 8% $^2H_2O$ in drinking water for the duration of the study. Mice received concurrent treatment with either 125 mg/kg Gem or 500 mg/kg HU. Gem was administered every other day, HU daily. At the end of 5 days tumors were removed, homogenized and DNA was isolated as described in Example 2, infra. Both chemotherapeutic agents suppressed tumor cell and bone marrow proliferation.

As shown in FIG. 20, cell proliferation can be reduced by anti-proliferative agents, in this case gemcitabine and hydroxyurea.

Example 3

DNA Synthesis in Rat Hippocampal Neuroprogenitor Cells as a Biomarker of Neurogenesis A compound or a combination of compounds or a mixture of compounds are tested on rats to determine whether they have effects on neurogenesis. Compounds with neurogenic potential (i.e., compounds that stimulate neurogenesis and/or inhibit neuroprogenitor cell death, including inhibition of apoptosis and/or inhibition of necrosis) may find use in treating spinal cord injury, Parkinson's disease, Huntington's disease, and other neurodegenerative disorders. By detecting neurogenesis and or inhibition of neuroprogenitor cell death, the methods allow for the selecting and/or characterizing of compounds for developing and evaluating the agents for treating the disorders listed, supra.

Rats are divided into exposed and control groups and administered labeled water as in Example 1, supra. After exposure to a compound or a combination of compounds or a mixture of compounds or vehicle if control rat, by gavage, intrathecal, or intracranial administration (route of administration is dependent on the chemistry of the compound, combination of compounds, or mixture of compounds, as is well known in the art) rats are euthanized by $CO_2$ asphyxiation and whole brains are removed.

For isolating tissue for neurogenesis analysis, the brain is bisected longitudinally and each hippocampal lobe is separated from the overlaying cortical white matter using the natural separation line along the alveus hippocampus. The white matter of the fimbria and subiculumis is removed.

Tissues are finely minced and digested for 45 min in a solution of papain (2.5 U/ml; Worthington, Freehold, N.J.), DNase (250 U/ml, Worthington), and neutral protease (1 U/ml Dispase; Boehringer Mannheim, Indianapolis, Ind.) dissolved in HibernateA.

Whole digested tissue is then suspended in HibernateA, triturated with a barely fire-polished siliconized Pasteur pipet, and thoroughly mixed with an equal volume of Percoll solution. The Percoll solution is made by mixing nine parts of Percoll (Amersham Pharmacia Biotech, Uppsala, Sweden) with one part 10×PBS (Irvine Scientific, Santa Ana, Calif.).

The cell suspension is then fractionated by centrifugation for 30 min, 18° C., at 20,000×g. Cell fractions are harvested and washed free of Percoll by three or more rinses in HibernateA.

DNA synthesis is measured as in Example 2, supra. DNA is labeled by $^2H$ as shown in FIGS. 2 and 3.

Exposed animals are then compared to unexposed animals to determine if a compound or a combination of compounds or a mixture of compounds increases DNA synthesis in hippocampal neuroprogenitor cells, which provides a basis for selecting and/or characterizing compounds for development and evaluation for treating neurodegenerative diseases and for evaluating efficacy, dosages, etc.

Example 4

DNA Synthesis in Mouse Hippocampal Neuroprogenitor Cells as a Biomarker of Neurogenesis Adult male mouse neuroprogenitor cell proliferation assays were prepared as described in Example 3, supra. Mice were chronically treated with either vehicle, fluoxetine (10 mg/kg/day), or imipramine (20 mg/kg/day). Two weeks after initiation of drug treatment, mice were labeled with 10% $^2H_2O$. Mice were sacrificed after 3 or 7 days of label, hippocampal progenitor cells were isolated, followed by DNA isolation and GC_MS analysis as described in Example 2, supra.

Figure 7:
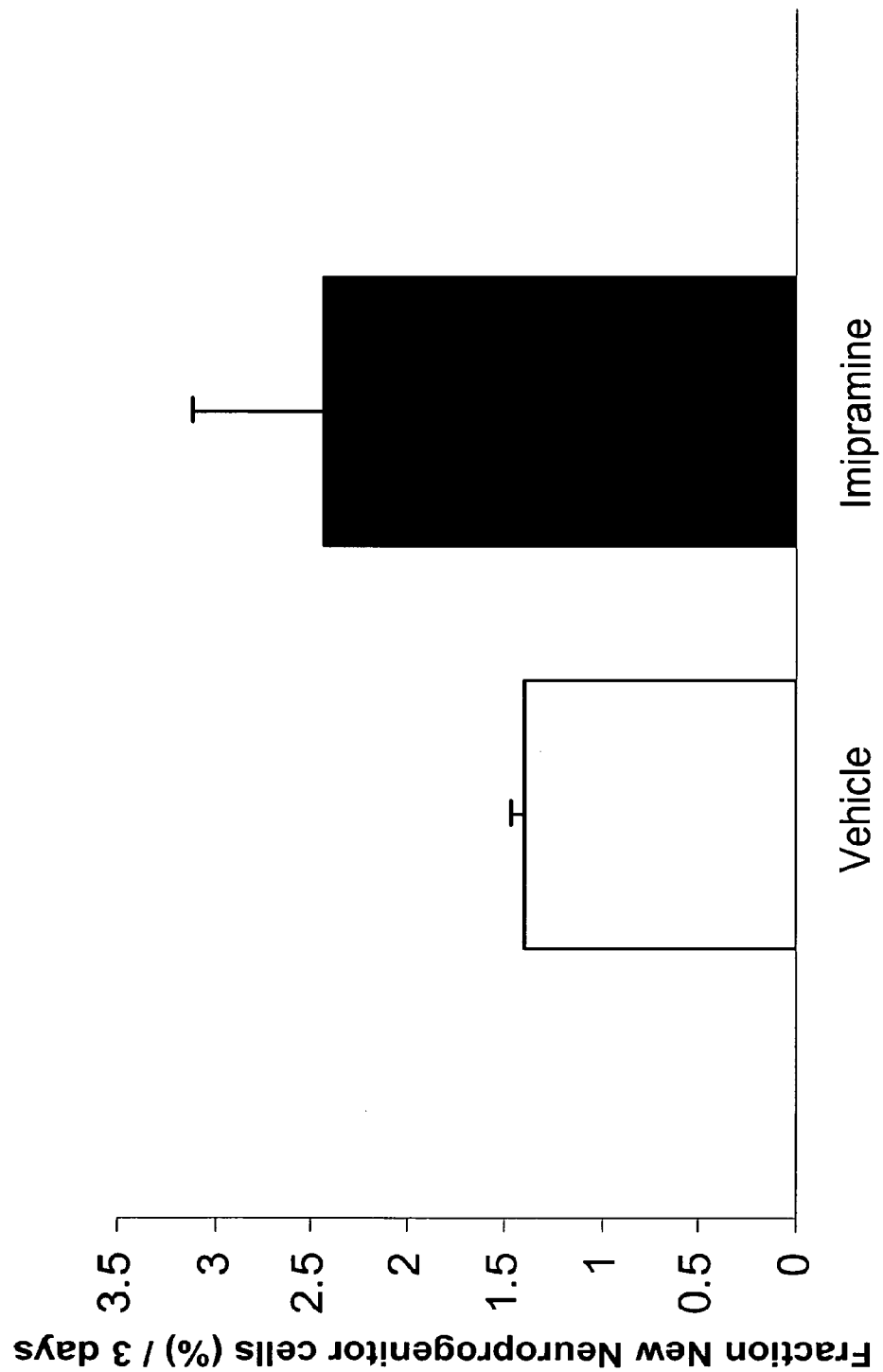
FIG. 7 depicts the effects of chronic imipramine treatment on hippocampal neuroprogenitor cell proliferation in male 129SvEv mice. Chronic Imipramine treatment increases progenitor cell proliferation in male 129SvEv mice. Mice received 3 weeks of treatment with imipramine (20 mg/kg/day) in drinking water and were labeled with 10% $^2$H$_2$O during the last 3 days of treatment. Data represent mean±SD, n=4 per group.
Figure 8:
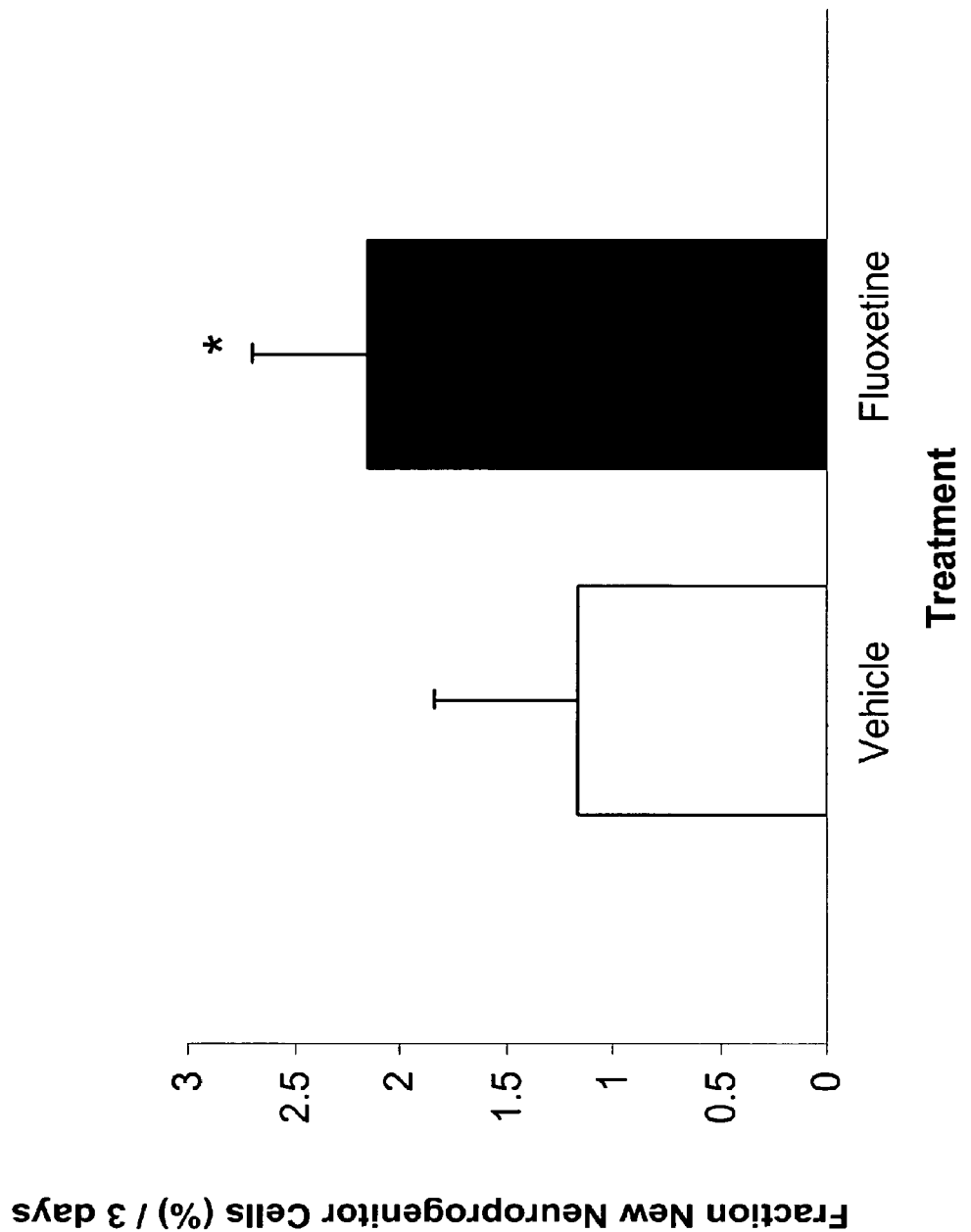
FIG. 8 depicts the effects of chronic fluoxetine treatment on hippocampal neuroprogenitor cell proliferation in male 129SvEv mice. Fluoxetine increases progenitor cell proliferation. Mice received 2 weeks of treatment with fluoxetine (10 mg/kg/day) in drinking water and were labeled with 10% $^2$H$_2$O during the last week of treatment. Data represent mean±SD, n=5 per group, *p<0.05 significantly different from vehicle group.

Chronic treatment with antidepressant drugs, imipramine and fluoxetine, produced a significant increase in the proliferation of mouse hippocampal neuroprogenitor cells in the hippocampus (see FIGS. 7 and 8). The magnitude of response is in accord with previous studies showing increased cell proliferation by BrdU labeling following antidepressant drug treatment.

Example 5

Measurement of Flux Rates of Aβ, APP, sAPP, and CTF in Mice as Biomarkers of Alzheimer's Disease Alzheimer Disease (AD) is a progressive neurodegenerative disorder that occurs spontaneously with aging. There are multiple factors that contribute to AD, but one of the most important components is the Aβ peptide, which forms insoluble deposits in the brains of patients, and leads to a range of neurodegenerative events. The Aβ peptide is derived from the beta-Amyloid Precursor Protein (APP), which is cleaved by a set of proteases to form Aβ. Perturbations in the processing of APP have been proposed to contribute to AD, as have changes in the rate of clearance of Aβ from the CNS. Therapeutic interventions aimed at altering the processing of APP, in order to reduce the generation of Aβ, provide a rational and widely pursued strategy for preventing or treating AD. Drugs that alter the processing of APP and/or Aβ are expected to make up the "next generation" of AD drugs.

Other drugs, including some in clinical trials, are focused on treating or slowing the events downstream of Aβ generation and deposition. Such downstream processes include neuroinflammation, memory loss, neuronal cell death, and impairment of neurogenesis.

As stated above, Aβ, APP, secreted amyloid precursor protein (sAPP), and the C-terminal fragment of APP (CTF) are important in the pathogenesis of AD. By measuring whether a compound, combination of compounds, or mixture of compounds can inhibit the synthesis of Aβ or APP or sAPP or CTF (or two or more of these proteins) one may in turn discover a novel means for treating AD.

The current benchmark for preclinical AD drug development is the APP transgenic mouse model. In these mice, total Aβ deposits in the brain are enumerated histologically. A reduction in this "plaque load" measurement is an indicator of drug effect. The formation of plaques in transgenic mice takes months to years, however, and the mice are expensive. A fast, quantitative preclinical assay of APP and/or Aβ kinetics that can be used in normal mice to test the actions of therapeutic interventions in the APP/Aβ pathway would greatly accelerate pre-clinical AD research. Isolation of Aβ or other peptides generated in this pathway from urine, plasma or cerebrospinal fluid could allow this kinetic approach to be applied in humans, as a biomarker of AD risk and response to therapies.

The flux of APP through the Aβ generating pathway will be a rapid and sensitive marker of efficacy for pre-clinical drug evaluation. Drugs that downregulate APP production or block the processing of APP by the Aβ generating protease β-secretase can be identified, compared for activity, and optimized through APP kinetics. An advantage of this approach is that these measurements can be made in young, wild-type animals, as well as in transgenic models of AD. A further advantage of this approach is that it is expected to be significantly faster (weeks to months vs. months to years) than waiting for transgenic animals to develop plaques.

Mice are labeled with $^2H_2O$ using the procedures described in Example 1, supra, for rats. Mice are given a compound, or a combination of compounds, or a mixture of compounds via gavage, intrathecal, or intracranial administration. Urine is collected to isolate Aβ protein. Total urinary protein is concentrated and exchanged in a suitable buffer for immunoaffinity purification. After immunoaffinity purification, Aβ can be further purified using size exclusion and/or reversed phase chromatography. The identity of purified peptides is confirmed by ELISA, western blot, and LC-MS (ESI).

Alternatively, mice are sacrificed and brain tissue is extracted and APP and CTF are obtained. Secreted APP is extracted from mouse cerebral spinal fluid (CSF) or brain. Proteins are extracted in neutral buffer, insoluble material is removed, and proteins precipitated. Resulting material is exchanged into an ion exchange buffer, and purified by ion exchange chromatography and then size exclusion and/or reversed phase chromatography. The identity of purified protein is confirmed by ELISA and western blot.

Purified proteins are hydrolyzed by treating with 6 N HCl, 16 hours at 110° C. Hydrolysates are dried and the N,O-penatfluorobenzyl derivative is generated by addition of PFBBr (Pierce) at 100° C. for 1 hour. Derivatized hydrolysates are extracted with ethyl acetate, dried with $NaSO_4$, and analyzed on a DB225 GC column, starting temp 100° C. increasing 10° C./min to 220° C. Alanine is analyzed with selected ion monitoring of m/z 448,449; other amino acids including glycine, methionine, leucine, isoleucine, and tyrosine also can be analyzed.

Enrichments for Aβ, APP, and CTF are performed as described, supra. Molecular flux rates for Aβ, APP, and CTF are calculated as described, supra. Exposed animals are then compared to unexposed animals to determine if a compound, or a combination of compounds, or a mixture of compounds inhibits Aβ, APP, sAPP, and CTF synthesis and/or stimulates their degradation, which provides a basis for selecting and/or characterizing compounds for development and evaluation for treating AD and for evaluating efficacy, dosages, etc.

Example 6

Glycolytic Disposal of Glucose in Normal Rats as a Biomarker for Insulin Resistance, Type II Diabetes, Metabolic Syndrome, and Cardiovascular Disease Glycolytic disposal of a glucose load reflects several insulin sensitive metabolic steps including uptake, phosphorylation, and glycolytic metabolism of blood glucose. Accordingly, whole body glycolytic rate is a biomarker for insulin resistance, metabolic syndrome, cardiovascular disease, and type II diabetes (see Reaven G M. Banting Lecture 1988. Role of insulin resistance in human disease. *Diabetes* 37(12):1595-607, 1988). Rats, as in Example 1, supra, are used to measure glycolytic disposal in vivo in response to a compound, or a combination of compounds, or a mixture of compounds for effects on insulin sensitivity. Because insulin resistance (lack of insulin sensitivity) underlies numerous diseases of Western society (Reaven), measurement of glycolytic disposal finds use in identifying and characterizing compounds for developing and evaluating therapeutics for insulin resistance, metabolic syndrome, cardiovascular disease, and type II diabetes.

More specifically, the method may be used to determine newly synthesized glycogen. Newly synthesized glycogen synthesis can be determined indirectly by subtracting glycolysis from the total amount of glucose initially administered since the total disappearance of glucose is equal to the total amount of glycolysis+the total amount of newly synthesized glycogen. The following equation can be used to calculate newly synthesized glycogen:

Total glucose utilization−glycolysis=newly synthesized glycogen

The $^2$H-glucose labeling protocol consists of an initial intraperitoneal (ip) injection or oral administration of 99.9% [6,6-$^2$H$_2$] glucose. For labeling rats, 2 mg labeled glucose per gram body weight is introduced. Body water is collected as serum at various timepoints. A compound or a combination of compounds or a mixture of compounds is administered by an appropriate route of administration such as gavage.

Glycolysis is measured by measuring deuterium in body water as a percent of administered [6,6-$^2$H$_2$]glucose normalized to account for different molar quantities of deuterium in molecular glucose and molecular water. Deuterated water is measured as described, supra. Glycolysis from exposed rats is compared with glycolysis from unexposed rats to determine if a compound or a combination of compounds or a mixture of compounds increased glycolysis, which provides the basis for selecting and characterizing compounds for development and evaluation for treating insulin resistance, type II diabetes, and/or other metabolic disorders and for evaluating efficacy, dosages, etc.

Figure 24:
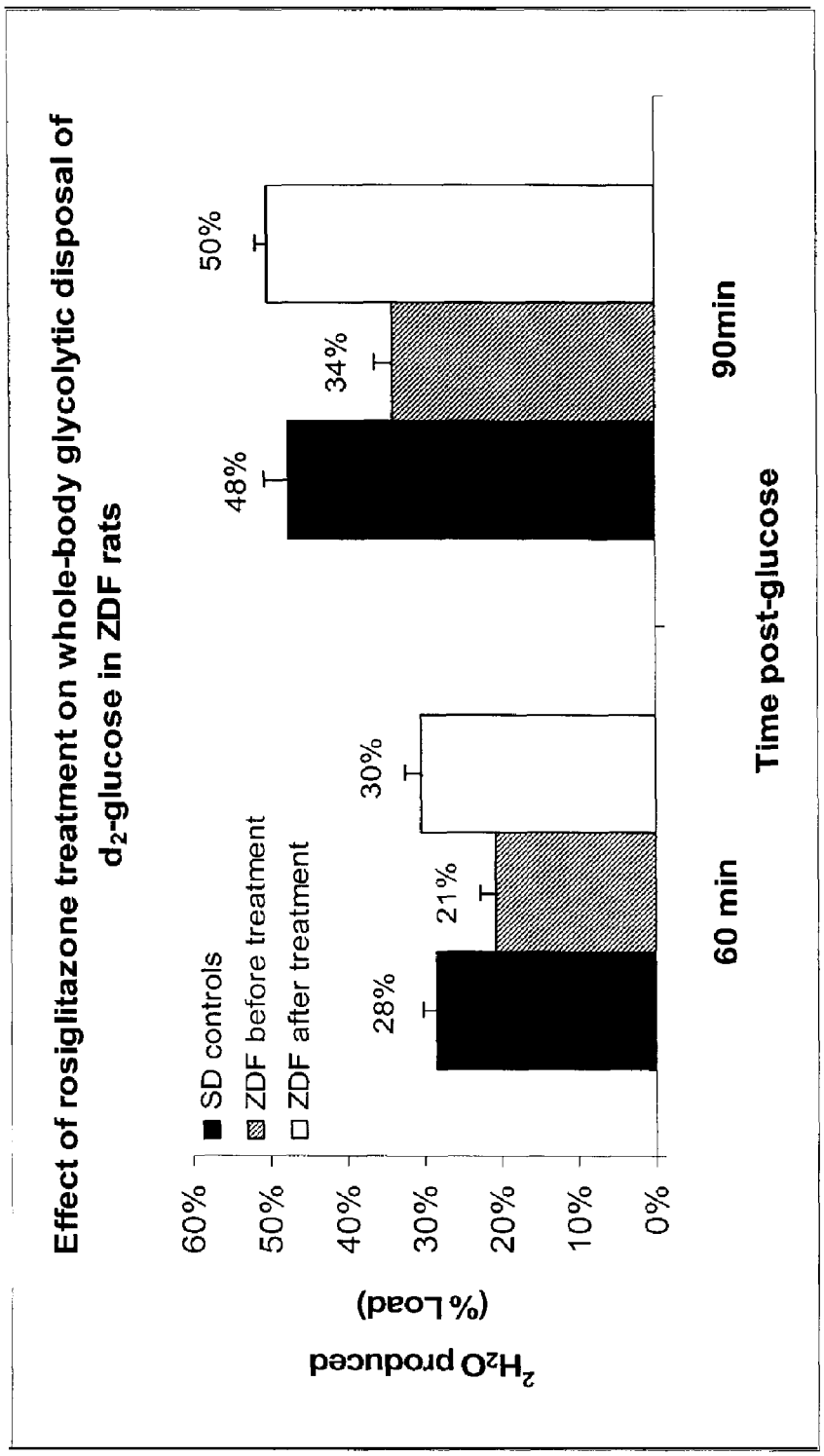
FIG. 24 depicts rates of glycolytic disposal as determined by measuring the production of deuterated water after administration of deuterated glucose. Blood was collected and analyzed 60 and 90 minutes after administration of deuterated glucose. SD controls represent normal animals, ZDF animals are a model of pre-diabetes, and show decreased glycolytic disposal. After treatment, ZDF animals have a glycolytic disposal rate that is similar to healthy control animals. This data shows a clear effect of a known insulin-sensitizing drug (rosiglitazone) in an animal model of disease.

As shown in FIG. 24, rosiglitazone, a known insulin sensitizing agent, can improve insulin sensitivity in Zucker-Diabetes-Fat (ZDF) rats, an animal model of insulin resistance and pre-diabetes.

Figure 29:
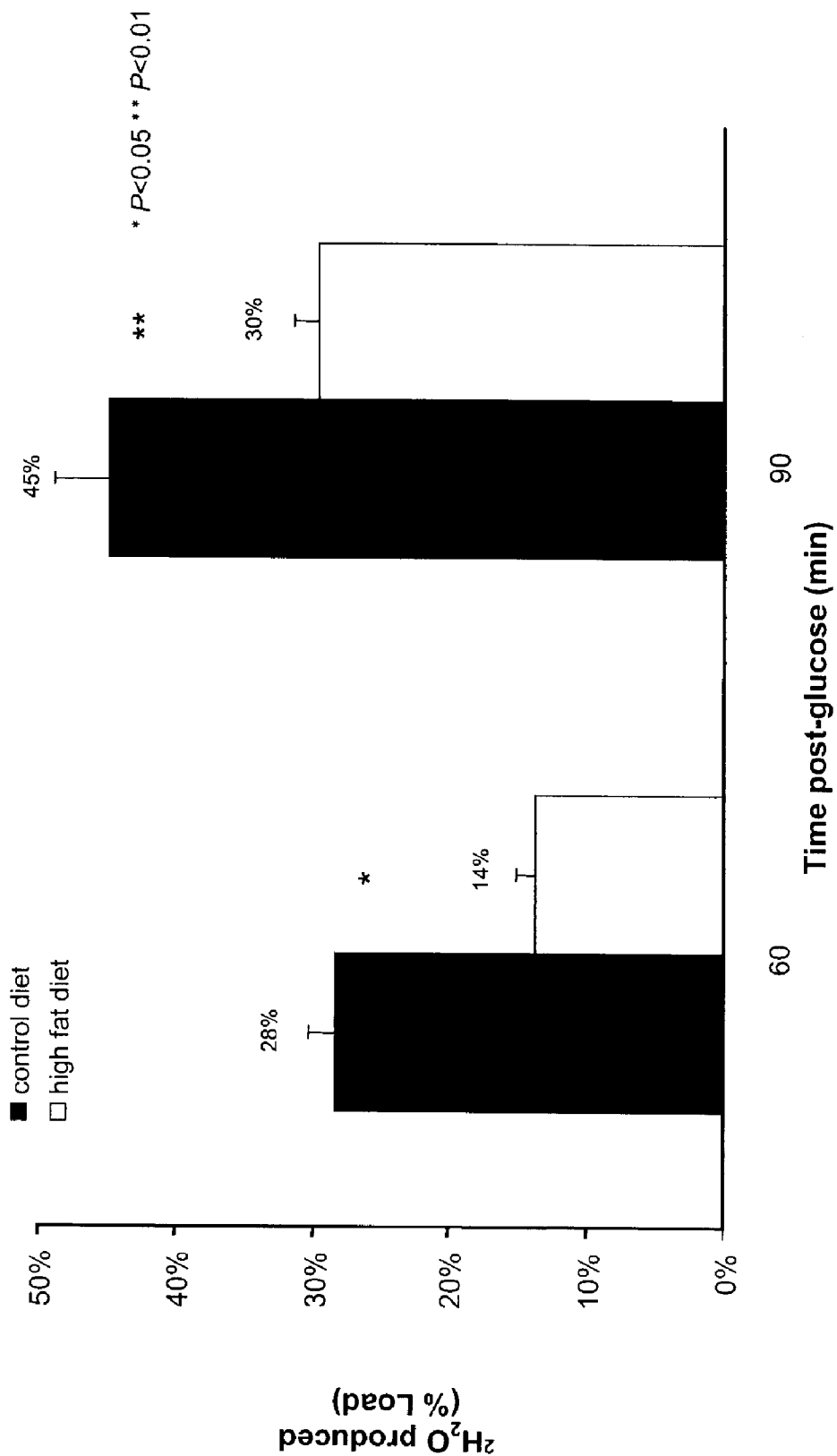
FIG. 29 depicts the effect of a high fat diet on normal rats as measured by the glycolytic disposal test. Deuterated water produced as a percentage of the total possible from the administered glucose load (% load) is shown for normal and high-fat diet (3 weeks) rats. Data was collected 60 and 90 minutes after administration of deuterated glucose.

FIG. 29 shows a decrease in glucose utilization as measured as a percent of total deuterated glucose administered. As can be seen, the rats fed a high fat diet for three weeks had an impaired ability to metabolize glucose compared to control rats who were fed a normal diet (results are statistically significant with $p<0.05$).

Figure 30:
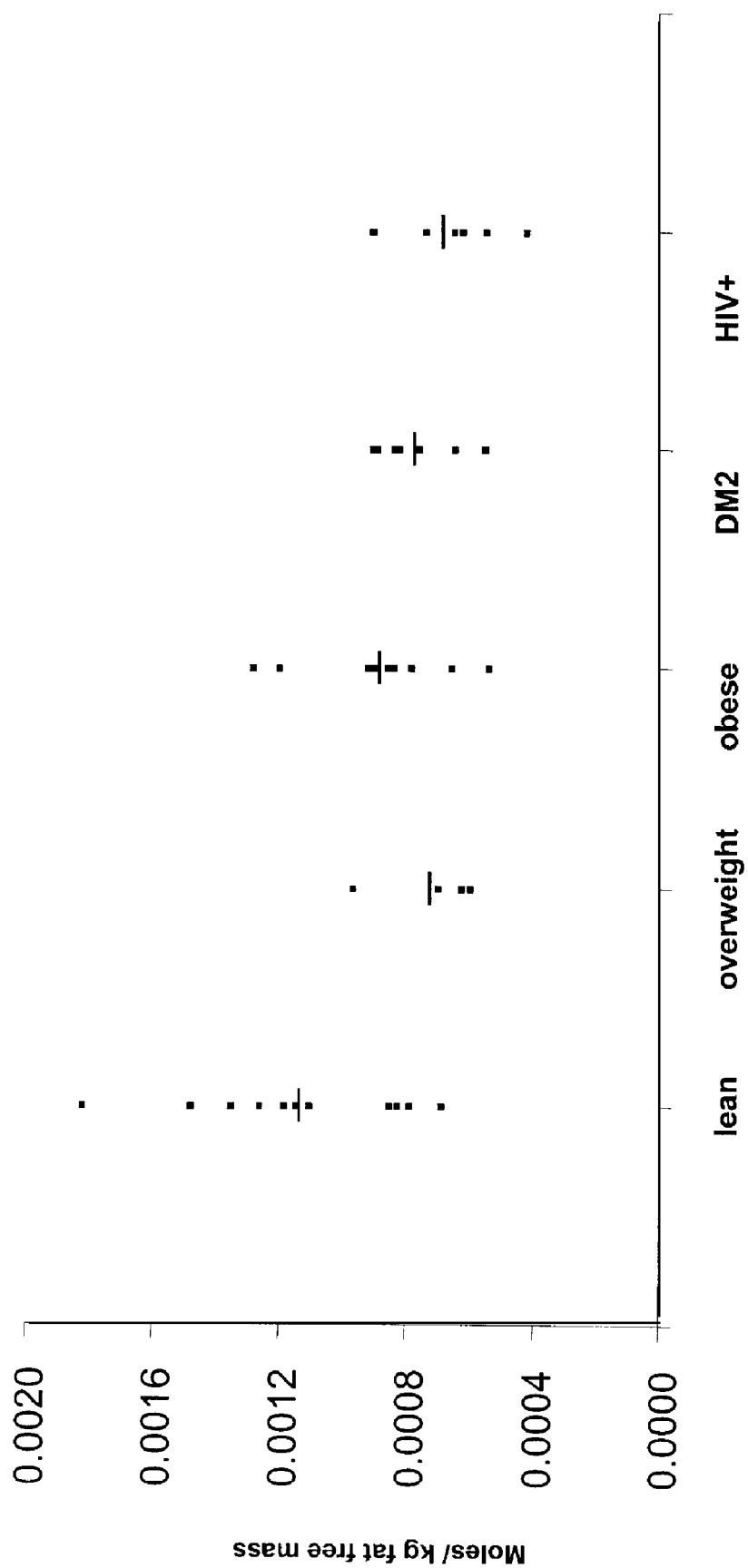
FIG. 30 depicts whole body glycolytic disposal in human patients with a variety of conditions. Lean=lean normal subjects. Overweight=overweight subjects. Obese=obese subjects. DM2=diabetes type II. HIV+=HIV positive patients. Results are presented as moles of $^2H_2O$ produced per kg of lean body mass. Measurements were made 4 hours after the administration of a 15 gram glucose load.

FIG. 30 shows glucose utilization in a number of human subjects grouped into lean, overweight, obese, type II diabetes, and HIV-infected individuals. All of the groups showed impaired glucose utilization with respect to the lean group, which is consistent with established data indicating overweight, obese, and HIV+ individuals are more likely to be insulin resistant. As expected, type II diabetes subjects were shown to be insulin resistant.

Example 7

Brain Galactocerebroside Turnover as a Biomarker of Remyelination in Demyelinating Diseases Brain galactocerebroside turnover is a fundamental biomarker for demyelination, the underlying biochemical process (metabolic pathway) in demyelination diseases such as multiple sclerosis (MS). Rats are given deuterated water as in Example 1, supra. Rats are administered a compound, or a combination of compounds, or a mixture of compounds via gavage, intrathecal, intraperitoneal, or intracranial administration. If it is found that a compound, or a combination of compounds, or a mixture of compounds stimulates remyelination and/or inhibits demyelination, this serves as a basis for selecting and characterizing compounds for development and evaluation for treating MS and other demyelinating diseases.

Weigh a set of 2-mL microcentrifuge tubes. Brains are collected from rat or mouse carcasses and weighed. The brain is put onto an ice-cooled glass plate, and 10 crystals of BHT are added. A razor blade is used to mince the brain for 1 minute. A spatula is used to put the minced brain back into the microcentrifuge tubes. The brain is minced well with a spatula. 80-120 mg of minced brain is put into 13×100 mm glass tubes with PTFE screw caps ensuring the tissue is at the bottom of the tube. The rest of the brain is stored in the microcentrifuge tubes at −20° C. 2 mL of chloroform-methanol 2:1 (v/v) with BHT is added into the glass tubes and the tubes are vortexed ensuring that all of the tissues are soaked in the solvent. Stand at least 5 minutes at room temperature. The tubes are centrifuged at 2000 RCF for 10 minutes at room temperature. The supernatant (lipid extracts) is poured into 2-mL screw capped vials and the solid residue is discarded.

TLC is performed. A 20 mL pipette is used to spot 20 mL of total cerebroside standard on lanes 1, 10, 19 of Whatman LK6DF silica gel 60 TLC plates. For each sample 40 µL of lipid extracts are spotted on each lane The TLC plates are developed using 69.2% chloroform, 26.6% methanol, 4.2% water developing solvent. After TLC plates develop, wait 15 minutes for the plates to dry. 20 iodine crystals are put into a tank specially used for iodine vapor. The tank is put on a heatblock set at 80° C. The dried TLC plates are put in the iodine tank to visualize the spots of lipids containing double bonds. The spots of total cerebroside standard are matched with those of samples. The silica gel is collected onto weighing paper and transferred to a 12×75 mm disposable glass tube. 2 ml of 65% dichloromethane/25% methanol/10% ammonium hydroxide solution is added and vortexed. Let stand until silica settles. The solvent is poured into a 13×100 mm screw cap tube and dried down. The sample is then resuspended in 1 ml of chloroform-methanol 2:1 with BHT and 1 mL of 3N methanolic HCl is added into the tube and the tube is capped tightly. The tubes are put on a heatblock at 80° C. for 1 h. The tubes are then removed from the heating block and allowed to cool to room temperature. 1.5 mL H$_2$O and 3 mL hexane are added into the tubes and the tubes are vortexed. 1.8-2 mL of the bottom layer (methyl glucose and methyl galactose) are transferred to GC vials. The GC vials dried in the speedvac. Following drying 100 µL of freshly made acetic anhydride-pyridine 2:1 (v/v) is added to the GC vials and the vials are covered and allowed to stand for 1 h at room temperature. The vials are then blown down under N$_2$ until dry. 100 µL ethyl acetate is. The samples are run on the GC/MS and galactocerebroside enrichments are determined. The molecular flux rates of galactocerebroside is determined as described supra, from rats exposed to a compound or a combination of compounds or a mixture of compounds and unexposed (vehicle control) rats. Enrichments of galactocerebroside greater than galactocerebroside enrichments in control animals indicates increases synthesis of galactocerebroside and possible remyelination (which, as discussed supra, provides a basis for selecting and/or characterizing a compound for development and evaluation for treating MS and other demyelinating diseases and for evaluating efficacy, dosages, etc.).

Enrichments that are less than controls indicates reduced myelin synthesis (pointing to neuronal toxicity, specifically toxicity to the myelin sheath; this will find use in identifying neurotoxic chemicals such as new industrial solvents).

Figure 26:
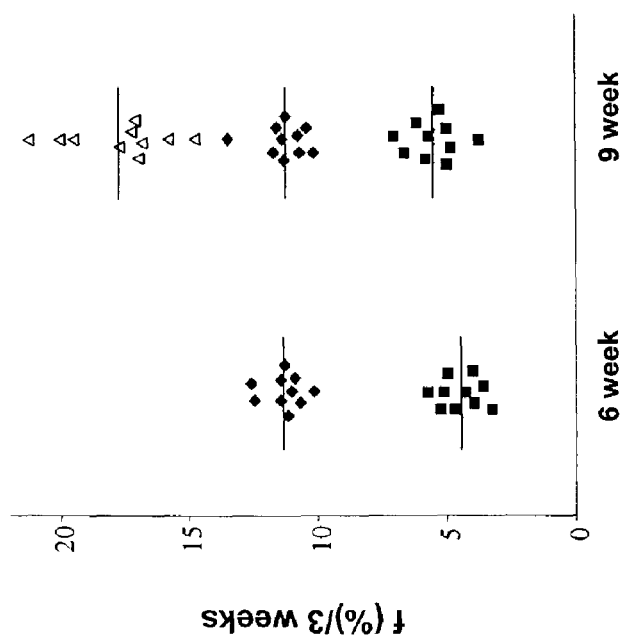
FIG. 26 depicts the fractional synthesis of myelin as determined by measuring deuterium incorporation into galactocerebroside (GalCer). Animals were treated as described for either 6 or 9 weeks, and labeled with deuterated water for the last 3 weeks of treatment. Control animals (closed diamonds) show a synthesis rate of 12% new (GalCer) in 3 weeks. Animals treated with a demyelinating toxin, cuprizone, show a decrease in the rate of fractional synthesis—reduced to about 5% new (closed squares). Animals treated with cuprizone for 6 weeks, and then given deuterated water for 3 weeks beginning at the time cuprizone treatment ceased show a dramatic increase in fractional synthesis (open triangles) as remyelination occurs.

As shown in FIG. 26, cuprizone, a known demyelinating toxic agent, is shown to suppress synthesis of galactocerebroside (GalCer) in the brain. After removal of cuprizone, fractional synthesis of GalCer is increased above the normal rate during the remyelinating phase.

Example 8

Collagen Turnover in Rats as a Biomarker of Osteoarthritis

The loss of cartilage from the articular surface is a principal feature in advanced osteoarthritis (OA). Considerable evidence supports the hypothesis that this loss is due, at least in part, to increased degradation rates of collagen. Thus, collagen turnover (degradation of collagen into its constituent breakdown products, which are principally hydroxyproline and telopeptides) is a fundamental biomarker in the underlying biochemical process (metabolic pathway) of OA and other joint diseases involving cartilage destruction (for a depiction of collagen labeling see FIG. 4; for its biosynthetic and degradative pathways, see FIG. 5).

Normal female rats (13 weeks of age, Sprague Dawley) will be labeled with $^2H_2O$ by the following protocol: at time 0 an ip injection of sterile 100% $^2H_2O$ 0.9% NaCl will be administered (30 ml/kg). Drinking water will be replaced with a solution containing 8% $^2H_2O$ and maintained until sacrifice.

Rats are administered a compound or a combination of compounds or a mixture of compounds via an appropriate route of administration. If it is found that a compound or a combination of compounds or a mixture of compounds inhibits collagen degradation (by, for example decreasing enrichment of degradation products of collagen including peptides, free hydroxyproline and/or telopeptides), this serves as a basis for selecting and/or characterizing compounds for development and evaluation for treating OA and other joint diseases involving cartilage destruction and for evaluating efficacy, dosages, etc.

Rats (five per time point) will be collected after 2, 4, 8, and 12 days of $^2H_2O$ labeling. Articular cartilage will be collected from hindlimb knee surfaces (MTP, LTP, MFC, LFC) and the femoral head and placed into pre-weighed RNAse free tubes, snap frozen and stored at −70 C until analyses.

Collagen is isolated by initially homogenizing tissue in 0.1 M NaOH. Collagen is purified from as little as 10 mg of fresh or frozen total liver homogenate as follows: using a Polytron homogenizer, collagen is isolated from soft tissue by homogenizing in 0.5 mL 100 mM NaOH. Under these conditions, collagen remains insoluble while most other proteins are readily dissolved. After centrifugation at 7,000×g for 10 minutes at 4° C., the supernatant is discarded. The pellet is washed briefly with 2 mL $H_2O$ and solubilized in reducing Laemmli sample buffer (Bio-Rad, Hercules, Calif.) after boiling for 3 minutes. The dissolved material is size-fractionated by SDS-PAGE. Using standard techniques, proteins are subsequently transferred onto PVDF, and a collagen band corresponding to the alpha monomer of collagen is excised from the resulting membrane after staining the membrane with Coomassie blue.

Degradative products of collagen (e.g., free hydroxyproline, collagen-derived peptides, telopeptides) are initially concentrated by reversed phase solid phase extraction. This is followed by a series of chromatographic steps which include size exclusion, anion exchange, and reversed phase separation. During the isolation protocol, the presence of specific degradation products is monitored both by commercially available immunological reagents Cartilaps (Nordic Bioscience, Herlew, Denmark) as well as by electrospray ionization mass spectrometry (ES/MS). For ES/MS, a selected ion monitoring is based on masses of the most commonly occurring variant of CTxII, with molecular weights of 1592.64 being used. The turnover of collagen measured in the articular cartilage will be compared between each site collected and to the CTxII peptides isolated from the synovial fluid.

Degradative products of collagen (e.g., free hydroxyproline, collagen-derived peptides, telopeptides) are hydrolyzed by treating with 6 N HCl, 16 hours at 110° C. Hydrolysates are dried and the N,O-penatfluorobenzyl derivative is generated by addition of PFBBr (Pierce) at 100° C. for 1 hour. The hydroxyl group of hydroxyproline is further derivatized with methyl imidizole/MTBSTFA. Hydroxyproline is analyzed on a DB225 GC column, starting temp 100° C. increasing 10° C./min to 220° C. with selected ion monitoring of m/z 424, 425.

Synthesis rates will be measured and calculated as described, supra.

Example 9

Liver Cell Turnover as a Biomarker for Subclinical Liver Toxicity or Disease

Liver cell turnover is a biomarker for liver injury and disease. In fact, liver cell proliferation (in response to exposure to environmental contaminants or therapeutic compounds or other factors such as hepatitis viruses) occurs well before clinical manifestations of injury or disease. Measuring liver cell proliferation in vivo, in response to exposure to a compound, or a combination of compounds, or a mixture of compounds, for example, exposure to a toxic chemical (e.g., a new industrial chemical, an environmental pollutant, or a known liver toxicant such as carbon tetrachloride) or an environmental toxin (e.g., biological factor elicting a toxic effect) or exposure to a chemical entity (whether new or old), or a drug candidate, or a drug lead, or an already-approved drug, or a biological factor is a sensitive method, therefore, for detecting liver changes before clinical injury or disease occurs. The deoxyribose (dR) moiety of dNTPs in replicating DNA can be labeled endogenously, through the de novo nucleotide synthesis pathway, using stable isotope-labeled glucose or $^2H_2O$ (FIG. 1). In this example, rats are labeled with $^2H_2O$ using the procedures described in Example 1, supra. Control and exposed groups are used as described in Example 1, supra.

Mice are given $CCl_4$ i.p. twice weekly for up to 4 weeks, and continuous oral $^2H_2O$ is given throughout, following an i.p. bolus of $^2H_2O$. Livers are perfused in situ with saline to minimize blood cell contamination. Livers are homogenized and DNA from 5-mg aliquots is analyzed for $^2H$ incorporation by gas chromatography/mass spectrometry analysis, after isolation and hydrolysis of genomic DNA, as described in Example 1, supra. Livers are collected 4 days after the last dose of $CCl_4$. The cell proliferation rate can then be calculated from the enrichment in the DNA of the target cell compared to measured body water enrichment or to a reference cell type which is fully replaced.

DNA is extracted from a liver sample, either by biopsy or liver homogenate. Liver cell proliferation can be determined on a sample a small as 2 mg (400,000 cells). The use of total liver, rather than isolated hepatocytes, allows for efficient scale-up and the sample processing can be adapted to a 96-well automated system for extremely high throughput. Total liver cell proliferation will be compared to the measured proliferation of isolated hepatocytes, and non-parenchymal cells for validation. Total liver cell proliferation is a simpler method to employ than isolated hepatocyte proliferation, therefore if it is found that measuring total liver cell proliferation approximates isolated hepatocyte proliferation, then using total liver cell proliferation will be preferable to using isolated hepatocyte proliferation in detecting subclinical liver toxicity.

Figure 13:
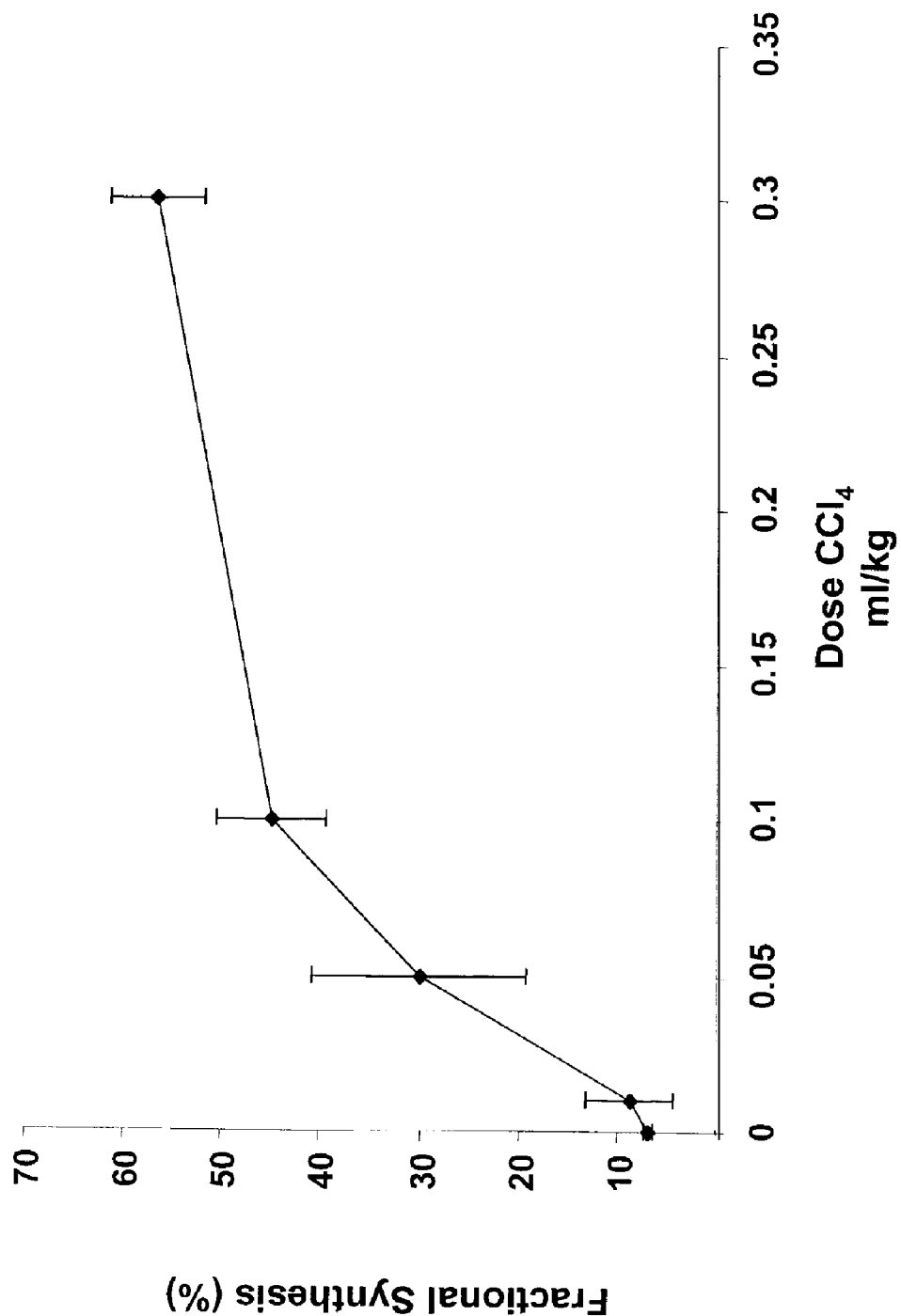
FIG. 13 depicts in vivo dose response of liver cell proliferation over 7 days of carbon tetrachloride treatment. Swiss Webster mice were given IP injections of CCl$_4$ over 7 days concurrent with $^2$H$_2$O.

FIG. 13 shows the effects of $CCl_4$ on liver cell proliferation over 7 days of treatment. Swiss Webster mice were given IP injections of $CCl_4$ over 7 days concurrent with $^2H_2O$. Total liver cell turnover (i.e., increased proliferation of liver cells)

was evident with increasing doses of $CCl_4$ reflecting the liver's response to the toxic insult.

Example 10

Collagen Synthesis as a Biomarker of Liver Fibrosis

Figure 4:
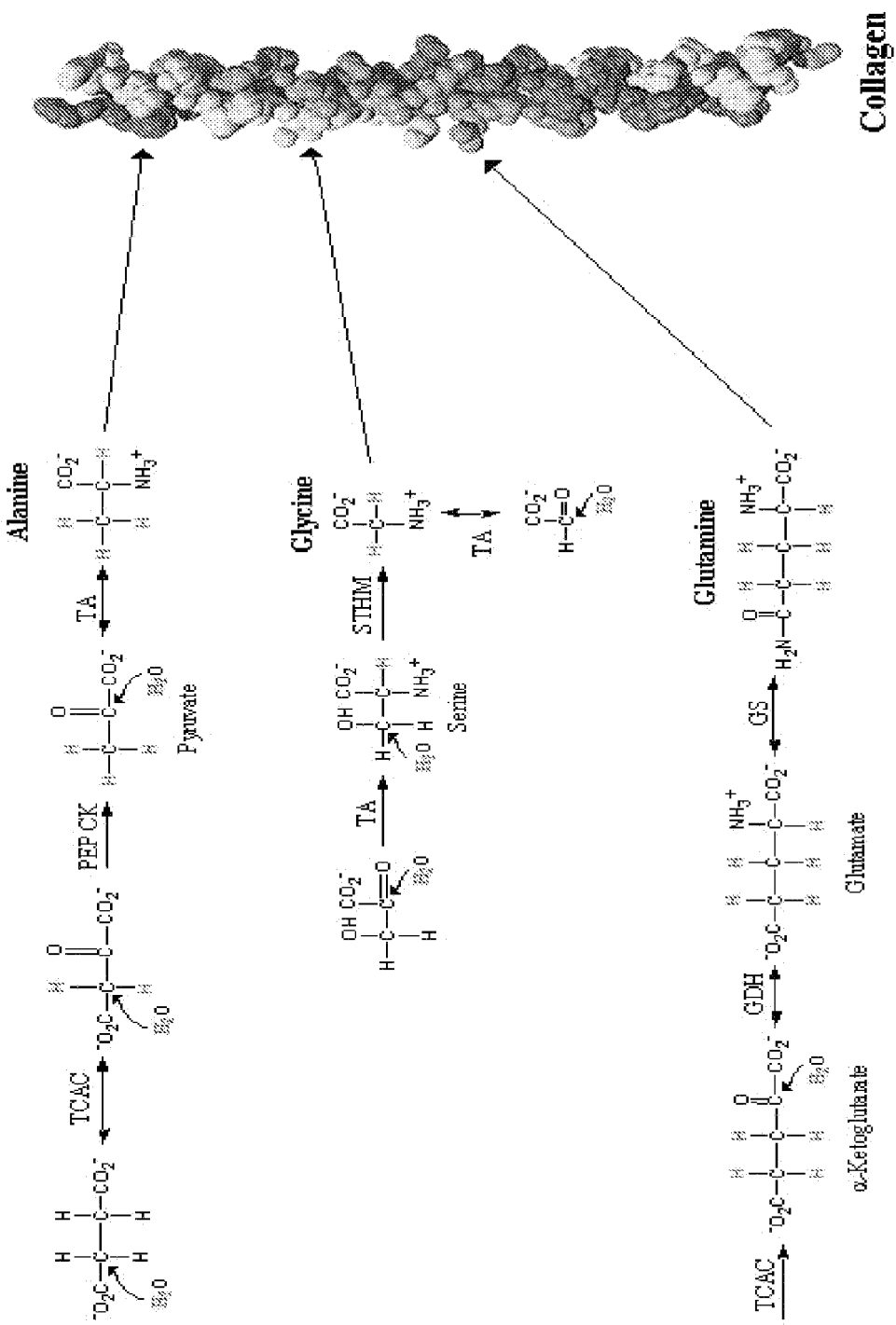
FIG. 4 shows label incorporation into collagen by way of labeled amino acids.
Figure 5:
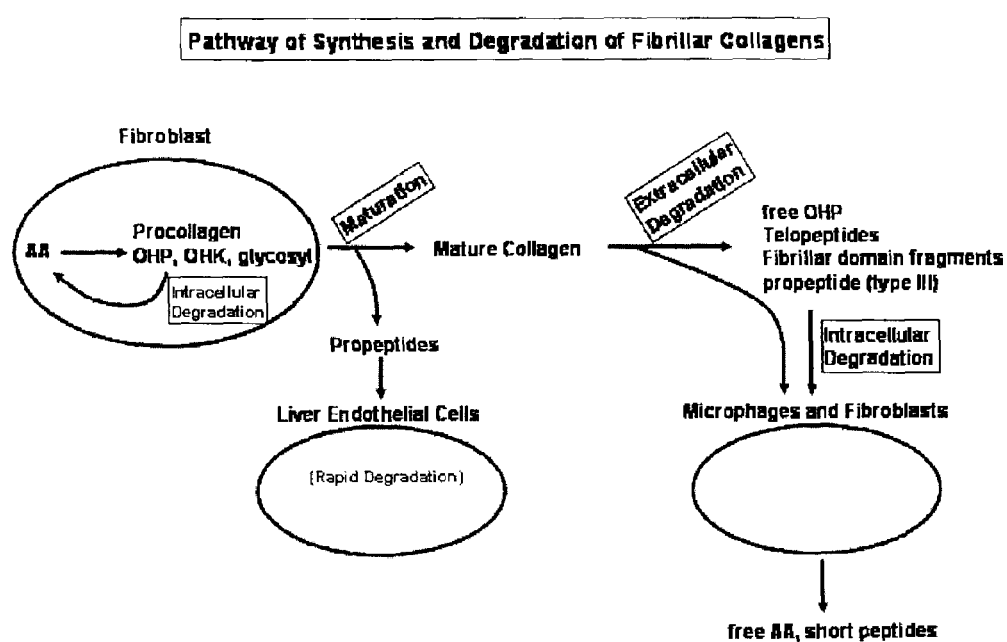
FIG. 5 shows the synthesis and degradation pathways for collagen.

Fibrosis, which is an overproduction of extracellular matrix (ECM) components, is a hallmark of many diseases of the vascular system, heart, lung, liver, and kidneys, and skin (for a depiction of collagen labeling see FIG. 4; for its biosynthetic and degradative pathways, see FIG. 5). Fibrosis generally occurs in response to tissue injury from toxicants such as alcohol as well as from mechanical and oxidative stresses. The most notable feature of tissue fibrosis is the chronic enhancement of biosynthesis and reduced degradation of collagen; eventually this buildup reduces organ function and leads to organ failure.

Early, predictive diagnosis of tissue fibrosis is critical for the assessment of drug toxicity and disease treatment. However, existing biomarkers of fibrosis are often expensive and insensitive. These include endpoint assays for measurement of increased collagen pool size and histochemical staining of ECM components within tissue biopsies. Measurements of alterations in collagen synthesis are more sensitive and quantitative than measurements of pool size or qualitative histopathology scoring.

Hepatic fibrosis, the accumulation of excessive extracellular matrix (collagen), is a common result of chronic liver injury or disease. Chronic, untreated fibrosis advances to cirrhosis, which is irreversible. Often associated with chronic alcohol abuse, fibrosis can result from other drug toxicities (including adverse effects from chemotherapeutics such as fenofibrate, griseofulvin, or methotrexate) and from exposure to environmental chemicals (e.g., new industrial chemicals or known industrial chemicals such as carbon tetrachloride). In fact, any drug that causes low persistent hepatic damage could lead to fibrosis which may not appear in clinical practice until many years after wide spread use.

In this example, rats are labeled with $^2H_2O$ using the procedures described in Example 1, supra. Control and exposed groups are used as described in Example 1, supra. Exposed rats are given a single dose of diethylnitroseamine (200 mg/kg). Diethylnitroseamine is a potent hepatotoxin, carcinogen and mutagen and has been shown to induce fibrosis from a single dose. Rats will receive $^2H_2O$ continuously for up to 2 weeks, then animals will be sacrificed at 7 and 14 days post treatment.

Collagen is purified from as little as 10 mg of fresh or frozen total liver homogenate as follows: using a Polytron homogenizer, collagen is isolated from soft tissue by homogenizing in 0.5 mL 100 mM NaOH. Under these conditions, collagen remains insoluble while most other proteins are readily dissolved. After centrifugation at 7,000×g for 10 minutes at 4° C., the supernatant is discarded. The pellet is washed briefly with 2 mL $H_2O$ and solubilized in reducing Laemmli sample buffer (Bio-Rad, Hercules, Calif.) after boiling for 3 minutes. The dissolved material is size-fractionated by SDS-PAGE. Using standard techniques, proteins are subsequently transferred onto PVDF, and a collagen band corresponding to the alpha monomer of collagen is excised from the resulting membrane after staining the membrane with Coomassie blue.

Collagen degradative products are derivatized and analyzed as described in Example 8, supra.

Hydroxyproline is a molecule of interest and is measured as OH-proline, the molecule being essentially unique to collagen. Because of this fact, total liver protein hydrolysate can be derivatized and the $^2H$ enrichment of hydroxyproline determined by GC/MS. Fractional synthesis of collagen in normal and diethylnitroseamine-treated animals is calculated from $^2H$ incorporation into hydroxyproline from total liver protein. In this fashion collagen synthesis can be determined with a minimal amount of sample preparation, lending itself to high-throughput analysis. Therefore, any entity (or combinations of entities) can be screened to determine whether collagen synthesis occurs in response to exposure. If collagen synthesis is observed, the organism is at increased risk for liver fibrosis. The method therefore allows for the screening of a compound, or a combination of compounds, or a mixture of compounds to determine whether they induce collagen synthesis in the liver and therefore possess hepatotoxic effects that place the exposed organism at increased risk for liver fibrosis and cirrhosis.

Conversely, if it is found that a compound, or a combination of compounds, or a mixture of compounds inhibits or reduces collagen synthesis and/or enhances collagen degradation, then this provides the basis for selecting and/or characterizing the compound for development and evaluation for treating liver fibrosis, and for evaluating efficacy, dosages, etc.

Figure 19:
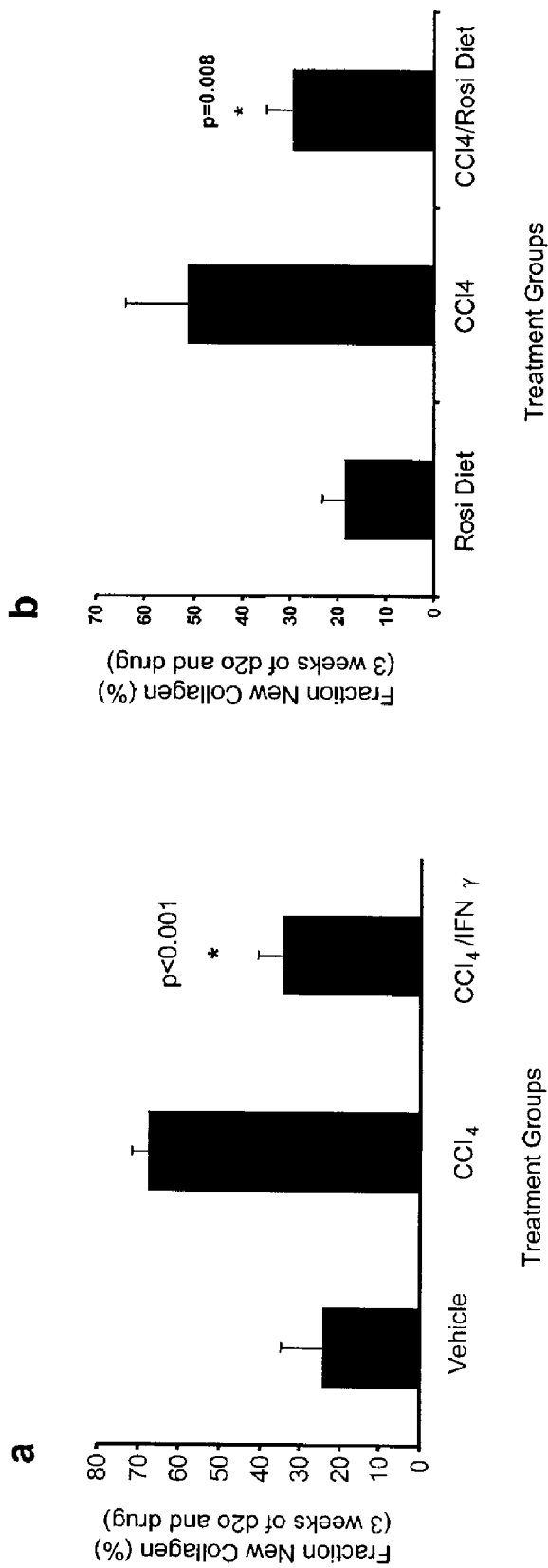
FIG. 19 depicts the effect of therapeutic agents on carbon tetrachloride ($CCl_4$)-induced liver fibrosis. Both Interferon-gamma (a) and rosiglitazone (b) reduce the rate of collagen synthesis in mice treated with $CCl_4$.

As shown in FIG. 19, $CCl_4$, a known fibrotic agent, increases collagen synthesis in mouse liver, an effect that is suppressed by two anti-fibrotic agents (a) interferon-gamma and (b) rosiglitazone.

Example 11

Collagen Synthesis as a Biomarker of Pulmonary Fibrosis

Fibrosis, which is an overproduction of extracellular matrix (ECM) components, is a hallmark of many diseases of the vascular system, heart, lung, liver, and kidneys, and skin (for a depiction of collagen labeling see FIG. 4; for its biosynthetic and degradative pathways, see FIG. 5). Fibrosis generally occurs in response to tissue injury from toxicants such as alcohol as well as from mechanical and oxidative stresses. The most notable feature of tissue fibrosis is the chronic enhancement of biosynthesis and reduced degradation of collagen; eventually this buildup reduces organ function and leads to organ failure.

Early, predictive diagnosis of tissue fibrosis is critical for the assessment of drug toxicity and disease treatment. However, existing biomarkers of fibrosis are often expensive and insensitive. These include endpoint assays for measurement of increased collagen pool size and histochemical staining of ECM components within tissue biopsies. Measurements of alterations in collagen synthesis are more sensitive and quantitative than measurements of pool size or qualitative histopathology scoring.

Pulmonary fibrosis may arise from exposure to a broad spectrum of airborne chemical pollutants and particulates, from sarcoidosis, as well as exposure to certain pharmacological agents such as carmustine. Idiopathic forms of pulmonary fibrosis in which etiology is unclear also exist.

Normal male rats (6 to 9 weeks of age, Sprague Dawley) are labeled with $^2H_2O$ by the following protocol: at time 0 an ip injection of sterile 100% $^2H_2O$ 0.9% NaCl is administered (30 mL/Kg). Drinking water is then replaced with a solution containing 8% $^2H_2O$ which is maintained until sacrifice.

Rats are administered a compound, or a combination of compounds, or a mixture of compounds via an appropriate route of administration such as ip injection. If it is found that a compound, or a combination of compounds, or a mixture of compounds inhibits or reduces collagen synthesis and/or enhances collagen degradation, this provides a basis for selecting and/or characterizing compounds for development and evaluation or treating pulmonary fibrosis and for evaluating efficacy, dosages, etc.

Conversely, if it is found that a compound, or a combination of compounds, or a mixture of compounds augments collagen synthesis and/or reduces collagen degradation, this provides a basis for reporting potential, hitherto unpublished toxicities of new chemical entities, drug candidates, drug leads, already-approved drugs, biological factors, environmental chemicals, new lead compounds and the like.

Rats (five per time point) are euthanized after 2, 7, 14, 21, and 28 days of $^2H_2O$ labeling. Tissues including but not limited to skin, lung, liver, heart, and kidney will be removed and stored at −20° C. until analyses.

Collagen is preferentially precipitated by initially homogenizing tissue in 0.1 M NaOH. The homogenate is centrifuged at 7,000×g, and the resulting pellet is size-fractionated by sodium dodecyl sulfate polyacrylamide gel electrophoresis. Proteins are transferred to PVDF solid support. Collagen is excised from the blot and hydrolyzed at 110° C. for 16 hours. Amino acids are derivatized and the $^2H$ content in treatment groups is measured and analyzed as a function of time, relative to control groups.

Collagen degradative products are derivatized and analyzed as described in Example 8, supra.

Example 12

Collagen Synthesis as a Biomarker of Myocardial Fibrosis

Fibrosis, which is an overproduction of extracellular matrix (ECM) components, is a hallmark of many diseases of the vascular system, heart, lung, liver, and kidneys, and skin (for a depiction of collagen labeling see FIG. 4; for its biosynthetic and degradative pathways, see FIG. 5). Fibrosis generally occurs in response to tissue injury from toxicants such as alcohol as well as from mechanical and oxidative stresses. The most notable feature of tissue fibrosis is the chronic enhancement of biosynthesis and reduced degradation of collagen; eventually this buildup reduces organ function and leads to organ failure.

Early, predictive diagnosis of tissue fibrosis is critical for the assessment of drug toxicity and disease treatment. However, existing biomarkers of fibrosis are often expensive and insensitive. These include endpoint assays for measurement of increased collagen pool size and histochemical staining of ECM components within tissue biopsies. Measurements of alterations in collagen synthesis are more sensitive and quantitative than measurements of pool size or qualitative histopathology scoring.

Myocardial fibrosis is a key feature of diseases of the heart. The most common cause is coronary arteriosclerosis. Other causes include: 1, relative coronary insufficiency due to cardiac hypertrophy due to hypertension, valvular disease; 2, healed rheumatic myocarditis; 3, healed infectious, immune, toxic, or idiopathic myocarditis; 4, scleroderma.

Normal male rats (6 to 9 weeks of age, Sprague Dawley) are labeled with $^2H_2O$ by the following protocol: at time 0 an ip injection of sterile 100% $^2H_2O$ 0.9% NaCl is administered (30 mL/Kg). Drinking water is then replaced with a solution containing 8% $^2H_2O$ which is maintained until sacrifice.

Rats are administered a compound, a combination of compounds, or a mixture of compounds via an appropriate route of administration such as ip injection. If it is found that a compound, or a combination of compounds, or a mixture of compounds reduces collagen synthesis and/or enhances collagen degradation in myocardial tissue, this provides a basis for selecting and/or characterizing compounds for development and evaluation for treating myocardial fibrosis and for evaluating efficacy, dosages, etc.

Contrastingly, if it is found that a compound, or a combination of compounds, or a mixture of compounds augments collagen synthesis and/or reduces collagen degradation, this provides a basis for reporting potential, hitherto unpublished myocardial toxicities of those compounds, combinations of compounds, or mixtures of compounds.

Rats (five per time point) are euthanized after 2, 7, 14, 21, and 28 days of $^2H_2O$ labeling. Tissues including but not limited to skin, lung, liver, heart, and kidney will be removed and stored at −20° C. until analyses.

Collagen is preferentially precipitated by initially homogenizing tissue in 0.1 M NaOH. The homogenate is centrifuged at 7,000×g, and the resulting pellet is size-fractionated by sodium dodecyl sulfate polyacrylamide gel electrophoresis. Proteins are transferred to PVDF solid support. Collagen is excised from the blot and hydrolyzed at 110° C. for 16 hours. Amino acids are derivatized and the $^2H$ content in treatment groups is measured and analyzed as a function of time, relative to control groups.

Collagen degradative products are derivatized and analyzed as described in Example 8, supra.

Example 13

Collagen Synthesis as a Biomarker of Dermal Fibrosis

Fibrosis, which is an overproduction of extracellular matrix (ECM) components, is a hallmark of many diseases of the vascular system, heart, lung, liver, kidneys, and skin (for a depiction of collagen labeling see FIG. 4; for its biosynthetic and degradative pathways, see FIG. 5). Fibrosis generally occurs in response to tissue injury from toxicants such as alcohol as well as from mechanical and oxidative stresses. The most notable feature of tissue fibrosis is the chronic enhancement of biosynthesis and reduced degradation of collagen; eventually this buildup reduces organ function and leads to organ failure.

Early, predictive diagnosis of tissue fibrosis is critical for the assessment of drug toxicity and disease treatment. However, existing biomarkers of fibrosis are often expensive and insensitive. These include endpoint assays for measurement of increased collagen pool size and histochemical staining of ECM components within tissue biopsies. Measurements of alterations in collagen synthesis are more sensitive, responsive, and quantitative than measurements of pool size or qualitative histopathology scoring.

Dermal fibrosis arises as a part of the pathology of scleroderma, sclerodermoid disorders, graft versus host disease, severe acne and other disorders. Halofuginone and other antifibrotic agents are being investigated and prescribed for such treatment, but this field would greatly accelerate with the advent of better tests for the early detection of such diseases and their animal models.

Normal male rats (6 to 9 weeks of age, Sprague Dawley) are labeled with $^2H_2O$ by the following protocol: at time 0 an ip injection of sterile 100% $^2H_2O$ 0.9% NaCl is administered (30 mL/Kg). Drinking water is then replaced with a solution containing 8% $^2H_2O$ which is maintained until sacrifice.

Rats are administered a compound, a combination of compounds, or a mixture of compounds via an appropriate route of administration such as ip injection. If it is found that a compound, or a combination of compounds, or a mixture of compounds reduces collagen synthesis and/or enhances collagen degradation, this provides a basis for selecting and/or characterizing compounds for development and evaluation for treating dermal fibrosis and for evaluating efficacy, dosages, etc.

Conversely, if it is found that a compound, or a combination of compounds, or a mixture of compounds augments collagen synthesis and/or reduces collagen degradation, this provides a basis for reporting potential, hitherto unpublished toxicities of those compounds, combinations of compounds, or mixtures of compounds.

Rats (five per time point) are euthanized after 2, 7, 14, 21, and 28 days of $^2H_2O$ labeling. Tissues including but not limited to skin, lung, liver, heart, and kidney will be removed and stored at $-20°$ C. until analyses.

Collagen is preferentially precipitated by initially homogenizing tissue in 0.1 M NaOH. The homogenate is centrifuged at 7,000×g, and the resulting pellet is size-fractionated by sodium dodecyl sulfate polyacrylamide gel electrophoresis. Proteins are transferred to PVDF solid support. Collagen is excised from the blot and hydrolyzed at $110°$ C. for 16 hours. Amino acids are derivatized and the $^2H$ content in treatment groups is measured and analyzed as a function of time, relative to control groups.

Collagen degradative products are derivatized and analyzed as described in Example 8, supra.

Example 14

Collagen Synthesis as a Biomarker of Renal Fibrosis

Fibrosis, which is an overproduction of extracellular matrix (ECM) components, is a hallmark of many diseases of the vascular system, heart, lung, liver, and kidneys (for a depiction of collagen labeling see FIG. 4; for its biosynthetic and degradative pathways, see FIG. 5). Fibrosis generally occurs in response to tissue injury from toxicants such as alcohol as well as from mechanical and oxidative stresses. The most notable feature of tissue fibrosis is the chronic enhancement of biosynthesis and reduced degradation of collagen; eventually this buildup reduces organ function and leads to organ failure.

Early, predictive diagnosis of tissue fibrosis is critical for the assessment of drug toxicity and disease treatment. However, existing biomarkers of fibrosis are often expensive and insensitive. These include endpoint assays for measurement of increased collagen pool size and histochemical staining of ECM components within tissue biopsies. Measurements of alterations in collagen synthesis are more sensitive and quantitative than measurements of pool size or qualitative histopathology scoring.

In the kidney, fibrosis is characterized by long, gradual replacement of healthy tissue with fibrotic tissue. Unlike typical wound healing responses, the kidney, when subjected to toxic insult or similar lesion-generating event, continues to produce extracellular matrix proteins including collagen long after the initial event. Antifibrotic agents for the treatment of renal fibrosis are the subject of intense research.

Normal male rats (6 to 9 weeks of age, Sprague Dawley) are labeled with $^2H_2O$ by the following protocol: at time 0 an ip injection of sterile 100% $^2H_2O$ 0.9% NaCl is administered (30 mL/Kg). Drinking water is then replaced with a solution containing 8% $^2H_2O$ which is maintained until sacrifice.

Rats are administered a compound, a combination of compounds, or a mixture of compounds via an appropriate route of administration such as ip injection. If it is found that a compound, a combination of compounds, or a mixture of compounds reduces collagen synthesis and/or enhances collagen degradation, this provides a basis for selecting and/or characterizing compounds for development and evaluation for treating renal fibrosis and for evaluating efficacy, dosages, etc.

Conversely, if it is found that a compound, or a combination of compounds, or a mixture of compounds augments collagen synthesis and/or reduces collagen degradation, this provides a basis for reporting potential, hitherto unpublished toxicities of compounds, combinations of compounds, or mixtures of compounds.

Rats (five per time point) are euthanized after 2, 7, 14, 21, and 28 days of $^2H_2O$ labeling. Tissues including but not limited to skin, lung, liver, heart, and kidney will be removed and stored at $-20°$ C. until analyses.

Collagen is preferentially precipitated by initially homogenizing tissue in 0.1 M NaOH. The homogenate is centrifuged at 7,000×g, and the resulting pellet is size-fractionated by sodium dodecyl sulfate polyacrylamide gel electrophoresis. Proteins are transferred to PVDF solid support. Collagen is excised from the blot and hydrolyzed at $110°$ C. for 16 hours. Amino acids are derivatized and the $^2H$ content in treatment groups is measured and analyzed as a function of time, relative to control groups.

Collagen degradative products are derivatized and analyzed as described in Example 8, supra.

Example 15

Neurogenesis as a Biomarker of Neurotoxicity and Neurodegeneration

Tissue from the cerebral cortex is isolated by dissection from freshly killed, $^2H_2O$-labeled mice. Total cerebral cortical DNA is isolated from approximately 25 mg of tissue using a commercially available kit (Qiagen, Valencia, Calif.), and then hydrolyzed and derivatized for GC/MS as described in Example 2, supra. Deuterium incorporation is determined by GC/MS and used to determine cell proliferation rates in the cerebral cortex. These rates can reflect a variety of processes, most notably gliogenesis (as part of brain development, as a response to injury, or as a response to an administered agent). Such rates may also reflect neuroinflammation, which can stimulate microglial cell proliferation. Neurotoxicity, which can cause neurodegeneration and subsequent gliogenesis or neuroinflammation, may also have effects on the cerebral cortex which can be detected by the above method. Neurogenesis, which occurs more slowly in the cerebral cortex, will also be detectable by the same method. These rates may also reflect the infiltration of other cell types, such as macrophages, into the cerebral cortex. This technique can be adapted to study cell proliferation in any substructure of the brain that can be isolated by dissection, and will yield the same type of information for that tissue. A compound, or a combination of compounds, or a mixture of compounds can therefore be tested for anti-inflammatory, microglial cell proliferation, neurogenesis, and/or gliogenesis activity. A compound, combination of compounds, or a mixture of compounds having such activity is a candidate for development and evaluation for treating brain injury and/or brain disease.

Figure 12:
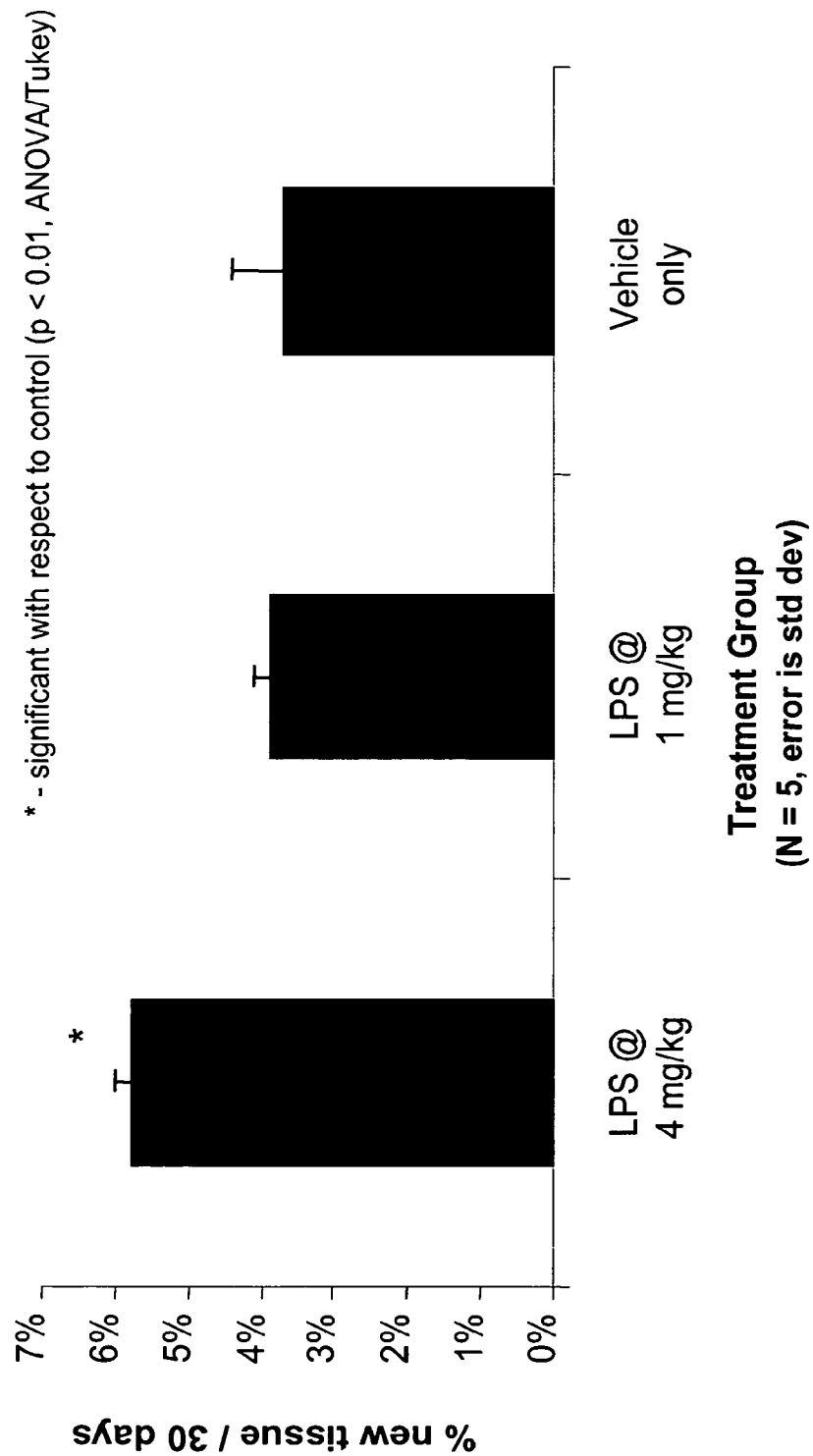
FIG. 12 depicts turnover of cerebral cortical tissue in response to bacterial toxin lipopolysaccharide (LPS). The high dose of LPS affected cortical tissue turnover representing the response of the brain to toxic insult.

Conversely, a compound, or a combination of compounds, or a mixture of compounds can be screened for neurotoxicity. FIG. 12 shows one such toxin, lipopolysaccharide (LPS), in which the high dose administered caused increased cortical cell turnover in response to the neurotoxic effects of LPS.

Example 16

Pancreatic βCell Turnover as a Biomarker for Diabetes

The number of functionally intact pancreatic β cells in the islet of Langerhans is of decisive importance for the development, course, and outcome of diabetes mellitus. Generally speaking, the total β-cell mass reflects the balance between the renewal and loss of these cells. Virtually all forms of diabetes mellitus are characterized by an insufficient extent of β cell replication needed to compensate for the loss or dysfunction of β cells occurring in diabetes. A reduction of the β-cell mass in the pancreas is, in fact, the critical clinical event in the development of type 1 diabetes and a reduced islet mass in combination with insulin resistance is necessary for type 2 diabetes to develop. Type 1 diabetes develops as a result of autoimmune destruction of the β cells; type 2 diabetes is characterized by development of early insulin resistance and a failure of the β cells to compensate for the hyperinsulinemia. Insufficient production of biologically active insulin is a common denominator in almost all forms of diabetes and the degree of insulin deficiency determines both the severity of the disease and the choice of therapy. Therefore, it is imperative to develop methods of measuring islet proliferation, as islet proliferation is a surrogate for pancreatic β-cell regeneration. A 50% partial pancreatectomy of rats can be performed to mimic the pre-diabetic state, especially in order to study β-cell regeneration (for reviews see Risbud M. V and Bhonde R. R. *Diabetes Res Clin Pract.* 2002 December; 58(3):155-65; Kulkarni R. N. *Int J Biochem Cell Biol.* 2004 March; 36(3):365-71).

Pancreatectomized (50%) male Wistar rats, and weight and age-match controls are obtained from commercial sources (Charles River, Wilmington, Mass.). Rats are given free access to water and standard chow. The animals are housed in a temperature-controlled room with a 12-h light, 12-dark cycle. Rats are treated with drugs or vehicles as determined by the study requirements.

Rats are killed by $CO_2$ gas, and the pancreatic duct is identified and cannulated for intraductal collagenase injection. 30 mL type V collagenase solution (20 mg/30 mL; Sigma Chemical Co. St Louis, Mo.) diluted in Hanks' Balanced Salt Solution (HBSS) buffer is injected into the pancreatic duct after cannulation. The pancreas is inflated, carefully removed, and placed in a 25-mL flask with 5 mL cold collagenase. The pancreas is digested in water bath at 37° C. for 15 min. At the end of the digestion, the pancreatic digest is washed with fresh HBSS. The islets are purified by Ficoll gradient. Approximately 200-250 intact islets are obtained per pancreas.

DNA is isolated from the islets and isotopic enrichment is measured as described in Example 2, supra.

A compound, or a combination of compounds, or a mixture of compounds can therefore be tested for the ability to stimulate islet proliferation or inhibit islet degradation. The islet of Langerhans serves as a surrogate marker for pancreatic β cell proliferation. A compound having such activity is a candidate for development and evaluation as an agent for treating diabetes.

Figure 9:
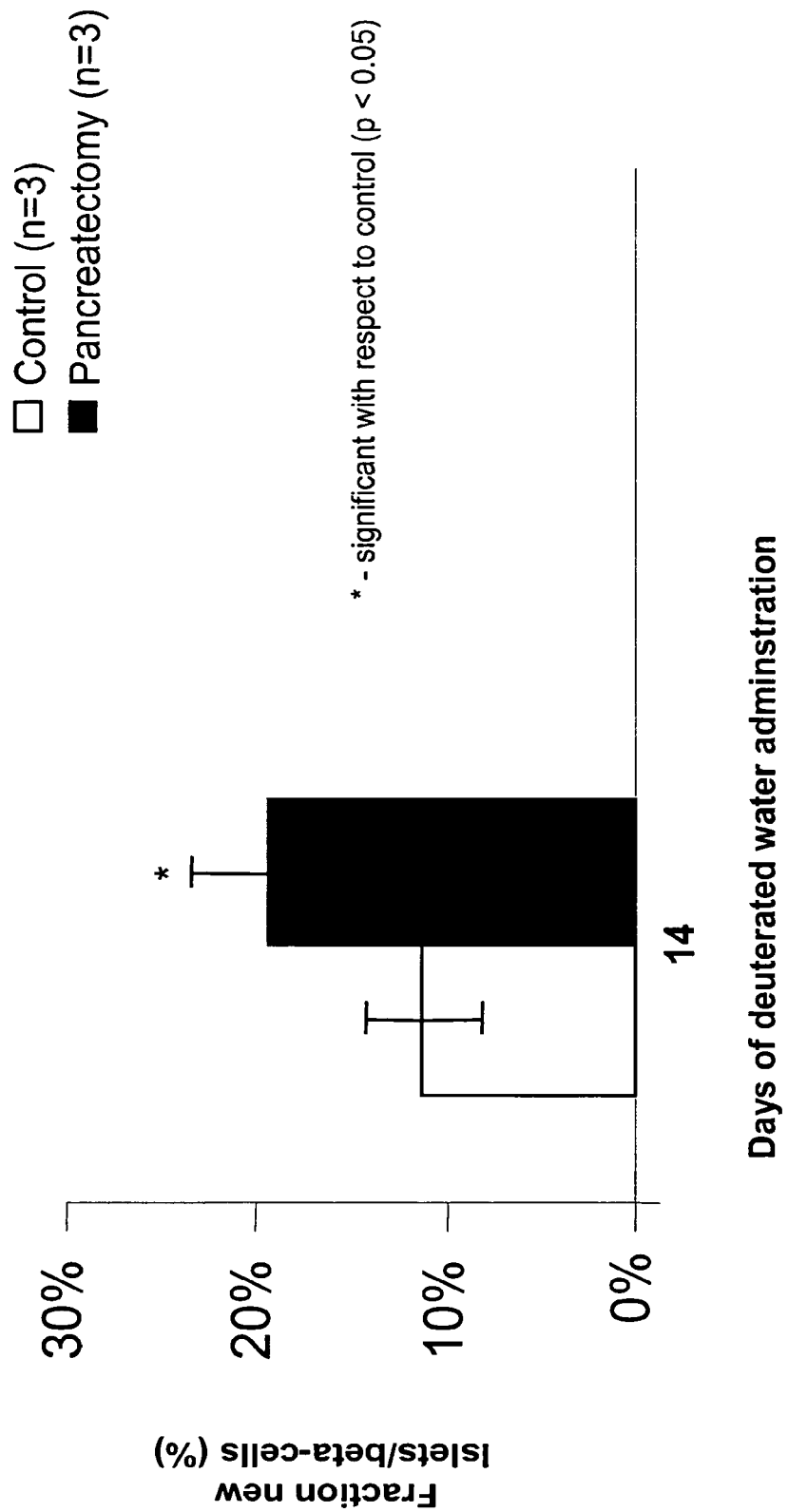
FIG. 9 depicts increased islet (beta-cell) proliferation after 50% pancreatectomy in Wistar rats.

Data obtained using the methods described herein is shown in FIG. 9. Control or pancreatectomized animals were administered $^2H_2O$ for 14 days, and Islet (beta-cell) proliferation was measured. Pancreatectomized animals showed increased proliferation after 14 days of $^2H_2O$ (19.31%±4.0, n=3, vs. 11.23%±3.0, n=3, P≤0.05 by t-test).

Figure 28:
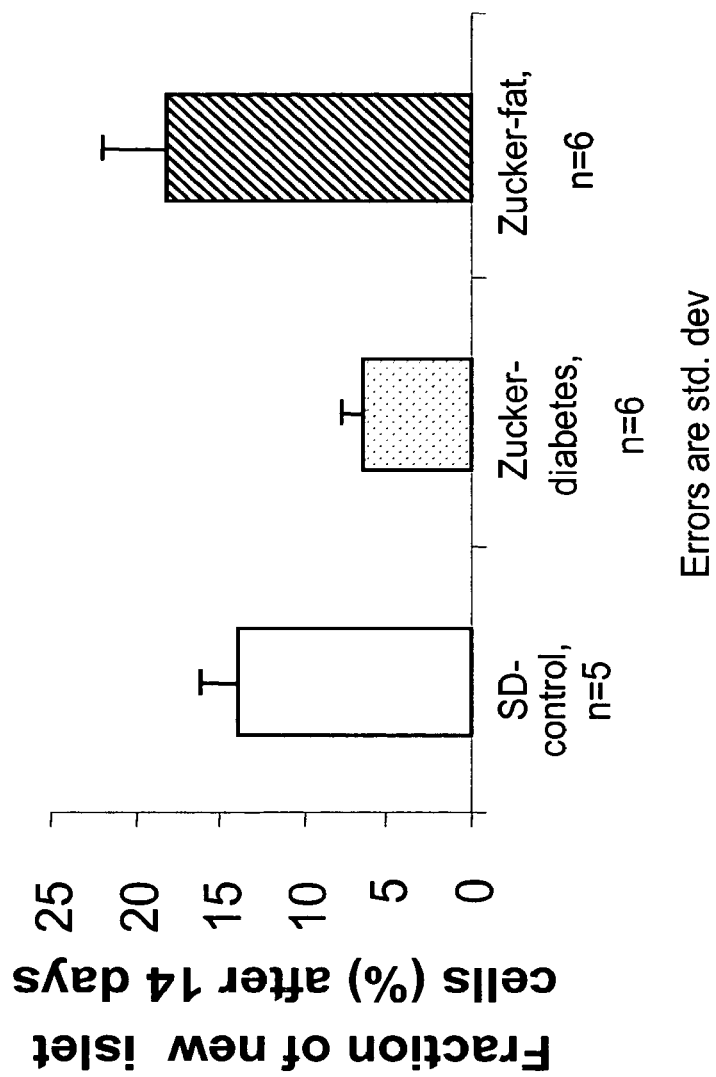
FIG. 28 depicts pancreatic islet/beta cell proliferation in a rat model of pre-diabetes (Zucker fat), a rat model of diabetes (Zucker-diabetes) and control animals (SD-control). Diabetic rats have impaired islet/beta cell proliferation, as expected from a diabetic animal. Pre-diabetic animals show increased proliferation of islet/beta cells, as the pancreas responds to decreasing insulin sensitivity.

FIG. 28 depicts pancreatic islet cell proliferation in a rat model of pre-diabetes (Zucker fat), a rat model of diabetes (Zucker-diabetes) and control animals (SD-control). Diabetic rats have impaired islet cell growth, as expected from a diabetic animal. Pre-diabetic animals show increased proliferation of islet cells, as the pancreas responds to decreasing insulin sensitivity.

Example 17

Endothelial Cell Proliferation as a Biomarker of Angiogenesis

Angiogenesis refers to the formation of new vessels from pre-existing vessels. Endothelial cell proliferation is one of the essential components of this complex biological process. Excessive angiogenesis is involved in the pathogenesis of cancer, blindness (retionopathy), psoriasis and other conditions, while insufficient angiogenesis can contribute to cerebrovascular disease, ulcer, scleroderma, and infertility.

Microvessel density is widely used in angiogenesis research, A positive correlation between microvessel density and tumor recurrence has been reported. However, other have pointed out that microvessel density is not a good indicator of angiogenesis or treatment efficacy. Rather, it reflects intrinsic metabolic demand of the supported tumor cells. At present, there is no other reliable measure of angiogenesis.

Disclosed herein is a new and reliable measurement of angiogenesis. The rate of angiogenesis in a tissue is measured by the endothelial cell proliferation rate. Endothelial cell proliferation is quantified by use of the heavy water ($^2H_2O$) labeling technique, as discussed extensively, supra.

The kinetics of angiogenesis are measured in liver and tumor xenografts. Balb/c Nu–/Nu– mice are transplanted with human breast tumor cells. After labeling with $^2H_2O$, individual animals are sacrificed, and both tumor tissue and liver tissue are harvested from the same animal. The tissue is then digested with collagenase (1 mg/mL) into a single cell suspension. Endothelial cells are enriched by Percoll gradient centrifugation, followed by FACS (sorting on isolection and CD31 positive cells). The proliferation rate of tumor endothelial cells, as well as liver endothelial cells is then measured by purifying, processing, derivatizing, and analyzing the DNA from the isolated endothelial cells, as described in example 2, supra.

A compound, or a combination of compounds, or a mixture of compounds can therefore be tested for the ability to stimulate or inhibit endothelial cell proliferation. Thus, endothelial cells can serve as a biomarker for angiogenesis. A compound or a combination or compounds, or a mixture of compounds having such activity is a candidate for development and evaluation for treating cancer, psoriasis, and other disorders and conditions such as wound healing.

Figure 18:
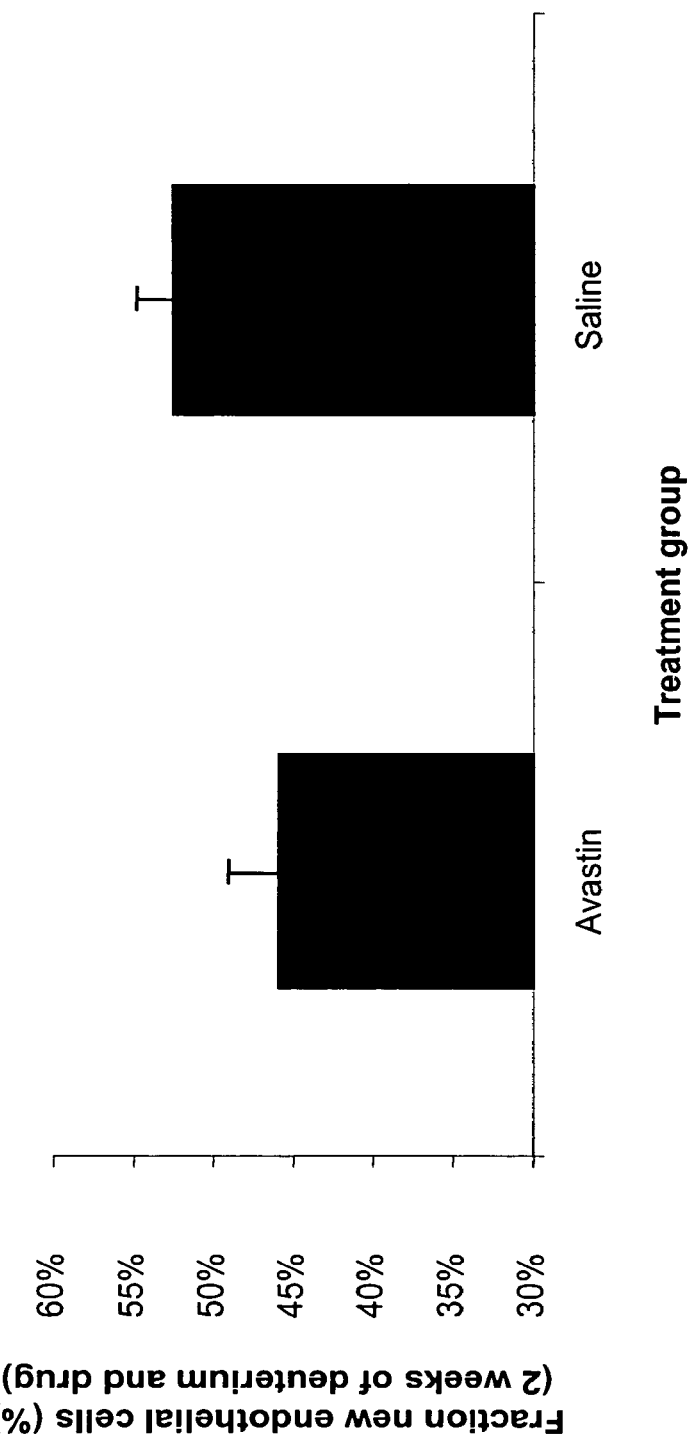
FIG. 18 depicts proliferation of endothelial cells from xenograft tumors in mice treated with an anti-angiogenic drug (Avastin) or a vehicle (saline). Endothelial cell proliferation is suppressed in animals treated with the drug.

As an example, Avastin (Genentech, CA), a known anti-angiogenesis drug had been tested with this method. With two weeks drug treatment, tumor endothelial cells in treated animals had shown significantly lower proliferation rate compare to the untreated group. (FIG. 18)

Example 18

Bone Marrow Cell Turnover as a Biomarker of Myelosuppression

Myeloid cells, which are critical to host defense against infections, are among the most rapidly turned-over cells in peripheral blood. The maintenance of normal myeloid cell numbers thus requires ongoing proliferation of bone marrow precursors. This is why neutropenia/myelosuppression is a common dose-limiting toxicity of antiproliferative agents used in cancer chemotherapy, which interferes with the proliferation of myeloid precursor cells. Prophylaxis with recombinant colony-stimulating factors can ameliorate or prevent neutropenia, but alternative, cheaper treatments are being sought.

Neutropenia is routinely detected and quantified by complete blood count. Due to a lag between proliferation of myeloid precursors and their progeny's appearance in blood, however, a substantial drop in the number of blood neutrophils does not occur until several days (rodents) or weeks (humans) after initiation of treatment. This translates into delays in preclinical toxicity screening. In humans, at onset of neutropenia, it can be too late to prevent the development of severe neutropenia and thus of life-threatening infections. Alternative markers, relying on in vitro surrogates of hematopoiesis, are being developed for preclinical testing but are difficult to translate into human use.

Incorporation of $^2H$ into newly synthesized cellular DNA after administration of heavy water ($^2H_2O$) provides a sensitive, quantitative measure of cell turnover. In animals, bone marrow toxicity after administration of antiproliferative agents can be detected as a decrease in $^2H$ incorporation into total bone marrow DNA following a short course of $^2H_2O$ labeling. More specifically, reduced $^2H$ incorporation into DNA of purified bone marrow myeloid cells provides a rapid readout of myelosuppression. In humans, reduced incorporation of $^2H$ label in the DNA of blood monocytes and granulocytes may serve as early warning of myelosuppression, before a drop in cell numbers becomes evident.

Mice are treated with compounds (as discussed in Example 1, supra) and labeled for 24 hours to 5 days with $^2H_2O$ (i.p. bolus to 5% $^2H$ in body water, followed by 8% $^2H_2O$ in drinking water to maintain body water enrichment). Humans are given oral $^2H_2O$ twice daily to 1-2.5% body water enrichment. DNA is isolated from total bone marrow, from bone marrow myeloid cells isolated using FACS, or immunomagnetic beads, from blood monocytes or granulocytes, or from phenotypic subsets of any of these cells. The DNA is enzymatically hydrolyzed, and deoxyribose is selectively released from purine deoxyribonucleosides and derivatized for analysis by gas chromatography/mass spectrometry, as discussed in Example 2, supra. The same animals can be studied for $^2H$ incorporation into other cells or proteins. For human studies, shorter, low-dose $^2H_2O$ labeling protocols are used in conjunction with highly sensitive isotope ratio mass spectrometry to detect low-level $^2H$ labeling.

A compound, or a combination of compounds, or a mixture of compounds can therefore be tested for the ability to stimulate bone marrow cell proliferation. Bone marrow cells are the precursor cells for the myeloid lineage and serve as a biomarker of myelosuppression. A compound, combination of compounds, or mixture of compounds having such activity is a candidate for development and evaluation for treating myelosuppression, for example, due to chemotherapeutic and radiotherapeutic treatment for cancer.

Figure 22:
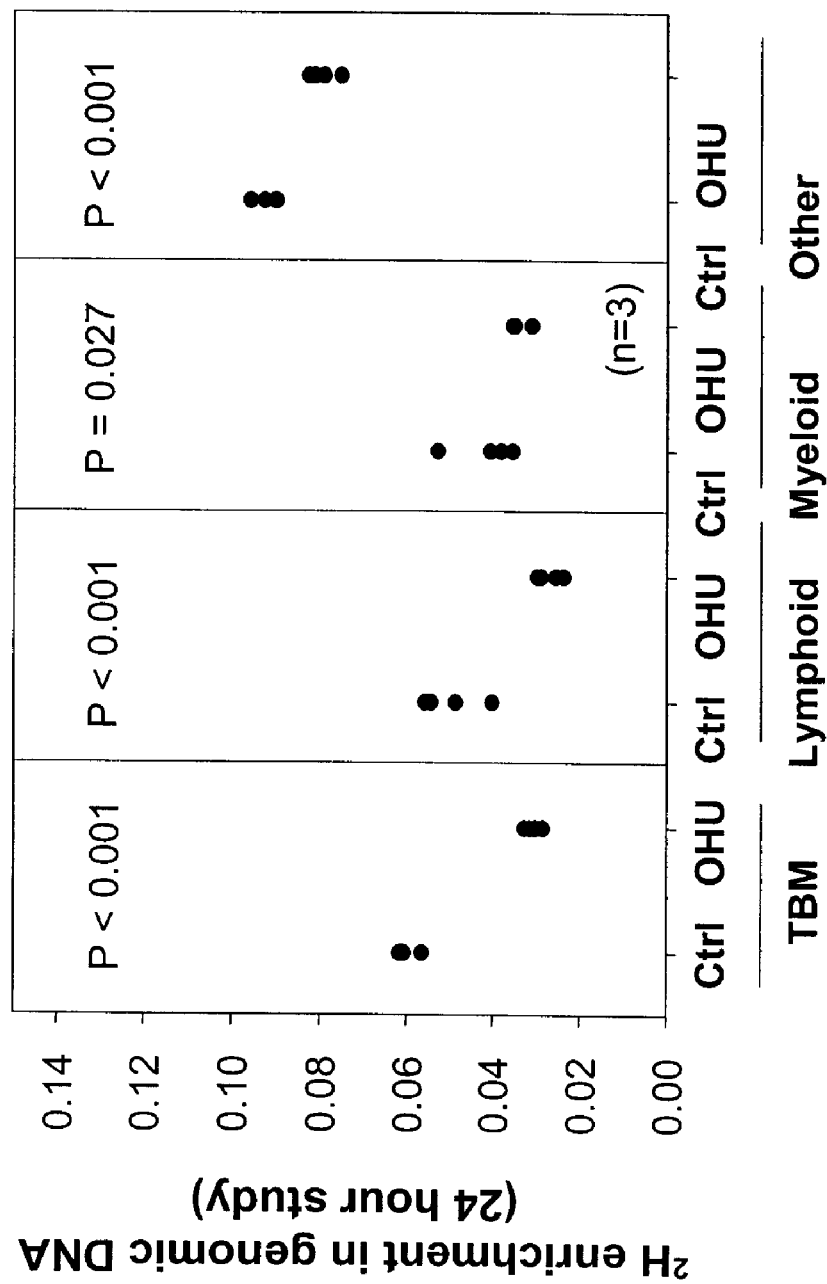
FIG. 22 depicts the response of different bone marrow cell subsets to treatment with hydroxyurea (OHU). Total bone marrow (TBM) was analyzed, or cells were divided into lymphoid, myeloid, or other cells, and analyzed separately. In three cases (indicated by **) OHU suppressed bone marrow proliferation.

FIG. 22 shows data depicting an experiment where Swiss Webster mice (n=4 per group except as indicated) were given a single dose of 500 mg/kg hydroxyurea ("OHU") i.p., or an equal volume of vehicle ("Ctrl"), and labeled with 8% $^2H_2O$ in drinking water for the subsequent 24 hours. Single cell suspensions were prepared from total bone marrow (TBM) of femora and tibiae at sacrifice. Lymphoid cells (expressing B220, CD3, DX5, and/or NK1.1) myeloid cells (expressing CD11b and Gr-1), and other cells (lacking the above antigens) were successively isolated by incubation with fluorochrome-labeled antibody cocktails, anti-fluorochrome-conjugated magnetic beads, and passage over MACS columns. DNA obtained from each fraction was hydrolyzed, purine dR was converted to the PFTA derivative, and $^2H$ incorporation into the M1 mass isotopomer was quantified. Complete turnover would be expected to result in EM1 values around 0.15. P values were determined by 2-way ANOVA for comparisons between cell types and treatments. As shown in FIG. 22, hydroxyurea has a statistically significant suppressive effect on proliferation in total bone marrow, lymphoid, and other bone marrow cells.

Figure 23:
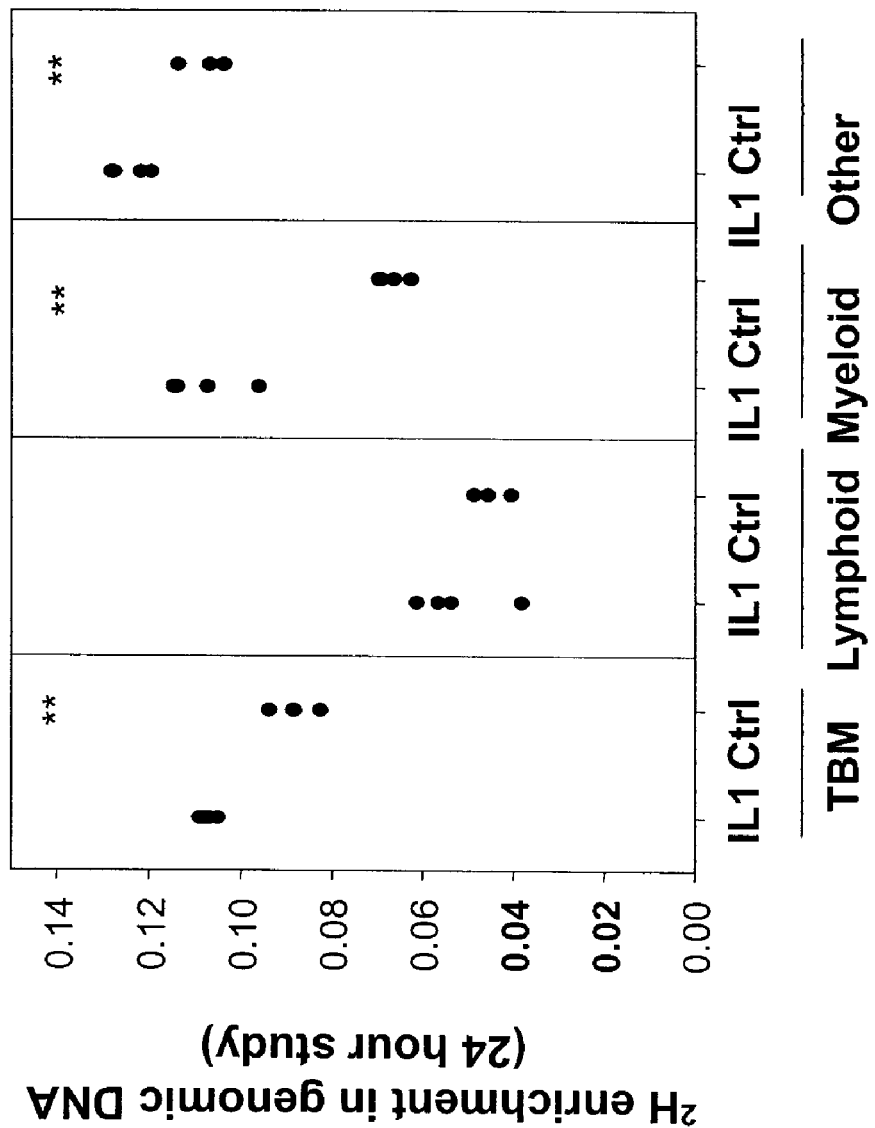
FIG. 23 depicts the response of different bone marrow cell subsets to treatment with interleukin-1 (IL-1) after OHU-mediated myelosuppression. TBM is total bone marrow, or cells were divided into lymphoid, myeloid, or other cells, and analyzed separately. In three cases (indicated by **) IL-1 is capable of stimulating myeloid cell proliferation. The effect in lymphoid cells is not statistically significant.

FIG. 23 shows data depicting an experiment where Swiss Webster mice (n=4 per group) were myelosuppressed with 500 mg/kg/d hydroxyurea i.p. for three days and rested on day 4. On day 5, mice received two i.p. injections of vehicle ("Ctrl") or 200 ng interleukin-1 (IL-1), 7-12 hours apart, and were labeled for 24 hours starting at the time of the first cytokine injection. Fractional DNA turnover (measured by EM1 in the PFTA derivative of purine dR) was determined for total bone marrow cells, or in lymphoid, myeloid, or non-lymphoid/non-myeloid ("other") bone marrow cell subsets. IL-1 has a statistically significant stimulatory effect on the proliferation of total bone marrow, myeloid, and other bone marrows after suppression by hydroxyurea.

Example 19

M Protein Turnover as a Biomarker of Multiple Myeloma

Multiple myeloma is a hematologic malignancy due to an accumulation of proliferating, monoclonal plasma cells in bone marrow and lymphoid organs. It is incurable except, in a small fraction of eligible patients, by bone marrow transplantation. Overproduction of M proteins (monoclonal antibodies secreted by myeloma cells) is detectable in serum; their fragments may appear in urine. Fatal complications arise due to the accumulation of malignant cells in bone marrow (competition with hematopoesis: anemia, immunodeficiency), M protein (immune complex disease) and other secreted products (bone erosion, hypercalcemia). Chemotherapy with antiproliferative and, more recently, anti-angiogenic drugs can delay or slow disease progression. Due to a lack of faithful animal models, efficacy studies in humans are particularly important.

M protein levels are tracked routinely to monitor disease progression and treatment response. However, overproduction of M proteins results in accelerated clearance compared to normal, polyclonal Ig of the same isotype, so M protein levels underestimate tumor burden in the bone marrow. M protein levels are often slow to change in response to chemotherapy; several month-long cycles of chemotherapy must therefore be completed before treatment efficacy becomes apparent, or before potentially toxic treatments can be abandoned if ineffective.

Malignant plasma cells can be sampled in bone marrow; expression of cell cycle markers by malignant cells, a measure of proliferation, may have prognostic utility, but its clinical utility remains controversial. Genetic markers of myeloma cells allow detection of residual disease and aid prognosis, but are less useful in evaluating tumor burden and response to treatment.

Measurement of absolute M protein synthesis promises improved accuracy in tracking tumor burden and early detection of response to treatment, compared to M protein levels.

Fractional M protein synthesis is measured as $^2$H label incorporation into newly synthesized M protein after in vivo labeling with $^2$H$_2$O. Fractional turnover rates are calculated using single-exponential kinetics as described, supra. Absolute turnover rates are calculated as the product of M protein level and fractional synthesis rate as described, supra.

Small (<5 mL) serum samples are obtained from patients with multiple myeloma who have received $^2$H$_2$O by mouth. Proteins of interest are isolated in a streamlined procedure, using affinity, size exclusion, and ion exchange chromatography. Proteins are hydrolyzed, and the resultant amino acids are derivatized for GC/MS analysis as described in Example 5, supra. Label incorporation into alanine is tracked as a measure of new protein synthesis.

A compound, or a combination of compounds, or a mixture of compounds can therefore be tested for the ability to inhibit M protein synthesis. M protein is a biomarker of multiple myeloma and thus a compound having such activity is a candidate for development and evaluation as an agent for treating multiple myeloma.

Figure 25:
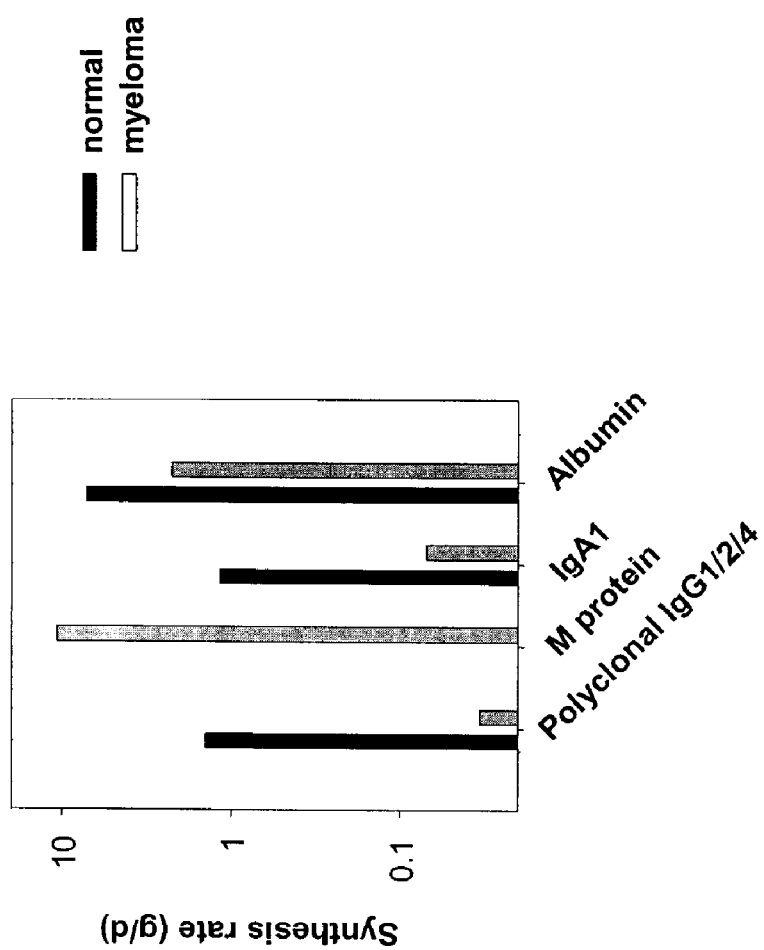
FIG. 25 depicts serum protein synthesis rates (calculated using total protein concentration and deuterium enrichment rates for each protein) in a normal volunteer or a myeloma patient. In the myeloma patient, the synthesis rates of the serum proteins evaluated are all suppressed in favor of the M-protein, which is produced by malignant cells. A kinetic analysis of the type described is very sensitive to such changes in synthesis.

As shown in FIG. 25, serum protein synthesis is altered in patients with multiple myeloma. Additionally, in a multiple myeloma patient, M-protein synthesis is shown to be significantly higher than other serum proteins including albumin.

Example 20

DNA Methylation as a Biomarker of Gene Expression

Hypermethylation of promoter regions of DNA is a frequent epigenetic event in many human cancers and is a potential pathway for tumor suppressor gene inactivation and the onset of cancer. Enzymes catalyzing this reaction belong to a family of methyltransferases that transfer the methyl group from cofactor S-adenosyl-l-methionine (SAM) to cytosine forming 5'-methylcytosine in DNA.

Monitoring of DNA methylation has attracted considerable attention. There are many DNA methylation methods known in the art and most of them suffer from limitations such as cross-reactivity (non-specific), incomplete reactions, unstable reagents, lengthy analysis time, toxic reagents, poor reproducibility, and the only measurable parameter is the content of methylcytosine not its rate of formation. This inability to measure methylation rate directly is a fundamental limitation of all of the well-known methods, in that changes in methylation can only be detected after methylcytosine content is substantially diluted, e.g., through repeated rounds of cell division.

In general, DNA methylation blocks gene expression whereas demethylation may result in gene activation. Newly increased or decreased DNA methylation in a tissue is measured by the amount and rate of label incorporation of $^2$H3-methyl group from administered methionine or $^2$H$_2$O entry into de novo synthesized methylene group of methylenefolate that is subsequently incorporated into homocysteine to form methionine by methionine Synthase. The newly incorporated label is detected by GC-MS after DNA extraction and hydrolysis as described in Example 2, supra. Briefly, 100 μl of 95% formic acid was added to the dried DNA sample in a GC vial. The vial was capped and incubated at 140° C. for 15 minutes.

The sample was dried, and 1-2 mg of sodium carbonate was added with 100 μL acetonitrile and 5 μl of pentafluorobenzyl bromide. The mixture was incubated at 70° C. for 15 minutes. Reaction was quenched with 0.5 mL water. The solution was then extracted twice with 0.5 mL ethyl acetate. The extracts were dried and 50 μL of pyridine was added along with 50 μL of MBTFA. The resulting solution was incubated for 15 min at 60° C. Two mL of water was added to the resulting solution that was then extracted twice with dichloromethane (2×0.8 mL). The organic extracts were then analyzed on the GCMS without further processing.

The expression of tumor suppressor genes that have been silenced by methylation can be activated by treatment of tumor cells with potential drugs. As an example, SW 1753 cells were cultured overnight in DMEM media (10% FBS) that had been supplemented with 20 μM $^2$H3-methyl methionine. Three different concentrations (125 nM, 250 nM, and 500 nM) of two known demethylating drugs (azacitidine and decitabine) were then added using methyldeoxycytidine as a negative control.

The methods of the present invention provide a fast and reliable test to measure DNA methylation and demethylation facilitating the development of newer and more efficacious drugs. For example, a compound, or a combination of compounds, or a mixture of compounds can therefore be tested for the ability to stimulate demethylation of DNA and thereby activate the expression of tumor suppressor genes, which may find use in treating various cancers.

Figure 10:
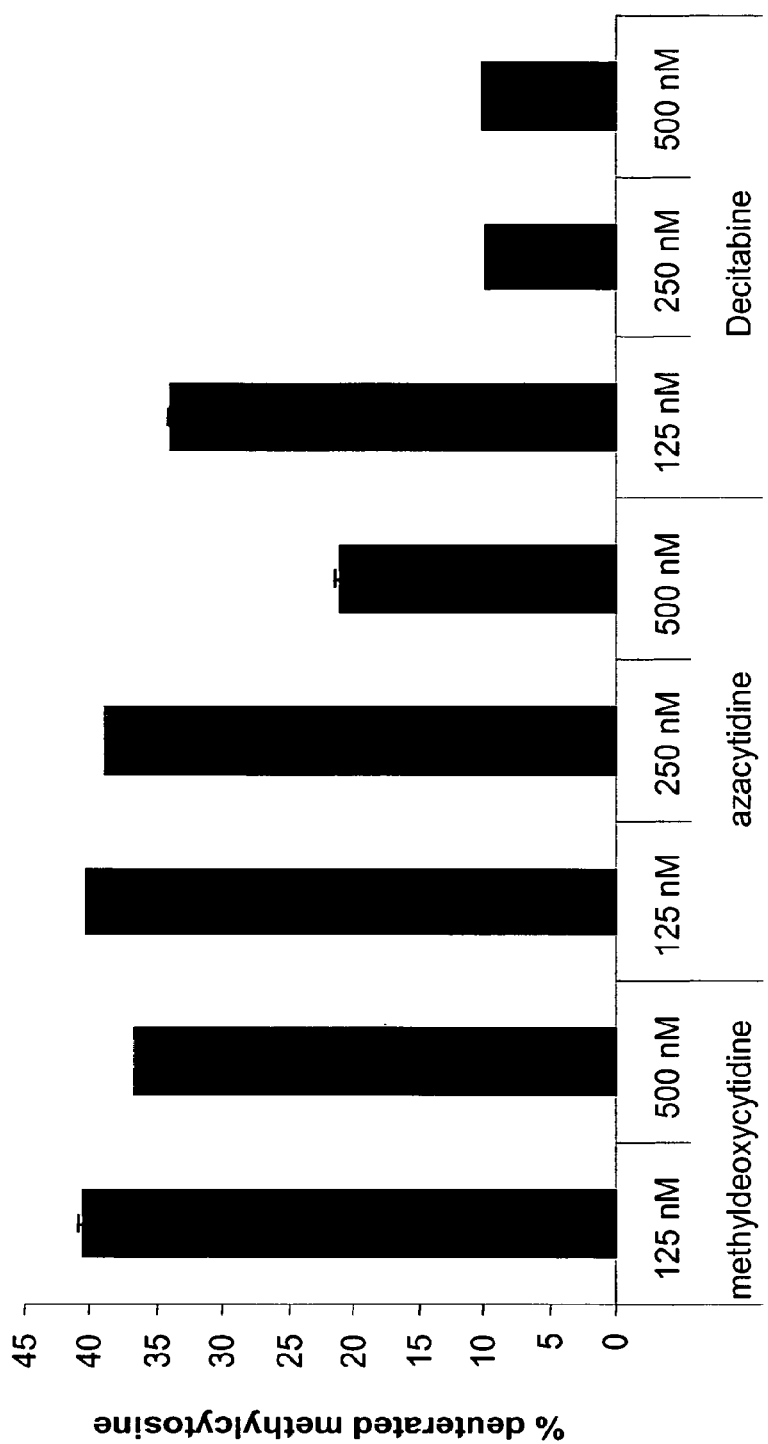
FIG. 10 depicts the effects of two demethylating drugs (azacitidine and decitabine) on SW 1753 cells that were cultured overnight in DMEM media (10% FBS) supplemented with 20 mM $^2$H3-methyl methionine. Three different concentrations (125 nM, 250 nM, and 500 nM) of azacitidine and decitabine were then added using methyldeoxycytidine (125 nM and 500 nM) as a negative control. Decitabine showed a better efficacy in inhibiting methylation (70% reduction) at 250 nM when compared to azacytidine (less than 10%).

As shown in FIG. 10, the fraction of methylcytosine that is new during a 24-hour labeling period is suppressed by two known antimethylating agents, azocitadine and decitabine.

Example 21

Neurogenesis as a Biomarker of Anti-Depressive Activity and Other Psychiatric or Cognitive Disorders and in Healing or Recovery from Neurological Diseases or Conditions Adult neurogenesis refers to the formation of new neurons in the brain of an adult organism. Neurogenesis is known to occur in discrete regions of the adult mammalian brain, particularly in the hippocampus of rodents, primates and humans. Hippocampal neuronal cells in the adult are formed from proliferating neuronal progenitor cells, and these new neurons form functional connections.

Currently, the most widely used marker for cell proliferation in the brain is through 5-bromo-2'-deoxyuridine (BrdU) labeling with immunohistochemical analysis. Neurogenesis is assessed by immunohistochemical co-labeling for BrdU and neuronal markers 2-4 weeks after BrdU administration. BrdU labeling for estimating neurogenesis is extremely labor intensive, it only labels cells that are in 'S' phase during a brief period (2 hours) before BrdU clearance from the brain, and has relatively poor reproducibility and precision. Also, immuno-labeling 1 month after BrdU administration to assess true neurogenesis results in further dilution of label. Moreover, high doses of BrdU are required, leading to possible toxicity.

Cell proliferation in the brain is measured from the synthesis of new DNA and, thus, new cells from heavy water ($^2$H$_2$O) as described, supra. Measurement of neurogenesis involves the isolation of neurons from labeled adult brain tissue.

Rodents are labeled with 8% $^2$H$_2$O in drinking water. Animals are sacrificed, brain is removed and the hippocampus is dissected out. Synthesis of hippocampal DNA reveals the cell proliferation rate in the hippocampus. Different durations of label administration can be used to differentiate between the kinetics of rapidly proliferating cells, such as the progenitor cell population, compared to the slower rate of label incorporation in neuronal cells. In order to assess neurogenesis directly, $^2$H$_2$O-labeled rats are sacrificed, the brain is removed, the hippocampus is dissected out and cut into 0.5 mm slices followed by digestion/dissociation with papain and trypsin. The isolated cells are stained for neuronal markers and sorted by flow cytometry. DNA is isolated and labeling is measured as described, supra.

Hippocampal neurogenesis has been shown to be involved in and required for anti-depressant drug action. Other potential applications include the assessment of neurogenic effects of drugs being developed for Alzheimer's disease, stroke, traumatic brain injury, as well as agents for learning and memory. For example, a compound, or a combination of compounds, or mixture of compounds can therefore be tested for the ability to stimulate neurogenesis (neuron proliferation as opposed to neuroprogenitor cell proliferation, which is discussed in Example 3, supra) and thereby identify for further development and evaluation compounds, or combinations of compounds, or mixtures of compounds for treating depression, AD, traumatic brain injury, damage due to neuroinflammation, stroke, memory, and learning.

Figure 27:
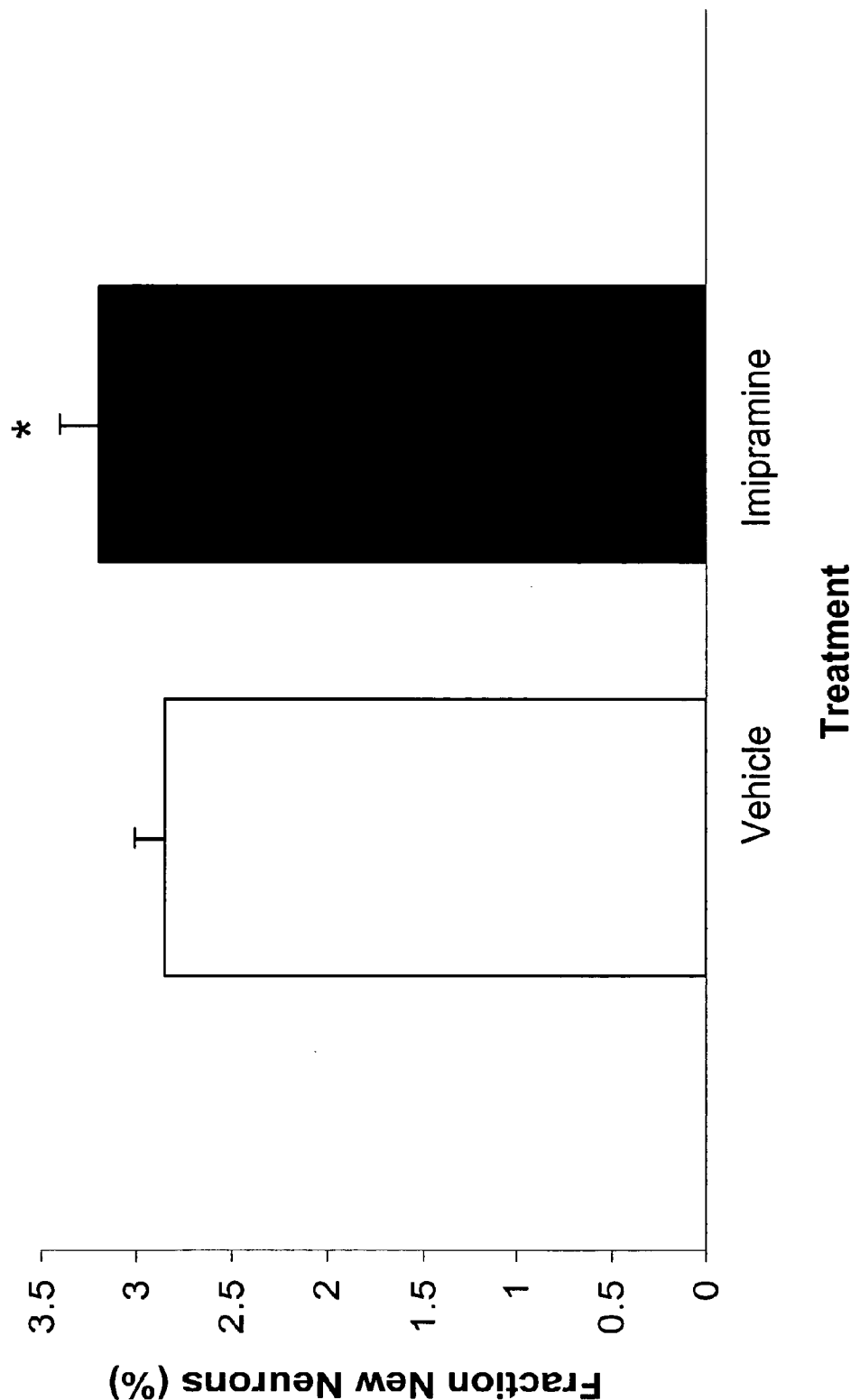
FIG. 27 depicts the proliferation of mature neurons in normal and antidepressant (imipramine)-treated adult mice. Neurons were isolated by flow cytometry and analyzed as described in Example 2, infra. Imipramine, a known antidepressant, increased the rate of mature neuron formation.

As shown in FIG. 27, a known antidepressant (imipramine) resulted in the increased formation of mature neurons in mice (i.e., neurogenesis).

Example 22

Spermatocyte Turnover as a Biomarker of Male Infertility

Infertility affects 15% of reproductive aged couples. Among those afflicted, a problem with the male partner is identified in 40% of cases. A significant proportion of male factor infertility is due to defects in spermatogenesis that are undefined.

Currently, histological semen analysis is the gold standard used to assess semen quality. This analysis includes the measures: volume of ejaculate, sperm quantity, sperm motility, progression, semen pH, and morphology. These static markers of semen quality, however, tell little about the underlying dynamic process of spermatogenesis and give few insights into the defects that may be causing abnormal sperm production/maturation and the ensuing male infertility.

Indeed, the current understanding of the kinetics of mitotic and meiotic activity in human spermatogenesis is very limited. Most contemporary data that characterizes spermatogenesis are derived from relatively simple microscopic analyses of testis histological features from healthy men of different ages. This and other approaches to measuring the dynamics of spermatogenesis are limited not only by inherent toxicity, but also because they are laborious, problematic, and expensive to perform.

The field has lacked a non-invasive measure of sperm production in vivo. The methods of the present invention provide such a measure.

The methods of the present invention for measuring spermatogenesis are applicable in humans or animals as $^2H_2O$ (heavy water) is administered via animals' drinking water or by providing human subjects with a few sips each day.

Deuterium ($^2H$) from the $^2H_2O$ is incorporated covalently into the deoxyribose (dR) moiety of replicating DNA synthesized during spermatogonia division. The deoxyribose dR moiety of dNTPs is labeled endogenously, through the de novo nucleotide synthesis pathway. By measuring the isotopic enrichment of deuterium in the dR moiety of purines (deoxyadenosine and deoxyguanosine), sperm production rates can be measured.

Figure 11:
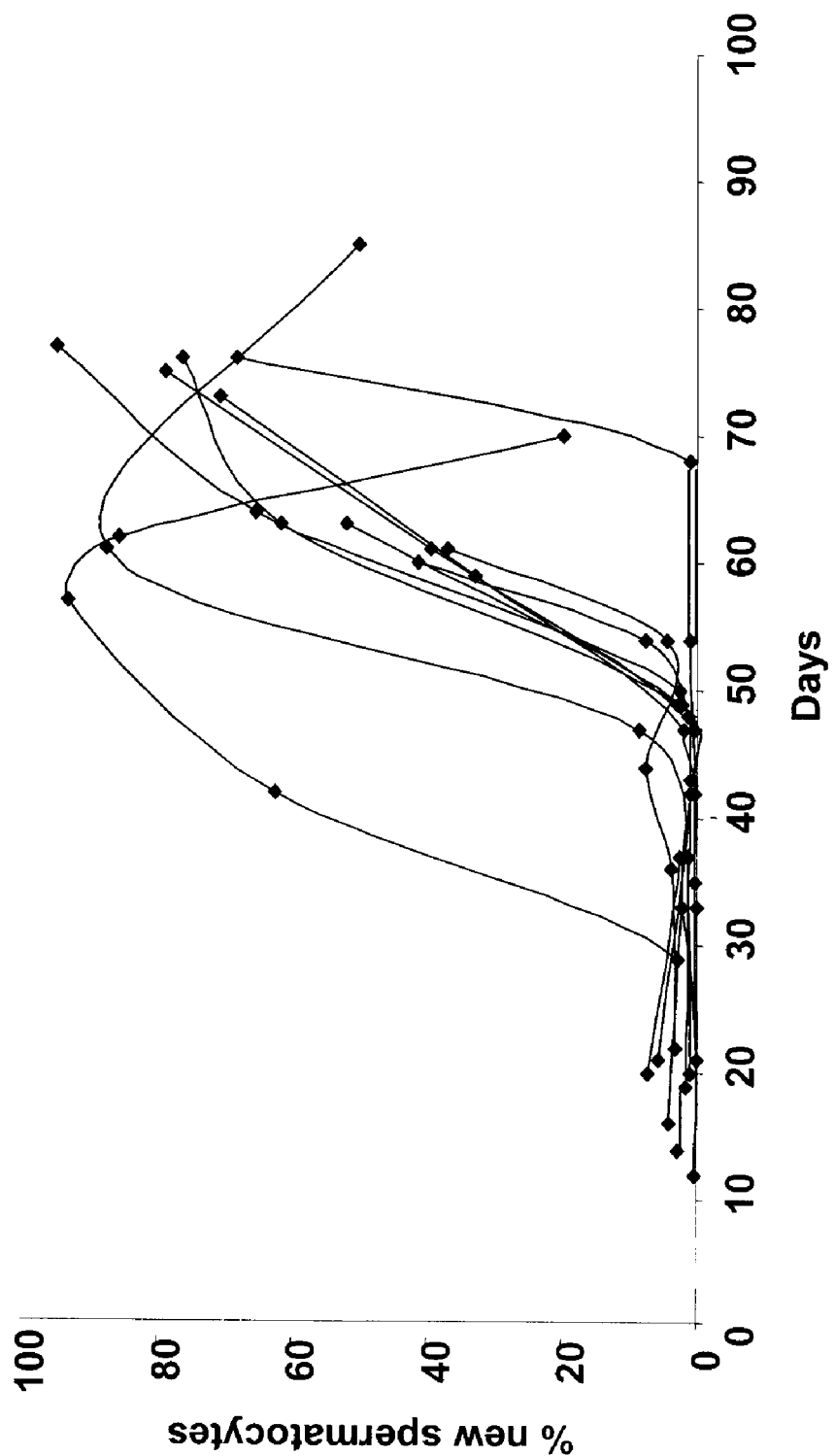
FIG. 11 depicts spermatocyte labeling curves for eleven subjects with normal semen analyses. Men were labeled with 50 ml of 70% $^2$H$_2$O twice daily for 3 weeks. Semen samples were collected every two weeks for 90 days from the start on $^2$H$_2$O, Spermatocyte DNA enrichment was measured by GC/MS and compared to that of a fully-turned over cell (monocyte) to calculate the percentage of new cells present.

After the subject is labeled with deuterated water, semen or testes biopsy tissue is obtained. Sperm is isolated from semen by Percoll gradient centrifugation. Sperm is isolated from testes tissue by enzymatic digestion and FACS sorting of haploid cells. Genomic DNA is extracted, hydrolyzed and the purine deoxyriboise moiety is derivatized for gas chromatographic/mass spectrometric (GC/MS) analysis as described in Example 2, supra. The DNA $^2H$-enrichment of the spermatocytes is compared to the $^2H$-enrichment of a fully turned over tissue (e.g., bone marrow for animal studies and blood granulocytes or blood monocytes for human studies) to calculate the rate of sperm proliferation (see FIG. 11). Both lag time of appearance of labeled sperm in ejaculate and the kinetics of label incorporation in the tissue or ejaculated cells are determined providing multiple insights into the biology of spermatogenesis and the etiology of male infertility.

The methods of the present invention enabling the measurement of spermatogenesis can be applied to male infertility clinical diagnostics and drug development in a variety of ways. It can be used to determine if a man is azospermic due to blockage or faulty spermatogenesis when applied to measuring spermatogenesis in testis biopsy samples. It can also be used to measure the effects of compounds, or combinations of compounds, or mixtures of compounds that are aimed at increasing spermatogonia division rates. In addition, it can be used to determine if compounds, or combinations of compounds, or mixtures of compounds alter maturation cycles and release into epidymus and/or affect transit time through the testes.

Example 23

Microglia Proliferation as a Biomarker of Neuroinflammation

Neuroinflammation is a feature of many neurodegenerative disorders, as well as a component of CNS damage due to stroke or traumatic brain injury (TBI). Microglia are the immune cells of the brain, and they mediate neuroinflammation and play a role in both neuroprotection and neurodegeneration. Microglia have complex signaling interactions with neurons, and can secrete a broad range of pro-inflammatory or neurotrophic factors, as well as acting as phagocytes and antigen presenting cells. They have been directly implicated in neurodegeneration in Alzheimer's Disease (AD), and have a role in post stroke or TBI brain damage and recovery. Microglia also have a lesser role in Parkinson's Disease (PD) and Multiple Sclerosis (MS).

In more severe cases of brain injury or disease, the blood brain barrier is breached, and hematogenous immune cells (such as T-cells in MS) also invade the CNS and play a role in neuroinflammation.

The ability to modulate the activity of microglia would be a valuable tool for the treatment or management of neurodegenerative disorders or CNS injury. Preventing or altering invasion of the CNS by circulating immune cells would be a similarly valuable tool.

Neuroinflammation and neuroprotection are currently studied using a variety of pre-clinical models. These models include the administration of toxins or inflammatory agents, the deliberate occlusion of arteries supplying the CNS, direct traumatic injury of the CNS, and others. While the range of models is broad, almost all of them rely on exhaustive histologic scoring of brain tissue to evaluate neuroinflammatory responses. The observation and enumeration of activated microglia and reactive astrocytes by immunohistochemistry is the current standard for evaluating neuroinflammation.

The methods of the present invention allow for an advanced capability to measure the proliferation rates of small populations of cells by monitoring the incoporation of deuterium from $^2H_2O$ into the ribose moiety of DNA as described, supra. Microglia, which often proliferate upon activation, can be isolated from animal brain tissues and their proliferation rates can be measured. In addition, circulating immune cells, which proliferate rapidly, can be pre-labeled and their infiltration into the brain can be measured after injury.

Using the methods of the present invention, the skilled artisan can evaluate the ability of potential compounds to reduce the proliferative response of microglia or the invasion of hematogenous immune cells. In the first case, the proliferation rates of microglia are measured, in the second, the appearance of highly labeled cells in the CNS is measured. This range of techniques allows for the study of compounds that can be used to treat chronic neurodegenerative disorders or acute CNS injury.

Glial fibrillary acidic protein synthesis and the rate of mitochondrial proliferation can also be used as biomarkers of astrocyte activation and oxidative damage, two other components of neuroinflammation, Mice are labeled with $^2H_2O$ for an appropriate period. Mice are anesthetized and perfused with 10 mL ice cold PBS (trans-cardiac perfusion). Brains are immediately harvested and placed on ice in cold PBS. Brains are then minced and shaken for 25 min at 37° C. in baffle flasks containing 30 mL of PBS supplemented with 0.05% DNAse, 0.25% trypsin, 0.8% glucose, and 0.16% EDTA. Subsequently, each flask is neutralized with 30 mL of ice cold media (1:1 DMEM:HAM's F10 supplemented with 10% FBS), and placed on ice. Tissue is then triturated repeatedly with a 10 mL pipette until all tissue fragments are dissociated. The resulting material is then filtered through a 100 micrometer filter, washed in media, and run on a discontinuous percoll gradient in order to remove non-cellular debris.

Figure 14:
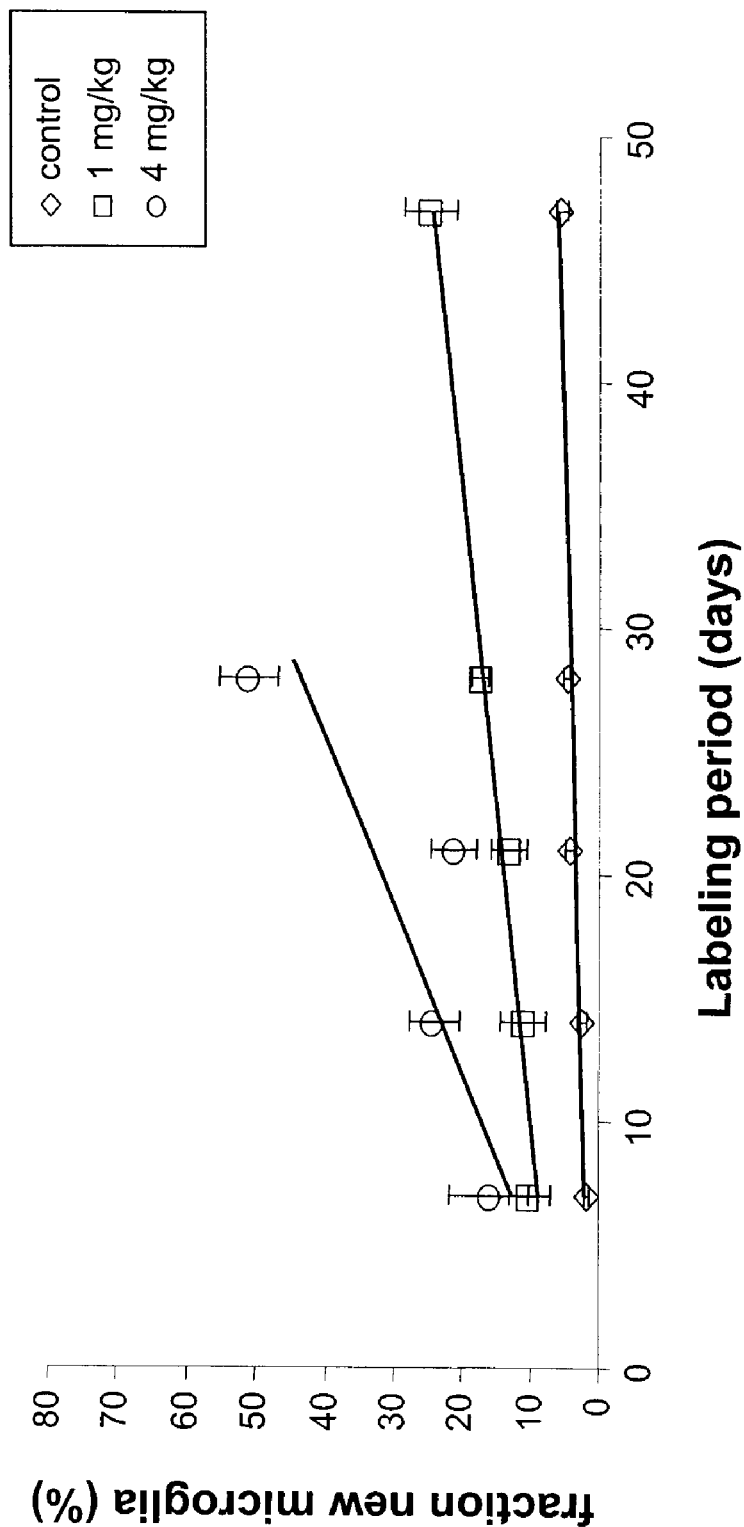
FIG. 14 depicts microglial response to the neuroinflammatory toxin lipopolysachamide (LPS). LPS is administered every other day to mice intraperitoneally at the two doses indicated (1 and 4 mg/kg body weight). $^2$H$_2$O was administered concurrently. Some animals were harvested at each of the indicated time points, and microglia were isolated and analyzed for deuterium incorporation. The increased proliferative response to both doses is significant with respect to control at every time point measured (p<0.05, ANOVA/Tukey), and dose dependence is observed from day 14 forward (p<0.05, ANOVA/Tukey). Error bars indicate standard deviation.
Figure 15:
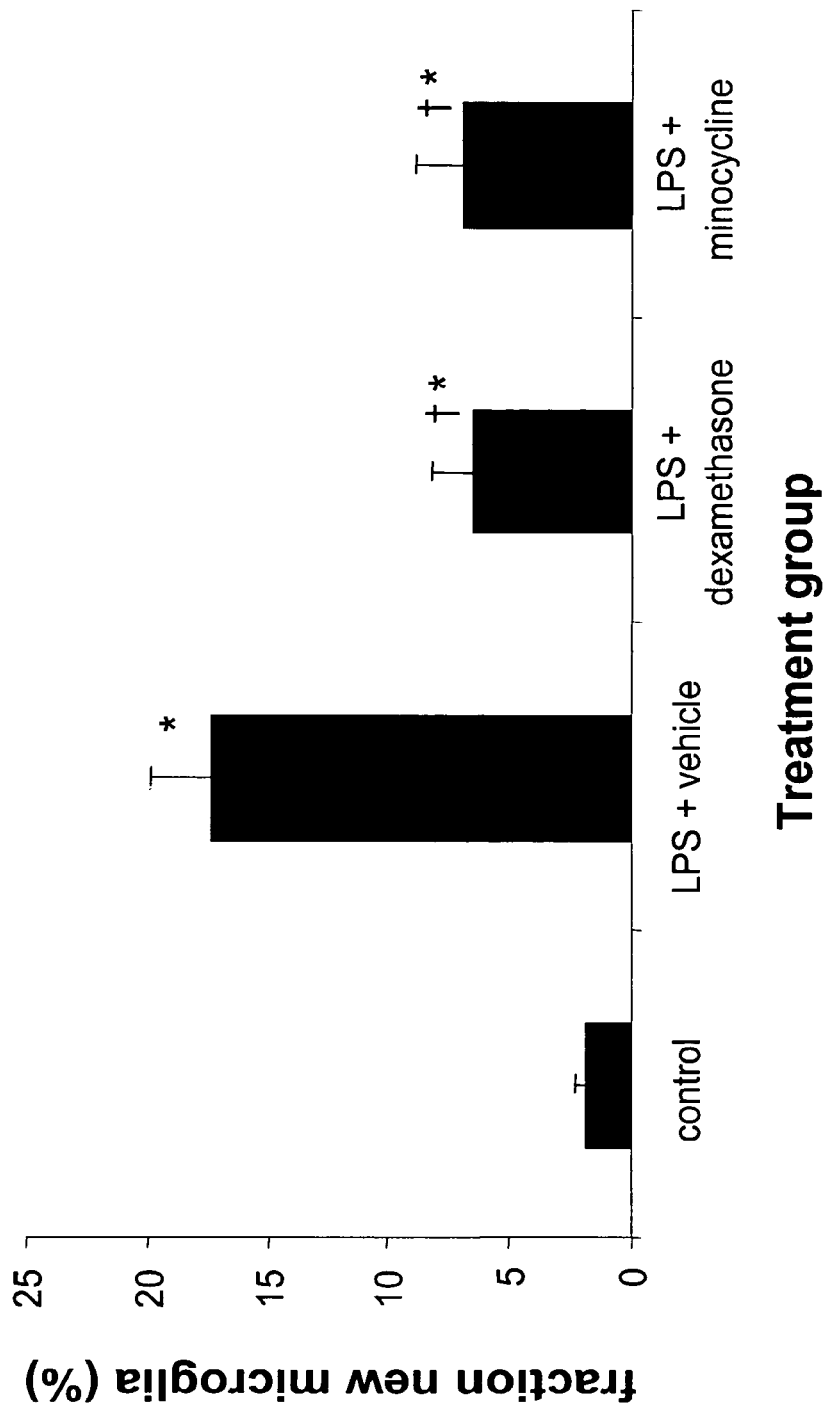
FIG. 15 depicts the effects of two anti-inflammatory chemotherapeutic agents (dexamethasone and minocycline) on microglial proliferation. Mice were given $^2$H$_2$O and either intraperitoneal lipopolysaccharide (LPS) to induce neuroinflammation, or a vehicle (control). Mice given LPS were treated with either a vehicle or dexamethasone or minocycline. Microglia were then isolated and analyzed for deuterium incorporation as described herein. The results show that the microglial proliferation assay is capable of detecting the activity, in vivo, of an effective anti-neuroinflammatory therapeutic. The LPS treated groups show increased proliferation with respect to the control group (p<0.01, ANOVA/Tukey) but the dexamethasone and minocycline treated groups show suppressed proliferation with respect to the vehicle treated groups (p<0.001, ANOVA/Tukey).

The resulting cells are stained with the macrophage specific markers F4/80 and CD11b, fixed in 4% paraformaldehyde (PFA), and then isolated by FACS. Alternatively, cells can be labeled with other cell surface or intracellular markers that can be used to sort microglia or microglial subsets by FACS or MACS. Cells can also be sorted immediately rather than fixing them in 4% PFA. DNA is extracted from sorted cells, hydrolyzed, derivatized, and analyzed by GC/MS as described in Example 2, supra. From this data, isotopic enrichment and cellular growth or migration rates are determined. The technique can also be used to isolate infiltrating leukocytes that enter the brain from the circulatory system. As shown in FIG. 14, LPS-induced neuroinflammation resulted in a statistically significant and dose-dependent increase in microglia proliferation. As shown in FIG. 15, the LPS-induced effect on microglia proliferation is suppressed by known anti-inflammatory or anti-microglial agents (dexamethasone and minocycline).

The methods of the present invention allow for the administration of a compound, or a combination of compounds, or a mixture of compounds to evaluate the ability to inhibit microglia proliferation and thereby identify for further development and evaluation treatments for neuroinflammation.

Example 24

Keratin Turnover as a Biomarker of Psoriasis and Other Skin Diseases and Conditions Keratins are a family of more than 50 structural proteins with a common architecture. Several keratins are expressed in skin and form the major protein component of epidermis. Basal cells of the epidermis produce daughter cells which migrate toward the skin surface, maturing until they contain little but keratins K1 and K10 and lipid. These cells ultimately die forming the many layered protective outer skin surface, the stratum corneum. In healthy human skin it takes on average about four weeks from the synthesis of new keratin until it is sloughed off at the skin surface.

Psoriasis is an important skin disease, affecting about 3% of the population in the USA with about one third of those judged to have moderate to severe disease. Both genetics and environment contribute to the auto-immune response which leads to psoriasis. Psoriasis is characteristically marked by hyperproliferation of the epidermis; transit time of epidermal keratin and keratinocyte may therefore take a few days rather than several weeks.

Current clinical and laboratory assessments for psoriasis involve a combination of physical examination measures including the Psoriasis Area Severity Index [PASI], Physician's Global Assessment [PGA] and photographs. The PASI combines scores for the degree of erythema, induration, desquamation, and the percentage of body-surface area affected in four anatomical regions. The PGA is an overall assessment of a patient's psoriasis, taking into consideration the quality and extent of plaques relative to the baseline assessment.

Keratin provides an accessible marker of skin turnover. Keratin turnover can be monitored by two methods. In one, whole epidermis is isolated from a skin sample using a simple proteolytic treatment; in the second, tape strips (CuDerm, Dallas Tex.) with a specially designed adhesive are applied to the skin surface and the outermost non-living tissue is removed a single layer at a time. Labeled keratin begins to appear quickly in whole epidermis upon administration of deuterated water but it takes about two and a half weeks before any label appears at the surface of normal human skin monitored by tape strips. At least 30 sequential tape applications are required to reach the underlying living portion of the epidermis in normal skin.

Keratins are very insoluble which makes it easy to isolate the keratin fraction from other proteins in the skin. The same procedure works well on both whole epidermis and tape strips. Samples are taken using skin harvesting strips First, the strips are washed in a high salt buffer containing a detergent, Triton X-100. This removes all epidermal proteins except keratins. Keratins are then solubilized by boiling in a solution of sodium dodecyl sulfate. Although hair is also composed of keratins (with a slightly different structure), hair keratins are not solubilized by this method and do not contaminate the samples. Virtually pure skin keratins are produced by this simple extraction. Keratin turnover is then measured using mass spectrometric analysis as described, supra, in example 4.

Keratinocyte proliferation can also be used alone, or in conjunction with, keratin turnover, as a biomarker for psoriasis and other skin conditions such as wrinkling (photo-aging). Once an animal or human subject ingests $^2H_2O$ (as described, supra) keratinocytes are isolated from the skin of the animal (such as the flaky skin mouse) or a human. Keratinocytes are isolated by removing the hair from a skin sample, washing it, and incubating it in a solution of dispase II, a proteolytic enzyme that separates the epidermis (mainly keratinocytes) from the dermis (a more complex tissue). DNA synthesis is then measured in the isolated samples, using the methods and techniques described, supra, in Example 2.

Figure 16:
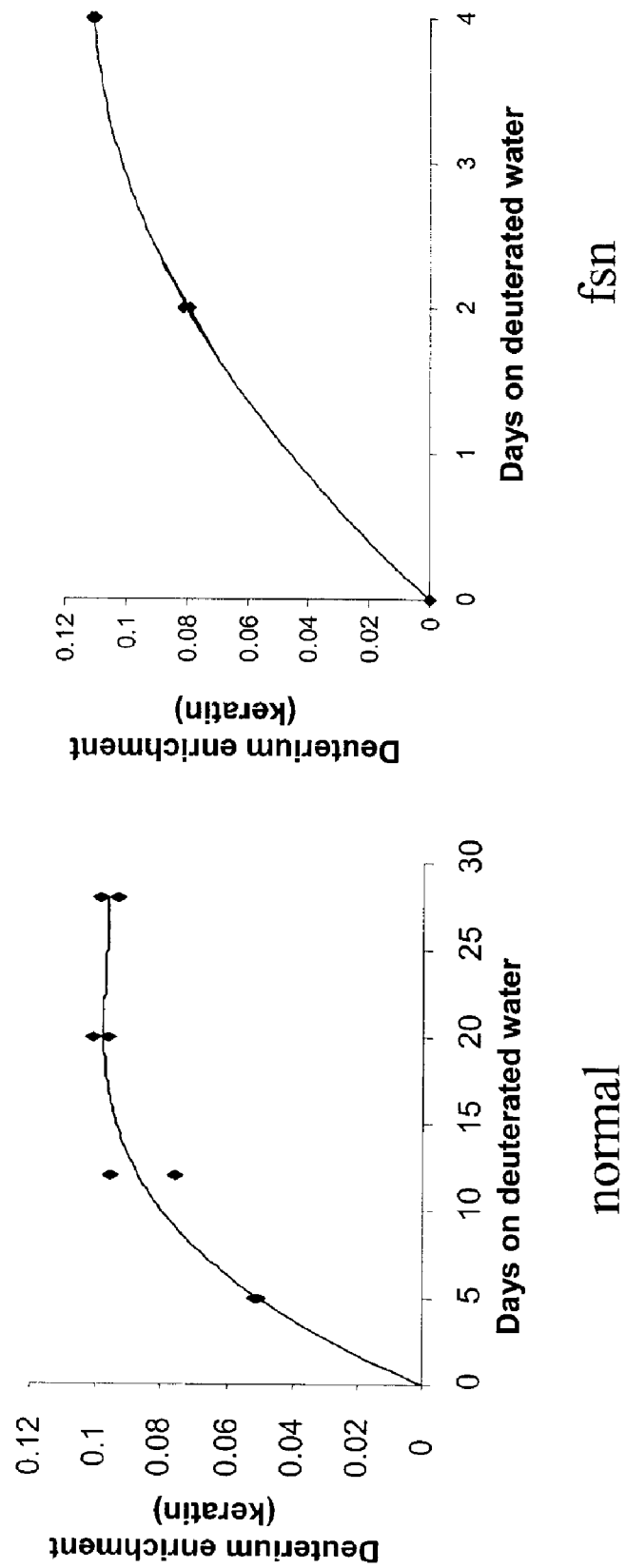
FIG. 16 depicts keratin kinetics in normal and fsn mice. Fsn mice are mutant mice with a psoriasis-like phenotype. Keratin turnover is dramatically enhanced in fsn mice as measured by deuterium incorporation into keratin—fsn mice reach maximal labeling in 4 days as opposed to 15 for control animals.
Figure 17:
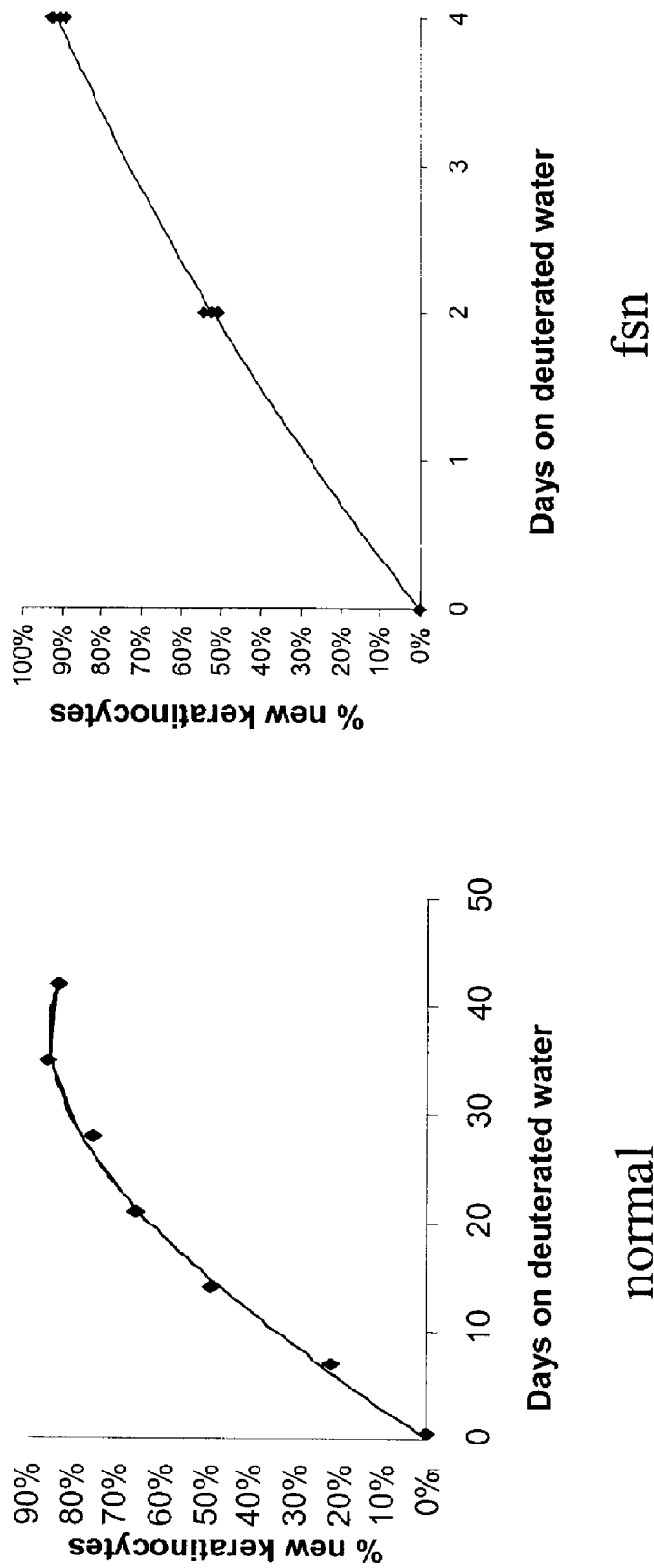
FIG. 17 depicts keratinocyte kinetics in normal and fsn mice. Fsn mice are mutant mice with a psoriasis-like phenotype. Keratinocyte turnover is enhanced in fsn mice as measured by deuterium incorporation into keratinocyte DNA—fsn mice reach maximal labeling in 4 days as opposed 30 for control animals.

Keratin turnover in normal and flaky skin ("fsn") mice is shown in FIG. 16, and keratinocyte proliferation, measured with the methods described herein, from normal and fsn mice is shown in FIG. 17. These results show increased keratin synthesis and keratinocyte proliferation in the fsn mouse model of psoriasis.

The methods of the present invention allow for the administration of a compound, or a combination of compounds or a mixture of compounds to evaluate the ability to inhibit keratinocyte proliferation or keratin synthesis and thereby identify for further development and evaluation treatments for psoriasis and other skin diseases and conditions.

I claim:

1. A method for evaluating an action of one or more compounds on a molecular flux rate through an adipose triglyceride metabolic pathway in a living system, said method comprising:
   a) administering a first isotope-labeled substrate to a first living system, not exposed to said one or more compounds, for a period of time sufficient for said first isotope-labeled substrate to enter into and label at least one glycerol or fatty acid derived from triglyceride to produce at least one first isotope-labeled glycerol or first isotope-labeled fatty acid derived from triglyceride within said first living system;
   b) obtaining one or more samples from said first living system, wherein said one or more samples comprise said at least one first isotope-labeled glycerol or first isotope-labeled fatty acid derived from triglyceride;
   c) measuring an isotopic content, rate of incorporation, and/or pattern or rate of change in isotopic content and/or pattern of isotope labeling of said at least one first isotope-labeled glycerol or first isotope-labeled fatty acid derived from triglyceride;
   d) calculating a molecular flux rate through said adipose triglyceride metabolic pathway based on the isotopic content, rate of incorporation, and/or pattern or rate of change of isotopic content and/or pattern of isotopic labeling in said at least one first isotope-labeled glycerol or first isotope-labeled fatty acid derived from triglyceride;
   e) exposing a second living system to said one or more compounds;
   f) administering a second isotope-labeled substrate to said second living system for a period of time sufficient for said second isotope-labeled substrate to enter into and label at least one glycerol or fatty acid derived from triglyceride to produce at least one second isotope-labeled glycerol or second isotope-labeled fatty acid derived from triglyceride;
   g) obtaining one or more samples from said second living system, wherein said one or more samples comprise said at least one second isotope-labeled glycerol or second isotope-labeled fatty acid derived from triglyceride;
   h) measuring an isotopic content, rate of incorporation, and/or pattern or rate of change in isotopic content and/or pattern of isotope labeling of said at least one second isotope-labeled glycerol or second isotope-labeled fatty acid derived from triglyceride;
   i) calculating a molecular flux rate through said adipose triglyceride metabolic pathway in said second living system based on the isotopic content, rate of incorporation, and/or pattern or rate of change in isotopic content and/or pattern of isotope labeling of said at least one second isotope-labeled glycerol or second isotope-labeled fatty acid derived from triglyceride; and
   j) comparing said molecular flux rate through said adipose triglyceride metabolic pathway in said first living system to said molecular flux rate through said adipose triglyceride metabolic pathway in said second living system to evaluate the action of said one or more compounds on said molecular flux rate through the adipose triglyceride metabolic pathway in said second living system.

2. The method of claim 1, wherein the molecular flux rate through said adipose triglyceride metabolic pathway is an indicator of obesity, lipoatrophy, fat distribution, or hyperplasia-hypertrophy.

3. The method of claim 2, wherein the molecular flux rate through said adipose triglyceride metabolic pathway contributes to the initiation, progression, severity, pathology, aggressiveness, grade, activity, disability, mortality, morbidity, disease sub-classification or other underlying pathogenic or pathologic feature of obesity, lipoatrophy, fat distribution, hyperplasia-hypertrophy, atherosclerosis, or risk of diabetes mellitus.

4. The method of claim 2, wherein the molecular flux rate through said adipose triglyceride metabolic pathway contributes to the prognosis, survival, morbidity, mortality, stage, therapeutic response, symptomology, disability or other clinical factor of obesity, lipoatrophy, fat distribution, hyperplasia-hypertrophy, atherosclerosis, or risk of diabetes mellitus.

5. The method of claim 2, wherein the molecular flux rate through said adipose triglyceride metabolic pathway in said first living system and the molecular flux rate through said adipose triglyceride metabolic pathway in said second living system are measured concurrently.

6. The method of claim 5, wherein said concurrent measurement is achieved by use of stable isotopic labeling techniques.

7. The method of claim 6, wherein said first isotope-labeled substrate and said second isotope-labeled substrate are stable, non-radioactive isotope-labeled substrates.

8. The method of claim 7, wherein said first isotope-labeled substrate and said second isotope-labeled substrate are both stable isotope-labeled water.

9. The method of claim 8, wherein the stable isotope-labeled water is $^2H_2O$.

10. The method of claim 5, wherein said concurrent measurement is achieved by use of radioisotope labeling techniques.

11. The method of claim 1, wherein said first living system and said second living system are each independently selected from the group consisting of a prokaryotic cell, a eukaryotic cell, a cell line, an isolated tissue preparation, a rabbit, a dog, a mouse, a rat, a guinea pig, a pig, a non-human primate, and a human.

12. The method of claim 11, wherein said first living system and said second living system are both a human.

13. The method of claim 1, wherein said first isotope labeled substrate and said second isotope labeled substrate are each independently selected from the group consisting of $^2H_2O$, $^2H$-glucose, $^2H$-labeled amino acids, $^2H$-labeled organic molecules, $^{13}C$-labeled organic molecules, $^{13}CO_2$, $^3H_2O$, $^3H$-labeled glucose, $^3H$-labeled amino acids, $^3H$-labeled organic molecules, $^{14}C$-labeled organic molecules, and $^{14}CO_2$.

14. The method of claim 1, wherein said isotope labeled substrate is $^2H_2O$.

15. An isotope-labeled glycerol or fatty acid derived from triglyceride generated by the method of claim 1.

16. The method of claim 1, wherein said first living system and said second living system are different individual living systems of the same species.

17. The method of claim 1, wherein said first living system is said second living system prior to exposure to said one or more compounds.

18. The method of claim 17, wherein said first living system and said second living system are both the same individual human subject.

19. The method of 1, wherein the glycerol or fatty acid derived from triglyceride is from adipose tissue.

* * * * *